(12) United States Patent
Adams et al.

(10) Patent No.: US 11,090,313 B2
(45) Date of Patent: *Aug. 17, 2021

(54) METHODS FOR INHIBITING MUSCLE ATROPHY

(71) Applicants: UNIVERSITY OF IOWA RESEARCH FOUNDATION, Iowa City, IA (US); THE UNITED STATES GOVERNMENT AS REPRESENTED BY THE DEPARTMENT OF VETERANS AFFAIRS, Washington, DC (US)

(72) Inventors: Christopher M. Adams, Iowa City, IA (US); Steven D. Kunkel, West Richland, WA (US); Michael Welsh, Riverside, IA (US)

(73) Assignees: UNIVERSITY OF IOWA RESEARCH FOUNDATION, Iowa City, IA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/661,660

(22) Filed: Oct. 23, 2019

(65) Prior Publication Data
US 2020/0061083 A1    Feb. 27, 2020

Related U.S. Application Data

(60) Continuation-in-part of application No. 16/157,767, filed on Oct. 11, 2018, now Pat. No. 10,668,087, (Continued)

(51) Int. Cl.
| | | |
|---|---|---|
| A61K 31/58 | (2006.01) |
| A61K 31/436 | (2006.01) |
| A61K 31/215 | (2006.01) |
| A61K 31/352 | (2006.01) |
| A61K 31/36 | (2006.01) |
| A61K 31/382 | (2006.01) |
| A61K 31/404 | (2006.01) |
| A61K 31/4164 | (2006.01) |

(Continued)

(52) U.S. Cl.
CPC ............ *A61K 31/58* (2013.01); *A61K 31/215* (2013.01); *A61K 31/352* (2013.01); *A61K 31/353* (2013.01); *A61K 31/36* (2013.01); *A61K 31/382* (2013.01); *A61K 31/404* (2013.01); *A61K 31/407* (2013.01); *A61K 31/4164* (2013.01); *A61K 31/4166* (2013.01); *A61K 31/435* (2013.01); *A61K 31/436* (2013.01); *A61K 31/437* (2013.01); *A61K 31/438* (2013.01); *A61K 31/4355* (2013.01); *A61K 31/4365* (2013.01); *A61K 31/4375* (2013.01); *A61K 31/473* (2013.01); *A61K 31/4706* (2013.01); *A61K 31/56* (2013.01); *A61K 31/565* (2013.01); *C12Q 1/6809* (2013.01); *G01N 33/5023* (2013.01); *C12Q 2600/136* (2013.01); *G01N 2800/10* (2013.01); *G01N 2800/52* (2013.01)

(58) Field of Classification Search
CPC combination set(s) only.
See application file for complete search history.

(56) References Cited

U.S. PATENT DOCUMENTS

| | | |
|---|---|---|
| 2,910,470 A | 10/1950 | Baran et al. |
| 3,466,279 A | 9/1969 | Marx |

(Continued)

FOREIGN PATENT DOCUMENTS

| | | | |
|---|---|---|---|
| CH | WO 2011/043827 | * | 10/2019 |
| CN | 1582990 A | | 2/2005 |

(Continued)

OTHER PUBLICATIONS

Reagen-Shaw et al. in The FASEB Journal 22, 659-661 (2007) (Year: 2007).*

(Continued)

*Primary Examiner* — Dennis Heyer
(74) *Attorney, Agent, or Firm* — Heslin Rothenberg Farley & Mesiti P.C.

(57) ABSTRACT

The invention provides a method for (a) increasing skeletal muscle mass; (b) reducing skeletal muscle atrophy; (c) increasing muscular strength; (d) promoting muscle growth; (e) decreasing muscle wasting; or (f) increasing strength per unit of muscle mass in an animal identified or having been identified to be in need of one or more of (a)-(f), the method comprising administering to the animal an effective amount of a compound of formula:

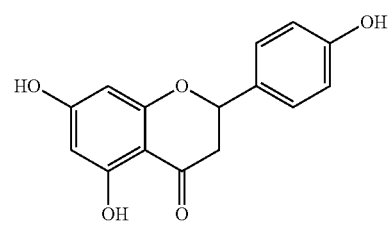

or a stereoisomer, solvate, or pharmaceutically acceptable salt thereof, thereby accomplishing one or more of (a)-(f).

21 Claims, 42 Drawing Sheets

Related U.S. Application Data which is a continuation of application No. 15/051,246, filed on Feb. 23, 2016, now Pat. No. 10,137,136, which is a division of application No. 14/124,582, filed as application No. PCT/US2012/041119 on Jun. 6, 2012, now Pat. No. 9,295,664, application No. 16/661,600, which is a continuation-in-part of application No. 15/804,590, filed on Nov. 6, 2017, now abandoned, which is a continuation of application No. 13/698,645, filed as application No. PCT/US2011/037238 on May 19, 2011, now Pat. No. 9,856,204, application No. 16/661,660, which is a continuation-in-part of application No. 16/003,184, filed on Jun. 8, 2018, now Pat. No. 10,576,091, which is a continuation of application No. 14/978,886, filed on Dec. 22, 2015, now Pat. No. 10,022,386, which is a continuation of application No. 14/612,636, filed on Feb. 3, 2015, now Pat. No. 9,254,295, which is a continuation of application No. PCT/US2013/053423, filed on Aug. 2, 2013.

(60) Provisional application No. 61/493,969, filed on Jun. 6, 2011, provisional application No. 61/445,488, filed on Feb. 22, 2011, provisional application No. 61/346,813, filed on May 20, 2010, provisional application No. 61/730,496, filed on Nov. 27, 2012, provisional application No. 61/679,432, filed on Aug. 3, 2012.

(51) Int. Cl.

| | | |
|---|---|---|
| *A61K 31/4166* | (2006.01) | |
| *A61K 31/4355* | (2006.01) | |
| *A61K 31/4365* | (2006.01) | |
| *A61K 31/437* | (2006.01) | |
| *A61K 31/4375* | (2006.01) | |
| *A61K 31/438* | (2006.01) | |
| *A61K 31/4706* | (2006.01) | |
| *A61K 31/56* | (2006.01) | |
| *A61K 31/353* | (2006.01) | |
| *A61K 31/407* | (2006.01) | |
| *A61K 31/435* | (2006.01) | |
| *A61K 31/473* | (2006.01) | |
| *A61K 31/565* | (2006.01) | |
| *G01N 33/50* | (2006.01) | |
| *C12Q 1/6809* | (2018.01) | |

(56) References Cited

U.S. PATENT DOCUMENTS

| | | | |
|---|---|---|---|
| 3,485,825 | A | 12/1969 | Marx |
| 3,539,449 | A | 11/1970 | Marx |
| 3,625,941 | A | 12/1971 | Pappo et al. |
| 3,903,089 | A | 9/1975 | Vanstone |
| 4,647,574 | A | 3/1987 | Ienaga et al. |
| 5,196,545 | A | 3/1993 | Schermanz et al. |
| 5,422,350 | A | 6/1995 | Woolf |
| 5,885,992 | A | 3/1999 | Ohgi et al. |
| 5,985,924 | A | 11/1999 | Ishikawa et al. |
| 6,096,364 | A | 8/2000 | Bok et al. |
| 6,770,630 | B2 | 8/2004 | Kashiwaba et al. |
| 7,612,045 | B2 | 11/2009 | Eldridge |
| 9,254,295 | B2 | 2/2016 | Adams et al. |
| 9,295,664 | B2 | 3/2016 | Adams et al. |
| 9,856,204 | B2 | 1/2018 | Adams et al. |
| 10,137,136 | B2 | 11/2018 | Adams et al. |
| 2003/0153538 | A1 | 8/2003 | Kuno et al. |
| 2003/0198684 | A1* | 10/2003 | Yegorova ............ A61K 31/352 424/520 |
| 2004/0086553 | A1 | 5/2004 | Shinohara et al. |
| 2004/0087557 | A1 | 5/2004 | Steiner et al. |
| 2004/0110663 | A1 | 6/2004 | Dudek et al. |
| 2005/0153968 | A1 | 7/2005 | Bi et al. |
| 2006/0025354 | A1 | 2/2006 | Nair et al. |
| 2006/0079562 | A1 | 4/2006 | Ewing et al. |
| 2007/0014719 | A1 | 1/2007 | Reading et al. |
| 2007/0259837 | A1 | 11/2007 | Meier et al. |
| 2008/0119426 | A1 | 5/2008 | Dale |
| 2008/0145322 | A1 | 6/2008 | Eldridge |
| 2009/0042857 | A1 | 2/2009 | Yamaoka et al. |
| 2009/0143279 | A1 | 6/2009 | Mootha et al. |
| 2009/0163580 | A1* | 6/2009 | Yatcilla ............ A61P 19/10 514/456 |
| 2010/0104669 | A1 | 4/2010 | Scheffler et al. |
| 2010/0112030 | A1 | 5/2010 | Parhami et al. |
| 2010/0204121 | A1 | 8/2010 | Romero et al. |
| 2010/0305068 | A1 | 12/2010 | Bulawa et al. |
| 2011/0008333 | A1 | 1/2011 | Dudek et al. |
| 2011/0097427 | A1 | 4/2011 | Ramakrishnan et al. |
| 2012/0177730 | A1 | 7/2012 | Baron et al. |
| 2013/0203712 | A1 | 8/2013 | Adams et al. |
| 2016/0243132 | A1 | 8/2016 | Adams et al. |
| 2018/0118657 | A1 | 5/2018 | Adams et al. |
| 2019/0105333 | A1 | 4/2019 | Adams et al. |

FOREIGN PATENT DOCUMENTS

| | | |
|---|---|---|
| CN | 101940616 A | 1/2011 |
| EP | 0020029 A1 | 12/1980 |
| EP | 0774255 A1 | 5/1997 |
| EP | 0920870 A1 | 6/1999 |
| EP | 1889850 A1 | 2/2008 |
| EP | 1987827 A1 | 11/2008 |
| JP | 56-154500 A | 11/1981 |
| JP | H09143076 A | 6/1997 |
| JP | 11171766 A | 6/1999 |
| JP | 2010-095459 A | 4/2010 |
| WO | 95/26330 | 10/1995 |
| WO | 2006/007910 A1 | 1/2006 |
| WO | 2006/034586 A1 | 4/2006 |
| WO | 2006/036638 A1 | 4/2006 |
| WO | 2007/011674 A2 | 1/2007 |
| WO | WO-2007053915 A2 | 5/2007 |
| WO | WO-2008063318 A2 | 5/2008 |
| WO | 2010056880 A1 | 5/2010 |
| WO | 2010/132776 A1 | 11/2010 |
| WO | WO-2010124847 A1 | 11/2010 |
| WO | 2011043827 A1 | 4/2011 |
| WO | WO-2011046978 A2 | 4/2011 |
| WO | 2011/146768 A1 | 11/2011 |
| WO | WO-2011153315 A1 | 12/2011 |
| WO | 2012033422 A1 | 3/2012 |

OTHER PUBLICATIONS

Herath et al. in Chem. Pharm. Bull. 56(4)418-422 (2008) (Year: 2008).*
Wilcox et al. in Cardiovascular Drug Reviews, 17(2), 160-178 (1999) (Year: 1999).*
Extended European Search Report for PCT/US2012/041119 dated Mar. 25, 2015.
Narici et al., *British Medical Bulletin* 2010; 95: 139-159.
M. C. Dyle, et al., Systems-based Discovery of Tomatidine as a Natural Small Molecule Inhibitor of Skeletal Muscle Atrophy, Journal of Biological Chemistry, Apr. 9, 2014, pp. 14913-14924, vol. 289, No. 21.
Richard F. Keeler, et al., Cyclopamine and related steroidal alkaloid teratogens: Their occurrence, structural relationship, and biologic effects, Lipids, Oct. 1, 1978, pp. 708-715, vol. 13, No. 10.
Shalender Bhasin, The Brave New World of Function-Promoting Anabolic Therapies: Testosterone and Fraility; Journal of Clinical Endocrinology & Metabolism, Feb. 1, 2010, pp. 509-511, vol. 95, No. 2.
Supplemental Search Report from EPO dated Nov. 24, 2014.
Ortiz-Andrade et al. in Diabetes, Obesity and Metabolism 10 1097-1104 (2007).

(56) References Cited

OTHER PUBLICATIONS

Jang et al. in International Immunopharmacology 9, 113-119 (2009).
Amendment filed Sep. 27, 2013 for Australian Patent Application No. 2011255495, which claims priority to PCT/US2011/037238, which published as WO 2011/146768 dated Sep. 24, 2011 (Applicant: University of Iowa Research Foundation // Inventor—Adams, et al) (10 pages).
Notice of Allowance of Amendment to the Specification dated Oct. 11, 2013 for for Australian Patent Application No. 2011255495, which claims priority to PCT/US2011/037238, which published as WO 2011/146768 dated Nov. 24, 2011 (Applicant: University of Iowa Research Foundation // Inventor—Adams, et al) (1 page).
Amendment filed Aug. 2, 2013 for Chinese National Phase Patent Application No. 201180035480X, which claims priority to PCT/US2011/037238, which published as WO 2011/146768 dated Nov. 24, 2011 (Applicant: University of Iowa Research Foundation // Inventor—Adams, et al) (7 pages).
Amendment filed Jul. 8, 2013 for European Patent Application No. 11784273.2, which claims priority to PCT/US2011/037238, which published as WO 2011/146768 dated Nov. 24, 2011 (Applicant: University of Iowa Research Foundation // Inventor—Adams, et al) (5 pages).
Communication pursuant to Rules 161(2) and 162 EPC dated Jan. 7, 2013 for Jul. 8, 2013 for European Patent Application No. 11784273.2, which claims priority to PCT/US2011/037238, which published as WO 2011/146768 dated Nov. 24, 2011 (Applicant: University of Iowa Research Foundation // Inventor—Adams, et al) (2 pages).
International Search Report dated Aug. 17, 2011 by the International Searching Authority for PCT Application No. PCT/US2011/037238, which published as WO 2011/146768 dated Nov. 24, 2011 8 Applicant: University of Iowa Research Foundation // Inventor—Adams, et al) (2 pages).
International Preliminary Report on Patentability dated Nov. 20, 2012 by the International Searching Authority for PCT Application No. PCT/US2011037238, which published as WO 2011/146768 dated Nov. 24, 2011 (Applicant: University of Iowa Research Foundation // Inventor—Adams, et al) (5 pages).
Written Opinion dated Aug. 17, 2011 by the International Searching Authority for PCT Application No. PCT/US2011/037238, which published as WO 2011/146768 dated Nov. 24, 2011 (Applicant: University of Iowa Research Foundation // Inventor—Adams, et al) (4 pages).
International Search Report dated Nov. 5, 2012 by the International Searching Authority for PCT Application No. PCT/US2012/041119, which published as WO 2012/170546 dated Dec. 13, 2012 (Applicant: University of Iowa Research Foundation // Inventor—Adams, et al) (5 pages).
International Search Report dated Feb. 8, 2013 by the International Searching Authority for PCT Application No. PCT/US2012/066341, which published as WO 2013/078372 dated Nov. 24, 2011 (Applicant: University of Iowa Research Foundation // Inventor—Adams, et al) (5 pages).
Written Opinion dated Feb. 8, 2013 by the International Searching Authority for PCT Application No. PCT/US2012/066341, which published as WO 2013/078372 dated Nov. 24, 2011 (Applicant: University of Iowa Research Foundation // Inventor—Adams, et al) (7 pages).
"Urosolic Acid Extract." http://www.ursolicare.com. Visited May 10, 2011.
Abbas T, et al. (2009). p21 in cancer; intricate networks and multiple; activities. Nat Rev Cancer 9: 400-414.
Abelian van Kan G. (2009) Epidemiology and consequences of sarcopenia. The Journal of Nutrition, Health & Aging 13: 708-712.
Acharyya S, et al. (2004) Cancer cachexia is regulated by selective targeting of skeletal muscle gene products. J Clin Investig 114: 370-378.
Acharyya S, et al. (2005) Dystrophin glycoprotein complex dysfunction: a regulatory link between muscular dystrophy and cancer cachexia. Cancer Cell 8(5): 421-432.

Adams CM, et al. (2011) Altered mRNA expression after long-term soleus electrical stimulation training in humans with paralysis. Muscle & Nerve 43(1): 65-75.ms.
Adams GR & Haddad F (1996) The relationships among IGP-1, DNA content, and protein accumulation during skeletal muscle hypertrophy. J Appl Physiol 81(6): 2509-2516.
Adams GR, et al. (1999) Time course of changes in markers of myogenesis in overloaded rat skeletal muscles. J Appl Physiol 87(5):1705-1712.
Adams V, et al. (2008) Induction of MuRF1 is essential for TNF-alpha-induced loss of muscle function in mice. Journal of molecular biology 384(1):48-59.
Adnyana, et al. (2001) Three new triterpenes from the seeds of combretum quadrangulate and their heparoprotective activity. J Nat Prod 64:360-363.
Almarasson O, et al. (2004) Crystal engineering of the composition of pharmaceutical phases. Do pharmaceutical co-crystals represent a new path to improved medicines? The Royal Science of Chemistry, 1889-1896.
Amthor H, et al. (2007) Lack of myostatin results in excessive muscle growth but impaired force generation. PROC Natl Acad Sci U.S.A., 104: 1835-1840.
Anderson R, et al. (2000). A simple method for the rapid generation of; recombinant adenovirus vectors. Gene therapy 7, 1034-1038.
Astley ST, et al. (1993) Hippeastrine synthesis: a comibined biodioxygenation/organoiron chirality relay approach. Tetrahedron Lett 34: 2035-2038.
Banduseela VC, et al. (2009) Gene expression and muscle fiber function in a porcine ICIJ model. Physiol. Genomics 39: 141-159.
Barres R, et al. (2009) Non-CpG methylation of the PGC-1α promoter through DNMT3B controls mitochondrial density, Cell Metabolism 10: 189-198.
Barres R, et al. (2012) Acute exercise remodels promoter methylation in human skeletal muscle. Cell Metabolism 15: 405-411.
Barreto G, et al. (2007), Gadd45a promotes epigenetic gene activation by repair-mediated DNA demethylation/ Nature 445: 671-675.
Barton-Davis ER, et al. (1998) Viral mediated expression of insulin-like growth factor I blocks the aging-related loss of skeletal muscle function. Proc Natl Acad Sci U.S.A. 95(26):15603-15607.
Bastida J, et al. (2011) Chemical and biological aspects of amaryllidaces alkaloids. Recent Advances in Pharmaceutical Sciences, 65-70.
Baumgartner RN, et al. (1998) Am J Epidemiol 147: 755-763.
Benmani-Baiti N and Walsh D, et al. (2011). Animal models of the cancer anorexia-cachexia syndrome. Support Care Cancer 19(9): 1451-1463.
Benson EK., et al. (2009) Single-vector inductible lentiviral RNAi system for oncology target validation, Cell cycle (Georgetown, Tex 8, 2002-2004.
Bird, A (2002) Genes & Development 16, 6-21.
Bodine SC., et al. (2001a) Identification of ubiquitin ligases required for skeletal muscle atrophy. Science 294: 1704-1708.
Bodine SC., et al., (2001b) Akt/mTOR pathway is a crucial regulator of skeletal muscle hypertrophy and can prevent muscle atrophy in vivo. Nat Cell Biol 3(11):1014-1019.
Bradley, et al. (2008) Myostatin as a therapeutic target for musculoskeletal disease. Cell Mol Life Sci, 65: 2119-2124.
Brfining JC, et al., (1998) A muscle-specific insulin receptor knockout exhibits features of the metabolic syndrome of NIDDM without altering glucose tolerance, Mol Cell 2: 559-569.
Burks TN, et al. (2011) Losartao restores skeletal muscle remodeling and protects against disuse atrophy in sarcopenia. Sci. Translat. Med. 3: 82ra3?.
Burridge S. (2011) Obesity and diabetes: lipid boosts muscle and shrinks fat. Nature Reviews Drug Discovery 10(8): 576.
Burton L.A. and Sumukadas D. (2010) Clin Interv Aging 5, 217-228.
Busquets S. et al. (2012) Myostatin blockage using actRIIB antabonsim in mice bearing the Lewis lung carcinoma results in the improvement of muscle wasting and physical performance. Journal of Cachexia, Sacropennia, and Muscle 3(1): 37-43.

(56) References Cited

OTHER PUBLICATIONS

Cai D, et al. (2004) LKKB/NF-κB activation causes severe muscle wasting in mice. Cell 119: 285-298.

Caron AZ, et al., (2009) A novel hindlimb immobilization procedure for studying skeletal muscle atrophy and recovery in mouse. J Appl Physiol. 106: 2049-2059.

Chadalapaka G, et al (2008) Structure-dependent inhibition of bladder and pancreatic cancer cell growth by 2-substituted glycynchetinic and ursolic acid derivatives. Biorganic and Medicinial Chemisty Letters 18(8): 2633-2639.

Chaturvedula, et al. (2004) A new ursane triterpene from Monochaetum vulcanicum that inhibits DNA polymerase beta lyase, J Nat Prod 67: 899-901.

Chedin F. (2011) Progress in molecular biology and translational science 101: 255-285.

Chen H, et al. (2010) Mitochondrial fusion is required for mtDNA stability in skeletal muscle and tolerance of mtDNA mutations. Cell 141: 280-289.

Chiu FL and Lin JK. (2008) Tomatidine inhibitors iNOS and COX-2 through supression of NF-kappaB and JNK pathways in LPS-stimulated mouse macrophages. FEBS letters 582(16): 2407-2412.

Choi SH, et al. (2012) Structure-acitvity relationships of alpha-, beta(1)-, gamma-, and delta-tomatine and tomatidine against human breast (MDA-MB-231), gastric (KATO-III), and prostate (PC3) cancer cells. Journal of Agricultural and Food Chemistry 60(15): 3891-3899.

Cohen S, et al. (2009) During muscle atrophy, thick, but not thin, filament components are degraded by McRF1-dependent ubiquitylation. The Journal of Cell Biology 185(6):1083-1095.

Cohn RD, et al. (2002) Disruption of DAG1 in differentiated skeletal muscle reveals a role for dystroglycan in muscle regeneration. Cell 110: 639-648.

Coker RH and Wolfe RR. (2011) Bedrest and sarcopenia. Curr Opin Clin Nutr Metab Care 15, 7-11.

Cornelissen B, et al. (2008). The level of insulin growth factor-1 receptor expression is directly correlated with the tumor uptake of (111)IN-IGF-1(ER3) in vivo and the clonogenic survival of breast cancer cells exposed in vitro to transuzumab (Herceptin). Nuclear Medicine and Biology 35(6): 645-653.

Cortellino S, et al. (2011) Thymine DNA glycosylase is essential for active DNA demethylation by linked deamination-base excision repais. Cell, 146: 67-79.

Coss CC, et al. (2011) Cancer cacexia therapy: a key weapon in the fight against cancer. Curr Opin Clin Nutr Mateb Care 14(3): 268-273.

Das SK, et al. (2011) Adipose triglyceride lipase contributes to cancer-associated cachexia. Science 333(6039):233-238.

De Angel RE, et al. (2010) Antitumor effects of ursolic acid in a mouse model of postmenopausal breast cancer. Nutrition and Cancer 62(8): 1074-1086.

de Melo CI., et al. (2010) Oleanolic acid a natural triterpenoid improves blood glucose tolerance in normal mice and ameliorates visceral obesity in mice fed a high-fat diet. Chem Biol Interact 185(1): 59-65.

Dedkov EI, et al. (2003) Dynamics of post-denervation atrophy of young and old skeletal muscles. Differential responses of fiber types and muscle types. J Gerontol 58: 984-991.

Delibergovie M, et al. (2007) Improved glucose homeostasis in mice with muscle-specific deletion of protein-tyrosine phosphatase 1B. Molecular and Cellular Biology 27(21):7727-7734.

Deng Y. et al. (2000). Peg3/Pw1 promotes p53-mediated apoptosis by inducing Bax translocation from cytosol to mitochondria. Proc Natl Acad Sci U.S.A. 97: 12050-12055.

Dobrowolny G, et al. (2005) Muscle expression of a local IgF-I isoform protects motor neurons in an ALS mouse model. The Journal of Cell Biology 168(2):193-199.

Doucet M, et al. (2007) Muscle atrophy and hypertrophy signlaing in patients with chronic obstructive pulmonary disease. American Journal of Respiratory and Critical Care Medicine 176(3):261-269.

Dubowicz V, et al. (2007) Muscle biopsy : a practical approach (Saunders Elsevier, Philadelphia) 3rd Ed pp. XIII, 611 s.

Dupors J, et al. (2001) Insulin-like growth factor I (IGF-1)-induced twist expression is involved in the anti-apoptotic effects of the IGF-1 receptor. The Journal of Biological Chemistry 276(28): 26699-26707.

Easwaran H P, et al. (2010) Role of nuclear architecture in epigenetic alterations in cancer. Cold Springs Harbor Symp Quant Biol 75: 507-515.

Ebert SM, et al. (2010) The transcription factor ATF4 promotes skeletal myofiber atrophy during fasting. Molecular endocrinology 24(4):790-799.

Ebert SM, et al. (2012) Stress-induced skeletal muscle Gadd45a expression reprograms myonuclei and causes muscle atrophy. The Journal of Biological Chemistry, 287: 27290-27301.

Edwards, MG, et al. (2007) Gene expression profiling of aging reveals activation of a p53-mediated transcriptional program. BMC Genomics 8: 80.

Elchehly et al. (1999) Increased insulin activity sensitivity and obesity resistance in mice lacking the protein tyrosine phosphatase-1B gene. Science, 283: 1544-1548.

el-Deiry WS, et al. (1995) Cancer research 55: 2910-2919.

Evidente A, et al. (Apr. 2009) Biological evaluation of structurally diverse amaryllidacase alkaloids and their synthetic derivatives: discovery of novel leads for anticancer drug design. Plants Med 75(5): 501-507.

Fearon KC. (2011) Cancer cachexia and fat-muscle physiology. The New England Journal of Medicine 365(6):565-567.

Fearon KC, et al. (2012) Cancer cachexia: mediators, signaling, and metaboloic pathways. Cell metabolism 16: 153-166.

Flood M and Newman AM. (2007) Journal of Gerontological Nursing 33, 19-35; quiz 36-17.

Frame S, et al. (2001) GSK3 takes center stage more than 20 years after its discovery. Biochem J 359: 1-16.

Fry CS, et al. (2011) Skeletal Muscle Protein Balance and Metabolism in the Elderly. Current Aging Science 4: 260-268.

Gao Y, et al. (2010) The Synthesis of Glycyrrhetinic Acid Derivatives Containing A Nitrogen Heterocycle and Their Antiproliferative Effects in Human Leukemin Cells. Molecules 15: 4439-4449.

Genet C., et al. (2010) Structure-activity relationship study of betulinic acid, a novel and selective TGR5 agonist, and its synthetic derivatives: potential impact in diabetes. J. Med. Chem. 53: 178-790.

Gentile MA, et al. (2010) Androgen-mediated improvement of body composition and muscle function involves a novel early transcriptional program including IGF1, mechano growth factor, and induction of (beta)-catenin. Journal of Molecular Endocrinology 44(1):55-73.

Glass D, et al. (2010) Recent advances in the biology and therapy of muscle wasting. Ann N Y Acad Sci 1211: 25-36.

Glass DJ. (2005) Skeletal muscle hypertrophy and atrophy signaling pathways. The international journal of biochemistry & cell biology 37(10):1974-1984.

Gomes MD, et al. (2001) Atrogin-1, a muscle-specific F-box protein highly expressed during muscle atrophy. Proc Natl Acad Sci U.S.A. 98: 14440-14445.

Goncalves DA, et al. (2009). Mechanisms involved in 3', 5'-cyclic adenosine monophosphate-mediated inhibition of the ubiquitin-proteasome system in skeletal; muscle, Endocrinology 15: 5395-5404.

Gonzalez de Aguilar JL., et al. (2008) Gene profiling of skeletal muscle in an amyotrophic lateral sclerosis mouse model. Physiol Genomics 32: 207-218.

Gundersen K, et al. (2008) Nuclear domains during muscle atrophy. Nuclei lost or paradigm lost? J Physiol 586: 2675-2681.

Hameed M. et al. (2004) The effect of recombinant human growth hormone and resistance training on IGF-1 mRNA expression in the muscles of elderly men. The Journal of Physiology 555(Pt1):231-240.

Haning H, et al. (2011) Total symbesis of the amarylidaceae alkaloid clivonine. Organic & Biomolecular Chemistry 9:2809-2820.

(56) References Cited

OTHER PUBLICATIONS

Harding HP, et al. (2003) An integrated stress response regulates amino acid metabolism and resistance to oxidative stress. Mol Cell 11: 619-633.
Hirose M, et al. (2011) Long-term denervation impairs insulin receptor substrate 1-mediated insulin signaling in skeletal muscle. Metabolism: Clinical and Experimental 50(2):216-222.
Hishiya A, et al. (2006) A novel ubiquitin-binding protein ZNF216 functioning in muscle atrophy. The EMBO journal 25(3):554-564.
Hu Z, et al. (2009) Endogenous glucocorticoids and impaired insulin signaling are both required to stimulate muscle wasting under pathophysiological conditions in mice. The Journal of Clinical Investigation 119(10):3059-3069.
Ikuta, et al. (2003) Ursane- and Oleanane-Type Triterpenes from Ternstroemia gymanthera Callus Tissues, J Nat Prod 66: 1051-1054.
Ishido M, et al. (2004) American Journal of Physiology 287: C484-493.
Izumiya Y, et al. (2008) Fast/Glycolytic muscle fiber growth reduces fat mass and improves metabolic parameters in obese mice. Cell Metabolism 7(2):159-172.
Jager S, et al. (2009) Pentacyclic Triterpene distribution in various plants—rich sources for a new group of multi-potent plant extracts. Molecules 14: 2016-2031.
Jagne RT, et al. (2002) Patterns of gene expression in atrophying skeletal muscles: response to flood deprivation. Faseb J 16(13):1697-1712.
Jang SM, et al. (2009) Ursolic acid enhances the cellular immune systems and pancreatic beta-cell function in streptozotocin-induced diabetic mice fed a high-fat diet. Int Immunopharmacol 9(1):113-119.
Janssen I, et al. (2004) The healthcare costs of sarcopenia in the United States J Am Geriatr Soc 52: 80-85.
Jayaprakasam B, et al. (2006) Amelioration of obesity and glucose intolerance in high-fat-fed C57BL/6 mice by anthocyanins and arsolic acid in Cornelian cherry (Cornus mas). J Agric Food Chem 54(1):243-248.
Jiang H. et al. (2007). The eukaryotic initiation factor-2 kinase pathway facilitates differential GADD45n expression in response to environmental stress. The Journal of Biological Chemistry 282: 3755-3765.
Jones (2010) Nature, 468: 752-753.
Jung SH, et al. (2007) Insulin-mimetic and insulin-sensitizing activities of a pentacyclic triterpenoid insulin receptor activator. The Biochemical journal 403(2):243-250.
Jung Y, et al. (2010). Examination of the expanding pathways for the regulation of p21 expression and activity. Cell Signal 22: 1003-1012.
Kajimura S. et al. (2010) Transcriptional control of brown fat development. cell Metabolism 11(4): 257-262.
Kamei Y, et al. (2004) Potential role of microsomal prostaglandin in E synthase-1 in tumorigenesis. The Journal of Biological Chemistry 279: 41114-41123.
Kandarian SC and Jackman RW (2006) Intracellular signaling during skeletal muscle atrophy. Muscle & nerve 33(2):155-165.
Kaneko-Ishino T, et al. (1995). Peg1/Mest imprinted gene on chromosome 6 identified by cDNA subtraction hybridization. Nature Genetics 11: 52-59.
Kastan M, et al. (1992) A mammalian cell cycle checkpoint pathway utilizing p53 and GADD45 is defective in anxia-telangiectasia. Cell 71: 587-597.
Kawamata Y, et al. (2003). A G protein-coupled receptor responsive to bile acids. J. Biol Chem 278: 9435-9440.
Kenner KA, et al. (1996). Protein-tyrosine phosphatase 1B is a negative regulator of insulin- and insulin-like growth factor-I-stimulated signaling. J Biol Chem 271: 19810-19816.
Kessar, et al. (1971) Synthetic studies in steroidal sapogenins and alkaloids—X: Synthesis of tomatid-5-Ene-3-ol and solasodine. Tetrahedron 27: 2869.

Klaman LD, et al. (2000) Increased energy expenditure, increased adiposity, and tissue-specific insulin sensitivity in protein-tyrosine phosphatase 1B-deficient mice. Molecular and Cellular Biology 20(15): 5479-5489.
Koh SJ, et al. (2012) Sensitization of ionizing radiation-induced apoptosis by ursolic acid. Free Radical Research 46(3): 339-345.
Korényi-Both AL. (1983) Muscle Pathology in Neuromuscular Disease, C.C. Thomas, Springfield, IL.
Kunkel S, et al. (2011) mRNA Expression Signatures of Human Skeletal: Muscle Atrophy Identify a Natural Compound that Increases Muscle Mass. Cell Metabolism; 13: 627-638.
Kunkel SD, et al. (2012) Ursolic Acid increases skeletal muscle and brown fat and decreases diet-induced obesity, glucose intolerance and Fatty liver disease. PloS one 7(6):e39332.
Kutner MH, et al. (2004) Applied Linear Regression Models, 4th ed., McGraw-Hill/Irwin, Boston.
Kwon SH, et al. (2010) Apoptotic action of ursolic isolated from corni fructus in RC-58T/h/SAH4 primary human prostate cancer cells. Bioorganic and Medicinal Chemistry Letters 20(22): 6435-6438.
Kwon TH, et al. (2009) Synthesis and NO production inhibitory activities of ursolic acid and oleanolic acid derivatives. Bull Korean Chem. Soc. 30(1): 119-123.
Lagirand-Cantaloube J. et al. (2008) The initiation factor eIFP3-f is a major target for atrogin1/MAFbx function in skeletal muscle atrophy. The EMBO Journal 27(8):266-1276
Lai KM, et al. (2004) Conditional activation of akt in adult skeletal muscle induces rapid hypertrophy. Molecular and Cellular Biology 24(21):9295-9304.
Lal A. and Garospe M. (2006) Cell Cycle (Georgetown Tex) 5: 1422-1425.
Lamb J, et al. (2006) The Connectivity Map: using gene-expression signatures to connect small molecules, genes, and disease. Science 313(5795):1929-1935.
Laure I., et al. (2009) Cardiac ankyrin repeat protein is a marker of skeletal muscle pathological remodeling. FEBS J 276: 669-68.
Lauthier F, et al. (2000) Ursolic acid triggers calcium-dependent apoptosis in human Daudi cells. Anti-Cancer Drugs 11: 737-745.
Le May N, et al. (2010) NER factors are recruited to active promoters and facilitate chromatin modification for transcription in the absence of esogenous genatoxic attack.. Mol Cell 38: 54-66.
Lecker SH, et al. (2004) Multiple types of skeletal muscle atrophy involve a common program of changes in gene expression FASEB J 18(1):39-51.
Lee SJ (2004) Regulation of muscle mass by myostatin. Annu Rev Cell Dev Biol 20:61-86.
Leger B, et al. (2006) Human skeletal muscle atrophy in amyotrophic lateral sclerosis reveals a reduction in Akt and an increase in atrogin-1, FASEB J 20(3):583-585.
Leinonen. (2006) Novel mass spectrometric analysis methods for anabolic androgenic steroids in sports drug testing. Department of Pharmaceutical Chemistry Faculty of Pharmacy University of Helsinki Finland.
Levine S, et al. (2008) Rapid disuse atrophy of diaphragm fibers in mechanically ventilated humans. The New England journal of medicine 358(13):1327-1335.
Li JB and Goldberg AI., (1976) Effets of food deprivation an protein synthesis and degradation in rat skeletal muscles. Am J Physiol 231: 441-448.
Liebermann DA and Hoffman B. (2008) Gadd45 in stress signaling. J. Mol. Signal 3, 15; Lin H, et al. (2010) Skp2 targeting suppresses tumorigenesis by Arf-p53-independent cellular senescence. Nature 464: 374-379.
Lin H, et al. Skp2 targeting suppresses tumorigenesis by Arf-p53-; independent cellular senescence Nature 464, 374-379.
Liu J, (1995) Pharmacology of cleanolic acid and ursolic acid. Journal of ethnopharmacology 49(2):57-68.
Liu J, (2005) Oleanolic acid and ursolic acid: research perspectives. Journal of Ethnopharmacology 100(1-2): 92-94.
Llano-Diez M, et al. (2011) BMC Genomics 12: 602.
Lonning PE & Helle SI (2004) IGF-1 and breast cancer. Novartis Foundation Symposium 262: 205-212; discussion 212-204, 265-208.

(56) References Cited

OTHER PUBLICATIONS

Ma J, et al. (1999) Prospective study of colorectal cancer risk in men and plasma levels of insulin-like growth factor (IGF)-1 and IGF-binding protein-3. Journal of the National Cancer Institute 91(7): 620-625.
Malmberg SE and Adams CM (2008) Insulin signaling and the general amino acid control response. Two distint pathways to amino acid synthesis and uptake. J Biol Chem 283: 19229-19234.
Mummucari C, et al. (2007) FoxO3 controls autophagy in skeletal muscle in vivo. Cell Metab 6: 458-471.
Manas CG, et al. (2010) Total synthesis of the lycorenine-type amaryllidaceae alkaloid- (+)-clinonine via a biomimetric ring-switch from a lycorine-type progenitor. J Am Chem Soc, 132: 5176-5178.
Masuoka H. et al. (2002) Targeted disruption of the activating transcription factor 4 gene results in severe fetal anemia in mice, Blood 99: 736-745.
Mendez J and Keys A. (1960) Density and composition of mammalian muscle. Metabolism: Clinical and Experimental 9:184-189.
Meng Y, et al. (2010) Molecules 15: 4033-4040.
Michael LF, et al. (2001) Restoration of insulin-sensitive glucose transporter (GLUT4) gene expression in muscle cells by the transcriptional coactivator PGC-1. Proc Natl Acad Sci U.S.A. 98: 3820-3825.
Miller RA and Nadon NL (2000) Principles of animal use for gerontological research. The Journals of Gerontology 55A: B117-123.
Moresi V, et al. (2010) Myogenin and class II HDACs control neurogenic muscle atrophy by inducing E3 ubiqultin ligases. Cell 143: 35-45.
Musarò A, et al. (2001) Localized igf-1 transgene expression sustains hypertrophy and regeneration in senescent skeletal muscle. Nature Genetics 27(2): 195-200.
Nathanson L. et al. (1994) Chemohormone therapy of metastic melanoma with megestrol acetate plus dacarbazine, carmustine, and cisplatin. Cancer 73(1):98-102.
Nichrs C. and Schafer A. (2012) Active DNA demethylation by Gadd45 and DNA repair Trends Cell Biol 22: 220-227.
Nishimura, et al. (1999) Activity-Guided Isolation of Triterpenoid Acyl CoA Cholesteryl Acyl Transferase (ACAT) Inhibitors from llex kudinchs. J Nat Prod 62: 1061-11064.
Novotny J., et al. (2001) Ursolic acid: an anti-tumorigenic and chemopreventive activity. Minireview Neoplasma 48(4): 241-246.
Pallafacchina G. et al. (2002) A protein kinase B-dependent and and rapamycin-sensitive pathway controls skeletal musle growth but not fiber type specification. Proceedings of the National Academy of Sciences of the United States of America 99(14):9213-9218.
Palus S, et al., (2011). Ghrelin and Its Analogues, BIM-28131 and BIM-; 28215, Improve Body Weight and Regulate the Expression of MuRF-1 and MAFbx in a Rat; Heart Failure Model. PLoS One, 6(11): e26865.
Pathak, et al. (2008) Expeditions microwave-assisted thionation with the system $PSCT3/H_2O/Et_3N$ under solvent-free condition. J Org Chem 73: 2890-2893.
Peterson JM, et al. (2011) NF-kB signaling in skeletal muscle health and disease. Curr Top Dev Biol 96: 85-119.
Plant PJ, et al. (2009) Absence of caspase-3 protects against denervation-induced skeletal muscle atrophy. J. Appl. Physiol 107: 224-234.
Porter DC, et al. (2012) Cyclin-depenent kinase 8 mediates chemotherapy induced tumor-promoting paracrine activities. Proc Natl Acad Sci U.S.A. 109: 13799-13804.
Powers SK, et al. (2012) Mitochondrial signaling contributes to disuse muscle atrophy. Am J Physiol Endocrinol Metab 303: E31-39.
Prasad S, et al. (2012) Ursolic acid inhibits growth and metastasis of human colorectal cancer in an orthotopic nude mouse model by targeting multiple cell signaling pathways: chemosensitization with capectiabine. Clin Cancer Res.

Proctor, et al. (2000) Synthesis of tacrine analogues and their structure-activity relationships. Curr Medical Chem 7: 295-302.
Qian S, et al. (2010) Synthesis and biological evaluation of oleanolic acid derivatives as inhibitors of protein tyrosine phosphatase 1B. J Nat Prod 73(11):1743-1750.
Reagan-Shaw S. et al. (2008) Dose translation from animal to human studies revisited. FASEB J 22(3):659-661.
Rodino-Klapec et al. (2009) Muscle Nerve 39: 283-296.
Sacheck J, et al. (2007). Rapid disuse and denervation atrophy involve; transcriptional changes similar to those of muscle wasting during systemic diseases. FASEB J: 21, 140-155.
Sacheck JM, et al. (2004) IGF-1 simulates muscle growth by suppressing protein breakdown and expression of atrophy-related ubiquitin ligases, atrogin-1 and MuRF1. Am J Physiol Endocrinol Metah 287(4):E591-601.
Sakuma K and Yamaguchi A. (2012) Novel intriguing strategies attenuating to sarcopenia. Journal of Aging Research 2012:251217.
Sandri M (2008) Signaling in muscle atrophy and hyertrophy. Physiology 23: 160-170.
Sandri M, et al. (2004) Foxo transcription factors induce the atrophy-related ubiquitin ligase atrogin-1 and cuase skeletal muscle atrophy. Cell 117(3): 399-412.
Sandri M, et al. (2006) PGC-1a protects skeletal muscle from atrophy by supressing FoxO3 action and atrophy-specific gene transcription. Proc Natl Acad Sci U.S.A. 103: 16260-16265.
Sartori R, et al. (2009) Smad2 and 3 transcription factors control muscle mass in adulthood. American Journal of Physiology 296: C1248-1257.
Schiaffino S and Mammucari C. (2011) Regulation of skeletal muscle growth by the IGF1-Akt/PKB pathway. Insights from genetic models. Skelet Muscle 1:4.
Schmitz KM, et al. (2009) TAF12 recruits Gadd45a and the nucleotide excision repair complex to the promoter of tRNA genes leading to active DNA demethylation. Mol Cell 33: 344-353.
Schwarzkopf M, et al. (2006) Muscle cachexia is regulated by a p53-PW1/Peg3-dependent pathway. Genes Dev. 20: 3440-3452.
Scime A., et al. (2005) Rb and p107 regulate preadipocyte differentiation into while versus brown fat through repression of PGC-1alpha. Cell metabolism 2: 283-295.
Sen Gl., et al. (2010) Nature 463: 563-567.
Shanmugam MK, et al. (2011) Ursolic acid inhibits multiiple cell survival pathways leading to suppression of growth of prostate cancer xenograft in jude mice. Journal of Molecular Medicine 89(7): 713-727.
Shavlakadze T, et al. (2005) Insulin-like growth factor I slows the rate of denervation induced skeletal muscle atrophy. Neuromuscul Disord 15(2):139-146.
Siegel R, et al. (2011) Cancer statistics, 2011: the impact of eliminating socioeconomic and racial disparities on premature cancer deaths. CA Cancer J Clin 61(4): 212-236.
Sivakumar G. et al.(2009) Plant-based corosolic acid: future antidiabetic drug? Biotechnol J 4(12):1704-1711.
Skipworth RJ, et al. (2007) Pathophysiology of cancer cachexia much more than host-tumor interaction. Clinical Nutrition 26(6): 667-676.
Sporn MB, et al (2011) New Synthric triterpenoids: potent agents for prevention and treatment of tissue injury caused by inflammatory and oxidative stress. J Nat Prod 74: 537-545.
Stevenson F, et al. (2003) Global analysis of gene expression patterns during disuse atrophy in rat skeletal muscle. The Journal of Physiology 551, 33-48.
Stitt TN, et al. (2004) The IGF-1/Pt3K/Akt pathway prevents expression of muscle atrophy-induced ubiquitin ligases by inhibiting FOXO transcription factors. Moll Cell 14(3): 395-403.
Subramanian A. et al. (2005). Gene ses enrichment analysis: a knowledge-based approach for interpreting genome-wide expression profiles. Proc Natl Acad Sci U.S.A. 102: 15545-15550.
Sun H, et al. (2006) Structure-activity relationships of oleanane- and ursane- type triterpenoids. Botanical Studies 47: 339-368.
Suneja BI., et al. (2010). The transcription factor ATF4 promotes skeletal myofiber atrophy during fasting. Mol. Endocrinol. 24, 790-799.

(56) References Cited

OTHER PUBLICATIONS

Sytnikova YA, et al. (2011) Gadd45a is an RNA-binding protein and is localized in nuclear speckles. PloS One 6, e14500.
Tan B and Fearon KC. (2008) Cachexia: prevalence and impact in medicine. Curr Opin Clin Nutr Metab Care 11(4): 400-407.
Tan BH, et al. (2009) Sarcopenia in an overweight or obese patient is an adverse prognosite factor in pancreatic cancer. Clin Cancer Res 15(22): 6973-6979.
Tian J, et al. (2011) Gadd45? is an inducible coactivator of transcription that facilitates rapid liver growth in mice. J Clin Investig 121: 4491-4502.
Tran H, et al. (2002) DNA repair pathway stimulated by the forkhead trascription factor FOXO3a through the Gadd45 protein. Science 296: 530-534.
Tureckova J, et al. (2001) Insulin-like growth factor-mediated muscle differentiation: collaboration between phosphatidylinositol 3-kinase-Akt-signaling pathways and myogenin. The Journal of Biological Chemistry 276(42):39264-39270.
Uhle. (1954) J Am Chem Soc 76: 6412.
Uhle. (1961) J Am Chem Soc 83: 1460.
Uldry M, et al. (2006) Complementary action of the PGC-1 coactivators in mitochondrial biogenesis and brown fat differentication. Cell Metab 3: 333-341.
Verhees KJ, et al. (2011) Glycogen synthase kinase-3? is required for the induction of skeletal muscle atrophy. Am J Physiol Cell Physiol 301: C995-C1007.
Volk KA, et al. (2005) The Journal of Biological Chemistry 280: 18348-18354.
von Haeling S and Anker SD, (2010) Cachexia as a major under estimated and unmet medical need: facts and numbers. Journal of Cachexia, Sacropenia, and Muscle 1(1): 1-5.
Wang JS, et al. (2012) Ursolic acid induces apoptosis by suppressing the expression of FoxMI in MCF-7 human breast cancer cells. Medical Oncology 29: 10-15.
Wang X, et al. (2005) Runx 1 prevents wasting, myofibrillar disorganization, and autophagy of skeletal muscle. Genes Dev 19: 1715-1722.
Wang X, et al. (2011) Ursolic acid inhibits proliferation and induces apoptosis of cancer cells in vitro and in vivo. Journal of Biomedicine and Biotechnology 2011: 419343.
Wang ZH, et al. (2010) Anti-glycative effects of cleanolic acid and ursolic acid in kidney of diabetic mice. European Journal of Pharmacology 628(1-3):255-260.
Watanabe M, et al. (2006). Bile acids induce energy expenditure by; promoting intracellular thyroid hormone activation. Nature 439: 484-489.
Weber M, et al. (2005). Chromosome-wide and promoter-specific analysis identify sites of differential DNA methylation in normal and transformed human cells. Nature Genetics 37; 853-862.
Welle S, et al. (2003) Gene expression profile of aging in human muscle. Physiol Genomics 14: 149-159.
Wells S, et al. (2004) Skeletal muscle gene expression profiles in 20-29-year-old and 65-71-year-old women. Exp Gerontol 39: 369-377.
Wenz T, et al. (2009) Increased muscle PGC-1alpha expression protects from sarcopenic and metabolic disease during aging. Proc Nat Acad Sci U.S.A. 106(48): 20405-20410.
Yakar S, et al. (1999) Normal growth and development in the abscence of hepatic insulin-like growth factor I. Proc Nat Acad Sci U.S.A. 96(13):7324-7329.
Yi YW, et al. (2000) Gadd45 family proteins are coactivators of nuclear hormone receptors. Biochem Biophys Res Commun 232: 193-198.
Ying QL., et al. (1991) Inhibition of human leucocyte elastase by ursolic acid. Biochem J, 277: 521-526.
Zabolotny JM, et al. (2004) Transgenic overexpression of proteintyrosine phosphatase 1B in muscle causes insulin resistance, but overexpression with leukocyte antigen-related phospharase does not additively impair insulin action. The Journal of Biological Chemistry 279(23):24844-24851.

Zeman R, et al. (2009). Differential skeletal muscle gene expression after; upper or lower motor neuron transection. Pflugers Arch 458: 525-535.
Zhan Q. (2005) Gadd45a, a p53- and BRCA1-regulated stress protein, in cellular response to DNA damage. Mutation Research 569: 133-143.
Zhang W, et al. (2006) Ursolic acid and its derivative inhibit protein tyrosine phosphatase 1B, enhancing insulin receptor phosphorylation and stimulating glucose uptake. Biochimica et Biophysica Acta 1760(10):1505-1512.
Zhang YN, et al. (2008) Oleanolic acid and its derivatives: new inhibitor of protein tyrosine phosphatase 1B with cellular activities. Bioorg Med Chem 16(18):8697-8705.
Zhang Z., et al. (2007) Sensitization of calcitonin gene-related peptide receptors by receptor activity-modifying protein-1 in the trigeminal ganglion. J Neurosci 27: 2693-270.
Zhao H, et al. (2000). The central region of Gadd45 is required for its interaction with p21/WAF1. Experimental Cell Research 258: 92-100.
Zhao J, et al. (2007) FoxO3 coordinately activates protein degradation by the autophagic/lysosomal and proteasomal pathways in atrophying muscle cells. Cell Metab 6: 472-483.
Zhon X. et al. (2010) Reversal of cancer cachexia and muscle wasting by ActRIIB antagonism lends in prolonged survival. Cell 142(4):531-43.
Yamada, K., et al., "Dietary Corosolic Acid Ameliorates Obesity and Hepatic Steatosis in KK-Ay Mice", Biol. Pharm. Bull., vol. 31, No. 4, pp. 651-655 (2008).
Baar, K., et al., "Phosphorylation of $p70^{s6k}$ correlates with increased skeletal muscle mass following resistance exercise", Am. J. Physiol., vol. 276 (Cell Physiol 45), pp. 120-127 (1999).
Belemtougri, R.G., et al., "Effects of two medicinal plants *Psidium guajava* L. (Myrataceae) and *Diospyros mespiliformis* L. (Ebenaceae) leaf extracts on rat skeletal muscle cells in primary culture" Journal of Zhejiang University, Science B, vol. 7, No. 1, pp. 56-63 (2006).
Liu, J., "Pharmacology of oleanolic acid and ursolic acid", Journal of Ethnopharmacology, vol. 49, pp. 57-68 (1995).
Rasmussen, B.B., et al., "The balancing act between the cellular processes of protein synthesis and breakdown: exercise as a model to understand the molecular mechanisms regulating muscle mass", J. Appl. Physiol., vol. 106, pp. 1365-1366 (2009).
Golovina, T.N., et al., "Effect of Ursolic Acid on Energy and Carbohydrate Metabolism in Muscles", Issled. Mekh. Vliyaniya Bal'neol. Faktorov Regul. Sist. Org, Editor(s): Shautsukova, L.K. Kabard.- Balkar. Gos. Univ.; Nalchik, USSR, pp. 101-102 (1976). Russian version and English translation.
Friedman, M., et al., "α-Tomatine Content in Tomato and Tomato Products Determined by HPLC with Pulsed Amperometric Detection", J. Agric. Food Chem., vol. 43, No. 6, pp. 1507-1511 (1995).
Koh, E., et al., "A long-term comparison of the influence of organic and conventional crop management practices on the content of the glycoalkaloid α-tomatine in tomatoes", J. Sci. Food Agric., vol. 93, pp. 1537-1542 (2013).
Rick, C.M., et al., "High α-tomatine content in ripe fruit of Andean *Lycopersicon esculentum* var. *Cerasiforme*: Developmental and genetic aspects", Proc. Natl. Acad. Sci. USA, vol. 91, pp. 12877-12881 (1994).
International Search Report for PCT/US2013/053423 dated Dec. 19, 2013.
Fugiwara, Y., et al., Tomatidine, a Tomato Sapogenol, Ameliorates Hyperlipidemia and Atherosclerosis in ApoE-Deficient Mice by Inhibiting Acyl-CoA: cholesterol Acyl-transferase (ACAT), American Chemical Society Publications, "Journal of Agricultural and Food Chemistry", vol. 60, pp. 2472-2479 (2012).
Azevedo, M.F., et al., "Ursolic Acid and Luteolin-7-Glucoside Improve Lipid Profiles and Increase Liver Glycogen Content through Glycogen Synthase Kinase-3", Phytotherapy Research, vol. 24, pp. S220-S224 (2010).
Kunkel, S.D., et al., "mRNA Expression Signatures of Human Skeletal Muscle Atrophy Identify a Natural Compound that Increases Muscle Mass", Cell Metabolism, vol. 13, pp. 627-638 (2011).
Narici et al., British Medical Bulletin, vol. 95, pp. 139-159 (2010).

(56) References Cited

OTHER PUBLICATIONS

Bodine, S.C., et al., "Akt/mTOR pathway is a crucial regulator of skeletal muscle hypertrophy and can prevent muscle atrophy in vivo", Nature Cell Biology, vol. 3, pp. 1014-1019 (2001).

Kuno, N., et al., "Antiobesity foods and beverages containing pentacyclic triterpenes, especially olives", Accession No. 2003-468459, Derwent Information LTD (2009).

Lee, S., et al., "Anabolic activity of ursolic acid in bone: Stimulating osteoblast differentiation in vitro and inducing new bone formation in vivo", Pharmacol Res., vol. 58, No. 5-6, pp. 290-296 (2008).

Kubica, N., et al., "Resistance Exercise Increasese Muscle Protein Synthesis and Translation of Eukaryotic Initiation Factor $2B_E$ mRNA in a Mammalian Target of Rapamycin-dependent Manner", The Journal of Biological Chemistry, vol. 280, No. 9, pp. 7570-7580 (2005).

Guttridge, D.C., "Signaling pathways weigh in on decisions to make or break skeletal muscle", vol. 7, No. 4, pp. 443-450 (2004) Abstract Only.

Lee et al., "Ursolic Acid Ameliorates Thymic Atrophy and Hyperglycemia in Streptozotocin-Nicotinamide-Induced Diabetic Mice," Chem Biol Interact. Dec. 5, 2010;188(3):635-42.

Fu et al., Obesity Impairs Skeletal Muscle Regeneration Through Inhibition of AMPK, Diabetes Jan;65(1):188-200 (2016).

Fujimaki et al., Diabetes-Induced Dysfunction of Mitochondria and Stem Cells in Skeletal Muscle and the Nervous System, International Journal of Molecular Sciences 18(10):2147 (2017).

Zygmunt et al., "Naringenin, a Citrus Flavonoid, Increases Muscle Cell Glucose Uptake Via AMPK," Biochemical and Biophysical Research Communications 398, 2010, pp. 178-183.

Mukai et al., "Quercetin Prevents Unloading-Derived Disused Muscle Atrophy by Attenuating the Induction of Ubiquitin Ligases in Tail-Suspension Mice," Journal of Natural Products 73(1), Sep. 2010, pp. 1708-1710.

Wilcox et al., "Antiatherogenic Properties of Naringenin, a Citrus Flavonoid," Cardiovascular Drug Reviews, vol. 17, No. 2, pp. 160-178.

Herath et al., "Microbial Metabolism Part 9.[1)] Structure and Antioxidant Significance of the Metabolites of 5,7-Dihydroxyflavone (Chrysin), and 5- and 6-Hydroxyflavones,".

Reagan-Shaw et al., "Dose Translation From Animal to Human Studies Revisited," The FASEB Journal, Life Sciences Forum, vol. 22, Mar. 2007, pp. 659-661.

Hsiu et al., "Comparison of Metabolic Pharmacokinetics of Naringin and Naringenin in Rabbits," Life Sciences, vol. 70, 2002, pp.

J.G. Cannon Chapter Nineteen in Burger's Medicinal Chemistry and Drug Discovery, Fifth Edition, vol. 1: Principles and Practice, Wiley-Interscience 1995, pp. 783-802.

\* cited by examiner

Human Muscle Atrophy Signature-1

Conserved Effects of Fasting on Human and Mouse Skeletal Muscle

| Induced mRNAs | Repressed mRNAs |
|---|---|
| ABCA1 | ACACA |
| ACOX1 | BPGM |
| ADPGK | CACNB1 |
| CALCOCO1 | CASQ1 |
| CAT | CNNM4 |
| CITED2 | DNMT3A |
| CPT1A | FEZ2 |
| GABARAPL1 | GAS2 |
| HERPUD1 | GRTP1 |
| HMOX1 | HSPH1 |
| IGF1R | JTB |
| INSR | MRPS15 |
| MED13L | MTSS1 |
| MYO5A | NEO1 |
| NBR1 | NFYA |
| NOX4 | P4HA2 |
| PDK4 | PBX1 |
| PPAP2B | PDE7B |
| RORA | PMP22 |
| SESN1 | PGC-1α |
| SFRS8 | PTX3 |
| SLC38A2 | SLC4A4 |
| SRPM2 | SPINT2 |
| SUPT6H | ST8SIA5 |
| TULP3 | SUV39H2 |
| TXNIP | TFRC |
| UBE4A | TGFB2 |
| UCP2 | TSPAN13 |
| UCP3 | TTLL1 |
| XPO4 | VEGFA |
| ZFAND5 | WDR1 |
|  | ZNF280B |

FIG. 2

Human Muscle Atrophy Signature-2

Conserved Effects of Fasting and SCI on Human Skeletal Muscle

| Induced mRNAs | Repressed mRNAs |
|---|---|
| CAV3 | CMAS |
| CTDSP2 | GUCY1B3 |
| CUGBP2 | HSPB7 |
| IGF1R | MRPS15 |
| IRS2 | PDE7B |
| KLF11 | PFDN6 |
| MLL | PGC-1α |
| NOX4 | SLC16A1 |
| NPC2 | TSPAN13 |
| NUPR1 | TTLL1 |
| OR1D4 | VEGFA |
| RHOBTB1 | VLDLR |
| SUPT6H | ZNF280B |
| TSPAN8 | ZNF32 |
| ZNF682 |  |

FIG. 3

| Conserved Effects of Fasting on Human and Mouse Skeletal Muscle ||
|---|---|
| Induced mRNAs | Repressed mRNAs |
| ABCA1 | ACACA |
| ACOX1 | BPGM |
| ADPGK | CACNB1 |
| CALCOCO1 | CASQ1 |
| CAT | CNNM4 |
| CITED2 | DNMT3A |
| CPT1A | FEZ2 |
| GABARAPL1 | GAS2 |
| HERPUD1 | GRTP1 |
| HMOX1 | HSPH1 |
| IGF1R | JTB |
| INSR | MRPS15 |
| MED13L | MTSS1 |
| MYO5A | NEO1 |
| NBR1 | NFYA |
| NOX4 | P4HA2 |
| PDK4 | PBX1 |
| PPAP2B | PDE7B |
| RORA | PMP22 |
| SESN1 | PGC-1α |
| SFRS8 | PTX3 |
| SLC38A2 | SLC4A4 |
| SRRM2 | SPINT2 |
| SUPT5H | ST8SIA5 |
| TULP3 | SUV39H2 |
| TXNIP | TFRC |
| UBE4A | TGFB2 |
| UCP2 | TSPAN13 |
| UCP3 | TTLL1 |
| XPO4 | VEGFA |
| ZFAND5 | WDR1 |
|  | ZNF280B |

FIG. 6A

FIG. 10A
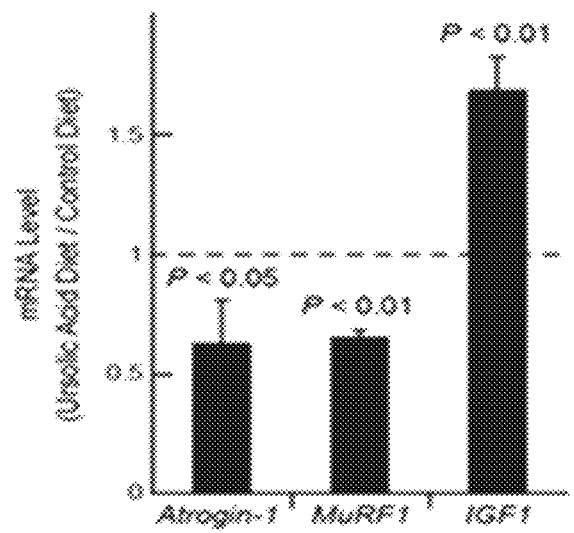
FIG. 10B
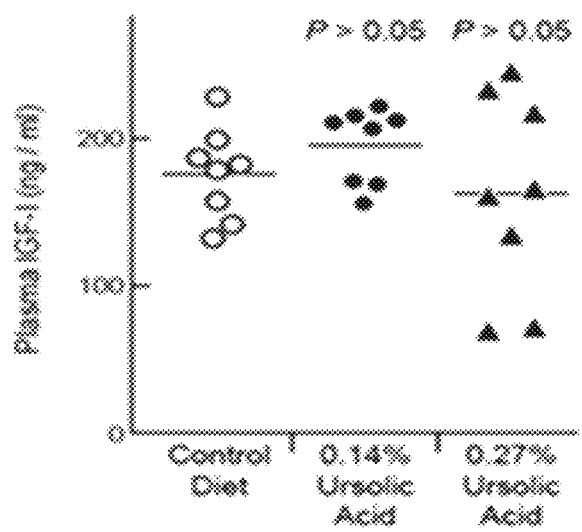
FIG. 10C

| Probe ID | Probe Position | IGF1 Exon | Log2 Hybridization Signals | | | p. |
|---|---|---|---|---|---|---|
| | | | Control | Ursolic Acid | Ursolic - Control | |
| 4803942 | chr10: 87322847 - 87323726 | 2 | 5.65 | 5.93 | 0.28 | 0.14 |
| 4714856 | chr10: 87324043 - 87324110 | 2 | 7.28 | 7.62 | 0.65 | 0.88 |
| 5397208 | chr10: 87327403 - 87327614 | 3 | 8.32 | 8.72 | 0.40 | 0.51 |
| 5261482 | chr10: 87376384 - 87376803 | 4 | 9.73 | 10.28 | 0.54 | 0.01 |
| 5254460 | chr10: 87378043 - 87378065 | 5 | 8.73 | 8.73 | 1.00 | 0.02 |
| 5265449 | chr10: 87378100 - 87378172 | 6 | 6.77 | 6.17 | 0.40 | 0.20 |
| 5275924 | chr10: 87378201 - 87378413 | 6 | 7.81 | 8.63 | 0.93 | 0.04 |
| 5467780 | chr10: 87393446 - 87393470 | 6 | 9.65 | 9.90 | 0.25 | 0.16 |

FIG. 11A

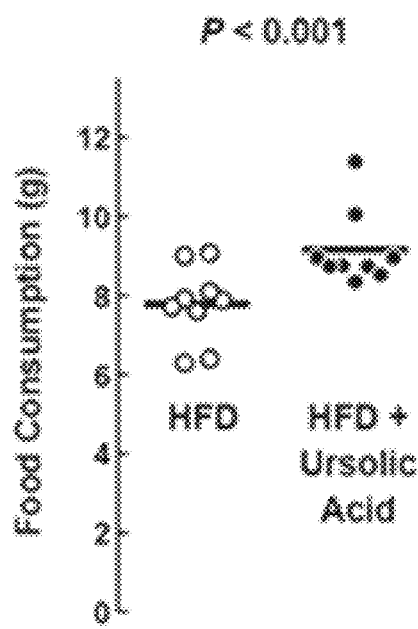
FIG. 14I
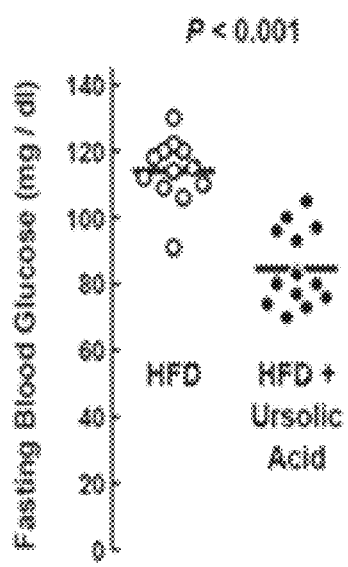 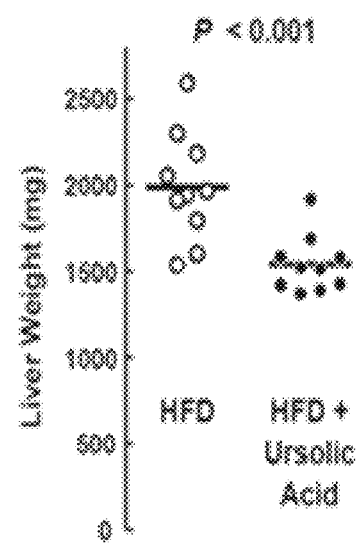
FIG. 15A          FIG. 15B

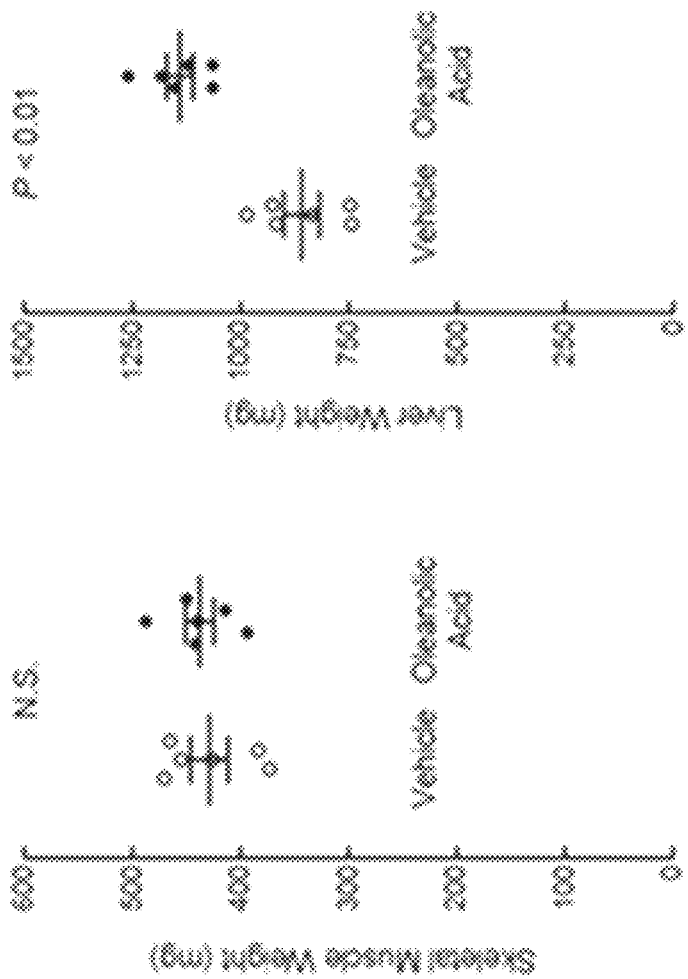
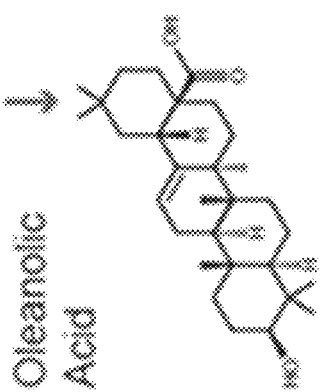
FIG. 16F
FIG. 16E
FIG. 16D

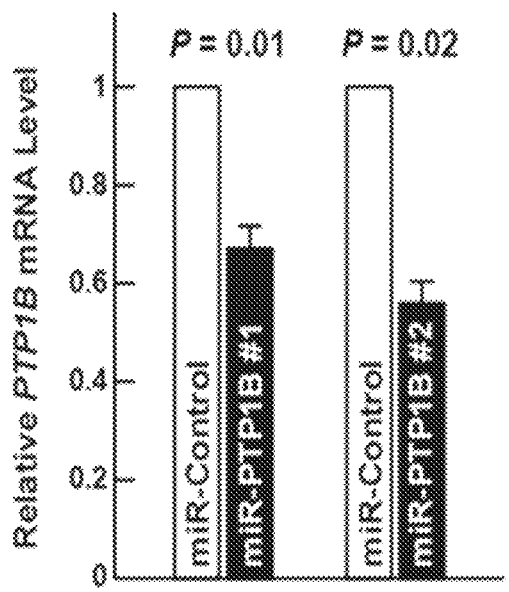
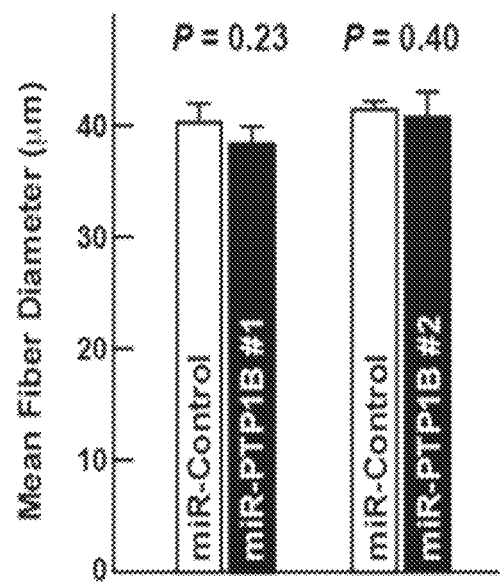
FIG. 17A
FIG. 17B
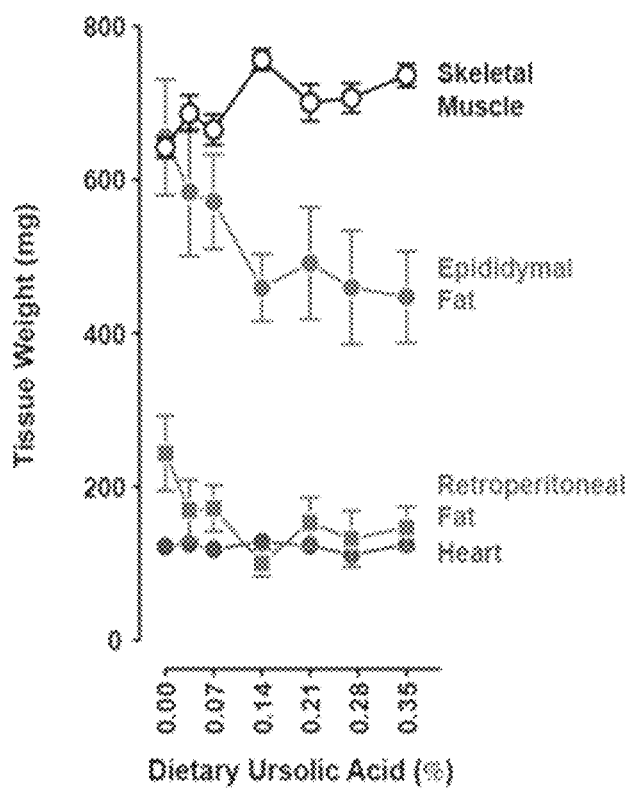
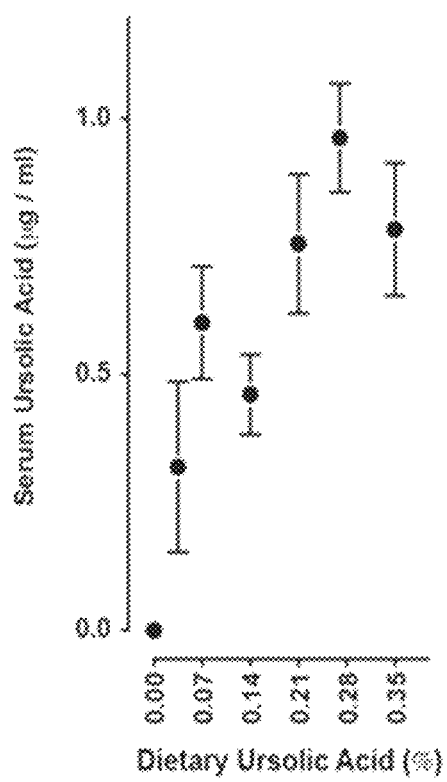
FIG. 18A
FIG. 18B

METHODS FOR INHIBITING MUSCLE ATROPHY

CROSS-REFERENCE TO RELATED APPLICATIONS

This application is a continuation-in-part of U.S. application Ser. No. 16/157,767, filed Oct. 11, 2018 (which published as US 2019-0105333 A1) which is a continuation of U.S. application Ser. No. 15/051,246, filed Feb. 23, 2016, which is a divisional of U.S. application Ser. No. 14/124,582 (which has a 371(c) date of Mar. 28, 2014), which is a national phase entry under 35 U.S.C. § 371 of International Application No. PCT/US2012/041119, filed Jun. 6, 2012, which claims the benefit of U.S. Provisional Application No. 61/493,969, filed on Jun. 6, 2011; this application is also a continuation-in-part of U.S. application Ser. No. 15/804,590, filed Nov. 6, 2017 (which published as US 2018-0118657 A1), which is a continuation of U.S. application Ser. No. 13/698,645 (having a 371(c) date of Apr. 22, 2013), which is a national phase application of International Application No. PCT/US11/37238, filed May 19, 2011, which claims the benefit of U.S. Provisional Application No. 61/346,813, filed on May 20, 2010, and 61/445,488, filed on Feb. 22, 2011; this application is also a continuation-in-part of U.S. application Ser. No. 16/003,184, filed Jun. 8, 2018 (which published as US 2018-0289725 A1), which is a continuation of U.S. application Ser. No. 14/978,886, filed Dec. 22, 2015, which is a continuation of U.S. application Ser. No. 14/612,636, filed Feb. 3, 2015, which is a continuation of PCT/US2013/053423, filed Aug. 2, 2013, which claims the benefit of U.S. Provisional Application No. 61/679,432, filed Aug. 3, 2012, and U.S. Provisional Application No. 61/730,496, filed Nov. 27, 2012. The contents of each of the prior applications are hereby incorporated herein by reference in their entireties.

STATEMENT REGARDING FEDERALLY SPONSORED RESEARCH

This invention was made with government support under T32 GM073610, 1R01 AR059115-01 and HL007121 awarded by the National Institutes of Health, as well as support from grant IBX000976A awarded by the Department of Veterans Affairs. This invention was also made with government support under R43 AR069400 awarded by National Institutes of Health and R41 AG047684 awarded by National Institutes of Health. The government has certain rights in the invention.

BACKGROUND

Skeletal muscle atrophy is characteristic of starvation and a common effect of aging. It is also a nearly universal consequence of severe human illnesses, including cancer, chronic renal failure, congestive heart failure, chronic respiratory disease, insulin deficiency, acute critical illness, chronic infections such as HIV/AIDS, muscle denervation, and many other medical and surgical conditions that limit muscle use. However, medical therapies to prevent or reverse skeletal muscle atrophy in human patients do not exist. As a result, millions of individuals suffer sequelae of muscle atrophy, including weakness, falls, fractures, opportunistic respiratory infections, and loss of independence. The burden that skeletal muscle atrophy places on individuals, their families, and society in general, is tremendous.

The pathogenesis of skeletal muscle atrophy is not well understood. Nevertheless, important advances have been made. For example, it has been described previously that insulin/IGF1 signaling promotes muscle hypertrophy and inhibits muscle atrophy, but is reduced by atrophy-inducing stresses such as fasting or muscle denervation (Bodine S C, et al. (2001) *Nat Cell Biol* 3(11):1014-1019; Sandri M, et al. (2004) *Cell* 117(3):399-4121; Stitt T N, et al. (2004) *Mol Cell* 14(3):395-403; Hu Z, et al. (2009) *The Journal of clinical investigation* 119(10):3059-3069; Dobrowolny G, et al. (2005) *The Journal of cell biology* 168(2):193-199; Kandarian S C & Jackman R W (2006) *Muscle & nerve* 33(2):155-165; Hirose M, et al. (2001) *Metabolism: clinical and experimental* 50(2):216-222; Pallafacchina G, et al. (2002) *Proceedings of the National Academy of Sciences of the United States of America* 99(14):9213-9218). The hypertrophic and anti-atrophic effects of insulin/IGF1 signaling are mediated at least in part through increased activity of phosphoinositide 3-kinase (PI3K) and its downstream effectors, including Akt and mammalian target of rapamycin complex 1 (mTORC1) Sandri M (2008) *Physiology (Bethesda)* 23:160-170; Glass D J (2005) *The international journal of biochemistry & cell biology* 37(10): 1974-1984).

Another important advance came from microarray studies of atrophying rodent muscle (Lecker S H, et al. (2004) *Faseb J* 18(1):39-51; Sacheck J M, et al. (2007) *Faseb J* 21(1): 140-155; Jagoe R T, et al. *Faseb J* 16(13):1697-1712). Those studies showed that several seemingly disparate atrophy-inducing stresses (including fasting, muscle denervation and severe systemic illness) generated many common changes in skeletal muscle mRNA expression. Some of those atrophy-associated changes promote muscle atrophy in mice; these include induction of the mRNAs encoding atroginI/MAFbx and MuRF1 (two E3 ubiquitin ligases that catalyze proteolytic events), and repression of the mRNA encoding PGC-1 α (a transcriptional co-activator that inhibits muscle atrophy) (Sandri M, et al. (2006) *Proceedings of the National Academy of Sciences of the United States of America* 103 (44): 16260-16265; Wenz T, et al. *Proceedings of the National Academy of Sciences of the United States of America* 106(48):20405-20410; Bodine S C, et al. (2001) *Science (New York, N.Y.* 294(5547):1704-1708; Lagirand-Cantaloube J, et al. (2008) *The EMBO journal* 27(8): 1266-1276; Cohen S, et al. (2009) *The Journal of cell biology* 185(6):1083-1095; Adams V, et al. (2008) *Journal of molecular biology* 384(1):48-59). However, the roles of many other mRNAs that are increased or decreased in atrophying rodent muscle are not yet defined. Data on the mechanisms of human muscle atrophy are even more limited, although atrogin-1 and MuRF1 are likely to be involved (Leger B, et al. (2006) *Faseb J* 20(3):583-585; Doucet M, et al. (2007) *American journal of respiratory and critical care medicine* 176(3):261-269; Levine S, et al. (2008) *The New England journal of medicine* 358(13):1327-1335).

Despite advances in understanding the physiology and pathophysiology of muscle atrophy, there is still a scarcity of compounds that are both potent, efficacious, and selective modulators of muscle growth and also effective in the treatment of muscle atrophy associated and diseases in which the muscle atrophy or the need to increase muscle mass is involved. These needs and other needs are satisfied by the present invention.

SUMMARY

In accordance with the purpose(s) of the invention, as embodied and broadly described herein, the invention, in one aspect, relates to compounds useful in methods to treat muscle atrophy. The compounds can be selected from a tacrine and analogs, naringenin and analogs, allantoin and analogs, conessine and analogs, tomatidine and analogs, ungerine/hippeastrine and analogs, and betulinic acid and analogs, or a mixture thereof.

Tacrine and analogs can have the structure:

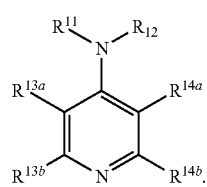

Naringenin and analogs can have the structure:

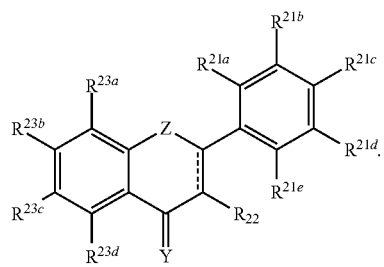

Allantoin and analogs can have the structure:

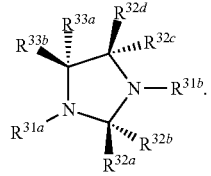

Conessine and analogs can have the structure:

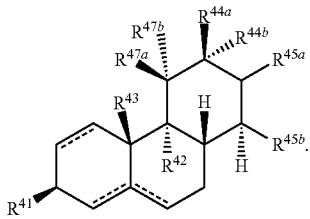

Tomatidine and analogs can have the structure:

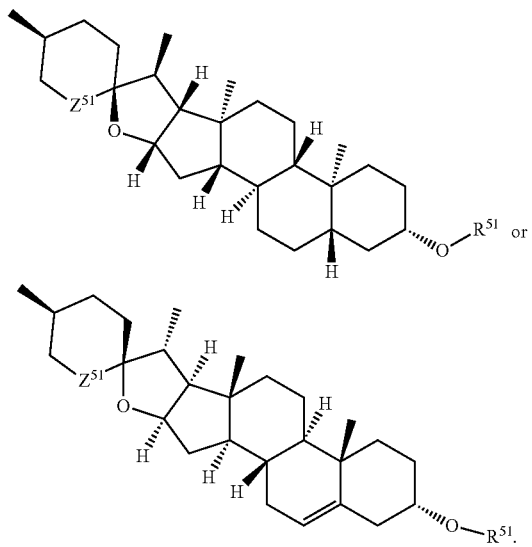

Ungerine/hippeastrine and analogs can have the structure:

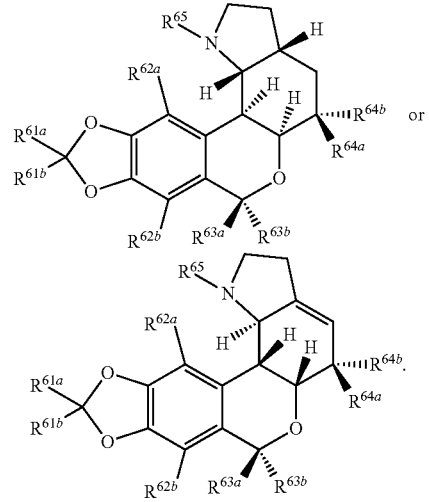

Betulinic acid and analogs can have the structure:

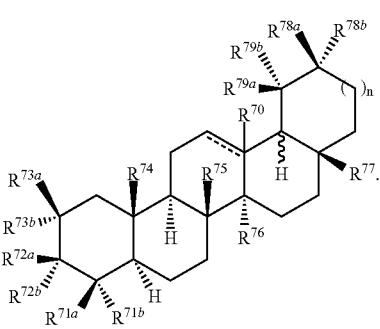

The disclosed compounds can treat muscle atrophy when administered in an effective amount to an animal, such as a mammal, fish or bird. For example, human.

Also disclosed in a method of lowering blood glucose in an animal by administering ursolic acid or ursolic acid analogs, such as betulininc acid analogs, and narigenin analogs, such as naringenin, in an effective amount to an animal.

Also disclosed in a method of lowering blood glucose in an animal by administering ungerine/hippeastrine analogs, such as hippeastrine, in an effective amount to an animal.

The disclosed compounds can also promote muscle health, promote normal muscle function, and/or promote healthy aging muscles by providing to a subject in need thereof an effective amount of a disclosed compound.

Also disclosed herein are pharmaceutical compositions comprising compounds used in the methods. Also disclosed herein are kits comprising compounds used in the methods.

In further aspects, the invention relates to compounds identified using muscle atrophy signature-1, muscle atrophy signature-2 or both muscle atrophy signatures. In still further aspects, the purpose(s) of the invention, as embodied and broadly described herein, the invention, in one aspect, relates to compounds useful in methods to modulate muscle health promote normal muscle function, and/or promote healthy aging muscles, methods to inhibit muscle atrophy, methods to increase insulin/IGF-I signaling, methods to reduce body fat; methods to reduce blood glucose, methods to reduce blood triglycerides, methods to reduce blood cholesterol, methods to reduce obesity, methods to reduce fatty liver disease, and methods to reduce diabetes, and pharmaceutical compositions comprising compounds used in the methods.

Disclosed are methods for treating muscle atrophy in a mammal, the method comprising administering to the mammal an effective amount of a compound, wherein the compound: (a) down regulates multiple induced mRNAs of a Muscle Atrophy Signature, compared to expression levels of the induced mRNAs of the Muscle Atrophy Signature in the same type of the muscle cell in the absence of the compound, and/or (b) up regulates multiple repressed mRNAs of the Muscle Atrophy Signature, compared to expression levels of the repressed mRNAs of the Muscle Atrophy Signature in the same type of the muscle cell in the absence of the compound, thereby inhibiting muscle atrophy in the mammal.

Also disclosed are methods for identifying a compound that inhibits muscle atrophy when administered in a effective amount to a animal in need of treatment thereof, the method comprising the steps of: (i) selecting a candidate compound; (ii) determining the effect of the candidate compound on a cell's expression levels of a plurality of induced mRNAs and/or repressed mRNAs of a Muscle Atrophy Signature, wherein the candidate compound is identified as suitable for muscle atrophy inhibition if: (a) more than one of the induced mRNAs of the Muscle Atrophy Signature are down regulated, compared to expression levels of the induced mRNAs of the Muscle Atrophy Signature in the same type of cell in the absence of the candidate compound; and/or (b) more than one of the repressed mRNAs of the Muscle Atrophy Signature are up regulated, compared to expression levels of the repressed mRNAs of the Muscle Atrophy Signature in the same type of cell in the absence of the candidate compound. In one aspect, the method further comprises administering the candidate compound to an animal. The candidate compound can be tacrine and analogs, naringenin and analogs, allantoin and analogs, conessine and analogs, tomatidine and analogs, ungerine/hippeastrine and analogs, and betulinic acid and analogs, or a mixture thereof.

Also disclosed are methods for manufacturing a medicament associated with muscle atrophy or the need to promote muscle health, promote normal muscle function, and/or promote healthy aging muscles comprising combining at least one disclosed compound or at least one disclosed product with a pharmaceutically acceptable carrier or diluent.

Also disclosed are uses of a disclosed compound or a disclosed product in the manufacture of a medicament for the treatment of a disorder associated with muscle atrophy or the need to promote muscle health, promote normal muscle function, and/or promote healthy aging muscles.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 2 shows human muscle atrophy signature-1.

FIG. 3 shows human muscle atrophy signature-2.

FIGS. 6A-6H show representative data on the identification of ursolic acid as an inhibitor of fasting-induced skeletal muscle atrophy.

FIGS. 10A-10K show representative data on the effect of ursolic acid on muscle growth, atrophic gene expression, trophic gene expression, and skeletal muscle IGF-I signaling.

FIGS. 11A-11F show representative data on the effect of ursolic acid on skeletal muscle expression of IGF1 gene exons, adipose IGF1 mRNA expression, and skeletal muscle insulin signaling.

FIGS. 14A-14I show representative data on the effect of ursolic acid on weight gain, white adipose tissue weight, skeletal muscle weight, brown adipose tissue weight and energy expenditure in a mouse model of obesity and metabolic syndrome.

FIGS. 15A-15H show representative data on the effect of ursolic acid on obesity-related pre-diabetes, diabetes, fatty liver disease and hyperlipidemia in a mouse model of obesity and metabolic syndrome.

FIGS. 16A-16I show representative data that oleanolic acid and metformin do not reduce skeletal muscle atrophy.

FIGS. 17A and 17B show representative data that targeted inhibition of PTP1B does not inhibit skeletal muscle atrophy.

FIGS. 18A and 18B show representative data on the effect of ursolic acid serum concentration on muscle mass and adiposity.

Figure 1:
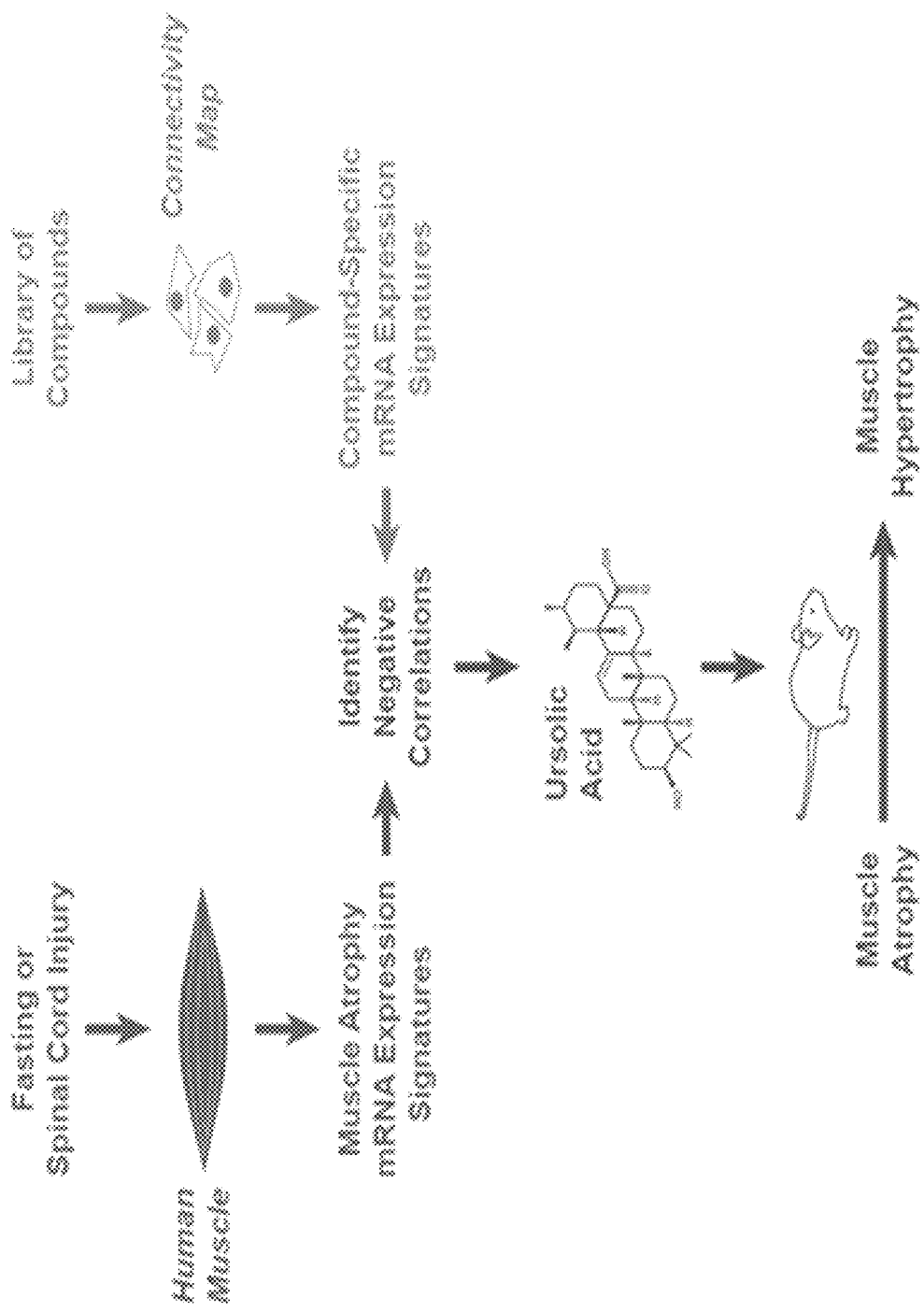
FIG. 1 shows a schematic overview of the discovery process leading to a pharmacological compound that promotes skeletal muscle growth and inhibits skeletal muscle atrophy.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "muscle atrophy signature-1" refers to the set of mRNAs with an altered expression pattern associated with muscle atrophy. The mRNAs comprise mRNAs that are either induced or repressed during the pathophysiology of muscle atrophy and which were identified using the methods described herein. For clarity, muscle atrophy signature-1 comprise the induced and repressed mRNAs described in FIG. 2.

As used herein, the term "muscle atrophy signature-2" refers to the set of mRNAs with an altered expression pattern associated with muscle atrophy. The mRNAs comprise mRNAs that are either induced or repressed during the pathophysiology of muscle atrophy and which were identified using the methods described herein. For clarity, muscle atrophy signature-2 comprise the induced and repressed mRNAs described in FIG. 3.

As used herein, the term "muscle atrophy signature-3" refers to the set of mRNAs with an altered expression pattern associated with muscle atrophy. The mRNAs comprise mRNAs that are either induced or repressed during the pathophysiology of muscle atrophy and which were identified using the methods described herein. For clarity, muscle atrophy signature-3 comprise the induced and repressed mRNAs described in Example 23.

As used herein, the term "muscle atrophy signature-4" refers to the set of mRNAs with an altered expression pattern associated with muscle atrophy. The mRNAs comprise mRNAs that are either induced or repressed during the pathophysiology of muscle atrophy and which were identified using the methods described herein. For clarity, muscle atrophy signature-4 comprise the induced and repressed mRNAs described in Example 24.

As used herein, the term "subject" refers to the target of administration, e.g. an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, fish, bird, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more muscle disorders prior to the administering step. In some aspects of the disclosed method, the subject has been diagnosed with a need for promoting muscle health prior to the administering step. In some aspects of the disclosed method, the subject has been diagnosed with a need for promoting muscle health prior, promote normal muscle function, and/or promote healthy aging muscles to the administering step.

As used herein, the term "treatment" refers to the medical management of a patient with the intent to cure, ameliorate, stabilize, or prevent a disease, pathological condition, or disorder. This term includes the use for astetic and self improvement purposes, for example, such uses include, but are not limited to, the administration of the disclosed compound in nutraceuticals, medicinal food, energy bar, energy drink, supplements (such as multivitamins). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, fish, bird, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a muscle atrophy disorder" means having been subjected to a physical examination by a person of skill, for example, a physician, and found to have a condition that can be diagnosed or treated by a compound or composition that can promote muscle health, promote normal muscle function, and/or promote healthy aging muscles. As a further example, "diagnosed with a need for promoting muscle health" refers to having been subjected to a physical examination by a person of skill, for example, a physician, and found to have a condition characterized by muscle atrophy or other disease wherein promoting muscle health, promoting normal muscle function, and/or promoting healthy aging muscles would be beneficial to the subject. Such a diagnosis can be in reference to a disorder, such as muscle atrophy, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to muscle atrophy) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in a in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein the a gene or genes has been introduced or knocked-out, as appropriate, to replicate a disease process.

As used herein, "$IC_{50}$," is intended to refer to the concentration or dose of a substance (e.g., a compound or a drug) that is required for 50% inhibition or diminuation of a biological process, or component of a process, including a protein, subunit, organelle, ribonucleoprotein, etc. $IC_{50}$ also refers to the concentration or dose of a substance that is required for 50% inhibition or diminuation in vivo, as further defined elsewhere herein. Alternatively, $IC_{50}$ also refers to the half maximal (50%) inhibitory concentration (IC) or inhibitory dose of a substance. The response can be measured in a in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein the a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl)$_2$ where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group.

For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R$; $-N(R^\circ)S(O)_2NR^\circ_2$; $-N(R^\circ)S(O)_2R$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR_3$; $-(C_{1-4}$ straight or branched alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_1$-6 aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R*_2))_{2-3}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\circ_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\circ$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

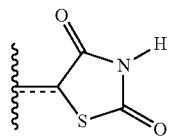

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

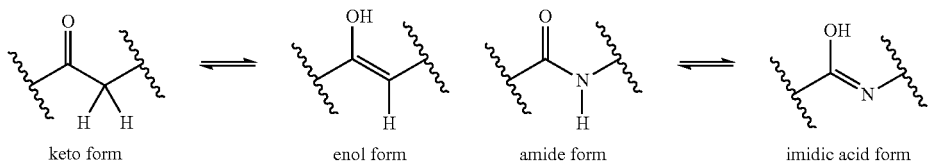 [SMILES: *CC(*)=O ; */C=C(/*)O ; *NC(*)=O ; */N=C(/*)O]

keto form     enol form     amide form     imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

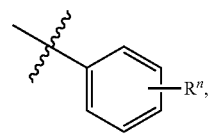

which is understood to be equivalent to a formula:

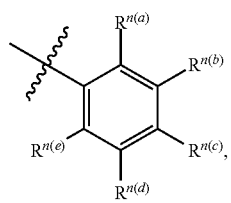

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in methods to inhibit muscle atrophy by providing to a subject in need thereof an effective amount of a compound or an analog thereof selected from among the compounds described herein, and pharmaceutical compositions comprising compounds used in the methods. In a further aspect, the invention relates to compounds identified using muscle atrophy signature-1, muscle atrophy signature-2, or both muscle atrophy signatures. In a further aspect, the invention relates to compounds useful in methods to modulate muscle health, methods to inhibit muscle atrophy, methods to increase insulin/IGF-I signaling, methods to reduce body fat; methods to reduce blood glucose, methods to reduce blood triglycerides, methods to reduce blood cholesterol, methods to reduce obesity, methods to reduce fatty liver disease, and methods to reduce diabetes, and pharmaceutical compositions comprising compounds used in the methods.

In one aspect, the compounds of the invention are useful in the treatment of muscle disorders. In a further aspect, the muscle disorder can be skeletal muscle atrophy secondary to malnutrition, muscle disuse (secondary to voluntary or involuntary bedrest), neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization, chronic disease (including cancer, congestive heart failure, chronic pulmonary disease, chronic renal failure, chronic liver disease, diabetes mellitus, Cushing syndrome, growth hormone deficiency, IGF-I deficiency, androgen deficiency, estrogen deficiency, and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, or age-related sarcopenia.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Tacrine and Analogs

In one aspect, the compound can be a tacrine analogs.

In one aspect, the tacrine analogs has a structure represented by a formula:

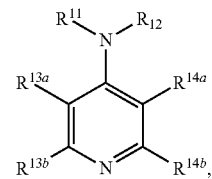

wherein $R^{13a}$ and $R^{13b}$ together comprise a cycle selected from:

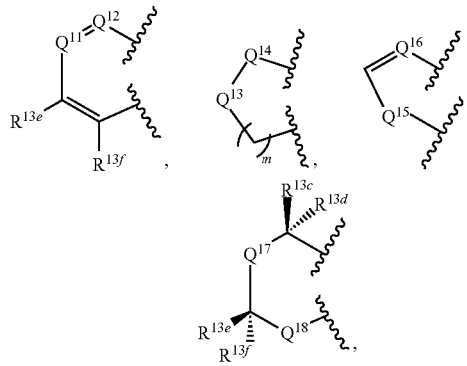

wherein $Q^{11}$ is selected from N and $CR^{13c}$;
wherein $Q^{12}$ is selected from N and $CR^{13d}$;
wherein $Q^{13}$ and $Q^{14}$ are independently selected from $CR^{13c}R^{13d}$, O, S, and $NR^{14c}$;
wherein $Q^{15}$ is selected from $CR^{13c}R^{13d}$, O, S, and $NR^{14c}$;
wherein $Q^{16}$ is selected from N and $CR^{13c}$;
wherein $Q^{17}$ and $Q^{18}$ are independently selected from $CR^{13c}R^{13d}$, O, S, and $NR^{14c}$;
wherein $R^{11}$ and $R^{12}$ are independently selected from H and C1-C6 alkyl;
wherein $R^{13c}$, $R^{13d}$, $R^{13e}$, and $R^{13f}$ are independently selected from H, C1-C6 alkyl, C1-C6 alkoxy, halo, hydroxyl, nitro, amino, cyano, $NHCOR^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;
wherein each $R^{14c}$ is independently selected from H and C1-C6 alkyl;
wherein $R^{14a}$ and $R^{14b}$ together comprise a cycle selected from:

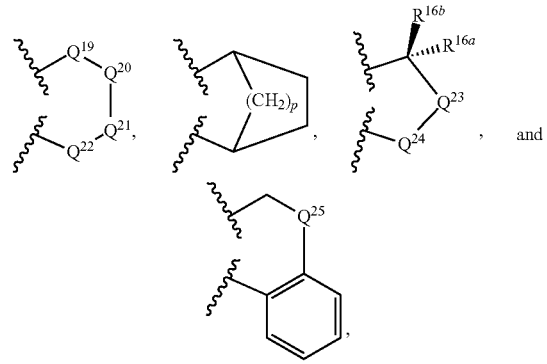

wherein each of $Q^{19}$, $Q^{20}$, $Q^{21}$, $Q^{22}$, $Q^{23}$, $Q^{24}$, and $Q^{25}$ are independently selected from $CR^{17a}R^{17b}$, O, S, and $NR^{18}$;
wherein $R^{16a}$ and $R^{16a}$ are independently selected from H, C1-C6 alkyl, C1-C6 alkoxy, halo, hydroxyl, nitro, amino, cyano, $NHCOR^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;
wherein $R^{17a}$ and $R^{17b}$ are independently selected from H, C1-C6 alkyl, C1-C6 alkoxy, halo, hydroxyl, nitro, amino, cyano, $NHCOR^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;
wherein each $R^{18}$ is independently selected from H and C1-C6 alkyl;
wherein each $R^{15}$ is independently selected from H and C1-C6 alkyl;
wherein each n is independently selected from 0, 1, and 2;
wherein m is selected from 1 and 2; and
wherein p is selected from 1, 2 and 3; or
a stereoisomer, tautomer, solvate, or pharmaceutically acceptable salt thereof.

In one aspect, compound (A) has the structure represented by the formula:

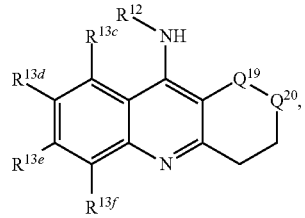

wherein $R^{12}$ is selected from H and C1-C6 alkyl;
wherein $R^{13c}$, $R^{13d}$, $R^{13e}$, and $R^{13f}$ are independently selected from H, C1-C6 alkyl, C1-C6 alkoxy, halo, hydroxyl, nitro, amino, cyano, $NHCOR^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;
wherein $Q^{19}$ and $Q^{20}$ are independently selected from $CR^{17a}R^{17b}$, O, S, and $NR^{18}$; wherein $R^{17a}$ and Rim are independently selected from H, C1-C6 alkyl, C1-C6 alkoxy, halo, hydroxyl, nitro, amino, cyano, $NHCOR^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, C2-C9 heterocyclyl, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein each $R^{18}$ is independently selected from H and C1-C6 alkyl; and wherein n is selected from 0, 1, and 2.

In another aspect, $R^{12}$ is H; $R^{13c}$, $R^{13d}$, $R^{13e}$, and $R^{13f}$ are independently selected from H, C1-C6 alkyl, C1-C6 alkoxy, halo, hydroxyl, nitro, and amino; $Q^{19}$ and $Q^{20}$ are independently selected from C $R^{17a}R^{17b}$, O, S, and $NR^{18}$; wherein $R^{17a}$ and Rim are independently selected from H, C1-C6 alkyl, C1-C6 alkoxy, halo, hydroxyl, nitro, and amino; wherein each $R^{18}$ is independently H; and n is selected from 0, 1, and 2.

In another aspect, $R^{12}$ is H; $R^{13c}$, $R^{13d}$, $R^{13e}$, and $R^{13f}$ are independently selected from H, C1-C6 alkyl, C1-C6 alkoxy, halo, hydroxyl, nitro, and amino; $Q^{19}$ and $Q^{20}$ are independently selected from C $R^{17a}R^{17b}$; wherein $R^{17a}$ and $R^{17b}$ are independently selected from H, C1-C6 alkyl, C1-C6 alkoxy, halo, hydroxyl, nitro, and amino; and n is 1.

In another aspect, $R^{12}$ is H; $R^{13c}$, $R^{13d}$, $R^{13e}$, and $R^{13f}$ are independently selected from H, C1-C6 alkyl, C1-C6 alkoxy, halo, and hydroxyl; $Q^{19}$ and $Q^{20}$ are independently selected from $CR^{17a}R^{17b}$; wherein $R^{17a}$ and Rim are independently H; and n is 1.

In another aspect, $R^{12}$ is H; $R^{12}$ is H; $R^{13c}$, $R^{13d}$, $R^{13e}$, and $R^{13f}$ are independently selected from H, C1-C6 alkyl, and halo; $Q^{19}$ and $Q^{20}$ are independently $CR^{17a}R^{17b}$; wherein $R^{17a}$ and $R^{17b}$ are independently H; and wherein n is 1.

In another aspect, the formula is:]

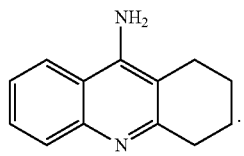

2. Naringenin and Analog

In one aspect, the compound can be a naringenin analog.

In one aspect, the naringenin analog has a structure represented by a formula:

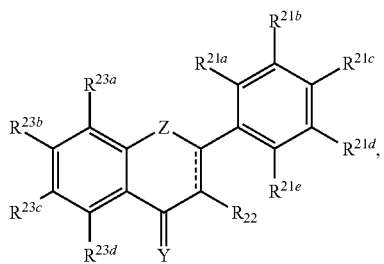

wherein each ----- represents a covalent bond selected from a single or double bond;

wherein $R^{21a}$, $R^{21b}$, $R^{21c}$, $R^{21d}$, and $R^{21e}$ are independently selected from H, OH, O-Glucosyl, halo, cyano, amino, nitro, nitroso, $NHCOR^{15}$, C1-C6 alkyl, C1-C6 alkoxy, C1-C6 monohaloalkyl, C1-C6 polyhaloalkyl, C1-C6 alkylamino, acyl, phenyl-C1-C6 alkoxy, benzyl-C1-C6 alkoxy, and C1-C6 dialkylamino;

wherein $R^{22}$ is selected from H, OH, O-Glucosyl, halo, cyano, amino, nitro, nitroso, $NHCOR^{15}$, C1-C6 alkyl, C1-C6 alkoxy, C1-C6 monohaloalkyl, C1-C6 polyhaloalkyl, C1-C6 alkylamino, acyl phenyl-C1-C6 alkoxy, benzyl-C1-C6 alkoxy, and C1-C6 dialkylamino; wherein $R^{23a}$, $R^{23b}$, $R^{23c}$, and $R^{23d}$ are independently selected from H, OH, O-Glucosyl halo, cyano, amino, nitro, nitroso, $NHCOR^{15}$, C1-C20 alkyl, C1-C20 alkenyl, C1-C20 alkynyl, C1-C20 alkenynyl, C1-C20 alkoxy, C1-C6 monohaloalkyl, C1-C6 polyhaloalkyl, C1-C6 alkylamino, acyl, phenyl-C1-C6 alkoxy, benzyl-C1-C6 alkoxy, and C1-C6 dialkylamino;

wherein $R^{15}$ is selected from H and C1-C6 alkyl;

wherein Z is selected from O and S; and wherein Y is selected from O and S; or a stereoisomer, tautomer, solvate, or pharmaceutically acceptable salt thereof;

wherein the compound does not have the structure:

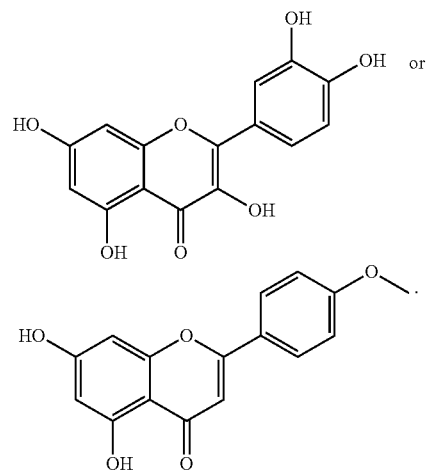

In one aspect, ----- indicates a covalent single bond. In another aspect, ----- indicates a covalent double bond.

In another aspect, Z is O, and Y is O.

In another aspect, $R^{21a}$, $R^{21b}$, $R^{21c}$, $R^{21d}$, and $R^{21e}$ are independently selected from H and OH; wherein $R^{22}$ is selected from H and OH; and wherein $R^{23a}$, $R^{23b}$, $R^{23c}$, $R^{23d}$, and $R^{23e}$ are independently selected from H and OH.

In another aspect, $R^{21a}$, $R^{21b}$, $R^{21c}$, $R^{21d}$, and $R^{21e}$ are independently selected from H, OH, O-Glucosyl, halo, cyano, amino, nitro, and nitroso.

In another aspect, $R^{22}$ is H.

In another aspect, $R^{21a}$, $R^{21b}$, $R^{21d}$, and $R^{21e}$ are H, and $R^{21c}$ is OH.

In another aspect, $R^{23a}$ and $R^{23c}$ are H, and $R^{23b}$ and $R^{23d}$ are OH.

In another aspect, $R^{21a}$, $R^{21b}$, $R^{21d}$, and $R^{21e}$ are H, $R^{21c}$ is OH, $R^{23a}$ and $R^{23c}$ are H, and $R^{23b}$ and $R^{23d}$ are OH.

In another aspect, $R^{21a}$, $R^{21d}$, and $R^{21e}$ are H, $R^{21b}$ and $R^{21c}$ are OH, $R^{23a}$ and $R^{23c}$ are H, and $R^{23b}$ and $R^{23d}$ are OH.

In another aspect, the compound has the structure:

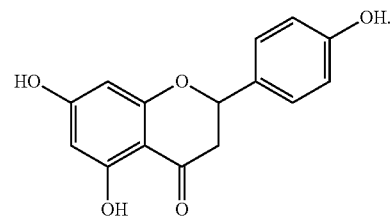 [SMILES: O=C1CC(c2ccc(O)cc2)Oc2cc(O)cc(O)c21]

3. Allantoin and Analogs

In one aspect, the compound can be a allantoin analog.

In one aspect, the allantoin analog has a structure represented by a formula:

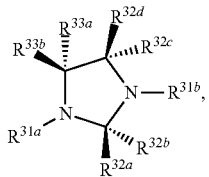

wherein $R^{31a}$ and $R^{31b}$ are independently selected from H, C1-C6 alkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{32a}$ and $R^{32b}$ are independently selected from H, C1-C6 alkyl, $OCl(OH)_4Al_2$, $OAl(OH)_2$, C1-C6 alkoxy, halo, hydroxyl, nitro, amino, cyano, $NHCOR^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl or taken together to form a double bond selected from =O and =S, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{32c}$ and $R^{32d}$ are independently selected from H, C1-C6 alkyl, $OCl(OH)_4Al_2$, $OAl(OH)_2$, C1-C6 alkoxy, halo, hydroxyl, nitro, amino, cyano, $NHCOR^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl or taken together to form a double bond selected from =O and =S, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{33a}$ and $R^{33b}$ are independently selected from H, $NR^{34a}CONR^{34b}R^{34c}$, C1-C6 alkyl, C1-C6 alkoxy, halo, hydroxyl, nitro, amino, cyano, $NHCOR^5$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino; and wherein $R^{34a}R^{34b}$ and $R^{34c}$ are independently selected from H, C1-C6 alkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently are substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino; or a stereoisomer, tautomer, solvate, or pharmaceutically acceptable salt thereof.

In one aspect, $R^{31a}$ and $R^{31b}$ are H.

In another aspect, $R^{32a}$ and $R^{32b}$ are taken together to form =O.

In another aspect, $R^{32c}$ and $R^{32d}$ are taken together to form =O.

In another aspect, $R^{32a}$ and $R^{32b}$ are taken together to form =O, and $R^{32c}$ and $R^{32d}$ are taken together to form =O.

In another aspect, $R^{31a}$ is H, $R^{31b}$ is H, $R^{32a}$ and $R^{32b}$ are taken together to form =O, and $R^{32c}$ and $R^{32d}$ are taken together to form =O.

In another aspect, $R^{31a}$ is H, $R^{31b}$ is H, $R^{32a}$ and $R^{32b}$ are taken together to form =O, $R^{32c}$ and $R^{32d}$ are taken together to form =O, and one of $R^{33a}$ and $R^{33b}$ is $NR^{34a}CONR^{34b}R^{34c}$ and the other one of $R^{33a}$ and $R^{33b}$ is H.

In another aspect, one of $R^{33a}$ and $R^{33b}$ is $NR^{34a}CONR^{34b}R^{34c}$ and the other one of $R^{33a}$ and $R^{33b}$ is H.

In another aspect, one of $R^{32a}$ and $R^{32b}$ is $OCl(OH)_4Al_2$ and the other one of $R^{32a}$ and $R^{32b}$ is H.

In another aspect, one of $R^{32c}$ and $R^{32d}$ is $OCl(OH)_4Al_2$ and the other one of $R^{32c}$ and $R^{32d}$ is H.

In another aspect, one of $R^{32a}$ and $R^{32b}$ is $OAl(OH)_2$ and the other one of $R^{32a}$ and $R^{32b}$ is H.

In another aspect, one of $R^{32c}$ and $R^{32d}$ is $OAl(OH)_2$ and the other one of $R^{32c}$ and $R^{32d}$ is H.

In another aspect, the compound has the structure:

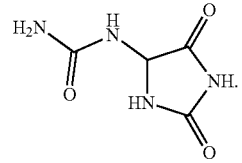 [SMILES: NC(=O)NC1NC(=O)NC1=O]

4. Conessine and Analogs

In one aspect, the compound can be a conessine analog.

In one aspect, the conessine analog has a structure represented by a formula:

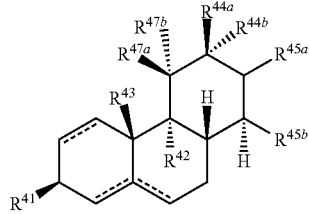

wherein each ----- represents a covalent bond independently selected from a single or double bond, wherein valency is satisfied;

wherein $R^{41}$ is selected from $NR^{48a}R^{48b}$, =O, =S, C1-C6 alkoxy and hydroxyl;

wherein $R^{48a}$ and $R^{48b}$ are independently selected from H, C1-C6 alkyl, C1-C6 heteroalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{42}$ is selected from H, C1-C6 alkoxy and hydroxyl;

wherein $R^{43}$ is selected from H and C1-C6 alkyl;

wherein $R^{44a}$ and $R^{44b}$ are independently selected from are independently selected from H, hydroxyl, and C1-C6 alkoxy;

wherein $R^{47a}$ and $R^{47b}$ are independently selected from are independently selected from H, hydroxyl, and C1-C6 alkoxy;

wherein $R^{45a}$ and $R^{45b}$ together comprise a cycle selected from:

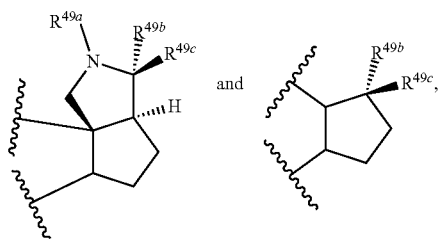

wherein $R^{49a}$ is selected from H and C1-C6 alkyl; and wherein $R^{49b}$ and $R^{49c}$ are independently selected from H and C1-C6 alkyl, or taken together to form =O; or a stereoisomer, tautomer, solvate, or pharmaceutically acceptable salt thereof.

In one aspect, $R^{47a}$ and $R^{47b}$ are independently selected from H, hydroxyl, and C1-C6 alkoxy.

In another aspect, $R^{44a}$ and $R^{44b}$ are independently selected from H, hydroxyl, and C1-C6 alkoxy.

In another aspect, $R^{42}$ is H.

In another aspect, $R^{47a}$ and $R^{47b}$ are selected from H, hydroxyl, and C1-C6 alkoxy; $R^{44a}$ and $R^{44b}$ are H.

In another aspect, $R^{41}$ is selected from $NR^{48a}R^{48b}$ and =O, wherein $R^{48a}$ and $R^{48b}$ are independently selected from H and C1-C6 alkyl.

In another aspect, $R^{43}$ is C1 alkyl.

In another aspect, the formula has the structure:

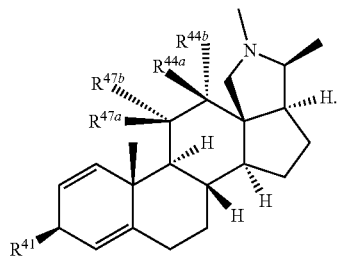

In another aspect, the formula has the structure:

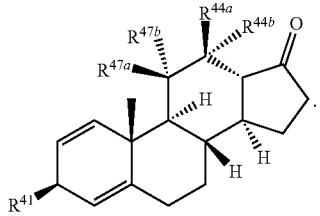

In another aspect, the formula has the structure:

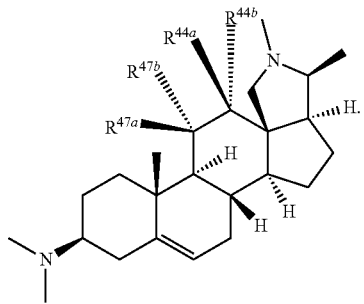

In another aspect, the formula has the structure:

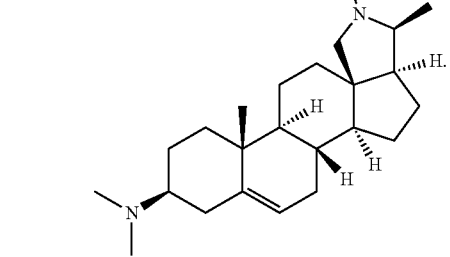

In another aspect, the formula has the structure:

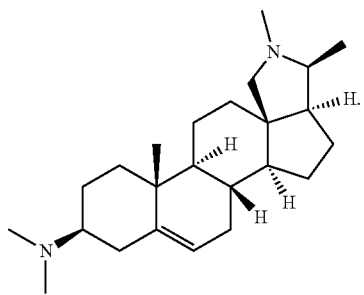

5. Tomatidine and Analogs

In one aspect, the compound can be a tomatidine analog.

In one aspect, the tomatidine analog has a structure represented by a formula:

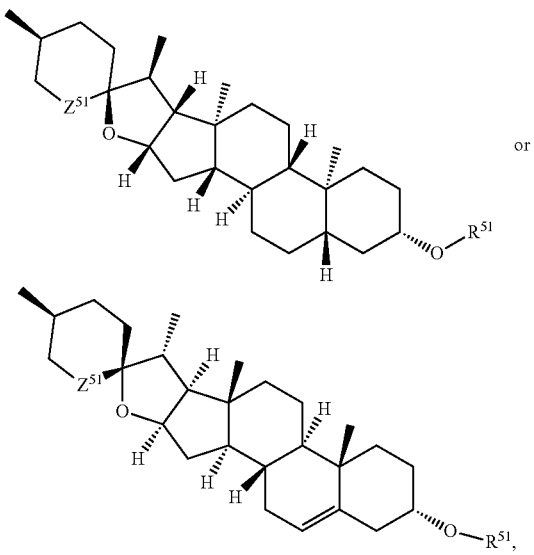

wherein $R^{51}$ is selected from H, C1-C6 alkyl, $COR^{53}$, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{53}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $Z^{51}$ is selected from O, S, and $NR^{54}$;

wherein $R^{54}$ is selected from H, C1-C6 alkyl, $COR^{55}$, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{55}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino; or a stereoisomer, tautomer, solvate, or pharmaceutically acceptable salt thereof.

In one aspect, $R^{51}$ is selected from H, C1-C6 alkyl and $COR^{53}$, wherein $R^{53}$ is C1-C6 alkyl.

In another aspect, $R^{51}$ is H.

In another aspect, $Z^{51}$ is $NR^{54}$. In another aspect, $Z^{51}$ is $NR^{54}$, wherein $R^{54}$ is selected from H, C1-C6 alkyl, and $COR^{55}$, wherein $R^{55}$ is C1-C6 alkyl.

In another aspect, $R^{51}$ is selected from H, C1-C6 alkyl and $COR^{53}$, wherein $R^{53}$ is C1-C6 alkyl; and $Z^{51}$ is $NR^{54}$, wherein $R^{54}$ is selected from H, C1-C6 alkyl, and $COR^{55}$, wherein $R^{55}$ is C1-C6 alkyl.

In another aspect, $R^{51}$ and $R^{54}$ are identical.

In another aspect, the structure is represented by the formula:

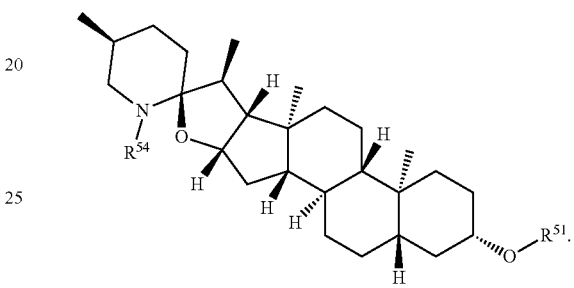

In another aspect, the structure is represented by the formula:

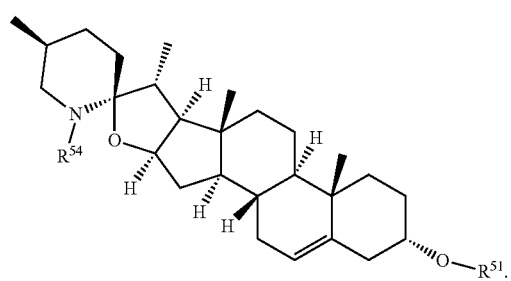

In another aspect, the formula has the structure:

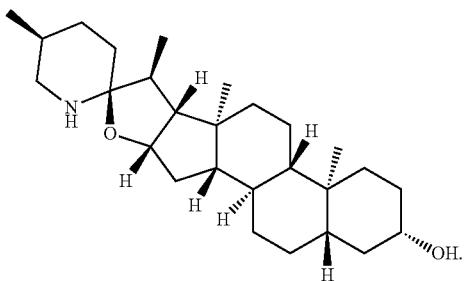 [SMILES: C[C@H]1CC[C@]2(NC1)O[C@H]1C[C@H]3[C@@H]4CC[C@H]5C[C@@H](O)CC[C@]5(C)[C@H]4CC[C@]3(C)[C@H]1[C@@H]2C]

6. Ungerine/Hippeastrine and Analogs

In one aspect, the compound can be a ungerine/hippeastrine analog.

In one aspect, the ungerine/hippeastrine has a structure represented by a formula:

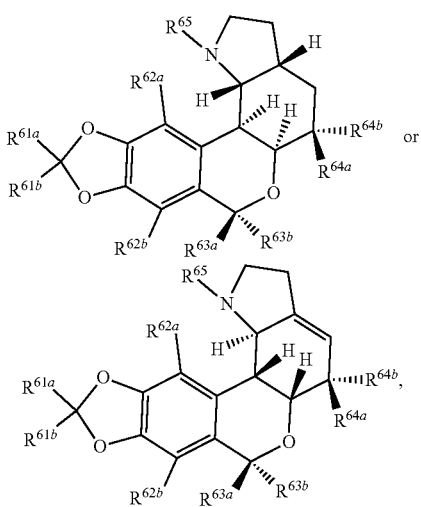

wherein $R^{62a}$ and $R^{62b}$ are independently selected from H, C1-C6 alkyl, C1-C6 alkoxy, halo, hydroxyl, nitro, amino, cyano, NHCOR$^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{63a}$ and $R^{63b}$ are independently selected from H, C1-C6 alkyl, C1-C6 alkoxy, halo, hydroxyl, nitro, amino, cyano, NHCOR$^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl, or taken together to form a group selected from =O and =S, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{64a}$ and $R^{64b}$ are independently selected from H, OR$^{67}$, C1-C6 alkyl, C1-C6 alkoxy, halo, hydroxyl, nitro, amino, cyano, NHCOR$^{15}$, C1-C6 monohaloalkyl, C1-C6 polyhaloalkyl, C1-C6 alkylamino, C1-C6 dialkylamino, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{65}$ is selected from H, C1-C6 alkyl, C1-C6 alkoxy, C1-C6 monohaloalkyl, C1-C6 polyhaloalkyl, C1-C6 alkylamino, C1-C6 dialkylamino, COR$^{66}$, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{66}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein $R^{67}$ is selected from C1-C6 alkyl, C1-C6 monohaloalkyl, C1-C6 polyhaloalkyl, C6-C10 aryl, C3-C10 cycloalkyl, C5-C9 heteroaryl, and C2-C9 heterocyclyl, wherein C6-C10 aryl, C3-C10 cycloalkyl, C5-C9 heteroaryl, and C2-C9 heterocyclyl are independently substituted with 0, 1, 2, or 3 substituents selected from halogen, hydroxyl, cyano, amino, C1-C6 alkyl, C1-C6 alkoxy, C1-C6 monohaloalkyl, C1-C6 polyhaloalkyl, C1-C6 alkylamino, and C1-C6 dialkylamino;

wherein each $R^{15}$ is independently selected from H and C1-C6 alkyl; or a stereoisomer, tautomer, solvate, or pharmaceutically acceptable salt thereof, wherein the compound is present in an effective amount.

In one aspect, the structure is represented by a formula:

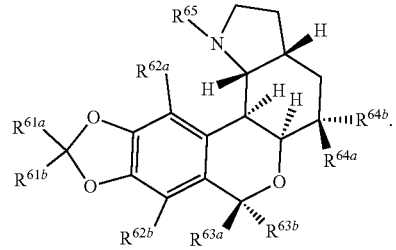

In another aspect, the structure is represented by a formula:

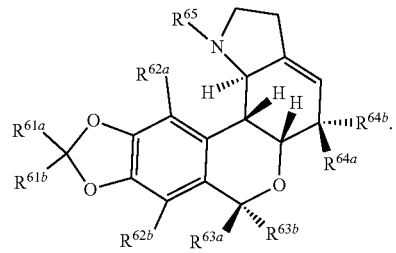

In another aspect, $R^{61a}$, $R^{61b}$, $R^{62a}$, and $R^{62b}$ are H.

In another aspect, one of $R^{63a}$ and $R^{63b}$ is hydroxyl and the other one of $R^{63a}$ and $R^{63b}$ is H.

In another aspect, $R^{63a}$ and $R^{63b}$ are taken together and form =O.

In another aspect, one of $R^{64a}$ and $R^{64b}$ is hydroxyl or OR$^{67}$ and the other one of $R^{64a}$ and $R^{64b}$ is H.

In another aspect, one of $R^{64a}$ and $R^{64b}$ is hydroxyl or OR$^{67}$ and the other one of $R^{64a}$ and $R^{64b}$ is H, wherein $R^{67}$ is C1-C6 alkyl.

In another aspect, $R^{65}$ is C1-C6 alkyl.

In another aspect, the structure is represented by a formula:

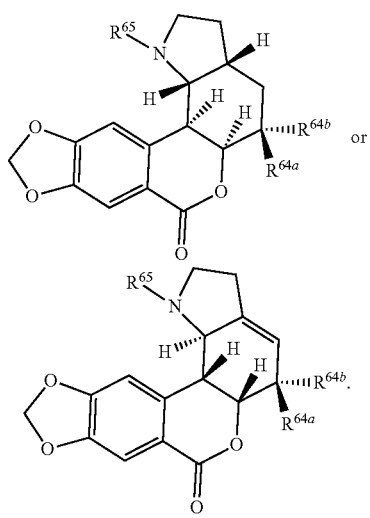

In another aspect, the structure is represented by a formula:

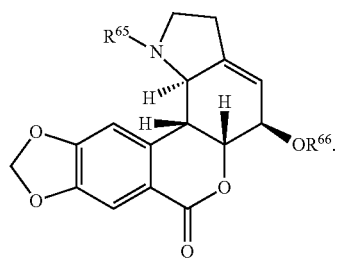

In another aspect, the structure is represented by a formula:

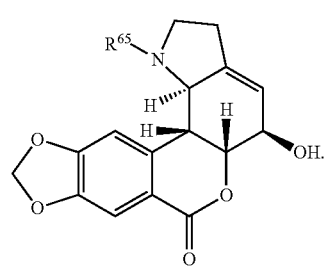

In another aspect, the structure is represented by a formula:

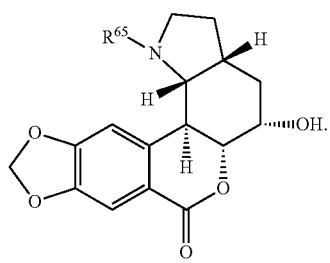

In another aspect, the structure is represented by a formula:

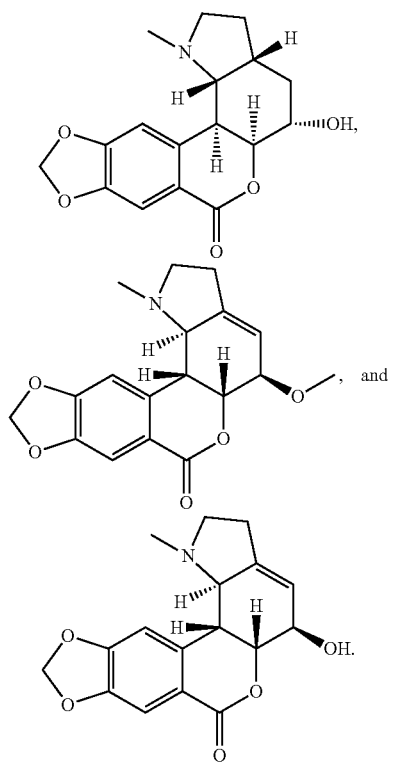

7. Betulinic Acid and Analogs

In one aspect, the compound can be a betulinic acid derivative.

In one aspect, has a structure represented by a formula:

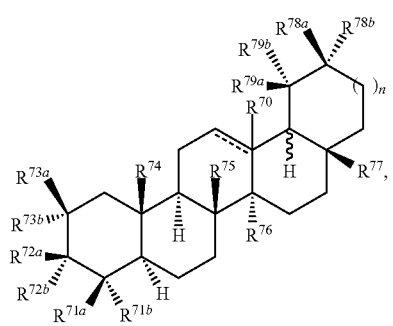

wherein ----- is an covalent bond selected from a single bond and a double bond, wherein valency is satisfied, and $R^{70}$ is optionally present; wherein n is 0 or 1; wherein $R^{70}$, when present, is hydrogen; wherein $R^{71a}$ is selected from C1-C6 alkyl and —C(O)Z$R^{82}$; wherein $R^{71b}$ is selected from C1-C6 alkyl, or wherein $R^{71a}$ and $R^{71b}$ are optionally covalently bonded and, together with the intermediate carbon, comprise an optionally substituted C3-C5 cycloalkyl or C2-C5 heterocycloalkyl; wherein one of $R^{72a}$ and $R^{72b}$ is —$Z^{72}$, and the other is hydrogen, or $R^{72a}$ and $R^{72b}$ together comprise =O; wherein each of $R^{73a}$ and $R^{73b}$ is independently selected from hydrogen, hydroxyl, C1-C6 alkyl, and C1-C6 alkoxyl, provided that $R^{73a}$ and $R^{73b}$ are not simultaneously hydroxyl, wherein $R^{73a}$ and $R^{73b}$ are optionally covalently bonded and, together with the intermediate carbon, comprise an optionally substituted C3-C5 cycloalkyl or C2-C5 heterocycloalkyl; wherein each of $R^{74}$, $R^{75}$, and $R^{76}$ is independently selected from C1-C6 alkyl; wherein $R^{77}$ is selected from C1-C6 alkyl, and —C(O)$Z^{71}R^{80}$; wherein $R^{80}$ is selected from hydrogen and C1-C6 alkyl; wherein $R^{78a}$ and $R^{78b}$ are independently selected from hydrogen and C1-C6 alkyl; wherein each of $R^{79a}$ and $R^{79b}$ is independently selected from hydrogen and C1-C6 alkyl, C2-C6 alkenyl, and C2-C6 alkynyl, provided that $R^{79a}$ and $R^{79b}$ are not simultaneously hydrogen; or wherein $R^{79a}$ and $R^{79b}$ are covalently bonded and, along with the intermediate carbon, together comprise C3-C5 cycloalkyl or C2-C5 heterocycloalkyl; wherein $R^{82}$ is selected from hydrogen and C1-C6 alkyl; wherein $Z^{71}$ and $Z^{72}$ are independently selected from —$OR^{81}$— and —$NR^{83}$—; wherein $R^{83}$ and $R^{83}$ are independently selected from hydrogen and C1-C4 alkyl; or, wherein $Z^{71}$ and $Z^{72}$ are independently N, $R^{84}$ and $R^{85}$ are covalently bonded and —$NR^{84}R^{85}$ comprises a moiety of the formula:

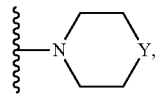

wherein Y is selected from —O—, —S—, —SO—, —$SO_2$—, —NH—, —$NCH_3$—, or a stereoisomer, tautomer, solvate, or pharmaceutically acceptable salt thereof.

In another aspect, the formula has the structure:

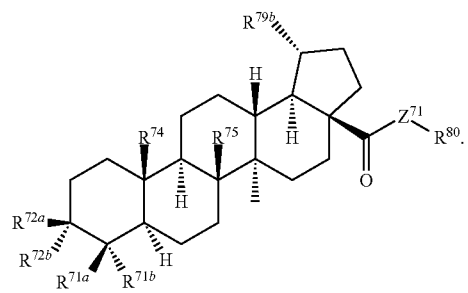

In another aspect, the formula has the structure:

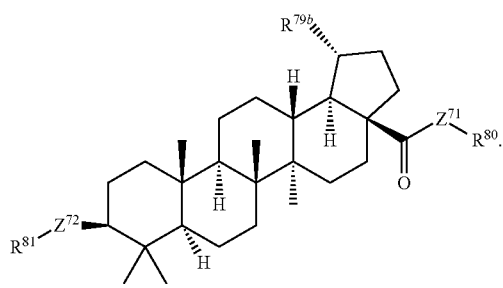

In another aspect, the formula has the structure:

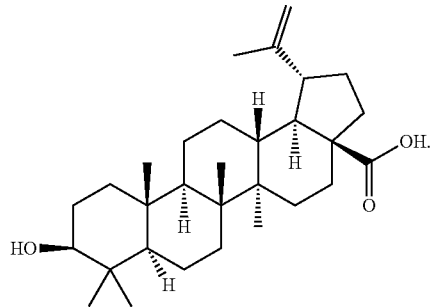

In one aspect, ----- is a single bond. In another aspect, ----- is a double bond.

In one aspect, n is 0. In another aspect, n is 1.

In another aspect, $R^{71a}$ is C1-C6 alkyl; $R^{71b}$ is selected from C1-C6 alkyl; one of $R^{72a}$ is —$Z^{72}$, and $R^{72b}$ is hydrogen; $R^{74}$, $R^{75}$ are independently selected from C1-C6 alkyl; wherein $R^{79b}$ is selected from C1-C6 alkyl, C2-C6 alkenyl, and C2-C6 alkynyl; $Z^{71}$ is —O—; and $Z^{72}$ is selected from —$OR^8$ and —$NR^{83}$—; $R^{81}$ and $R^{83}$ are independently selected from hydrogen and C1-C4 alkyl.

In another aspect, $R^{71a}$ is C1 alkyl; $R^{71b}$ is C1 alkyl; $R^{72a}$ is —$Z^{72}$, and $R^{72b}$ is hydrogen; $R^{74}$, $R^{75}$ are independently selected from C1 alkyl; wherein $R^{79b}$ is selected from C1-C6 alkyl, C2-C6 alkenyl, and C2-C6 alkynyl; $Z^{71}$ is —O—; and $Z^{72}$ is selected from —$OR^{81}$ and —$NR^{83}$—; wherein $R^{81}$ and $R^{83}$ are hydrogen.

In another aspect, $R^{71a}$ is C1 alkyl; $R^{71b}$ is C1 alkyl; $R^{72a}$ is —$Z^{72}$, and $R^{72b}$ is hydrogen; $R^{74}$, $R^{75}$ are independently selected from C1 alkyl; $R^{79b}$ is C2-C6 alkenyl; $Z^{71}$ is —O—; and $Z^{72}$ is selected from —$OR^{81}$ and —$NR^{83}$—; wherein $R^{81}$ and $R^{83}$ are hydrogen.

8. Compounds Identified by Muscle Atrophy Signature-1 and Muscle Atrophy Signature-2.

In various aspects, the invention relates to uses of one or more compounds selected from tacrine analogs, naringenin analogs, allantoin analogs, conessine analogs, tomatidine analogs, hippeastrine/ungerine analogs and betulinic acid analogs.

a. Muscle Atrophy Signature-1

In one aspect, the disclosed compounds comprise compounds identified using muscle atrophy signature-1. Such compounds include, but are not limited to, allantoin; conessine; naringenin; tacrine; tomatidine or a pharmaceutically acceptable salt, tautomer, stereoisomer, hydrate, solvate, or polymorph thereof. In a yet further aspect, the compound is an analog of one the preceding compounds as defined above.

b. Muscle Atrophy Signature-2

In a further aspect, the disclosed compounds comprise compounds identified using muscle atrophy signature-2. Such compounds include, but are not limited to, allantoin; betulinic acid; conessine; naringenin; tacrine; tomatidine or a pharmaceutically acceptable salt, tautomer, stereoisomer, hydrate, solvate, or polymorph thereof. In a yet further aspect, the compound is an analog of one the preceding compounds as defined above.

c. Muscle Atrophy Signature-1 or Muscle Atrophy Signature-2

In a further aspect, the disclosed compounds comprise compounds identified using either muscle atrophy signature-1 or muscle atrophy signature-2. Such compounds include, but are not limited to, allantoin; betulinic acid; conessine; naringenin; tacrine; tomatidine or a pharmaceutically acceptable salt, tautomer, stereoisomer, hydrate, solvate, or polymorph thereof. In a yet further aspect, the compound is an analog of one the preceding compounds as defined above.

d. Muscle Atrophy Signature-1 and Muscle Atrophy Signature-2

In a further aspect, the disclosed compounds comprise compounds identified using both muscle atrophy signature-1 and muscle atrophy signature-2, and is a compound associated with both muscle atrophy signatures. Such compounds include, but are not limited to, allantoin; conessine; naringenin; tacrine; tomatidine or a pharmaceutically acceptable salt, tautomer, stereoisomer, hydrate, solvate, or polymorph thereof. In a yet further aspect, the compound is an analog of one the preceding compounds as defined above.

9. Inhibition of Muscle Atrophy

In one aspect, the disclosed compounds inhibit muscle atrophy. In a further aspect, the disclosed compounds promoting muscle health, promoting normal muscle function, and/or promoting healthy aging muscles. In a yet further aspect, the disclosed compounds inhibit of muscle atrophy and promote muscle health, promote normal muscle function, and/or promote healthy aging muscles. In a further aspect, the inhibition of muscle atrophy is in an animal. In an even further aspect, the promoting muscle health, promoting normal muscle function, and/or promoting healthy aging muscles is in an animal. In a still further aspect, the animal is a mammal, In a yet further aspect, the mammal is a human. In a further aspect, the mammal is a mouse. In a yet further aspect, the mammal is a rodent.

In a further aspect, the disclosed compounds inhibit muscle atrophy when administered at an oral dose of greater than about 5 mg per day in a human. In a further aspect, the disclosed compounds inhibit muscle atrophy when administered at an oral dose of greater than about 10 mg per day in a human. In a further aspect, the disclosed compounds inhibit muscle atrophy when administered at an oral dose of greater than about 25 mg per day in a human. In a further aspect, the disclosed compounds inhibit muscle atrophy when administered at an oral dose of greater than about 50 mg per day in a human. In a further aspect, the disclosed compounds inhibit muscle atrophy when administered at an oral dose of greater than about 75 mg per day in a human. In a further aspect, the disclosed compounds inhibit muscle atrophy when administered at an oral dose of greater than about 100 mg per day in a human. In a further aspect, the disclosed compounds inhibit muscle atrophy when administered at an oral dose of greater than about 150 mg per day in a human. In a further aspect, the disclosed compounds inhibit muscle atrophy when administered at an oral dose of greater than about 200 mg per day in a human. In a further aspect, the disclosed compounds inhibit muscle atrophy when administered at an oral dose of greater than about 250 mg per day in a human. In a yet further aspect, the disclosed compounds inhibit muscle atrophy when administered at an oral dose of greater than about 300 mg per day in a human. In a still further aspect, the disclosed compounds inhibit muscle atrophy when administered at an oral dose of greater than about 400 mg per day in a human. In an even further aspect, the disclosed compounds inhibit muscle atrophy when administered at an oral dose of greater than about 500 mg per day in a human. In a further aspect, the disclosed compounds inhibit muscle atrophy when administered at an oral dose of greater than about 750 mg per day in a human. In a yet further aspect, the disclosed compounds inhibit muscle atrophy when administered at an oral dose of greater than about 1000 mg per day in a human. In a still further aspect, the disclosed compounds inhibit muscle atrophy when administered at an oral dose of greater than about 1500 mg per day in a human. In an even further aspect, the disclosed compounds inhibit muscle atrophy when administered at an oral dose of greater than about 2000 mg per day in a human.

It is contemplated that one or more compounds can optionally be omitted from the disclosed invention.

C. Pharmaceutical Compositions

In one aspect, the invention relates to pharmaceutical compositions comprising the disclosed compounds. That is, a pharmaceutical composition can be provided comprising a therapeutically effective amount of at least one disclosed compound. In another example, a pharmaceutical composition can be provided comprising a prophylactically effective amount of at least one disclosed compound In one aspect, the invention relates to pharmaceutical compositions comprising a pharmaceutically acceptable carrier and a compound, wherein the compound is present in an effective amount. The compound can be selected from a tacrine analog, allantoin analog, naringenin analog, conessine analog, tomatidine analog, ungerine/hippeastrine analog and betulinic acid analog. For example, the compound can be a tacrine analog. In another example, the compound can be a naringenin analog. In another example, the compound can be a conessine analog. In another example, the compound can be a tomatidine analog. In another example, the compound can be an ungerine/hippeastrine analog. In another example, the compound can be a betulinic acid analog.

In one aspect, the compound is present in an amount greater than about an amount selected from 5 mg, 10 mg, 25 mg, 50 mg, 100 mg, 150 mg, 200 mg, 250 mg, 300 mg, 400, mg, 500 mg, 750 mg, 1000 mg, 1,500 mg, or 2,000 mg.

A pharmaceutical composition comprising a pharmaceutically acceptable carrier and an effective amount of one or more of: (a) a compound selected from a tacrine analog, allantoin analog, naringenin analog, conessine analog, tomatidine analog, ungerine/hippeastrine analog and betulinic acid analog; (b) a compound that down regulates multiple induced mRNAs of Muscle Atrophy Signature 1, compared to expression levels in the same type of the muscle cell in the absence of the compound; (c) a compound that up regulates multiple repressed mRNAs of Muscle Atrophy Signature 1, compared to expression levels in the same type of the muscle cell in the absence of the compound; (d) a compound that down regulates multiple induced mRNAs of Muscle Atrophy Signature 2, compared to expression levels in the same type of the muscle cell in the absence of the compound; and/or (e) a compound that up regulates multiple mRNAs of Muscle Atrophy Signature 2, compared to expression levels in the same type of the muscle cell in the absence of the compound.

In a further aspect, the amount is a therapeutically effective amount. In a still further aspect, the amount is a prophylactically effective amount.

In a further aspect, pharmaceutical composition is administered to an animal. In a still further aspect, the animal is a mammal, fish or bird. In a yet further aspect, the mammal is a primate. In a still further aspect, the mammal is a human. In an even further aspect, the human is a patient.

In a further aspect, the pharmaceutical composition comprises a compound identified using muscle atrophy signature-1. In a yet further aspect, the pharmaceutical composition comprises a compound identified using muscle atrophy signature-2. In a yet further aspect, the pharmaceutical composition comprises a compound identified using both muscle atrophy signature-1 and muscle atrophy signature-2.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, the muscle disorder is muscle atrophy. In an even further aspect, the muscle disorder is a condition in need of promoting muscle health, promoting normal muscle function, and/or promoting healthy aging muscles.

In a further aspect, the pharmaceutical composition is administered following identification of the mammal in need of treatment of muscle atrophy. In a still further aspect, the pharmaceutical composition is administered following identification of the mammal in need of prevention of muscle atrophy. In an even further aspect, the mammal has been diagnosed with a need for treatment of muscle atrophy prior to the administering step.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared thereof, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of cellular function related to muscle health, muscle function and/or healthy muscle aging an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating cellular activity related to muscle health, muscle function, and/or healthy aging muscles (e.g., treatment of one or more disorders associated with muscle dysfunction or atrophy) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

D. Methods of Using the Compounds and Compositions

1. Muscle Atrophy

Muscle atrophy is defined as a decrease in the mass of the muscle; it can be a partial or complete wasting away of muscle. When a muscle atrophies, this leads to muscle weakness, since the ability to exert force is related to mass. Muscle atrophy is a co-morbidity of several common diseases, and patients who have "cachexia" in these disease settings have a poor prognosis.

Muscle atrophy can also be skeletal muscle loss or weakness caused by malnutrition, aging, muscle disuse (such as voluntary and involuntary bed rest, neurologic disease (such as multiple sclerosis, amyotrophic lateral sclerosis, spinal muscular atrophy, critical illness neuropathy, spinal cord injury, peripheral neuropathy, or peripheral nerve injury), injury to the limbs or joints, casting, other post-surgical forms of limb immobilization, or spaceflight), chronic disease (such as cancer, congestive heart failure, chronic pulmonary disease, chronic renal failure, chronic liver disease, diabetes mellitus, glucocorticoid excess, growth hormone deficiency, IGF-I deficiency, estrogen deficiency, and chronic infections such as HIV/AIDS or tuberculosis), burn injuries, sepsis, other illnesses requiring mechanical ventilation, drug-induced muscle disease (such as glucocorticoid-induced myopathy and statin-induced myopathy), genetic diseases that primarily affect skeletal muscle (such as muscular dystrophy, myotonic dystrophy and inclusion body myositis), or autoimmune diseases that affect skeletal muscle (such as polymyositis and dermatomyositis).

There are many diseases and conditions which cause muscle atrophy, including malnutrition, muscle disuse (secondary to voluntary or involuntary bed rest, neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization), chronic disease (including cancer, congestive heart failure, chronic pulmonary disease, chronic renal failure, chronic liver disease, diabetes mellitus, Cushing syndrome, growth hormone deficiency, IGF-I deficiency, estrogen deficiency, and chronic infections such as HIV/AIDS or tuberculosis), burns, sepsis, other illnesses requiring mechanical ventilation, drug-induced muscle disease (such as glucocorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, and aging.

Muscle atrophy occurs by a change in the normal balance between protein synthesis and protein degradation. During atrophy, there is a down-regulation of protein synthesis pathways, and an activation of protein breakdown pathways. The particular protein degradation pathway which seems to be responsible for much of the muscle loss seen in a muscle undergoing atrophy is the ATP-dependent, ubiquitin/proteasome pathway. In this system, particular proteins are targeted for destruction by the ligation of at least four copies of a small peptide called ubiquitin onto a substrate protein. When a substrate is thus "poly-ubiquitinated," it is targeted for destruction by the proteasome. Particular enzymes in the ubiquitin/proteasome pathway allow ubiquitination to be directed to some proteins but not others—specificity is gained by coupling targeted proteins to an "E3 ubiquitin ligase." Each E3 ubiquitin ligase binds to a particular set of substrates, causing their ubiquitination. For example, in skeletal muscle, the E3 ubiquitin ligases atrogin-1 and MuRF1 are known to play essential roles protein degradation and muscle atrophy.

Muscle atrophy can be opposed by the signaling pathways which induce muscle hypertrophy, or an increase in muscle size. Therefore one way in which exercise induces an promote muscle health, promote normal muscle function, and/or promote healthy aging muscles is to downregulate the pathways which have the opposite effect. One important rehabilitation tool for muscle atrophy includes the use of functional electrical stimulation to stimulate the muscles which has had limited success in the rehabilitation of paraplegic patients.

In certain aspects, the disclosed compounds can be used as a therapy for illness- and age-related muscle atrophy. It can be useful as a monotherapy or in combination with other strategies that have been considered, such as myostatin inhibition (Zhou, X., et al. (2010) Cell 142(4): 531-543). Given its capacity to reduce adiposity, fasting blood glucose and plasma lipid levels, a disclosed compound derivatives can also be used as a therapy for obesity, metabolic syndrome and type 2 diabetes.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

Systemic administration of one or more disclosed compounds (e.g., by parenteral injection or by oral consumption) can be used to promote muscle health, promote normal muscle function, and/or promote healthy aging muscles, and reduce muscle atrophy in all muscles, including those of the limbs and the diaphragm. Local administration of a disclosed compound (by a topical route or localized injection) can be used to promote local muscle health, as can be required following a localized injury or surgery.

In one aspect, the subject compounds can be coadministered with agents that stimulate insulin signaling, IGF1 signaling and/or muscle health including ursolic acid, insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type inhibitors, myostatin signaling inhibitors, beta-2 adrenergic agents including clenbuterol, androgens, selective androgen receptor modulator (such as GTx-024, BMS-564,929, LGD-4033, AC-262,356, JNJ-28330835, LGD-2226, LGD-3303, S-40503, or S-23), aromatase inhibitors (such as anastrozole, letrozole, exemestane, vorozole, formestane, fadrozole, 4-hydroxyandrostenedione, 1,4,6-androstatrien-3,17-dione, and 4-androstene-3,6,17-trione), growth hormone, a growth hormone analog, ghrelin, a ghrelin analog. A disclosed compound or salt thereof can be administered orally, intramuscularly, intravenously or intraarterially. A disclosed compound or salt thereof can be substantially pure. A disclosed compound or salt thereof can be administered at about 10 mg/day to 10 g/day.

In another aspect, the subject compounds can be administered in combination with agents that stimulate ursolic acid, insulin, insulin analogs, insulin-like growth factor 1, metformin, thiazoladinediones, sulfonylureas, meglitinides, leptin, dipeptidyl peptidase-4 inhibitors, glucagon-like peptide-1 agonists, tyrosine-protein phosphatase non-receptor type inhibitors, myostatin signaling inhibitors, beta-2 adrenergic agents including clenbuterol, androgens, selective androgen receptor modulator (such as GTx-024, BMS-564, 929, LGD-4033, AC-262,356, JNJ-28330835, LGD-2226, LGD-3303, S-40503, or S-23), aromatase inhibitors (such as anastrozole, letrozole, exemestane, vorozole, formestane, fadrozole, 4-hydroxyandrostenedione, 1,4,6-androstatrien-3,17-dione, and 4-androstene-3,6,17-trione), growth hormone, a growth hormone analog, ghrelin, or a ghrelin analog. A disclosed compound or salt thereof can be administered orally, intramuscularly, intravenously or intraarterially. A disclosed compound or salt thereof can be substantially pure. A disclosed compound or salt thereof can be administered at about 10 mg/day to 10 g/day.

The pharmaceutical compositions and methods of the present invention can further comprise other therapeutically active compounds as noted herein which are usually applied in the treatment of the above mentioned pathological conditions.

2. Treatment Methods

The compounds disclosed herein are useful for treating, preventing, ameliorating, controlling or reducing the risk of a variety of muscle disorders. Examples of such muscle disorders include, but are not limited to, skeletal muscle atrophy secondary to malnutrition, muscle disuse (secondary to voluntary or involuntary bedrest), neurologic disease (including multiple sclerosis, amyotrophic lateral sclerosis, spinal muscular atrophy, critical illness neuropathy, spinal cord injury or peripheral nerve injury), orthopedic injury, casting, and other post-surgical forms of limb immobilization, chronic disease (including cancer, congestive heart failure, chronic pulmonary disease, chronic renal failure, chronic liver disease, diabetes mellitus, Cushing syndrome and chronic infections such as HIV/AIDS or tuberculosis), burns, sepsis, other illnesses requiring mechanical ventilation, drug-induced muscle disease (such as glucorticoid-induced myopathy and statin-induced myopathy), genetic diseases that primarily affect skeletal muscle (such as muscular dystrophy and myotonic dystrophy), autoimmune diseases that affect skeletal muscle (such as polymyositis and dermatomyositis), spaceflight, or age-related sarcopenia. In still further aspects, the invention is related to methods to modulate muscle health, methods to inhibit muscle atrophy.

Thus, provided is a method for treating or preventing muscle atrophy, comprising: administering to a subject at least one disclosed compound; at least one disclosed pharmaceutical composition; and/or at least one disclosed product in a dosage and amount effective to treat the disorder in the subject.

Also provided is a method for promoting muscle health, promote normal muscle function, and/or promote healthy aging muscles comprising: administering to a subject at least one disclosed compound; at least one disclosed pharmaceutical composition; and/or at least one disclosed product in a dosage and amount effective to treat the disorder in the subject.

The compounds disclosed herein are useful for treating, preventing, ameliorating, controlling or reducing the risk of a variety of metabolic disorders. In a further aspect, the disclosed compounds in treating disorders associated with a dysfunction of insulin/IGF-I signaling. Thus, are provided methods to increase insulin/IGF-I signaling, methods to reduce body fat; methods to reduce blood glucose, methods to reduce blood triglycerides, methods to reduce blood cholesterol, methods to reduce obesity, methods to reduce fatty liver disease, and methods to reduce diabetes, and pharmaceutical compositions comprising compounds used in the methods.

a. Treating Muscle Atrophy

Disclosed herein is a method of treating muscle atrophy in an animal comprising administering to the animal an effective amount of a compound. The compound can be selected from a tacrine and analogs, naringenin and analogs, allantoin and analogs, conessine and analogs, tomatidine and analogs, ungerine/hippeastrine and analogs, and betulinic acid and analogs, or a mixture thereof. For example, the compound can be a tacrine analog. In another example, the compound can be a naringenin analog. In another example, the compound can be an allantoin analog. In another example, the compound can be a conessine analog. In another example, the compound can be a tomatidine analog. In another example, the compound can be a ungerine/hippeastrine analog. In another example, the compound can be a betulinic acid analog.

In one aspect, the compound is administered in an amount between about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response In one aspect, the disclosed compounds inhibit muscle atrophy. In a further aspect, the disclosed compounds promote muscle health, promote normal muscle function, and/or promote healthy aging muscles. In a yet further aspect, the disclosed compounds inhibit of muscle atrophy and promoting muscle health, promoting normal muscle function, and/or promoting healthy aging muscles. In an even further aspect, the disclosed compounds inhibit of muscle atrophy.

In a further aspect, the compound administered is a disclosed compound or a product of a disclosed method of making a compound. In a yet further aspect, the invention relates to a pharmaceutical composition comprising at least one compound as disclosed herein.

In a further aspect, the compound is co-administered with an anabolic agent. In a further aspect, wherein the compound is co-administered with ursolic acid or a ursolic acid derivative.

In a further aspect, the animal is a mammal, fish or bird. In a yet further aspect, the mammal is a primate. In a still further aspect, the mammal is a human. In an even further aspect, the human is a patient.

In a further aspect, the Muscle Atrophy Signature is Muscle Atrophy Signature 1. In a still further aspect, the Muscle Atrophy Signature is Muscle Atrophy Signature 2.

In a further aspect, prior to the administering step the mammal has been diagnosed with a need for treatment of a disorder selected muscle atrophy, diabetes, obesity, and fatty liver disease. In a yet further aspect, the disorder is muscle atrophy.

In a further aspect, prior to the administering step the mammal has been diagnosed with a need for treatment of a disorder associated with a dysfunction in insulin/IGF-I signaling.

In a further aspect, the treatment of the disorder increases muscle IGF-I signaling. In a still further aspect, the treatment of the disorder increases muscle IGF-I production.

In a further aspect, prior to the administering step the mammal has been diagnosed with a need for treatment of a disorder associated with circulating levels of leptin. In a still further aspect, the treatment decreases the circulating levels of leptin.

In a further aspect, administration the methods are promoting muscle health, promoting normal muscle function, and/or promoting healthy aging muscles in the mammal. In a yet further aspect, administration increases energy expenditure. In a still further aspect, increases brown fat. In an even further aspect, administration increases the ratio of brown fat to white fat. In a still further aspect, administration increases the ratio of skeletal muscle to fat. In a yet further aspect, the compound is co-administered with a disclosed compound or a derivative thereof.

In a further aspect, the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, muscle atrophy is prevented by administration of the compound. In an even further aspect, muscle atrophy is treated by administration of the compound. In a still further aspect, the method further comprises the step of identifying the mammal in need of treatment of muscle atrophy. In a yet further aspect, the method further comprises the step of identifying the mammal in a need of prevention of muscle atrophy. In an even further aspect, the mammal has been diagnosed with a need for treatment of muscle atrophy prior to the administering step.

b. Promoting Muscle Health

In one aspect, the invention relates to a method for promoting muscle health, promoting normal muscle function, and/or promoting healthy aging muscles in an animal, the method comprising administering to the animal an effective amount of a compound selected from a tacrine and analogs, naringenin and analogs, allantoin and analogs, conessine and analogs, tomatidine and analogs, ungerine/hippeastrine and analogs, and betulinic acid and analogs, or a mixture thereof, thereby promoting muscle health in the animal. For example, the compound can be a tacrine analog. In another example, the compound can be a naringenin analog. In another example, the compound can be an allantoin analog. In another example, the compound can be a conessine analog. In another example, the compound can be a tomatidine analog. In another example, the compound can be a ungerine/hippeastrine analog. In another example, the compound can be a betulinic acid analog. In one aspect, the invention relates to a method for promoting muscle health. In another aspect, the invention relates to a method for promoting normal muscle function. In another aspect, the invention relates to a method for promoting healthy aging muscles.

In one aspect, the invention relates to a method for promoting muscle health, promoting normal muscle function, and/or promoting healthy aging muscles in an animal, the method comprising administering to the animal an effective amount of a compound, wherein the compound down regulates at least one of the induced mRNAs of Muscle Atrophy Signature 1 or Muscle Atrophy Signature 2, compared to expression levels in the same type of the muscle cell in the absence of the compound, and/or wherein the compound up regulates at least one of the repressed mRNAs of Muscle Atrophy Signature 1 or Muscle Atrophy Signature 2, compared to expression levels in the same type of the muscle cell in the absence of the compound, thereby promoting muscle health, promoting normal muscle function, and/or promoting healthy aging muscles in the animal.

In a further aspect, the animal is a mammal, fish or bird. In a yet further aspect, the mammal is a primate. In a still further aspect, the mammal is a human. In an even further aspect, the human is a patient.

In a further aspect, the Muscle Atrophy Signature is Muscle Atrophy Signature 1. In a still further aspect, the Muscle Atrophy Signature is Muscle Atrophy Signature 2.

In a further aspect, prior to the administering step the mammal has been diagnosed with a need for treatment of a disorder selected muscle atrophy, diabetes, obesity, and fatty liver disease. In a yet further aspect, the disorder is muscle atrophy.

In a further aspect, prior to the administering step the mammal has been diagnosed with a need for treatment of a disorder associated with a dysfunction in insulin/IGF-I signaling.

In a further aspect, the treatment of the disorder increases muscle IGF-I signaling. In a still further aspect, the treatment of the disorder increases muscle IGF-I production.

In a further aspect, prior to the administering step the mammal has been diagnosed with a need for treatment of a disorder associated with circulating levels of leptin. In a still further aspect, the treatment decreases the circulating levels of leptin.

In a further aspect, administration promoting muscle health, promoting normal muscle function, and/or promoting healthy aging muscles in the mammal. In a yet further aspect, administration increases energy expenditure. In a still further aspect, increases brown fat. In an even further aspect, administration increases the ratio of brown fat to white fat. In a still further aspect, administration increases the ratio of skeletal muscle to fat. In a yet further aspect, the compound is co-administered with a disclosed compound or a derivative thereof.

In a further aspect. the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, muscle atrophy is prevented by administration of the compound. In an even further aspect, muscle atrophy is treated by administration of the compound. In a still further aspect, the method further comprises the step of identifying the mammal in need of treatment of muscle atrophy. In a yet further aspect, the method further comprises the step of identifying the mammal in a need of prevention of muscle atrophy. In an even further aspect, the mammal has been diagnosed with a need for treatment of muscle atrophy prior to the administering step.

c. Enhancing Muscle Formation

In one aspect, the invention relates to a method of enhancing muscle formation in a mammal, the method comprising administering to the animal an effective amount of a compound selected from a tacrine and analogs, naringenin and analogs, allantoin and analogs, conessine and analogs, tomatidine and analogs, ungerine/hippeastrine and analogs, and betulinic acid and analogs, or a mixture thereof, thereby promoting muscle health, promoting normal muscle function, and/or promoting healthy aging muscles in the animal. For example, the compound can be a tacrine analog. In another example, the compound can be a naringenin analog. In another example, the compound can be an allantoin analog. In another example, the compound can be a conessine analog. In another example, the compound can be a tomatidine analog. In another example, the compound can be a ungerine/hippeastrine analog. In another example, the compound can be a betulinic acid analog.

In a further aspect, the invention relates to a method of enhancing muscle formation in a mammal, the method comprising administering to the animal an effective amount of a compound, wherein the compound down regulates at least one of the induced mRNAs of Muscle Atrophy Signature 1 or Muscle Atrophy Signature 2, compared to expression levels in the same type of the muscle cell in the absence of the compound, and/or wherein the compound up regulates at least one of the repressed mRNAs of Muscle Atrophy Signature 1 or Muscle Atrophy Signature 2, compared to expression levels in the same type of the muscle cell in the absence of the compound, thereby promoting muscle health, promoting normal muscle function, and/or promoting healthy aging muscles in the animal.

In a further aspect, the mammal is a human. In a still further aspect, the human is a patient. In a yet further aspect, administration of the compound prevents muscle atrophy in the mammal. In an even further aspect, administration of the compound treats muscle atrophy in the mammal. In a still further aspect, administration of the compound promote muscle health, promote normal muscle function, and/or promote healthy aging muscles in the mammal.

In a further aspect, the compound is administered in an effective amount. In a yet further aspect, the effective amount is a therapeutically effective amount. In a still further aspect, the effective amount is a prophylactically effective amount. In a still further aspect, the method further comprises the step of identifying the mammal in need of treatment of muscle atrophy. In a yet further aspect, the method further comprises the step of identifying the mammal in need of prevention of muscle atrophy. In an even further aspect, the mammal has been diagnosed with a need for treatment of muscle atrophy prior to the administering step.

In a further aspect. the mammal is a domesticated animal. In a yet further aspect, domesticated animal is livestock. In a yet further aspect, the livestock animal is selected from pig, cow, horse, goat, bison, and sheep.

3. Facilitating Tissue Formation In Vitro

In one aspect, the invention relates to a method of enhancing tissue health in vitro, the method comprising administering to the tissue an effective amount of a compound wherein the compound down regulates at least one of the induced mRNAs of Muscle Atrophy Signature 1 or Muscle Atrophy Signature 2, compared to expression levels in the same type of the muscle cell in the absence of the compound, and/or wherein the compound up regulates at least one of the repressed mRNAs of Muscle Atrophy Signature 1 or Muscle Atrophy Signature 2, compared to expression levels in the same type of the muscle cell in the absence of the compound, thereby promoting muscle health, promoting normal muscle function, and/or promoting healthy aging muscles.

In a further aspect, the compound administered is a disclosed compound. In a further aspect, the compound is selected from a tacrine and analogs, naringenin and analogs, allantoin and analogs, conessine and analogs, tomatidine and analogs, ungerine/hippeastrine and analogs, and betulinic acid and analogs, or a mixture thereof, thereby facilitating tissue formation in vitro. For example, the compound can be a tacrine analog. In another example, the compound can be a naringenin analog. In another example, the compound can be an allantoin analog. In another example, the compound can be a conessine analog. In another example, the compound can be a tomatidine analog. In another example, the compound can be a ungerine/hippeastrine analog. In another example, the compound can be a betulinic acid analog.

In a further aspect, the tissue comprises animal cells. In a still further aspect, the animal cells are muscle cells. In a yet further aspect, the muscle cells are skeletal muscle stem or progenitor cells. In an even further aspect, the skeletal muscle stem or progenitor cells are grown on a scaffold.

4. Manufacture of a Medicament

In one aspect, the invention relates to a method for the manufacture of a medicament for inhibiting muscle atrophy and for promoting muscle health, promoting normal muscle function, and/or promoting healthy aging muscles in a mammal comprising combining a therapeutically effective amount of a disclosed compound or product of a disclosed method with a pharmaceutically acceptable carrier or diluent.

In one aspect, the invention relates to a method for manufacturing a medicament associated with muscle atrophy or the need to promote muscle health, promote normal muscle function, and/or promote healthy aging muscles, the method comprising the step of combining an effective amount of one or more of: (a) a compound selected from tacrine analog, naringenin analog, allantoin analog, conessine analog, tomatidine analog, ungerine/hippeastrine analog and betulinic acid analog, or a mixture thereof; (b) a compound that down regulates multiple induced mRNAs of Muscle Atrophy Signature 1, compared to expression levels in the same type of the muscle cell in the absence of the compound; (c) a compound that up multiple repressed mRNAs of Muscle Atrophy Signature 1, compared to expression levels in the same type of the muscle cell in the absence of the compound; (d) a compound that down regulates multiple induced mRNAs of Muscle Atrophy Signature 2, compared to expression levels in the same type of the muscle cell in the absence of the compound; and/or (e) a compound that up regulates at least one of the repressed mRNAs of Muscle Atrophy Signature 2, compared to expression levels in the same type of the muscle cell in the absence of the compound, with a pharmaceutically acceptable carrier or diluent.

In a further aspect, the medicament comprises a disclosed compound. In a still further aspect, the compound is selected from a tacrine and analogs, naringenin and analogs, allantoin and analogs, conessine and analogs, tomatidine and analogs, ungerine/hippeastrine and analogs, and betulinic acid and analogs, or a mixture thereof. For example, the compound can be a tacrine analog. In another example, the compound can be a naringenin analog. In another example, the compound can be an allantoin analog. In another example, the compound can be a conessine analog. In another example, the compound can be a tomatidine analog. In another example, the compound can be a ungerine/hippeastrine analog. In another example, the compound can be a betulinic acid analog.

In a further aspect, the medicament is modulates muscle health. In a still further aspect, the medicament inhibits muscle atrophy. In a yet further aspect, the medicament promote muscle health, promote normal muscle function, and/or promote healthy aging muscles.

5. Kits

Also disclosed herein are kit comprising a tacrine analog, naringenin analog, allantoin analog, conessine analog, tomatidine analog, ungerine/hippeastrine analog and betulinic acid analog, or a mixture thereof, and one or more of: a) at least one agent known to treat muscle atrophy in an animal; b) at least one agent known to decrease the risk of obtaining muscle atrophy in an animal; c) at least one agent known to have a side effect of muscle atrophy; d) instructions for treating muscle atrophy; or e) at least one anabolic agent. For example, the compound can be a tacrine analog. In another example, the compound can be a naringenin analog. In another example, the compound can be a allantoin analog. In another example, the compound can be a conessine analog. In another example, the compound can be a tomatidine analog. In another example, the compound can be a ungerine/hippeastrine analog. In another example, the compound can be a betulinic acid analog.

In one aspect, the kit further comprises at least one agent, wherein the compound and the agent are co-formulated.

In another aspect, the compound and the agent are co-packaged. The agent can be any agent as disclosed herein, such as anabolic agent, agent known to have a side effect of muscle atrophy, agent known to decrease the risk of obtaining muscle atrophy in an animal, or agent known to treat muscle atrophy in an animal.

In one aspect, the invention relates to a kit comprising an effective amount of one or more of: (a) a compound selected from a tacrine analog, naringenin analog, allantoin analog, conessine analog, tomatidine analog, ungerine/hippeastrine analog and betulinic acid analog; (b) a compound that down regulates multiple induced mRNAs of Muscle Atrophy Signature 1, compared to expression levels in the same type of the muscle cell in the absence of the compound; (c) a compound that up regulates multiple repressed mRNAs of Muscle Atrophy Signature 1, compared to expression levels in the same type of the muscle cell in the absence of the compound; (d) a compound that down regulates multiple induced mRNAs of Muscle Atrophy Signature 2, compared to expression levels in the same type of the muscle cell in the absence of the compound; and/or (e) a compound that up regulates multiple repressed mRNAs of Muscle Atrophy Signature 2, compared to expression levels in the same type of the muscle cell in the absence of the compound, (f) and one or more of: (i) a protein supplement; (ii) an anabolic agent; (iii) a catabolic agent; (iv) a dietary supplement; (v) at least one agent known to treat a disorder associated with muscle wasting; (vi) instructions for treating a disorder associated with cholinergic activity; or (vii) instructions for using the compound to promote muscle health, promote normal muscle function, and/or promote healthy aging muscles.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

6. Method of Lowering Blood Glucose

In one aspect, the invention relates to a method of lowering blood glucose in an animal comprising administering to the animal an effective amount of a composition comprising ursolic acid and a naringenin analog, thereby lowering the blood glucose in the animal. In one aspect, the naringenin analog can be naringenin. In one aspect, the ursolic acid can be a ursolic acid derivative.

In another aspect, invention relates to a method of lowering blood glucose in an animal comprising administering to the animal an effective amount of a hippeastrine analog, thereby lowering the blood glucose in the animal. In one aspect, the hippeastrine analog can be hippeastrine.

In another aspect, invention relates to a method of lowering blood glucose in an animal comprising administering to the animal an effective amount of a conessine analog, thereby lowering the blood glucose in the animal. In one aspect, the conessine analog can be conessine.

In a further aspect, the animal is a mammal, fish or bird. In a yet further aspect, the mammal is a primate. In a still further aspect, the mammal is a human. In an even further aspect, the human is a patient.

In a further aspect, prior to the administering step the mammal has been diagnosed with a need for treatment of a disorder associated with the need of lowering blood glucose.

In a further aspect, prior to the administering step the mammal has been diagnosed with a need for treatment of a disorder associated with a dysfunction in insulin/IGF-I signaling.

In a further aspect, the treatment of the disorder increases muscle IGF-I signaling. In a still further aspect, the treatment of the disorder increases muscle IGF-I production.

In a further aspect, prior to the administering step the mammal has been diagnosed with a need for treatment of a disorder associated with circulating levels of leptin. In a still further aspect, the treatment decreases the circulating levels of leptin.

In a further aspect. the animal is a domesticated animal. In a still further aspect, the domesticated animal is a domesticated fish, domesticated crustacean, or domesticated mollusk. In a yet further aspect, the domesticated animal is poultry. In an even further aspect, the poultry is selected from chicken, turkey, duck, and goose. In a still further aspect, the domesticated animal is livestock. In a yet further aspect, the livestock animal is selected from pig, cow, horse, goat, bison, and sheep.

In a further aspect, the effective amount is a therapeutically effective amount. In a still further aspect, the effective amount is a prophylactically effective amount. In a yet further aspect, high blood glucose is prevented by administration of the compound. In a still further aspect, the method further comprises the step of identifying the mammal in need of treatment of lowering of blood glucose. In a yet further aspect, the method further comprises the step of identifying the mammal in a need of prevention the need of lowering blood glucose. In an even further aspect, the mammal has been diagnosed with a need for lowering of blood glucose prior to the administering step.

7. Identification of Compounds that Inhibit Muscle Atrophy

Also disclosed are methods for identifying a compound that inhibits muscle atrophy when administered in a effective amount to a animal in need of treatment thereof, the method comprising the steps of: (i) selecting a candidate compound; (ii) determining the effect of the candidate compound on a cell's expression levels of a plurality of induced mRNAs and/or repressed mRNAs of a Muscle Atrophy Signature, wherein the candidate compound is identified as suitable for muscle atrophy inhibition if: (a) more than one of the induced mRNAs of the Muscle Atrophy Signature are down regulated, compared to expression levels of the induced mRNAs of the Muscle Atrophy Signature in the same type of cell in the absence of the candidate compound; and/or (b) more than one of the repressed mRNAs of the Muscle Atrophy Signature are up regulated, compared to expression levels of the repressed mRNAs of the Muscle Atrophy Signature in the same type of cell in the absence of the candidate compound. In one aspect, the method further comprises administering the candidate compound to an animal. In yet another aspect, the method further comprises writing a report. In yet another aspect, the method further comprises reporting the results. In yet another aspect, the method further comprises performing further tests on the candidate compound, such as confirmatory tests. In yet another aspect, the method further comprises performing toxicity studies on the candidate compound.

In a further aspect, the candidate compound comprises a disclosed compound. In a still further aspect, the compound is selected from a tacrine analog, naringenin analog, allantoin analog, conessine analog, tomatidine analog, ungerine/hippeastrine analog and betulinic acid analog, as defined elsewhere herein. For example, the compound can be a tacrine analog. In another example, the compound can be a naringenin analog. In another example, the compound can be an allantoin analog. In another example, the compound can be a conessine analog. In another example, the compound can be a tomatidine analog. In another example, the compound can be a ungerine/hippeastrine analog. In another example, the compound can be a betulinic acid analog.

In a further aspect, the animal is a mammal, fish or bird. In a yet further aspect, the mammal is a primate. In a still further aspect, the mammal is a human. In an even further aspect, the human is a patient.

In a further aspect, the Muscle Atrophy Signature is Muscle Atrophy Signature 1. In a still further aspect, the Muscle Atrophy Signature is Muscle Atrophy Signature 2.

In a further aspect, the Muscle Atrophy Signature is determined according to steps comprising: a) determining mRNA expression levels in a muscle cell undergoing muscle atrophy, b) determining mRNA expression levels in a muscle cell not undergoing muscle atrophy, wherein an mRNA is determined to be part of the Muscle Atrophy Signature if: (a0 the mRNA is up regulated in the muscle cell undergoing muscle atrophy compared to the muscle cell not undergoing muscle atrophy, or (b) the mRNA is down regulated in the muscle cell undergoing muscle atrophy compared to the muscle cell not undergoing muscle atrophy.

In one aspect, the muscle cell undergoing atrophy and the muscle cell not undergoing atrophy are harvested from an animal. In another aspect, the muscle cell undergoing atrophy is harvested while the animal is in a state of fasting and the muscle cell not undergoing atrophy is harvested prior to the state of fasting. In yet another aspect, the muscle cell undergoing atrophy is harvested from an immobilized muscle and the muscle cell not undergoing atrophy is harvested from a mobile muscle. In yet another aspect, the muscle cell undergoing atrophy is harvested from an animal with spinal cord injury and the muscle cell not undergoing atrophy is harvested from a muscle that has received electrical stimulation. In yet another aspect, the Muscle Atrophy Signature is determined by selecting mRNAs commonly up regulated or commonly down regulated between two or more of the Muscle Atrophy Signatures of the methods described herein.

In a further aspect, the invention relates to a method for inhibiting muscle atrophy in a mammal, the method comprising administering to the mammal a therapeutically effective amount of a compound of identified using the method described above.

8. Non-Medical Uses

Also provided are the uses of the disclosed compounds and products as pharmacological tools in the development and standardization of in vitro and in vivo test systems for the evaluation of the effects of inhibitors of muscle atrophy related activity in laboratory animals such as cats, dogs, rabbits, monkeys, rats, fish, birds, and mice, as part of the search for new therapeutic agents of promoting muscle health, promoting normal muscle function, and/or promoting healthy aging muscles.

E. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Certain materials, reagents and kits were obtained from specific vendors as indicated below, and as appropriate the vendor catalog, part or other number specifying the item are indicated. Vendors indicated below are as follows: "Ambion" is Ambion, a division of Life Technologies Corporation, Austin, Tex., USA; "Applied Biosystems" is Applied Biosystems, a division of Life Technologies Corporation, Carlsbad, Calif., USA; "Boehringer Mannheim" is Boehringer Mannheim Corporation, Indiapolis, Ind., USA; "CardinalHealth" is Cardinal Health, Inc., Dublin, Ohio, USA; "Cell Signaling" is Cell Signaling Technology, Inc., Beverly, Massachussetts, USA; "Columbus Inst" is Columbus Instruments International, Columbus, Ohio, USA; "Harlan" is Harlan Laboratories, Indianapolis, Ind., USA; "Instrumedics" is Instrumedics, Inc., Richmond, Ill., USA; "Invitrogen" is Invitrogen Corporation, Carlsbad, Calif., USA; "Microm" is the Microm division (Walldorf, Germany) of Thermo Fisher Scientific Inc., Rockford, Ill., USA; "Millipore" is Millipore Corporation, Billerica, Massachussetts, USA; a division of Merck KGaA, Darmstadt, Germany; "Ortho" is Ortho Clinical Diagnostics, Rochester, N.Y., USA; "Pierce" is Pierce Biotechnology, Inc., Milwaukee, Wis., USA, a division of Thermo Fisher Scientific, Inc.; "R&D Systems" is R&D Systems Inc., Minneapolis, Minn., USA; "Roche Diagnostics" is Roche Diagnostics Corporation, Indianapolis, Ind., USA; "Sakura" is Sakura Finetek USA, Inc., Torrance, Calif., USA; "Santa Cruz" is Santa Cruz Biotechnology, Inc., Santa Cruz, Calif., USA; and, "Sigma" is Sigma-Aldrich Corporation, Saint Louis, Mo., USA.

1. General Methods a. Human Subject Protocol.

The study referred to herein was approved by the Institutional Review Board at the University of Iowa, and involved seven healthy adults who gave their informed consent before participating. One week prior to the fasting study, subjects made one visit to the Clinical Research Unit ("CRU") for anthropometric measurements, a dietary interview that established each subject's routine food intake and food preferences, and baseline determinations of blood hemoglobin ("Hb") A1c turbidimetric immunoinhibition using the BM/Hitachi 911 analyzer (Boehringer Mannheim); plasma triglycerides and plasma free T4 and TSH by electrochemiluminescence immunoassay using the Elecsys® System (Roche Diagnostics); plasma CRP by immunoturbidimetric assay using the Roche Cobas Integra® high-sensitivity assay (Roche Diagnostics); and, plasma TNF-α levels using the Quantikine® Kit (R&D Systems). To ensure that subjects were eating their routine diet prior to the fasting study, subjects ate only meals prepared by the CRU dietician (based on the dietary interview) for 48 hours before the fasting study. The fasting study began at t=0 hours, when subjects were admitted to the CRU and began fasting. While fasting, subjects remained in the CRU and were encouraged to maintain their routine physical activities. Water was allowed ad libitum, but caloric intake was not permitted. At about 40 hours, a percutaneous biopsy was taken from the vastus lateralis muscle using a Temno® Biopsy Needle (CardinalHealth; Cat #T1420) under ultrasound guidance. Subjects then ate a CRU-prepared mixed meal, and at t=46 hours, a muscle biopsy was taken from the contralateral vastus lateralis muscle. Plasma glucose and insulin levels were measured at t=36, 40, 42 and 46 hours; the Elecsys® system was used to quantitate plasma insulin. Our study protocol of humans with spinal cord injury was described previously (Adams C M, et al. (2011) *Muscle Nerve*. 43(1): 65-75).

b. Microarray Analysis of Human Skeletal Muscle mRNA Levels.

Following harvest, skeletal muscle samples were immediately placed in RNAlater (Ambion) and stored at −80° C. until further use. Total RNA was extracted using TRIzol solution (Invitrogen), and microarray hybridizations were performed at the University of Iowa DNA Facility, as described previously (Lamb J, et al. (2006) *Science* (*New York, N.Y.* 313(5795):1929-1935). The $\log_2$ hybridization signals as shown herein reflect the mean signal intensity of all exon probes specific for an individual mRNA. To determine which human skeletal muscle mRNAs were significantly altered by fasting ($P \leq 0.02$), paired t-tests were used to compare fasted and fed $\log_2$ signals. To determine which mouse skeletal muscle mRNAs were significantly altered by ursolic acid ($P \leq 0.005$), unpaired t-tests were used to compare $\log_2$ signals in mice fed control diet or diet supplemented with ursolic acid. Highly expressed mRNAs were defined as those significantly altered mRNAs that were repressed from or induced to a $\log_2$ signal >8. These raw microarray data from humans and mice have been deposited in NCBI's Gene Expression Omnibus ("GEO") and are accessible through GEO Series accession numbers GSE28016 and GSE28017, respectively. Exon array studies of the effects of fasting on mouse skeletal muscle, and the effects of spinal cord injury on human skeletal muscle were described previously (Adams C M, et al. (2011) *Muscle & nerve* 43(1):65-75; Ebert S M, et al. (2010) *Molecular Endocrinology* 24(4):790-799).

c. Quantitative Real-Time RT-PCR (qPCR).

TRIzol-extracted mRNA was treated with DNase I using the Turbo DNA-free kit (Ambion). qPCR analysis of human mRNA and mouse IGF-I mRNA was performed using TaqMan Gene Expression Assays (Applied Biosystems). First strand cDNA was synthesized from 2 µg of RNA using the High Capacity cDNA Reverse Transcription Kit (Applied Biosystems, Part No. 4368814). The real time PCR contained, in a final volume of 20 al, 20 ng of reverse transcribed RNA, 1 µl of 20× TaqMan Gene Expression Assay, and 10 µl of TaqMan Fast Universal PCR Master Mix (Applied Biosystems; Part No. 4352042). qPCR was carried out using a 7500 Fast Real-Time PCR System (Applied Biosystems) in 9600 emulation mode. qPCR analysis of mouse atrogin-1 and MuRF1 mRNA levels was performed as previously described (Ebert S M, et al. (2010) *Molecular Endocrinology* 24(4):790-799). All qPCR reactions were performed in triplicate and the cycle threshold (Ct) values were averaged to give the final results. To analyze the data, the $\Delta$Ct method was used, with the level of 36B4 mRNA serving as the invariant control.

d. Mouse Protocols.

Male C57BL/6 mice, ages 6-8 weeks, were obtained from NCI, housed in colony cages with 12 h light/12 h dark cycles, and used for experiments within 3 weeks of their arrival. Unless otherwise indicated, mice were maintained on standard chow (Harlan; Teklad Diet, Formula 7013, NIH-31 Modified Open Formula Mouse/Rat Sterilizable Diet). Metformin (Sigma) was dissolved in 0.9% NaCl at a concentration of 250 mg/ml. Ursolic acid (Enzo Life Sciences) was dissolved in corn oil at a concentration of 200 mg/ml (for i.p. injections); alternatively, the ursolic acid was added directly to standard chow (Harlan; Teklad Diet, Formula 7013) or standard high fat diet (Harlan; Teklad Diet, Formula TD.93075) as a customized chow. Oleanolic acid (Sigma) was dissolved in corn oil at a concentration of 200 mg/ml. Mice were fasted by removing food, but not water, for 24 hours. Fasting blood glucose levels were obtained from the tail vein with an ACCU-CHEK® Aviva glucose meter (Roche Diagnostics). Unilateral hindlimb muscle denervation was performed by transsecting the sciatic nerve under anesthesia, and was followed by administration of ursolic acid (200 mg/kg) or vehicle alone (corn oil) via i.p injection twice daily for 7 days. Forelimb grip strength was determined using a grip strength meter equipped with a triangular pull bar (Columbus Inst). Each mouse was subjected to 5 consecutive tests to obtain the peak value. Plasma IGF-I and leptin levels were measured by RIA at the Vanderbilt University Hormone Assay Core Facility. Plasma cholesterol, triglyceride, creatinine, bilirubin and ALT were measured using the VITROS® 350 Chemistry System (Ortho). All animal procedures were approved by the Institutional Animal Care and Use Committee of the University of Iowa.

e. Histological Analysis.

Following harvest, tissues were immediately placed in isopentane that had been chilled to −160° C. with liquid $N_2$. Muscles were embedded in tissue freezing medium, and 10 µm sections from the mid-belly were prepared using a Microm HM 505 E cryostat equipped with a CryoJane sectioning system (Instrumedics). Adipose tissue was fixed in 10% neutral buffered formalin, embedded in paraffin, and then 4 μm sections were prepared using a Microm HM355 S motorized microtome (Microm). Hematoxylin and eosin stains were performed using a DRS-601 automatic slide stainer (Sakura), and examined on an Olympus IX-71 microscope equipped with a DP-70 camera. Image analysis was performed using ImageJ software (public domain, available from the National Institutes of Health, USA). Muscle fiber diameter was measured using the lesser diameter method, as described elsewhere (Dubowitz V, et al. (2007) *Muscle biopsy: a practical approach* (Saunders Elsevier, Philadelphia) 3rd Ed pp XIII, 611 s).

f. Analysis of IGF-I and Insulin-Mediated Protein Phosphorylation.

Mouse quadriceps muscles were snap frozen in liquid $N_2$, and Triton-X 100 soluble protein extracts were prepared as described previously (Ebert S M, et al. (2010) *Molecular endocrinology* 24(4):790-799). Mouse C2C12 myoblasts were obtained from American Type Culture Collection ("ATCC"), and maintained in Dulbecco's modified Eagle's medium (DMEM; ATCC #30-2002) containing antibiotics (100 units/ml penicillin, 100 μg/ml streptomycin sulfate) and 10% (v/v) fetal bovine serum (FBS). On day 0, myotubes were set-up in 6-well plates at a density of $2.5 \times 10^5$ cells/well. On day 2, differentiation into myotubes was induced by replacing 10% FBS with 2% horse serum. On day 7, myotubes were serum-starved by washing 2 times with phosphate buffered saline, and then adding fresh serum-free media. After 16 hours of serum-starvation, 10 μM ursolic acid (from a 10 mM stock prepared in DMSO), or an equal volume of DMSO, with or without 10 nM mouse IGF-I (Sigma; Cat. No. 18779) or 10 nM bovine insulin (Sigma; Cat. No. 16634) was directly added to the media. For analysis of Akt, S6K, ERK and FoxO phosphorylation, myotubes were incubated in the presence or absence of ursolic acid, IGF-I and/or insulin for 20 min, and then harvested into SDS lysis buffer (10 mM Tris-HCl, pH 7.6, 100 mM NaCl, 1% (w/v) SDS, 1 μg/ml pepstatin A, 2 μg/ml aprotinin, 10 μg/ml leupeptin, 200 μM phenylmethylsulfonyl fluoride and a 1:100 dilution of phosphatase inhibitor cocktail 3 (Sigma). An aliquot of each muscle extract or cell lysate was mixed with 0.25 volume of sample buffer (250 mM Tris-HCl, pH 6.8, 10% SDS, 25% glycerol, 0.2% (w/v) bromophenol blue, and 5% (w/v) 2-mercaptoethanol) and heated for 5 min at 95° C., whereas a separate aliquot was used to determine protein concentration by the BCA kit (Pierce). Samples (25 μg) were subjected to 8% SDS-PAGE, then transferred to Hybond-C extra nitrocellulose filters (Millipore). Immunoblots were performed at 4° C. for 16 h using a 1:2000 dilution of antibodies detecting total Akt, phospho-Akt(Ser473), total S6K, phospho-S6K(T421/S424), total ERK1/2, phospho-ERK(T202/Y204), FoxO3a, or phospho-FoxO1 (T24)/FoxO3a(T32) (Cell Signaling). For analysis of IGF-1 receptor or insulin receptor phosphorylation, myotubes were incubated in the presence or absence of ursolic acid, IGF-I and/or insulin for 2 min, and then harvested into RIPA buffer (10 mM Tris-HCL, pH 7.4, 150 mM NaCl, 0.1% (w/v) SDS, 1% (w/v) Triton X-100, 1% Na deoxycholate, 5 mM EDTA, 1 mM NaF, 1 mM Na orthovanadate, 1 μg/ml pepstatin A, 2 μg/ml aprotinin, 10 μg/ml leupeptin, 200 μM phenylmethylsulfonyl fluoride, 1:100 dilution of phosphatase inhibitor cocktail 2 (Sigma) and a 1:100 dilution of phosphatase inhibitor cocktail 3 (Sigma). The protein concentration was measured using the BCA kit, after which the extract was diluted to a concentration of 1 mg/ml in RIPA buffer (final volume 500 μl).

Then 2 μg anti-IGF-1 receptor β antibody (Cell Signaling) or 2 μg anti-insulin receptor β antibody (Santa Cruz) was added with 50 μl protein G plus Sepharose beads (Santa Cruz), and then the samples were rotated at 4° C. for 16 h. Immunoprecipitates were washed three times for 20 min with 1 ml RIPA buffer and then mixed with 100 μl sample buffer (50 mM Tris-HCl (pH 6.8), 2% SDS, 5% glycerol, 0.04% (w/v) bromophenol blue and 5% (w/v) 2-mercaptoethanol), then boiled for 5 min. Immunoprecipitates were subjected to 8% SDS-PAGE. For analysis of total IGF-1 receptor, phospho-insulin receptor and total insulin receptor, proteins were transferred to Hybond-C extra nitrocellulose filters (Millipore). For analysis of phospho-IGF-1 receptor, proteins were transferred to PVDF membranes (Bio-Rad). Immunoblots were performed at room temperature using a 1:2000 dilution of anti-IGF-1 receptor β antibody, 1:5000 dilution of mouse anti-phospho-tyrosine 4G10 monoclonal antibody (Millipore), a 1:2000 dilution of anti-insulin receptor β, or 1:2000 dilution of anti-phospho-insulin receptor β (Y1162/1163) (Santa Cruz).

g. PTP1B Inhibition Via RNA Interference.

The plasmids pCMV-miR-PTP1B #1 and pCMV-miR-PTP1B #2 were generated by ligating PTPN1-specific oligonucleotide duplexes (Invitrogen) into the pcDNA6.2GW/EmGFP miR plasmid (Invitrogen), which contains a CMV promoter driving co-cistronic expression of engineered pre-miRNAs and EmGFP. pCMV-miR-control encodes a non-targeting pre-miRNA hairpin sequence (miR-neg control; Invitrogen) in pcDNA6.2GW/EmGFP miR plasmid. Male C57BL/6 mice were obtained from NCI at ages 6-8 weeks, and used for experiments within 3 weeks of their arrival. Electroporation of mouse tibialis anterior muscles and isolation of skeletal muscle RNA was performed as described previously (Ebert S M, et al. (2010) *Molecular endocrinology* 24(4):790-799). First strand cDNA was synthesized in a 20 μl reaction that contained 2 μg of RNA, random hexamer primers and components of the High Capacity cDNA reverse transcription kit (Applied Biosystems). qPCR analysis of PTPN1 mRNA levels was performed using a Taqman expression assay as described previously (Ebert S M, et al. (2010) *Molecular endocrinology* 24(4):790-799). qPCR was carried out using a 7500 Fast Real-Time PCR System (Applied Biosystems). All qPCR reactions were performed in triplicate and the cycle threshold (Ct) values were averaged to give the final results. Fold changes were determined by the ΔCt method, with level of 36B4 mRNA serving as the invariant control. Skeletal muscle sections were prepared and transfected (EmGFP-positive) muscle fibers were identified and measured as described previously (Ebert S M, et al. (2010) *Molecular endocrinology* 24(4):790-799).

h. Measurement of Serum Ursolic Acid Levels.

Ursolic acid is extracted from serum using a 10:1 mixture of hexane:propanol (recovery>90%), and then conjugated via its carboxylic acid group to 2-(2,3-naphthalimino)ethyl trifluoromethanesulfonate (Invitrogen; Ne-OTf), a moiety that enhances TUV and fluorescence detection. Derivatized samples are then analyzed on a Waters Acquity UPLC equipped with a 100×2.1 mm C18 HSS column with 1.8 μm beads (Waters Part No. 186003533) and a TUV detector.

2. Identification of Therapeutics to Treat Muscle Atrophy

Skeletal muscle atrophy is common and debilitating condition that lacks a pharmacologic therapy. To identify and develop new therapeutic approaches to this pathophysiological condition (FIG. 1), an approach using gene expression signatures to connect small molecules, genes, and disease was used. Briefly, 63 mRNAs were identified that were regulated by fasting in both human and mouse muscle, and 29 mRNAs that were regulated by both fasting and spinal cord injury in human muscle. These two unbiased mRNA expression signatures of muscle atrophy were used to query the Connectivity Map, an algorithm that allows gene signature datasets to be used to find relationships between small molecules, genes, and disease.

Three complimentary studies to characterize global atrophy-associated changes in skeletal muscle mRNA levels in humans and mice were carried out. These three studies determined the effects of: A) fasting on human skeletal muscle mRNA levels as described herein, B) spinal cord injury ("SCI") on human skeletal mRNA levels (Adams C M, et al. (2011) *Muscle & nerve* 43(1):65-75) and C) fasting on mouse skeletal muscle mRNA levels (Ebert S M, et al. (2010) *Molecular endocrinology* 24(4):790-799). In each study, exon expression arrays were used to quantitate levels of more than 16,000 mRNAs. Although there were many significant changes in each study, analysis focused on mRNAs whose levels were similarly altered in at least two atrophy models. Thus, by comparing the effects of fasting on human and mouse skeletal muscle, there were two sets of mRNAs identified: a) 31 mRNAs that were increased by fasting in both species, and b) 32 mRNAs that were decreased by fasting in both species. These evolutionarily conserved, fasting-regulated skeletal muscle mRNAs were termed "muscle atrophy signature-1" (see FIG. 2). Next, the effects of fasting and SCI on human skeletal muscle were determined and two sets of mRNAs were identified: a) 18 mRNAs that were increased by fasting and SCI, and b) 17 mRNAs that were decreased by fasting and SCI. This second group of mRNAs was termed "muscle atrophy signature-2" (see FIG. 3). Almost all of the mRNAs in muscle atrophy signatures-1 and -2 have previously uncharacterized roles in normal or atrophied skeletal muscle. It was next hypothesized that pharmacologic compounds whose effects on cellular mRNA levels were opposite to muscle atrophy signatures-1 and -2 might inhibit skeletal muscle atrophy. To identify candidate compounds, the Connectivity Map (Lamb J, et al. (2006) *Science (New York, N.Y.* 313(5795): 1929-1935) was used to compare muscle atrophy signatures-1 and -2 to mRNA expression signatures of >1300 bioactive small molecules. These results identified several predicted inhibitors of human skeletal muscle atrophy, including ursolic acid. The predicted inhibitors of human skeletal muscle atrophy, i.e. compounds with negative connectivity with the muscle atrophy signatures, are shown in Tables 2 and 3 below. Table 2 shows compounds with negative connectivity to human muscle atrophy signature-1 (see FIG. 2 for mRNAs in the signature), whereas Table 3 shows compounds with negative connectivity to human muscle atrophy signature-2 (see FIG. 3 for mRNAs in the signature).

As a proof-of-concept of the utility of muscle atrophy signatures-1 and -2 described herein, the effects of ursolic acid were assessed in mice, and surprisingly it was discovered ursolic acid inhibited muscle atrophy and promoted muscle hypertrophy.

TABLE 2

Compounds with negative connectivity to human muscle atrophy signature-1.

| Cmap name/ cell line | Connectivity score | n | Enrichment | p | Specificity | % Non-null |
|---|---|---|---|---|---|---|
| conessine - HL60 | −0.752 | 1 | −0.991 | — | — | 100 |
| allantoin - HL60 | −0.622 | 1 | −0.954 | — | — | 100 |
| conessine - PC3 | −0.598 | 1 | −0.941 | — | — | 100 |
| tacrine - HL60 | −0.551 | 1 | −0.91 | — | — | 100 |
| tomatidine - HL60 | −0.497 | 1 | −0.873 | — | — | 100 |
| tomatidine - PC3 | −0.483 | 1 | −0.861 | — | — | 100 |
| naringenin - PC3 | −0.462 | 1 | −0.846 | — | — | 100 |
| allantoin - MCF7 | −0.347 | 2 | −0.735 | 0.13873 | 0.1118 | 50 |
| tomatidine - MCF7 | −0.343 | 2 | −0.78 | 0.09489 | 0.2263 | 50 |
| naringenin - MCF7 | −0.219 | 2 | −0.546 | 0.4127 | 0.6589 | 50 |
| allantoin - PC3 | −0.077 | 2 | −0.414 | 0.78446 | 0.7654 | 50 |

TABLE 3

Compounds with negative connectivity to human muscle atrophy signature-2.

| Cmap name/ cell line | Connectivity score | n | Enrichment | p | Specificity | % Non-null |
|---|---|---|---|---|---|---|
| tacrine - HL60 | −0.870 | 1 | −0.998 | — | — | 100 |
| tomatidine - PC3 | −0.861 | 1 | −0.998 | — | — | 100 |
| naringenin - PC3 | −0.754 | 1 | −0.990 | — | — | 100 |
| betulinic acid - HL60 | −0.569 | 1 | −0.929 | — | — | 100 |
| conessine - HL60 | −0.543 | 1 | −0.915 | — | — | 100 |
| allantoin - MCF7 | −0.486 | 2 | −0.840 | 0.05114 | 0.04710 | 100 |
| naringenin - MCF7 | −0.314 | 2 | −0.460 | 0.64871 | 0.84500 | 50 |
| tomatidine - MCF7 | −0.281 | 2 | −0.611 | 0.30586 | 0.65260 | 50 |

3. Effects of Fasting on Skeletal Muscle mRNA Expression in Humans.

Figure 4A:
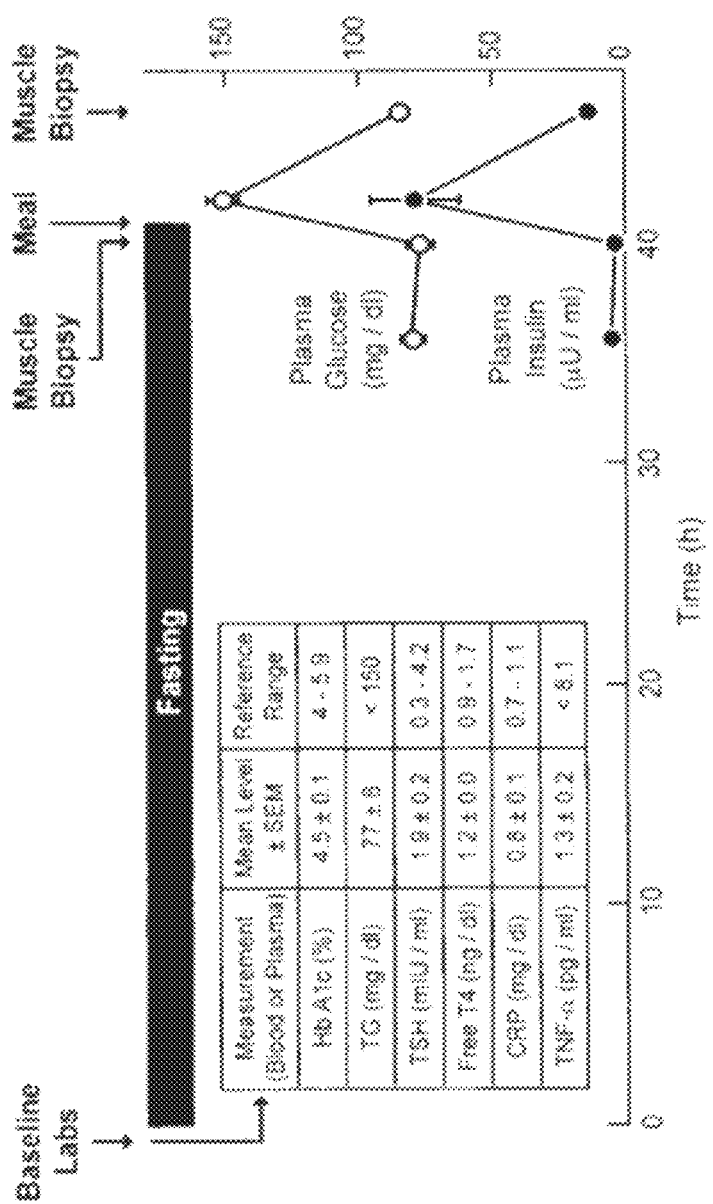
FIGS. 4A and 4B show representative data on the effect of fasting on skeletal muscle mRNA expression in healthy human adults.

Prolonged fasting induces muscle atrophy, but its effects on global mRNA expression in human skeletal muscle were not known heretofore. In order to determine the relationship between global mRNA expression and human skeletal muscle status, seven healthy adult human volunteers (3 male and 4 female) with ages ranging from 25 to 69 years (mean=46 years) were studied. The overall study design is shown in FIG. 4A. The mean body mass index of these subjects (±SEM) was 25±1. Their mean weight was 69.4±4.8 kg. Baseline circulating levels of hemoglobin A1c (HbA1c), triglycerides (TG), thyroid-stimulating hormone (TSH), free thyroxine (free T4), C-reactive protein (CRP) and tumor necrosis factor-α (TNF-α) were within normal limits (FIG. 4A). The table (FIG. 4A, insert) shows baseline circulating metabolic and inflammatory markers. The graph shows plasma glucose and insulin levels (FIG. 4A). Data are means±SEM from the seven study subjects. In some cases, the error bars are too small to see. While staying in the University of Iowa Clinical Research Unit, the subjects fasted for 40 h by forgoing food but not water. The mean weight loss during the fast was 1.7±0.1 kg (3±0% of the initial body weight).

After the 40 h fast, a muscle biopsy was obtained from the subjects' vastus lateralis (VL) muscle. Immediately after the muscle biopsy, the subjects ate a mixed meal. Five hours later (six hours after the first biopsy), a second muscle biopsy from their contralateral VL muscle. Thus, each subject had a muscle biopsy under fasting and nonfasting conditions. As expected, plasma glucose and insulin levels were low at the end of the 40 h fast, rose after the meal, and returned to baseline by the time of the second biopsy (FIG. 4A). These data indicate comparable levels of plasma glucose and insulin at the times of the first (fasting) and second (nonfasting) muscle biopsies.

To determine the effect of fasting on skeletal muscle mRNA expression, RNA was isolated from the paired muscle biopsies and then analyzed it with exon expression arrays. Using P≤0.02 (by paired t-test) as criteria for statistical significance, it was found that 281 mRNAs were higher in the fasting state and 277 were lower (out of >17,000 mRNAs measured; see FIG. 4B). A complete list of these fasting-responsive mRNAs is shown below in Table X1 ("Change" is the mean $\log_2$ change or difference between fasting and fed states). The data in Table X1 is for all mRNAs in this study whose levels were increased or decreased by fasting (P≤0.02 by paired t-test).

Figure 4B:
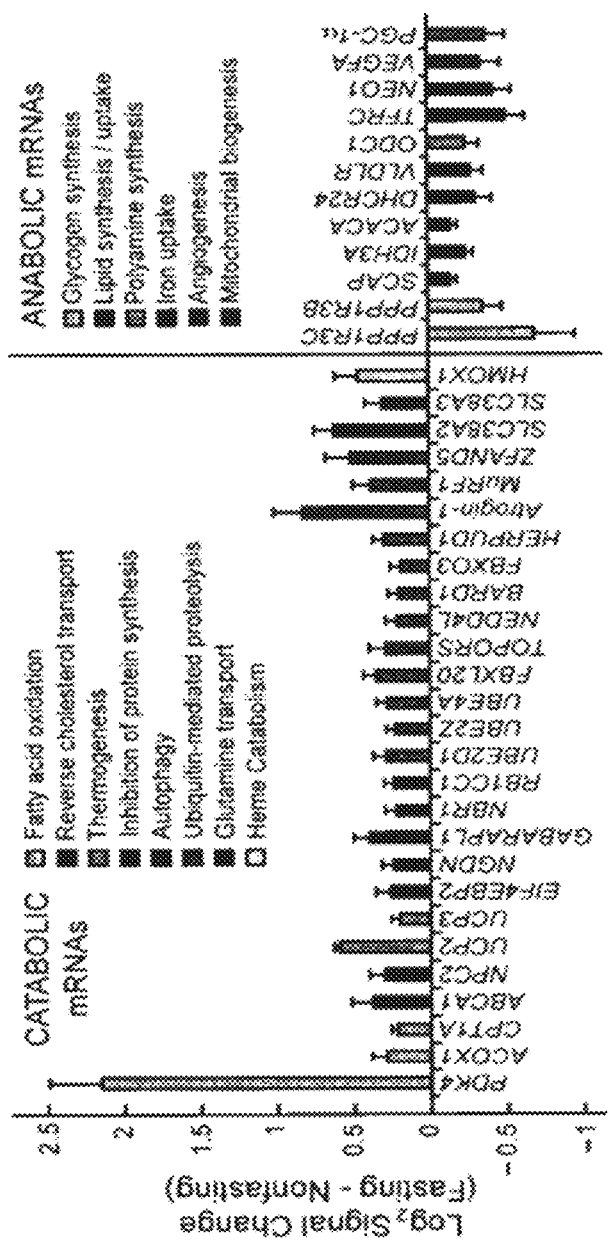

Representative fasting-responsive human skeletal muscle mRNAs, and the effect of fasting on their log 2 hybridization signals, as assessed by Affymetrix Human Exon 1.0 ST arrays are shown in FIG. 4B. In each subject, the fasting signal was normalized to the nonfasting signal from the same subject. Data are means±SEM from 7 subjects. P≤0.02 by paired t-test for all mRNAs shown. The complete set of 458 fasting-responsive mRNAs is shown in Table X1. Most of the differentially expressed mRNAs identified as altered by fasting surprisingly did not have previously known roles in muscle atrophy. However, fasting increased several mRNAs that encode proteins with known roles in catabolic processes such as fat oxidation, reverse cholesterol transport, thermogenesis, inhibition of protein synthesis, autophagy, ubiquitin-mediated proteolysis, glutamine transport and heme catabolism (FIG. 4B). Of these, atrogin-1, MuRF1 and ZFAND5 mRNAs encode proteins known to be required for skeletal muscle atrophy in mice (Bodine S C, et al. (2001) *Science (New York, N.Y.* 294(5547): 1704-1708; Hishiya A, et al. (2006) *The EMBO journal* 25(3):554-564). Conversely, fasting significantly decreased several mRNAs encoding proteins with known roles in anabolic processes such as glycogen synthesis, lipid synthesis and uptake, polyamine synthesis, iron uptake, angiogenesis, and mitochondrial biogenesis (FIG. 4B). Of these, PGC-1α mRNA encodes a protein that inhibits atrophy-associated gene expression and skeletal muscle atrophy in mice (Sandri M, et al. (2006) *Proceedings of the National Academy of Sciences of the United States of America* 103(44): 16260-16265).

Figure 5:
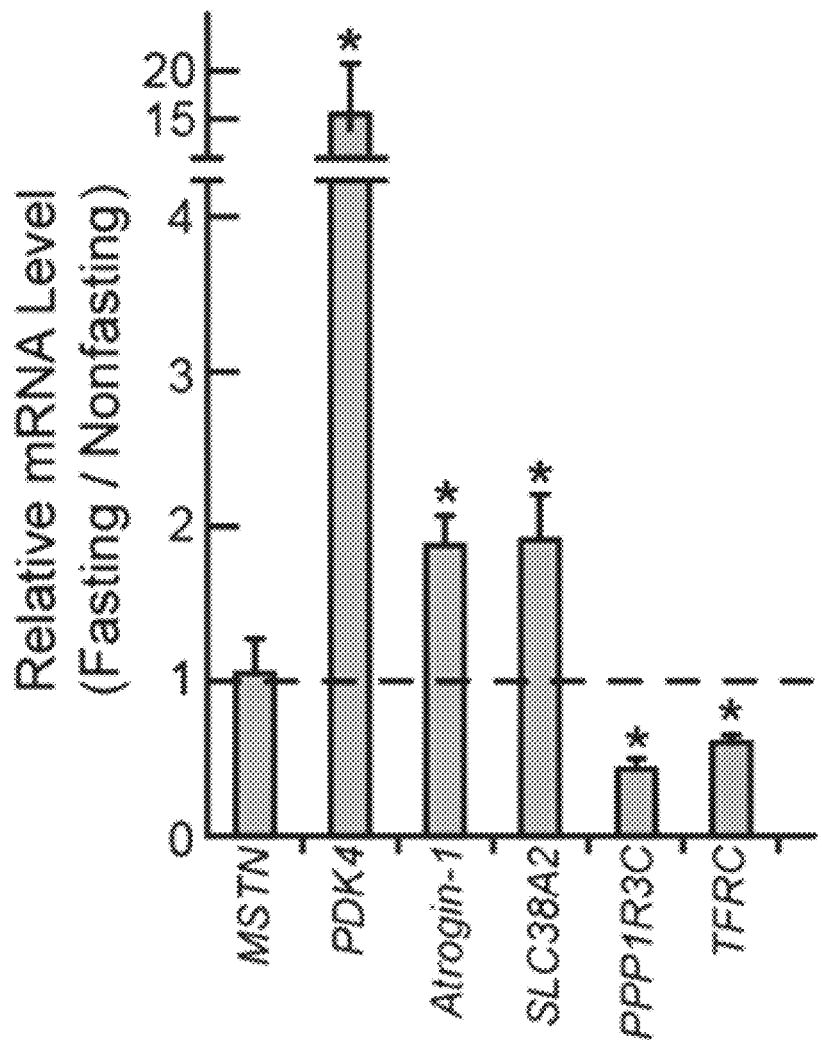
FIG. 5 shows qPCR analysis of representative fasting-responsive mRNAs from human skeletal muscle.

The results were further validated using qPCR to analyze RNA from paired fed and fasted skeletal muscle biopsy samples obtained from seven healthy human subjects (see FIG. 5; data are means±SEM; * P≤0.01 by paired t-test.). In each subject, the fasting mRNA level was normalized to the nonfasting level, which was set at 1. The mRNA encoding myostatin (MSTN) is a control transcript whose level was not altered by fasting, as assessed by exon expression arrays. Taken together, these data established an mRNA expression signature of fasting in human skeletal muscle.

TABLE X1

Fasting-responsive human mRNAs.

| Affymetrix ID | mRNA | Gene Assignment | Accession No. | (Fasting-Fed) | Change SEM | P |
|---|---|---|---|---|---|---|
| 3062082 | PDK4 | NM_002612 // PDK4 // pyruvate dehydrogenase kinase, isozyme 4 // 7q21.3 // 5166 | NM_002612 | 2.15 | 0.34 | 0.000 |
| 2319340 | SLC25A33 | NM_032315 // SLC25A33 // solute carrier family 25, member 33 // 1p36.22 // 84275 | NM_032315 | 1.42 | 0.41 | 0.007 |
| 3165957 | IFNK | NM_020124 // IFNK // interferon, kappa //—// 56832 /// ENST00000276943 // IF | NM_020124 | 0.96 | 0.28 | 0.007 |
| 3424158 | MYF6 | NM_002469 // MYF6 // myogenic factor 6 (herculin) // 12q21 // 4618 /// ENST00000 | NM_002469 | 0.95 | 0.12 | 0.000 |
| 3422144 | LGR5 | NM_003667 // LGR5 // leucine-rich repeat-containing G protein-coupled receptor 5 | NM_003667 | 0.88 | 0.12 | 0.000 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2356115 | TXNIP | NM_006472 // TXNIP // thioredoxin interacting protein // 1q21.1 // 10628 /// ENS | NM_006472 | 0.85 | 0.22 | 0.004 |
| 3233605 | PFKFB3 | NM_004566 // PFKFB3 // 6-phosphofructo-2-kinase/fructose-2,6-biphosphatase 3 // | NM_004566 | 0.84 | 0.18 | 0.002 |
| 3151607 | FBXO32 | NM_058229 // FBXO32 // F-box protein 32 // 8q24.13 // 114907 /// NM_148177 // FB | NM_058229 | 0.82 | 0.19 | 0.002 |
| 2745547 | GAB1 | NM_207123 // GAB1 // GRB2-associated binding protein 1 // 4q31.21 // 2549 /// NM | NM_207123 | 0.71 | 0.08 | 0.000 |
| 3173479 | FOXD4L3 | NM_199135 // FOXD4L3 // forkhead box D4-like 3 // 9q13 // 286380 /// NM_012184 / | NM_199135 | 0.68 | 0.25 | 0.017 |
| 3199500 | CER1 | NM_005454 // CER1 // cerberus 1, cysteine knot superfamily, homolog (Xenopuslae | NM_005454 | 0.64 | 0.24 | 0.019 |
| 3444309 | TAS2R9 | NM_023917 // TAS2R9 // taste receptor, type 2, member 9 // 12p13 // 50835 /// EN | NM_023917 | 0.63 | 0.22 | 0.015 |
| 3452323 | SLC38A2 | NM_018976 // SLC38A2 // solute carrier family 38, member 2 // 12q // 54407 /// E | NM_018976 | 0.62 | 0.13 | 0.001 |
| 3381843 | UCP3 | NM_003356 // UCP // uncoupling protein 3 (mitochondrial, proton carrier) // 11q | NM_003356 | 0.59 | 0.04 | 0.000 |
| 3147508 | KLF10 | NM_005655 // KLF10 // Kruppel-like factor 10 // 8q22.2 // 7071 /// NM_001032282 | NM_005655 | 0.58 | 0.11 | 0.001 |
| 3982534 | LPAR4 | NM_005296 // LPAR4 // lysophosphatidic acid receptor 4 // Xq13-q21.1 // 2846 /// | NM_005296 | 0.57 | 0.17 | 0.008 |
| 3384321 | RAB30 | NM_014488 // RAB30 // RAB30, member RAS oncogene family // 11q12-q14 // 27314 // | NM_014488 | 0.56 | 0.21 | 0.019 |
| 3256192 | C10orf116 | NM_006829 // C10orf116 // chromosome 10 open reading frame 116 // 10q23.2 // 109 | NM_006829 | 0.55 | 0.19 | 0.013 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2705690 | GHSR | NM_198407 // GHSR // growth hormone secretagogue receptor // 3q26.31 // 2693 /// | NM_198407 | 0.54 | 0.20 | 0.016 |
| 3326938 | LOC100130104 | AF274942 // LOC100130104 // PNAS-17 // 11p13 // 100130104 | AF274942 | 0.53 | 0.16 | 0.009 |
| 2318656 | PER3 | NM_016831 // PER3 // period homolog 3 (Drosophila) // 1p36.23 // 8863 /// ENST00 | NM_016831 | 0.52 | 0.16 | 0.009 |
| 3209623 | ZFAND5 | NM_001102420 // ZFAND5 // zinc finger, AN1-type domain 5 // 9q13-q21 // 7763 /// | NM_001102420 | 0.51 | 0.13 | 0.005 |
| 3741300 | OR1D4 | NM_003552 // OR1D4 // olfactory receptor, family 1, subfamily D, member 4 // 17p | NM_003552 | 0.50 | 0.19 | 0.019 |
| 2899176 | HIST1H2BD | NM_138720 // HIST1H2BD // histone cluster 1, H2bd // 6p21.3 // 3017 /// NM_02106 | NM_138720 | 0.49 | 0.16 | 0.010 |
| 3439256 | RPS11 | ENST00000270625 // RPS11 // ribosomal protein S11 // 19q13.3 // 6205 /// BC10002 | ENST00000270625 | 0.49 | 0.11 | 0.002 |
| 2973232 | KIAA0408 | NM_014702 // KIAA0408 // KIAA0408 // 6q22.33 // 9729 /// NM_001012279 // C6orf17 | NM_014702 | 0.49 | 0.14 | 0.006 |
| 3291151 | RHOBTB1 | NM_014836 // RHOBTB1 // Rho-related BTB domain containing 1 // 10q21.2 // 9886/ | NM_014836 | 0.48 | 0.09 | 0.001 |
| 2358136 | C1orf51 | BC027999 // C1orf51 // chromosome 1 open reading frame 51 // 1q21.2 // 148523 // | BC027999 | 0.48 | 0.17 | 0.016 |
| 3948936 | — | — | — | 0.47 | 0.18 | 0.020 |
| 3944129 | HMOX1 | NM_002133 // HMOX1 // hemeoxygenase (decycling) 1 // 22q12|22q13.1 // 3162 /// | NM_002133 | 0.46 | 0.13 | 0.006 |
| 2968652 | SESN1 | NM_014454 // SESN1 // sestrin 1 // 6q21 // 27244 /// ENST00000302071 // SESN1 // | NM_014454 | 0.46 | 0.12 | 0.004 |
| 2951881 | PXT1 | NM_152990 // PXT1 // peroxisomal, testis specific 1 // 6p21.31 // 222659 /// ENS | NM_152990 | 0.45 | 0.14 | 0.008 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2819747 | POLR3G | NM_006467 // POLR3G // polymerase (RNA) III (DNA directed) polypeptide G (32 kD) | NM_006467 | 0.45 | 0.13 | 0.007 |
| 2957384 | GSTA2 | NM_000846 // GSTA2 // glutathione S-transferase A2 // 6p12.1 // 2939 /// NM_1536 | NM_000846 | 0.44 | 0.10 | 0.002 |
| 4014387 | RPSA | NM_002295 // RPSA // ribosomal protein SA // 3p22.2 // 3921 /// NM_001012321 // | NM_002295 | 0.44 | 0.16 | 0.018 |
| 3021158 | C7orf58 | NM_024913 // C7orf58 // chromosome 7 open reading frame 58 // 7q31.31 // 79974 / | NM_024913 | 0.44 | 0.07 | 0.000 |
| 2976155 | OLIG3 | NM_175747 // OLIG3 // oligodendrocyte transcription factor 3 // 6q23.3 // 167826 | NM_175747 | 0.44 | 0.12 | 0.006 |
| 3261886 | C10orf26 | NM_017787 // C10orf26 // chromosome 10 open reading frame 26 // 10q24.32 // 5483 | NM_017787 | 0.44 | 0.17 | 0.019 |
| 2489169 | — | — | — | 0.42 | 0.12 | 0.006 |
| 2790062 | TMEM154 | NM_152680 // TMEM154 // transmembrane protein 154 // 4q31.3 // 201799 /// ENST00 | NM_152680 | 0.42 | 0.14 | 0.012 |
| 3792656 | CCDC102B | NM_024781 // CCDC102B // coiled-coil domain containing 102B // 18q22.1 // 79839 | NM_024781 | 0.42 | 0.12 | 0.007 |
| 3554282 | INF2 | NM_022489 // INF2 // inverted formin, FH2 and WH2 domain containing // 14q32.33 | NM_022489 | 0.41 | 0.14 | 0.012 |
| 2614142 | NR1D2 | NM_005126 // NR1D2 // nuclear receptor subfamily 1, group D, member 2 // 3p24.2 | NM_005126 | 0.39 | 0.15 | 0.019 |
| 3404636 | GABARAPL1 | NM_031412 // GABARAPL1 // GABA(A) receptor-associated protein like 1 // 12p13.2 | NM_031412 | 0.39 | 0.10 | 0.004 |
| 3063856 | tcag7.1177 | ENST00000292369 // tcag7.1177 // opposite strand transcription unit to STAG3 // | ENST00000292369 | 0.39 | 0.09 | 0.003 |
| 3461981 | TSPAN8 | NM_004616 // TSPAN8 // tetraspanin 8 // 12q14.1-q21.1 // 7103 /// ENST0000039333 | NM_004616 | 0.39 | 0.14 | 0.015 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2908154 | C6orf206 | BC029519 // C6orf206 // chromosome 6 open reading frame 206 // 6p21.1 // 221421 | BC029519 | 0.39 | 0.09 | 0.003 |
| 3415046 | FLJ33996 | AK091315 // FLJ33996 // hypothetical protein FLJ33996 // 12q13.13 // 283401 /// | AK091315 | 0.39 | 0.15 | 0.019 |
| 3326400 | CAT | NM_001752 // CAT // catalase // 11p13 // 847 /// ENST00000241052 // CAT // catal | NM_001752 | 0.39 | 0.09 | 0.003 |
| 2390322 | OR2M5 | NM_001004690 // OR2M5 // olfactory receptor, family 2, subfamily M, member 5 // | NM_001004690 | 0.38 | 0.12 | 0.011 |
| 2402536 | TRIM63 | NM_032588 // TRIM63 // tripartite motif-containing 63 // 1p34-p33 // 84676 /// E | NM_032588 | 0.38 | 0.12 | 0.009 |
| 2976768 | CITED2 | NM_006079 // CITED2 // Cbp/p300-interacting transactivator, with Glu/Asp-rich ca | NM_006079 | 0.37 | 0.10 | 0.005 |
| 3218528 | ABCA1 | NM_005502 // ABCA1 // ATP-binding cassette, sub-family A (ABC1), member 1 // 9q3 | NM_005502 | 0.37 | 0.14 | 0.016 |
| 3377861 | DKFZp761E198 | NM_138368 // DKFZp761E198 // DKFZp761E198 protein // 11q13.1 // 91056 /// BC1091 | NM_138368 | 0.37 | 0.06 | 0.000 |
| 2961347 | FILIP1 | NM_015687 // FILIP1 // filamin A interacting protein 1 // 6q14.1 // 27145 /// EN | NM_015687 | 0.37 | 0.10 | 0.005 |
| 3097580 | C8orf22 | NM_001007176 // C8orf22 // chromosome 8 open reading frame 22 // 8q11 // 492307 | NM_001007176 | 0.37 | 0.08 | 0.002 |
| 3755655 | FBXL20 | NM_032875 // FBXL20 // F-box and leucine-rich repeat protein 20 // 17q12 // 8496 | NM_032875 | 0.35 | 0.08 | 0.002 |
| 3057505 | CCL26 | NM_006072 // CCL26 // chemokine (C-C motif) ligand 26 // 7q11.23 // 10344 /// EN | NM_006072 | 0.35 | 0.12 | 0.012 |
| 3307795 | C10orf118 | NM_018017 // C10orf118 // chromosome 10 open reading frame 118 // 10q25.3 // 550 | NM_018017 | 0.35 | 0.13 | 0.020 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3654699 | NUPR1 | NM_001042483 // NUPR1 // nuclear protein 1 // 16p11.2 // 26471 /// | NM_001042483 | 0.35 | 0.10 | 0.007 |
| 3778252 | ANKRD12 | NM_012385 // NM_015208 // ANKRD12 // ankyrin repeat domain 12 // 18p11.22 // 23253 /// NM_001 | NM_015208 | 0.34 | 0.08 | 0.002 |
| 2662560 | C3orf24 | NM_173472 // C3orf24 // chromosome 3 open reading frame 24 // 3p25.3 // 115795 / | NM_173472 | 0.34 | 0.08 | 0.002 |
| 3896370 | RP5-1022P6.2 | NM_019593 // RP5-1022P6.2 // hypothetical protein KIAA1434 // 20p12.3 // 56261 / | NM_019593 | 0.34 | 0.10 | 0.007 |
| 3389566 | KBTBD3 | NM_198439 // KBTBD3 // kelch repeat and BTB (POZ) domain containing 3 // 11q22.3 | NM_198439 | 0.34 | 0.08 | 0.003 |
| 3247818 | FAM133B | NM_152789 // FAM133B // family with sequence similarity 133, member B // 7q21.2 | NM_152789 | 0.34 | 0.11 | 0.010 |
| 2457988 | ZNF706 | AF275802 // ZNF706 // zinc finger protein 706 // 8q22.3 // 51123 /// BC015925 // | AF275802 | 0.34 | 0.12 | 0.016 |
| 3525234 | IRS2 | NM_003749 // IRS2 // insulin receptor substrate 2 // 13q34 // 8660 /// ENST00000 | NM_003749 | 0.34 | 0.09 | 0.004 |
| 2730281 | ODAM | NM_017855 // ODAM // odontogenic, ameloblast asssociated // 4q13.3 // 54959 /// | NM_017855 | 0.34 | 0.12 | 0.016 |
| 3768969 | ABCA5 | NM_018672 // ABCA5 // ATP-binding cassette, sub-family A (ABC1), member 5 // 17q | NM_018672 | 0.33 | 0.10 | 0.008 |
| 3687494 | MAPK3 | NM_001040056 // MAPK3 // mitogen-activated protein kinase 3 // 16p11.2 // 5595 / | NM_001040056 | 0.33 | 0.09 | 0.004 |
| 3405396 | CREBL2 | NM_001310 // CREBL2 // cAMP responsive element binding protein-like 2 // 12p13 / | NM_001310 | 0.33 | 0.07 | 0.002 |
| 3647504 | PMM2 | NM_000303 // PMM2 // phosphomannomutase 2 // 16p13.3-p13.2 // 5373 /// ENST00000 | NM_000303 | 0.33 | 0.10 | 0.008 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3392840 | BUD13 | NM_032725 // BUD13 // BUD13 homolog (S. cerevisiae) // 11q23.3 // 84811 /// ENST | NM_032725 | 0.33 | 0.07 | 0.002 |
| 3453837 | TUBA1A | NM_006009 // TUBA1A // tubulin, alpha 1a // 12q12-q14.3 // 7846 /// ENST00000301 | NM_006009 | 0.33 | 0.07 | 0.002 |
| 2409310 | ELOVL1 | NM_022821 // ELOVL1 // elongation of very long chain fatty acids (FEN1/Elo2, SUR | NM_022821 | 0.32 | 0.09 | 0.005 |
| 3837707 | ZNF114 | NM_153608 // ZNF114 // zinc finger protein 114 // 19q13.32 // 163071 /// ENST000 | NM_153608 | 0.31 | 0.09 | 0.007 |
| 3504434 | XPO4 | NM_022459 // XPO4 // exportin 4 // 13q11 // 64328 /// ENST00000255305 // XPO4 // | NM_022459 | 0.31 | 0.10 | 0.009 |
| 2431877 | — | — | — | 0.31 | 0.11 | 0.017 |
| 3837836 | PSCD2 | NM_017457 // PSCD2 // pleckstrin homology, Sec7 and coiled-coil domains 2 (cytoh | NM_017457 | 0.31 | 0.05 | 0.000 |
| 3869396 | ZNF432 | NM_014650 // ZNF432 // zinc finger protein 432 // 19q13.33 // 9668 /// ENST00000 | NM_014650 | 0.31 | 0.09 | 0.006 |
| 3981120 | OGT | NM_181672 // OGT // O-linked N-acetylglucosamine (GlcNAc) transferase (UDP-N-ace | NM_181672 | 0.31 | 0.10 | 0.013 |
| 2622607 | SLC38A3 | NM_006841 // SLC38A3 // solute carrier family 38, member 3 // 3p21.3 // 10991 // | NM_006841 | 0.30 | 0.11 | 0.016 |
| 3978812 | FOXR2 | NM_198451 // FOXR2 // forkhead box R2 // Xp11.21 // 139628 /// ENST00000339140 / | NM_198451 | 0.30 | 0.09 | 0.008 |
| 3571904 | NPC2 | NM_006432 // NPC2 // Niemann-Pick disease, type C2 // 14q24.3 // 10577 /// NM_00 | NM_006432 | 0.30 | 0.10 | 0.011 |
| 2417945 | PTGER3 | NM_198715 // PTGER3 // prostaglandin E receptor 3 (subtype EP3) // 1p31.2 // 573 | NM_198715 | 0.30 | 0.11 | 0.017 |
| 3059393 | SEMA3E | NM_012431 // SEMA3E // sema domain, immunoglobulin domain (Ig), short basic doma | NM_012431 | 0.30 | 0.09 | 0.009 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2336456 | MGC52498 | NM_001042693 // MGC52498 // hypothetical protein MGC52498 // 1p32.3 // 348378 // | NM_001042693 | 0.30 | 0.10 | 0.011 |
| 3726772 | CROP | NM_016424 // CROP // cisplatin resistance-associated overexpressed protein // 17 | NM_016424 | 0.30 | 0.11 | 0.016 |
| 2784265 | IL2 | NM_000586 // IL2 // interleukin 2 // 4q26-q27 // 3558 /// ENST00000226730 // IL2 | NM_000586 | 0.29 | 0.11 | 0.019 |
| 2495782 | LIPT1 | NM_145197 // LIPT1 // lipoyltransferase 1 // 2q11.2 // 51601 /// NM_145198 // LI | NM_145197 | 0.29 | 0.10 | 0.012 |
| 2377094 | PFKFB2 | NM_006212 // PFKFB2 // 6-phosphofructo-2-kinase/fructose-2,6-biphosphatase 2 // | NM_006212 | 0.29 | 0.10 | 0.012 |
| 2469213 | KLF11 | NM_003597 // KLF11 // Kruppel-like factor 11 // 2p25 // 8462 /// ENST00000305883 | NM_003597 | 0.29 | 0.10 | 0.011 |
| 3662387 | HERPUD1 | NM_014685 // HERPUD1 // homocysteine-inducible, endoplasmic reticulum stress-ind | NM_014685 | 0.29 | 0.07 | 0.003 |
| 3771215 | ACOX1 | NM_004035 // ACOX1 // acyl-Coenzyme A oxidase 1, palmitoyl // 17q24-q25| 17q25.1 | NM_004035 | 0.29 | 0.10 | 0.013 |
| 3203135 | TOPORS | NM_005802 // TOPORS // topoisomerase I binding, arginine/serine-rich // 9p21 // | NM_005802 | 0.28 | 0.11 | 0.018 |
| 2805482 | — | — | — | 0.28 | 0.09 | 0.008 |
| 3247757 | UBE2D1 | NM_003338 // UBE2D1 // ubiquitin-conjugating enzyme E2D 1 (UBC4/5 homolog, yeast | NM_003338 | 0.28 | 0.08 | 0.007 |
| 3444147 | KLRC1 | NM_002259 // KLRC1 // killer cell lectin-like receptor subfamily C, member 1 // | NM_002259 | 0.28 | 0.10 | 0.015 |
| 3348891 | C11orf57 | NM_018195 // C11orf57 // chromosome 11 open reading frame 57 // 11q23.1 // 55216 | NM_018195 | 0.28 | 0.09 | 0.011 |
| 3906942 | SERINC3 | NM_006811 // SERINC3 // serine incorporator 3 // 20q13.1-q13.3 // 10955 /// NM_1 | NM_006811 | 0.28 | 0.07 | 0.003 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2930418 | UST | NM_005715 // UST // uronyl-2-sulfotransferase // 6q25.1 // 10090 /// ENST0000036 | NM_005715 | 0.28 | 0.06 | 0.002 |
| 3188200 | OR1L1 | NM_001005236 // OR1L1 // olfactory receptor, family 1, subfamily L, member 1 // | NM_001005236 | 0.28 | 0.09 | 0.011 |
| 3856075 | ZNF682 | NM_033196 // ZNF682 // zinc finger protein 682 // 19p12 // 91120 /// NM_00107734 | NM_033196 | 0.28 | 0.10 | 0.017 |
| 3385951 | NOX4 | NM_016931 // NOX4 // NADPH oxidase 4 // 11q14.2-q21 // 50507 /// ENST00000263317 | NM_016931 | 0.28 | 0.06 | 0.002 |
| 3523881 | KDELC1 | NM_024089 // KDELC1 // KDEL (Lys-Asp-Glu-Leu) containing 1 // 13q33 // 79070 /// | NM_024089 | 0.28 | 0.06 | 0.002 |
| 2632778 | EPHA6 | NM_001080448 // EPHA6 // EPH receptor A6 // 3q11.2 // 285220 /// ENST00000389672 | NM_001080448 | 0.28 | 0.09 | 0.010 |
| 3373272 | OR5W2 | NM_001001960 // OR5W2 // olfactory receptor, family 5, subfamily W, member 2 // | NM_001001960 | 0.28 | 0.10 | 0.015 |
| 4017694 | IRS4 | NM_003604 // IRS4 // insulin receptor substrate 4 // Xq22.3 // 8471 /// ENST0000 | NM_003604 | 0.28 | 0.10 | 0.016 |
| 3545311 | KIAA1737 | NM_033426 // KIAA1737 // KIAA1737 // 14q24.3 // 85457 /// ENST00000361786 // KIA | NM_033426 | 0.28 | 0.07 | 0.003 |
| 3753860 | CCL5 | NM_002985 // CCL5 // chemokine (C-C motif) ligand 5 // 17q11.2-q12 // 6352 /// E | NM_002985 | 0.28 | 0.05 | 0.001 |
| 3617312 | SLC12A6 | NM_001042496 // SLC12A6 // solute carrier family 12 (potassium/chloride transpor | NM_001042496 | 0.27 | 0.07 | 0.005 |
| 3351315 | UBE4A | NM_004788 // UBE4A // ubiquitination factor E4A (UFD2 homolog, yeast) // 11q23.3 | NM_004788 | 0.27 | 0.07 | 0.004 |
| 3755396 | CCDC49 | NM_017748 // CCDC49 // coiled-coil domain containing 49 // 17q12 // 54883 /// EN | NM_017748 | 0.27 | 0.09 | 0.013 |
| 2870889 | C5orf13 | NM_004772 // C5orf13 // chromosome 5 open reading frame 13 // 5q22.1 // 9315 /// | NM_004772 | 0.27 | 0.09 | 0.010 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2775259 | RASGEF1B | NM_152545 // RASGEF1B // RasGEF domain family, member 1B // 4q21.21-q21.22 // 15 | NM_152545 | 0.27 | 0.10 | 0.015 |
| 3165624 | — | — | — | 0.27 | 0.06 | 0.003 |
| 2771654 | CENPC1 | NM_001812 // CENPC1 // centromere protein C 1 // 4q12-q13.3 // 1060 /// ENST0000 | NM_001812 | 0.27 | 0.09 | 0.013 |
| 3784670 | C18orf21 | NM_031446 // C18orf21 // chromosome 18 open reading frame 21 // 18q12.2 // 83608 | NM_031446 | 0.27 | 0.08 | 0.008 |
| 2364231 | DDR2 | NM_001014796 // DDR2 // discoidin domain receptor tyrosine kinase 2 // 1q23.3 // | NM_001014796 | 0.26 | 0.10 | 0.018 |
| 3921442 | SH3BGR | NM_007341 // SH3BGR // SH3 domain binding glutamic acid-rich protein // 21q22.3 | NM_007341 | 0.26 | 0.08 | 0.007 |
| 2627368 | C3orf49 | BC015210 // C3orf49 // chromosome 3 open reading frame 49 // 3p14.1 // 132200 | BC015210 | 0.26 | 0.06 | 0.003 |
| 3250699 | EIF4EBP2 | NM_004096 // EIF4EBP2 // eukaryotic translation initiation factor 4E binding pro | NM_004096 | 0.26 | 0.10 | 0.018 |
| 3237788 | PLXDC2 | NM_032812 // PLXDC2 // plexin domain containing 2 // 10p12.32-p12.31 // 84898 // | NM_032812 | 0.26 | 0.09 | 0.013 |
| 3285926 | ZNF33B | NM_006955 // ZNF33B // zinc finger protein 33B // 10q11.2 // 7582 /// ENST000003 | NM_006955 | 0.26 | 0.10 | 0.018 |
| 3304475 | ARL3 | NM_004311 // ARL3 // ADP-ribosylation factor-like 3 // 10q23.3 // 403 /// ENST00 | NM_004311 | 0.26 | 0.08 | 0.008 |
| 3364306 | SOX6 | NM_017508 // SOX6 // SRY (sex determining region Y)-box 6 // 11p15.3 // 55553 // | NM_017508 | 0.26 | 0.08 | 0.010 |
| 3185498 | SLC31A2 | NM_001860 // SLC31A2 // solute carrier family 31 (copper transporters), member 2 | NM_001860 | 0.25 | 0.09 | 0.015 |
| 3998766 | KAL1 | NM_000216 // KAL1 // Kallmann syndrome 1 sequence // Xp22.32 // 3730 /// ENST000 | NM_000216 | 0.25 | 0.07 | 0.006 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3143266 | PSKH2 | NM_033126 // PSKH2 // protein serine kinase H2 // 8q21.2 // 85481 /// ENST000002 | NM_033126 | 0.25 | 0.07 | 0.006 |
| 3458911 | CTDSP2 | NM_005730 // CTDSP2 // CTD (carboxy-terminal domain, RNA polymerase II, polypept | NM_005730 | 0.25 | 0.06 | 0.003 |
| 3195034 | PTGDS | NM_000954 // PTGDS // prostaglandin D2 synthase 21 kDa (brain) // 9q34.2-q34.3 // | NM_000954 | 0.25 | 0.08 | 0.010 |
| 3854066 | C19orf42 | NM_024104 // C19orf42 // chromosome 19 open reading frame 42 // 19p13.11 // 7908 | NM_024104 | 0.25 | 0.08 | 0.010 |
| 3819474 | ANGPTL4 | NM_139314 // ANGPTL4 // angiopoietin-like 4 // 19p13.3 // 51129 /// NM_001039667 | NM_139314 | 0.25 | 0.06 | 0.004 |
| 3944084 | TOM1 | NM_005488 // TOM1 // target of myb1 (chicken) // 22q13.1 // 10043 /// ENST000003 | NM_005488 | 0.25 | 0.07 | 0.006 |
| 3848243 | INSR | NM_000208 // INSR // insulin receptor // 19p13.3-p13.2 // 3643 /// NM_001079817 | NM_000208 | 0.24 | 0.09 | 0.014 |
| 3168415 | CLTA | NM_007096 // CLTA // clathrin, light chain (Lca) // 9p13 // 1211 /// NM_00107667 | NM_007096 | 0.24 | 0.08 | 0.009 |
| 2609462 | CAV3 | NM_033337 // CAV3 // caveolin 3 // 3p25 // 859 /// NM_001234 // CAV3 // caveolin | NM_033337 | 0.24 | 0.07 | 0.007 |
| 3393834 | C11orf60 | BC022856 // C11orf60 // chromosome 11 open reading frame 60 // 11q23.3 // 56912 | BC022856 | 0.24 | 0.06 | 0.003 |
| 3755614 | STAC2 | NM_198993 // STAC2 // SH3 and cysteine rich domain 2 // 17q12 // 342667 /// ENST | NM_198993 | 0.24 | 0.07 | 0.009 |
| 3627363 | NARG2 | NM_024611 // NARG2 // NMDA receptor regulated 2 // 15q22.2 // 79664 /// NM_00101 | NM_024611 | 0.24 | 0.06 | 0.003 |
| 3212976 | ZCCHC6 | NM_024617 // ZCCHC6 // zinc finger, CCHC domain containing 6 // 9q21 // 79670 // | NM_024617 | 0.24 | 0.08 | 0.014 |
| 3275922 | PRKCQ | NM_006257 // PRKCQ // protein kinase C, theta // 10p15 // 5588 /// ENST000002631 | NM_006257 | 0.24 | 0.05 | 0.002 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3023825 | C7orf45 | BC017587 // C7orf45 // chromosome 7 open reading frame 45 // 7q32.2 // 136263 // | BC017587 | 0.23 | 0.09 | 0.020 |
| 3832906 | IL29 | NM_172140 // IL29 // interleukin 29 (interferon, lambda 1) // 19q13.13 // 282618 | NM_172140 | 0.23 | 0.08 | 0.015 |
| 3529156 | NGDN | NM_015514 // NGDN // neuroguidin, EIF4E binding protein // 14q11.2 // 25983 /// | NM_015514 | 0.23 | 0.08 | 0.012 |
| 2620448 | CLEC3B | NM_003278 // CLEC3B // C-type lectin domain family 3, member B // 3p22-p21.3 // | NM_003278 | 0.23 | 0.08 | 0.014 |
| 3481296 | SGCG | NM_000231 // SGCG // sarcoglycan, gamma (35 kDa dystrophin-associated glycoprotei | NM_000231 | 0.23 | 0.09 | 0.019 |
| 3135184 | RB1CC1 | NM_014781 // RB1CC1 // RB1-inducible coiled-coil 1 // 8q11 // 9821 /// NM_001083 | NM_014781 | 0.23 | 0.07 | 0.008 |
| 2421843 | GBP3 | NM_018284 // GBP3 // guanylate binding protein 3 // 1p22.2 // 2635 /// ENST00000 | NM_018284 | 0.23 | 0.06 | 0.004 |
| 3385003 | CREBZF | NM_001039618 // CREBZF // CREB/ATF bZIP transcription factor // 11q14 // 58487 / | NM_001039618 | 0.23 | 0.09 | 0.020 |
| 3610804 | IGF1R | NM_000875 // IGF1R // insulin-like growth factor 1 receptor // 15q26.3 // 3480 / | NM_000875 | 0.23 | 0.08 | 0.013 |
| 3606304 | AKAP13 | NM_006738 // AKAP13 // A kinase (PRKA) anchor protein 13 // 15q24-q25 // 11214 / | NM_006738 | 0.23 | 0.04 | 0.000 |
| 2565579 | ANKRD39 | NM_016466 // ANKRD39 // ankyrin repeat domain 39 // 2q11.2 // 51239 /// ENST0000 | NM_016466 | 0.23 | 0.05 | 0.003 |
| 2722151 | RBPJ | NM_005349 // RBPJ // recombination signal binding protein for immunoglobulin kap | NM_005349 | 0.22 | 0.07 | 0.008 |
| 3031533 | GIMAP4 | NM_018326 // GIMAP4 // GTPase, IMAP family member 4 // 7q36.1 // 55303 /// ENST0 | NM_018326 | 0.22 | 0.08 | 0.017 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3725481 | UBE2Z | NM_023079 // UBE2Z // ubiquitin-conjugating enzyme E2Z // 17q21.32 // 65264 /// | NM_023079 | 0.22 | 0.06 | 0.004 |
| 3549575 | IFI27 | NM_005532 // IFI27 // interferon, alpha-inducible protein 27 // 14q32 // 3429 // | NM_005532 | 0.22 | 0.08 | 0.016 |
| 3725035 | NFE2L1 | NM_003204 // NFE2L1 // nuclear factor (erythroid-derived 2)-like 1 // 17q21.3 // | NM_003204 | 0.22 | 0.07 | 0.011 |
| 3348748 | C11orf1 | NM_022761 // C11orf1 // chromosome 11 open reading frame 1 // 11q13-q22 // 64776 | NM_022761 | 0.22 | 0.07 | 0.008 |
| 3722039 | RAMP2 | NM_005854 // RAMP2 // receptor (G protein-coupled) activity modifying protein 2 | NM_005854 | 0.22 | 0.05 | 0.003 |
| 3886704 | STK4 | NM_006282 // STK4 // serine/threonine kinase 4 // 20q11.2-q13.2 // 6789 /// ENST | NM_006282 | 0.22 | 0.07 | 0.012 |
| 3645901 | FLJ14154 | NM_024845 // FLJ14154 // hypothetical protein FLJ14154 // 16p13.3 // 79903 /// N | NM_024845 | 0.22 | 0.06 | 0.005 |
| 3367673 | MPPED2 | NM_001584 // MPPED2 // metallophosphoesterase domain containing 2 // 11p13 // 74 | NM_001584 | 0.22 | 0.08 | 0.017 |
| 3219885 | PTPN3 | NM_002829 // PTPN3 // protein tyrosine phosphatase, non-receptor type 3 // 9q31 | NM_002829 | 0.22 | 0.05 | 0.003 |
| 3791466 | — | — | — | 0.22 | 0.06 | 0.007 |
| 3717635 | ZNF207 | NM_001098507 // ZNF207 // zinc finger protein 207 // 17q11.2 // 7756 /// NM_0034 | NM_001098507 | 0.22 | 0.08 | 0.015 |
| 2648141 | MBNL1 | NM_021038 // MBNL1 // muscleblind-like (Drosophila) // 3q25 // 4154 /// NM_20729 | NM_021038 | 0.22 | 0.07 | 0.009 |
| 2436938 | PBXIP1 | NM_020524 // PBXIP1 // pre-B-cell leukemia homeobox interacting protein 1 // 1q2 | NM_020524 | 0.21 | 0.05 | 0.002 |
| 3299705 | PANK1 | NM_148977 // PANK1 // pantothenate kinase 1 // 10q23.31 // 53354 /// NM_148978 / | NM_148977 | 0.21 | 0.06 | 0.007 |

TABLE X1-continued

Fasting-responsive human mRNAs.

| Affymetrix ID | mRNA | Gene Assignment | Accession No. | (Fasting-Fed) Change | SEM | P |
|---|---|---|---|---|---|---|
| 3628923 | FAM96A | NM_032231 // FAM96A // family with sequence similarity 96, member A // 15q22.31 | NM_032231 | 0.21 | 0.05 | 0.003 |
| 2353669 | CD2 | NM_001767 // CD2 // CD2 molecule // 1p13 // 914 /// ENST00000369478 // CD2 // CD | NM_001767 | 0.21 | 0.06 | 0.006 |
| 3474450 | PLA2G1B | NM_000928 // PLA2G1B // phospholipase A2, group IB (pancreas) // 12q23-q24.1 // | NM_000928 | 0.21 | 0.08 | 0.016 |
| 3722417 | NBR1 | NM_031858 // NBR1 // neighbor of BRCA1 gene 1 // 17q21.31 // 4077 /// NM_005899 | NM_031858 | 0.21 | 0.08 | 0.017 |
| 3234760 | CUGBP2 | NM_001025077 // CUGBP2 // CUG triplet repeat, RNA binding protein 2 // 10p13 // | NM_001025077 | 0.21 | 0.06 | 0.004 |
| 3627422 | RORA | NM_134260 // RORA // RAR-related orphan receptor A // 15q21-q22 // 6095 /// NM_0 | NM_134260 | 0.21 | 0.06 | 0.006 |
| 3382061 | XRRA1 | NM_182969 // XRRA1 // X-ray radiation resistance associated 1 // 11q13.4 // 1435 | NM_182969 | 0.21 | 0.08 | 0.017 |
| 3015338 | STAG3 | NM_012447 // STAG3 // stromal antigen 3 // 7q22.1 // 10734 /// ENST00000317296 / | NM_012447 | 0.21 | 0.06 | 0.007 |
| 2665720 | ZNF385D | NM_024697 // ZNF385D // zinc finger protein 385D // 3p24.3 // 79750 /// ENST0000 | NM_024697 | 0.21 | 0.07 | 0.013 |
| 3154185 | TMEM71 | NM_144649 // TMEM71 // transmembrane protein 71 // 8q24.22 // 137835 /// ENST000 | NM_144649 | 0.21 | 0.06 | 0.009 |
| 3789947 | NEDD4L | NM_015277 // NEDD4L // neural precursor cell expressed, developmentally down-reg | NM_015277 | 0.21 | 0.08 | 0.016 |
| 2688933 | CD200R2 | ENST00000383679 // CD200R2 // CD200 cell surface glycoprotein receptor isoform 2 | ENST00000383679 | 0.21 | 0.08 | 0.016 |
| 3379644 | CPT1A | NM_001876 // CPT1A // carnitine palmitoyltransferase 1A (liver) // 11q13.1-q13.2 | NM_001876 | 0.21 | 0.04 | 0.001 |
| 3677795 | CREBBP | NM_004380 // CREBBP // CREB binding protein (Rubinstein-Taybi syndrome) // 16p13 | NM_004380 | 0.21 | 0.05 | 0.004 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2358320 | TARS2 | NM_025150 // TARS2 // threonyl-tRNA synthetase 2, mitochondrial (putative) // 1q | NM_025150 | 0.21 | 0.06 | 0.007 |
| 3228373 | TSC1 | NM_000368 // TSC1 // tuberous sclerosis 1 // 9q34 // 7248 /// NM_001008567 // TS | NM_000368 | 0.20 | 0.06 | 0.006 |
| 3362795 | RNF141 | NM_016422 // RNF141 // ring finger protein 141 // 11p15.4 // 50862 /// ENST00000 | NM_016422 | 0.20 | 0.08 | 0.019 |
| 3673684 | CDT1 | NM_030928 // CDT1 // chromatin licensing and DNA replication factor 1 // 16q24.3 | NM_030928 | 0.20 | 0.07 | 0.015 |
| 3042881 | HOXA7 | NM_006896 // HOXA7 // homeobox A7 // 7p15-p14 // 3204 /// ENST00000396347 // HOX | NM_006896 | 0.20 | 0.02 | 0.000 |
| 3381817 | UCP2 | NM_003355 // UCP2 // uncoupling protein 2 (mitochondrial, proton carrier) // 11q | NM_003355 | 0.20 | 0.05 | 0.005 |
| 3415068 | ANKRD33 | NM_182608 // ANKRD33 // ankyrin repeat domain 33 // 12q13.13 // 341405 /// ENST0 | NM_182608 | 0.20 | 0.06 | 0.006 |
| 3633403 | SIN3A | NM_015477 // SIN3A // SIN3 homolog A, transcription regulator (yeast) // 15q24.2 | NM_015477 | 0.20 | 0.07 | 0.014 |
| 3380901 | NUMA1 | NM_006185 // NUMA1 // nuclear mitotic apparatus protein 1 // 11q13 // 4926 /// E | NM_006185 | 0.19 | 0.04 | 0.002 |
| 2598099 | BARD1 | NM_000465 // BARD1 // BRCA1 associated RING domain 1 // 2q34-q35 // 580 /// ENST | NM_000465 | 0.19 | 0.07 | 0.015 |
| 3139722 | NCOA2 | NM_006540 // NCOA2 // nuclear receptor coactivator 2 // 8q13.3 // 10499 /// ENST | NM_006540 | 0.19 | 0.06 | 0.010 |
| 3641871 | LINS1 | NM_018148 // LINS1 // lines homolog 1 (Drosophila) // 15q26.3 // 55180 /// NM_00 | NM_018148 | 0.19 | 0.06 | 0.013 |
| 3401217 | TULP3 | NM_003324 // TULP3 // tubby like protein 3 // 12p13.3 // 7289 /// ENST0000022824 | NM_003324 | 0.19 | 0.06 | 0.008 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3741997 | ANKFY1 | NM_016376 // ANKFY1 // ankyrin repeat and FYVE domain containing 1 // 17p13.3 // | NM_016376 | 0.19 | 0.06 | 0.008 |
| 2622742 | C3orf45 | BC028000 // C3orf45 // chromosome 3 open reading frame 45 // 3p21.31 // 132228 / | BC028000 | 0.19 | 0.06 | 0.013 |
| 3845352 | UQCR | NM_006830 // UQCR // ubiquinol-cytochrome c reductase, 6.4 kDa subunit // 19p13.3 | NM_006830 | 0.19 | 0.06 | 0.014 |
| 3960356 | BAIAP2L2 | NM_025045 // BAIAP2L2 // BAI1-associated protein 2-like 2 // 22q13.1 // 80115 // | NM_025045 | 0.19 | 0.07 | 0.018 |
| 3645947 | CLUAP1 | NM_015041 // CLUAP1 // clusterin associated protein 1 // 16p13.3 // 23059 /// NM | NM_015041 | 0.19 | 0.06 | 0.012 |
| 3835544 | ZNF227 | NM_182490 // ZNF227 // zinc finger protein 227 // — // 7770 /// ENST0000031304 | NM_182490 | 0.18 | 0.06 | 0.011 |
| 3368748 | FBXO3 | NM_033406 // FBXO3 // F-box protein 3 // 11p13 // 26273 /// NM_012175 // FBXO3 / | NM_033406 | 0.18 | 0.07 | 0.020 |
| 3621623 | ELL3 | NM_025165 // ELL3 // elongation factor RNA polymerase II-like 3 // 15q15.3 // 80 | NM_025165 | 0.18 | 0.05 | 0.005 |
| 3430552 | PWP1 | NM_007062 // PWP1 // PWP1 homolog (S. cerevisiae) // 12q23.3 // 11137 /// ENST00 | NM_007062 | 0.18 | 0.07 | 0.016 |
| 2844908 | BTNL9 | NM_152547 // BTNL9 // butyrophilin-like 9 // 5q35.3 // 153579 /// ENST0000032770 | NM_152547 | 0.18 | 0.05 | 0.005 |
| 4021508 | ZNF280C | NM_017666 // ZNF280C // zinc finger protein 280C // Xq25 // 55609 /// ENST000003 | NM_017666 | 0.18 | 0.07 | 0.018 |
| 2489071 | TET3 | NM_144993 // TET3 // tet oncogene family member 3 // 2p13.1 // 200424 /// ENST00 | NM_144993 | 0.18 | 0.04 | 0.003 |
| 2516879 | HOXD8 | NM_019558 // HOXD8 // homeobox D8 // 2q31.1 // 3234 /// ENST00000313173 // HOXD8 | NM_019558 | 0.18 | 0.06 | 0.015 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3740704 | SMYD4 | NM_052928 // SMYD4 // SET and MYND domain containing 4 // 17p13.3 // 114826 /// | NM_052928 | 0.18 | 0.06 | 0.012 |
| 3975467 | UTX | NM_021140 // UTX // ubiquitously transcribed tetratricopeptide repeat, X chromos | NM_021140 | 0.18 | 0.06 | 0.013 |
| 3699044 | RFWD3 | NM_018124 // RFWD3 // ring finger and WD repeat domain 3 // 16q22.3 // 55159 /// | NM_018124 | 0.18 | 0.06 | 0.011 |
| 3473083 | MED13L | NM_015335 // MED13L // mediator complex subunit 13-like // 12q24.21 // 23389 /// | NM_015335 | 0.18 | 0.02 | 0.000 |
| 2332711 | PPIH | NM_006347 // PPIH // peptidylprolyl isomerase H (cyclophilin H) // 1p34.1 // 104 | NM_006347 | 0.17 | 0.06 | 0.017 |
| 3556990 | JUB | NM_032876 // JUB // jub, ajuba homolog (Xenopus laevis) // 14q11.2 // 84962 /// | NM_032876 | 0.17 | 0.04 | 0.004 |
| 2780143 | BDH2 | NM_020139 // BDH2 // 3-hydroxybutyrate dehydrogenase, type 2 // 4q24 // 56898 // | NM_020139 | 0.17 | 0.05 | 0.006 |
| 3899495 | C20orf12 | NM_001099407 // C20orf12 // chromosome 20 open reading frame 12 // 20p11.23 // 5 | NM_001099407 | 0.17 | 0.05 | 0.008 |
| 3290875 | ANK3 | NM_020987 // ANK3 // ankyrin 3, node of Ranvier (ankyrin G) // 10q21 // 288 /// | NM_020987 | 0.17 | 0.03 | 0.001 |
| 3576014 | C14orf102 | NM_017970 // C14orf102 // chromosome 14 open reading frame 102 // 14q32.11 // 55 | NM_017970 | 0.17 | 0.04 | 0.002 |
| 3644887 | ATP6V0C | NM_001694 // ATP6V0C // ATPase, H+ transporting, lysosomal 16 kDa, V0 subunit c / | NM_001694 | 0.17 | 0.06 | 0.017 |
| 2648378 | RAP2B | NM_002886 // RAP2B // RAP2B, member of RAS oncogene family // 3q25.2 // 5912 /// | NM_002886 | 0.17 | 0.06 | 0.017 |
| 2362892 | ATP1A2 | NM_000702 // ATP1A2 // ATPase, Na+/K+ transporting, alpha 2 (+) polypeptide // 1 | NM_000702 | 0.16 | 0.06 | 0.015 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2361488 | RHBG | NM_020407 // RHBG // Rh family, B glycoprotein // 1q21.3 // 57127 /// ENST000003 | NM_020407 | 0.16 | 0.06 | 0.014 |
| 3415915 | PFDN5 | NM_002624 // PFDN5 // prefoldin subunit 5 // 12q12 // 5204 /// NM_145897 // PFDN | NM_002624 | 0.16 | 0.05 | 0.011 |
| 3433796 | PEBP1 | NM_002567 // PEBP1 // phosphatidylethanolamine binding protein 1 // 12q24.23 // | NM_002567 | 0.16 | 0.04 | 0.004 |
| 3788302 | SMAD4 | NM_005359 // SMAD4 // SMAD family member 4 // 18q21.1 // 4089 /// ENST0000039841 | NM_005359 | 0.16 | 0.05 | 0.012 |
| 3436236 | ZNF664 | NM_152437 // ZNF664 // zinc finger protein 664 // 12q24.31 // 144348 /// ENST000 | NM_152437 | 0.16 | 0.06 | 0.016 |
| 3441542 | TMEM16B | NM_020373 // TMEM16B // transmembrane protein 16B // 12p13.3 // 57101 /// ENST00 | NM_020373 | 0.16 | 0.06 | 0.018 |
| 3456353 | CALCOCO1 | NM_020898 // CALCOCO1 // calcium binding and coiled-coil domain 1 // 12q13.13 // | NM_020898 | 0.16 | 0.05 | 0.010 |
| 3888721 | PTPN1 | NM_002827 // PTPN1 // protein tyrosine phosphatase, non-receptor type 1 // 20q13 | NM_002827 | 0.16 | 0.06 | 0.020 |
| 3138204 | CYP7B1 | NM_004820 // CYP7B1 // cytochrome P450, family 7, subfamily B, polypeptide 1 // | NM_004820 | 0.15 | 0.05 | 0.014 |
| 3278401 | FRMD4A | NM_018027 // FRMD4A // FERM domain containing 4A // 10p13 // 55691 /// ENST00000 | NM_018027 | 0.15 | 0.05 | 0.009 |
| 3904226 | RBM39 | NM_184234 // RBM39 // RNA binding motif protein 39 // 20q11.22 // 9584 /// NM_00 | NM_184234 | 0.15 | 0.05 | 0.015 |
| 3791850 | SERPINB13 | NM_012397 // SERPINB13 // serpin peptidase inhibitor, clade B (ovalbumin), membe | NM_012397 | 0.15 | 0.04 | 0.005 |
| 3665603 | CTCF | NM_006565 // CTCF // CCCTC-binding factor (zinc finger protein) // 16q21-q22.3 / | NM_006565 | 0.15 | 0.04 | 0.004 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3969802 | BMX | NM_203281 // BMX // BMX non-receptor tyrosine kinase // Xp22.2 // 660 /// NM_001 | NM_203281 | 0.15 | 0.05 | 0.016 |
| 3621276 | HISPPD2A | NM_014659 // HISPPD2A // histidine acid phosphatase domain containing 2A // 15q1 | NM_014659 | 0.14 | 0.04 | 0.005 |
| 2325113 | C1orf213 | NM_138479 // C1orf213 // chromosome 1 open reading frame 213 // 1p36.12 // 14889 | NM_138479 | 0.14 | 0.05 | 0.012 |
| 3681956 | KIAA0430 | NM_014647 // KIAA0430 // KIAA0430 // 16p13.11 // 9665 /// ENST00000396368 // KIA | NM_014647 | 0.14 | 0.05 | 0.018 |
| 3415193 | GRASP | NM_181711 // GRASP // GRP1 (general receptor for phosphoinositides 1)-associated | NM_181711 | 0.14 | 0.05 | 0.019 |
| 3249369 | LRRTM3 | NM_178011 // LRRTM3 // leucine rich repeat transmembrane neuronal 3 // 10q21.3 / | NM_178011 | 0.14 | 0.05 | 0.011 |
| 3874023 | PTPRA | NM_002836 // PTPRA // protein tyrosine phosphatase, receptor type, A // 20p13 // | NM_002836 | 0.14 | 0.04 | 0.004 |
| 3809621 | FECH | NM_001012515 // FECH // ferrochelatase (protoporphyria) // 18q21.3 // 2235 /// N | NM_001012515 | 0.14 | 0.04 | 0.009 |
| 3351385 | MLL | NM_005933 // MLL // myeloid/lymphoid or mixed-lineage leukemia (trithorax homolo | NM_005933 | 0.14 | 0.05 | 0.016 |
| 3288707 | ERCC6 | NM_000124 // ERCC6 // excision repair cross-complementing rodent repair deficien | NM_000124 | 0.14 | 0.05 | 0.016 |
| 3624607 | MYO5A | NM_000259 // MYO5A // myosin VA (heavy chain 12, myoxin) // 15q21 // 4644 /// EN | NM_000259 | 0.14 | 0.04 | 0.006 |
| 3353859 | OR4D5 | NM_001001965 // OR4D5 // olfactory receptor, family 4, subfamily D, member 5 // | NM_001001965 | 0.14 | 0.05 | 0.017 |
| 2823797 | TSLP | NM_033035 // TSLP // thymic stromal lymphopoietin // 5q22.1 // 85480 /// NM_1385 | NM_033035 | 0.14 | 0.05 | 0.013 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2414366 | PPAP2B | NM_003713 // PPAP2B // phosphatidic acid phosphatase type 2B // 1pter-p22.1 // 8 | NM_003713 | 0.13 | 0.04 | 0.007 |
| 3878308 | CSRP2BP | NM_020536 // CSRP2BP // CSRP2 binding protein // 20p11.23 // 57325 /// NM_177926 | NM_020536 | 0.13 | 0.05 | 0.019 |
| 4025771 | CD99L2 | NM_031462 // CD99L2 // CD99 molecule-like 2 // Xq28 // 83692 /// NM_134446 // CD | NM_031462 | 0.13 | 0.04 | 0.007 |
| 3414776 | LETMD1 | NM_015416 // LETMD1 // LETM1 domain containing 1 // 12q13.13 // 25875 /// NM_001 | NM_015416 | 0.13 | 0.05 | 0.014 |
| 3645253 | SRRM2 | NM_016333 // SRRM2 // serine/arginine repetitive matrix 2 // 16p13.3 // 23524 // | NM_016333 | 0.13 | 0.04 | 0.007 |
| 2440700 | ADAMTS4 | NM_005099 // ADAMTS4 // ADAM metallopeptidase with thrombospondin type 1 motif, | NM_005099 | 0.13 | 0.03 | 0.005 |
| 2609870 | BRPF1 | NM_001003694 // BRPF1 // bromodomain and PHD finger containing, 1 // 3p26-p25 // | NM_001003694 | 0.13 | 0.04 | 0.012 |
| 3632298 | ADPGK | NM_031284 // ADPGK // ADP-dependent glucokinase // 15q24.1 // 83440 /// ENST0000 | NM_031284 | 0.13 | 0.04 | 0.007 |
| 3184940 | GNG10 | NM_001017998 // GNG10 // guanine nucleotide binding protein (G protein), gamma 1 | NM_001017998 | 0.13 | 0.04 | 0.011 |
| 3223776 | C5 | NM_001735 // C5 // complement component 5 // 9q33-q34 // 727 /// ENST00000223642 | NM_001735 | 0.13 | 0.04 | 0.008 |
| 3922100 | MX1 | NM_002462 // MX1 // myxovirus (influenza virus) resistance 1, interferon-inducib | NM_002462 | 0.12 | 0.04 | 0.015 |
| 3960478 | CSNK1E | NM_001894 // CSNK1E // casein kinase 1, epsilon // 22q13.1 // 1454 /// NM_152221 | NM_001894 | 0.12 | 0.04 | 0.018 |
| 3715703 | SUPT6H | NM_003170 // SUPT6H // suppressor of Ty 6 homolog (S. cerevisiae) // 17q11.2 // | NM_003170 | 0.11 | 0.03 | 0.005 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2322818 | PADI3 | NM_016233 // PADI3 // peptidyl arginine deiminase, type III // 1p36.13 // 51702 | NM_016233 | 0.11 | 0.03 | 0.006 |
| 2393740 | KIAA0562 | NM_014704 // KIAA0562 // KIAA0562 // 1p36.32 // 9731 /// ENST00000378230 // KIAA | NM_014704 | 0.11 | 0.03 | 0.009 |
| 3784509 | ZNF271 | NM_001112663 // ZNF271 // zinc finger protein 271 // 18q12 // 10778 /// NM_00662 | NM_001112663 | 0.11 | 0.04 | 0.020 |
| 3372253 | CUGBP1 | NM_006560 // CUGBP1 // CUG triplet repeat, RNA binding protein 1 // 11p11 // 106 | NM_006560 | 0.11 | 0.04 | 0.011 |
| 2948259 | TRIM26 | NM_003449 // TRIM26 // tripartite motif-containing 26 // 6p21.3 // 7726 /// ENST | NM_003449 | 0.11 | 0.03 | 0.006 |
| 3191900 | NUP214 | NM_005085 // NUP214 // nucleoporin 214 kDa // 9q34.1 // 8021 /// ENST00000359428 | NM_005085 | 0.11 | 0.03 | 0.003 |
| 3105581 | CA3 | NM_005181 // CA3 // carbonic anhydrase III, muscle specific // 8q13-q22 // 761 / | NM_005181 | 0.11 | 0.03 | 0.003 |
| 3832457 | RYR1 | NM_000540 // RYR1 // ryanodine receptor 1 (skeletal) // 19q13.1 // 6261 /// NM_0 | NM_000540 | 0.11 | 0.03 | 0.006 |
| 3936256 | BCL2L13 | NM_015367 // BCL2L13 // BCL2-like 13 (apoptosis facilitator) // 22q11 // 23786 / | NM_015367 | 0.10 | 0.02 | 0.002 |
| 3599280 | PIAS1 | NM_016166 // PIAS1 // protein inhibitor of activated STAT, 1 // 15q // 8554 /// | NM_016166 | 0.10 | 0.04 | 0.017 |
| 3755976 | MED24 | NM_014815 // MED24 // mediator complex subunit 24 // 17q21.1 // 9862 /// NM_0010 | NM_014815 | 0.10 | 0.04 | 0.019 |
| 3656418 | SRCAP | NM_006662 // SRCAP // Snf2-related CREBBP activator protein // 16p11.2 // 10847 | NM_006662 | 0.10 | 0.04 | 0.017 |
| 3943101 | DEPDC5 | NM_014662 // DEPDC5 // DEP domain containing 5 // 22q12.3 // 9681 /// NM_0010071 | NM_014662 | 0.09 | 0.01 | 0.000 |
| 3960685 | DMC1 | NM_007068 // DMC1 // DMC1 dosage suppressor of mck1 homolog, meiosis-specific ho | NM_007068 | 0.09 | 0.03 | 0.013 |
| 2434776 | CDC42SE1 | NM_001038707 // CDC42SE1 // CDC42 small | NM_001038707 | 0.08 | 0.03 | 0.014 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| | | effector 1 // 1q21.2 // 56882 /// NM_020 | | | | |
| 3438417 | SFRS8 | NM_004592 // SFRS8 // splicing factor, arginine/serine-rich 8 (suppressor-of-whi | NM_004592 | 0.08 | 0.03 | 0.016 |
| 3457696 | PAN2 | NM_014871 // PAN2 // PAN2 polyA specific ribonuclease subunit homolog (S. cerevi | NM_014871 | 0.08 | 0.02 | 0.008 |
| 2534615 | SCLY | NM_016510 // SCLY // selenocysteine lyase // 2q37.3 // 51540 /// ENST00000254663 | NM_016510 | 0.08 | 0.02 | 0.004 |
| 2765865 | RELL1 | NM_001085400 // RELL1 // RELT-like 1 // 4p14 // 768211 /// NM_001085399 // RELL1 | NM_001085400 | 0.07 | 0.02 | 0.002 |
| 3765642 | INTS2 | NM_020748 // INTS2 // integrator complex subunit 2 // 17q23.2 // 57508 /// ENST0 | NM_020748 | 0.05 | 0.01 | 0.005 |
| 2906607 | NFYA | NM_002505 // NFYA // nuclear transcription factor Y, alpha // 6p21.3 // 4800 /// | NM_002505 | −0.07 | 0.02 | 0.011 |
| 3168102 | CREB3 | NM_006368 // CREB3 // cAMP responsive element binding protein 3 // 9pter-p22.1 / | NM_006368 | −0.07 | 0.02 | 0.010 |
| 3939365 | SMARCB1 | NM_003073 // SMARCB1 // SWI/SNF related, matrix associated, actin dependent regu | NM_003073 | −0.07 | 0.02 | 0.013 |
| 3415229 | NR4A1 | NM_002135 // NR4A1 // nuclear receptor subfamily 4, group A, member 1 // 12q13 / | NM_002135 | −0.07 | 0.03 | 0.015 |
| 2437801 | ARHGEF2 | NM_004723 // ARHGEF2 // rho/rac guanine nucleotide exchange factor (GEF) 2 // 1q | NM_004723 | −0.09 | 0.02 | 0.002 |
| 3645565 | THOC6 | NM_024339 // THOC6 // THO complex 6 homolog (Drosophila) // 16p13.3 // 79228 /// | NM_024339 | −0.10 | 0.04 | 0.018 |
| 2406766 | MRPS15 | NM_031280 // MRPS15 // mitochondrial ribosomal protein S15 // 1p35-p34.1 // 6496 | NM_031280 | −0.11 | 0.03 | 0.003 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3553141 | KIAA0329 | NM_014844 // KIAA0329 // KIAA0329 // 14q32.31 // 9895 /// ENST00000359520 // KIA | NM_014844 | −0.11 | 0.04 | 0.018 |
| 3297666 | DYDC1 | NM_138812 // DYDC1 // DPY30 domain containing 1 // 10q23.1 // 143241 /// ENST000 | NM_138812 | −0.11 | 0.02 | 0.000 |
| 3625674 | RFXDC2 | NM_022841 // RFXDC2 // regulatory factor X domain containing 2 // 15q21.3 // 648 | NM_022841 | −0.12 | 0.04 | 0.012 |
| 2926969 | PDE7B | NM_018945 // PDE7B // phosphodiesterase 7B // 6q23-q24 // 27115 /// ENST00000308 | NM_018945 | −0.12 | 0.04 | 0.013 |
| 3525313 | COL4A1 | NM_001845 // COL4A1 // collagen, type IV, alpha 1 // 13q34 // 1282 /// ENST00000 | NM_001845 | −0.12 | 0.04 | 0.014 |
| 2438892 | FCRL5 | NM_031281 // FCRL5 // Fc receptor-like 5 // 1q21 // 83416 /// ENST00000361835 // | NM_031281 | −0.12 | 0.04 | 0.009 |
| 3220846 | SUSD1 | NM_022486 // SUSD1 // sushi domain containing 1 // 9q31.3-q33.1 // 64420 /// ENS | NM_022486 | −0.12 | 0.03 | 0.006 |
| 3598430 | SLC24A1 | NM_004727 // SLC24A1 // solute carrier family 24 (sodium/potassium/calcium excha | NM_004727 | −0.12 | 0.05 | 0.019 |
| 3506431 | RNF6 | NM_005977 // RNF6 // ring finger protein (C3H2C3 type) 6 // 13q12.2 // 6049 /// | NM_005977 | −0.12 | 0.04 | 0.011 |
| 3696057 | SLC12A4 | NM_005072 // SLC12A4 // solute carrier family 12 (potassium/chloride transporter | NM_005072 | −0.12 | 0.02 | 0.001 |
| 2519577 | COL3A1 | NM_000090 // COL3A1 // collagen, type III, alpha 1 (Ehlers-Danlos syndrome type | NM_000090 | −0.12 | 0.04 | 0.012 |
| 3734479 | TMEM104 | NM_017728 // TMEM104 // transmembrane protein 104 // 17q25.1 // 54868 /// ENST00 | NM_017728 | −0.13 | 0.04 | 0.015 |
| 3345157 | PIWIL4 | NM_152431 // PIWIL4 // piwi-like 4 (Drosophila) // 11q21 // 143689 /// ENST00000 | NM_152431 | −0.13 | 0.05 | 0.015 |
| 2949471 | NEU1 | NM_000434 // NEU1 // sialidase 1 (lysosomal | NM_000434 | −0.13 | 0.04 | 0.013 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2599670 | CRYBA2 | sialidase) // 6p21.3 // 4758 /// ENS NM_057093 // CRYBA2 // crystallin, beta A2 // 2q34-q36 // 1412 /// NM_005209 // | NM_057093 | −0.13 | 0.04 | 0.014 |
| 3922444 | ABCG1 | NM_207628 // ABCG1 // ATP-binding cassette, sub-family G (WHITE), member 1 // 21 | NM_207628 | −0.13 | 0.03 | 0.003 |
| 2760371 | WDR1 | NM_017491 // WDR1 // WD repeat domain 1 // 4p16.1 // 9948 /// NM_005112 // WDR1 | NM_017491 | −0.14 | 0.05 | 0.019 |
| 2835440 | TCOF1 | NM_001008656 // TCOF1 // Treacher Collins-Franceschetti syndrome 1 // 5q32-q33.1 | NM_001008656 | −0.14 | 0.04 | 0.007 |
| 2451544 | MYOG | NM_002479 // MYOG // myogenin (myogenic factor 4) // 1q31-q41 // 4656 /// ENST00 | NM_002479 | −0.14 | 0.05 | 0.018 |
| 3745504 | SCO1 | NM_004589 // SCO1 // SCO cytochrome oxidase deficient homolog 1 (yeast) // 17p12 | NM_004589 | −0.14 | 0.03 | 0.003 |
| 2835213 | PPARGC1B | NM_133263 // PPARGC1B // peroxisome proliferator-activated receptor gamma, coact | NM_133263 | −0.14 | 0.04 | 0.006 |
| 3704567 | CBFA2T3 | NM_005187 // CBFA2T3 // core-binding factor, runt domain, alpha subunit 2; trans | NM_005187 | −0.14 | 0.05 | 0.020 |
| 2893562 | RREB1 | NM_002955 // RREB1 // ras responsive element binding protein 1 // 6p25 // 6239 / | NM_002955 | −0.14 | 0.04 | 0.006 |
| 2672712 | SCAP | NM_012235 // SCAP // SREBF chaperone // 3p21.31 // 22937 /// ENST00000265565 // | NM_012235 | −0.14 | 0.04 | 0.009 |
| 2768197 | CORIN | NM_006587 // CORIN // corin, serine peptidase // 4p13-p12 // 10699 /// ENST00000 | NM_006587 | −0.14 | 0.05 | 0.011 |
| 2495279 | VWA3B | NM_144992 // VWA3B // von Willebrand factor A domain containing 3B // 2q11.2 | NM_144992 | −0.14 | 0.04 | 0.006 |
| 2903588 | PFDN6 | NM_014260 // PFDN6 // prefoldin subunit 6 // 6p21.3 // 10471 /// ENST00000399112 | NM_014260 | −0.14 | 0.05 | 0.014 |
| 3031383 | REPIN1 | NM_013400 // REPIN1 // replication initiator | NM_013400 | −0.15 | 0.05 | 0.018 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3754469 | ACACA | 1 // 7q36.1 // 29803 /// NM_014374 NM_198839 // ACACA // acetyl-Coenzyme A carboxylase alpha // 17q21 // 31 /// NM_ | NM_198839 | −0.15 | 0.05 | 0.010 |
| 3767480 | AXIN2 | NM_004655 // AXIN2 // axin 2 (conductin, axil) // 17q23-q24 // 8313 /// ENST0000 | NM_004655 | −0.15 | 0.05 | 0.013 |
| 2954506 | CRIP3 | NM_206922 // CRIP3 // cysteine-rich protein 3 // 6p21.1 // 401262 /// ENST000003 | NM_206922 | −0.15 | 0.06 | 0.018 |
| 3845263 | ADAMTSL5 | NM_213604 // ADAMTSL5 // ADAMTS-like 5 // 19p13.3 // 339366 /// ENST00000330475 | NM_213604 | −0.15 | 0.06 | 0.016 |
| 2565143 | STARD7 | NM_020151 // STARD7 // StAR-related lipid transfer (START) domain containing 7 / | NM_020151 | −0.15 | 0.06 | 0.016 |
| 2321960 | PLEKHM2 | NM_015164 // PLEKHM2 // pleckstrin homology domain containing, family M (with RU | NM_015164 | −0.16 | 0.05 | 0.009 |
| 3829174 | GPATCH1 | NM_018025 // GPATCH1 // G patch domain containing 1 // 19q13.11 // 55094 /// ENS | NM_018025 | −0.16 | 0.03 | 0.001 |
| 2798586 | AHRR | NM_020731 // AHRR // aryl-hydrocarbon receptor repressor // 5p15.3 // 57491 /// | NM_020731 | −0.16 | 0.05 | 0.011 |
| 2362991 | CASQ1 | NM_001231 // CASQ1 // calsequestrin 1 (fast-twitch, skeletal muscle) // 1q21 // | NM_001231 | −0.16 | 0.06 | 0.015 |
| 3954525 | ZNF280B | NM_080764 // ZNF280B // zinc finger protein 280B // 22q11.22 // 140883 /// ENST0 | NM_080764 | −0.16 | 0.04 | 0.005 |
| 4020991 | ACTRT1 | NM_138289 // ACTRT1 // actin-related protein T1 // Xq25 // 139741 /// ENST000003 | NM_138289 | −0.16 | 0.05 | 0.007 |
| 3982975 | POU3F4 | NM_000307 // POU3F4 // POU class 3 homeobox 4 // Xq21.1 // 5456 /// ENST00000373 | NM_000307 | −0.16 | 0.05 | 0.013 |
| 3963990 | PKDREJ | NM_006071 // PKDREJ // polycystic kidney disease (polycystin) and REJ homolog (s | NM_006071 | −0.16 | 0.03 | 0.001 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2436401 | JTB | NM_006694 // JTB // jumping translocation breakpoint // 1q21 // 10899 /// NM_002 | NM_006694 | −0.16 | 0.06 | 0.014 |
| 2759654 | ABLIM2 | NM_032432 // ABLIM2 // actin binding LIM protein family, member 2 // 4p16-p15 // | NM_032432 | −0.16 | 0.05 | 0.007 |
| 2437329 | CLK2 | NM_003993 // CLK2 // CDC-like kinase 2 // 1q21 // 1196 /// NR_002711 // CLK2P // | NM_003993 | −0.16 | 0.06 | 0.016 |
| 3401119 | ITFG2 | NM_018463 // ITFG2 // integrin alpha FG-GAP repeat containing 2 // 12p13.33 // 5 | NM_018463 | −0.16 | 0.04 | 0.004 |
| 3599709 | GLCE | NM_015554 // GLCE // glucuronic acid epimerase // 15q23 // 26035 /// ENST0000026 | NM_015554 | −0.16 | 0.06 | 0.014 |
| 3882413 | C20orf114 | NM_033197 // C20orf114 // chromosome 20 open reading frame 114 // 20q11.21 // 92 | NM_033197 | −0.16 | 0.06 | 0.020 |
| 3712922 | C17orf39 | NM_024052 // C17orf39 // chromosome 17 open reading frame 39 // 17p11.2 // 79018 | NM_024052 | −0.16 | 0.06 | 0.017 |
| 2473376 | EFR3B | BC049384 // EFR3B // EFR3 homolog B (S. cerevisiae) // 2p23.3 // 22979 /// ENST0 | BC049384 | −0.17 | 0.05 | 0.009 |
| 2607262 | STK25 | NM_006374 // STK25 // serine/threonine kinase 25 (STE20 homolog, yeast) // 2q37. | NM_006374 | −0.17 | 0.06 | 0.015 |
| 3755580 | CACNB1 | NM_199247 // CACNB1 // calcium channel, voltage-dependent, beta 1 subunit // 17q | NM_199247 | −0.17 | 0.06 | 0.013 |
| 3402150 | NTF3 | NM_001102654 // NTF3 // neurotrophin 3 // 12p13 // 4908 /// NM_002527 // NTF3 // | NM_001102654 | −0.17 | 0.06 | 0.020 |
| 3014714 | ARPC1B | NM_005720 // ARPC1B // actin related protein 2/3 complex, subunit 1B, 41 kDa // 7 | NM_005720 | −0.17 | 0.06 | 0.020 |
| 3723071 | DBF4B | NM_145663 // DBF4B // DBF4 homolog B (S. cerevisiae) // 17q21.31\|17q21 // 80174 | NM_145663 | −0.17 | 0.04 | 0.002 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2371255 | SMG7 | NM_173156 // SMG7 // Smg-7 homolog, nonsense mediated mRNA decay factor (C. eleg | NM_173156 | −0.17 | 0.06 | 0.014 |
| 3217487 | ALG2 | NM_033087 // ALG2 // asparagine-linked glycosylation 2 homolog (S. cerevisiae, a | NM_033087 | −0.17 | 0.06 | 0.011 |
| 3352159 | LOC100130353 | AK130019 // LOC100130353 // hypothetical protein LOC100130353 // 11q23.3 // 1001 | AK130019 | −0.17 | 0.06 | 0.018 |
| 3401259 | TEAD4 | NM_003213 // TEAD4 // TEA domain family member 4 // 12p13.3-p13.2 // 7004 /// NM | NM_003213 | −0.17 | 0.07 | 0.020 |
| 3114618 | RNF139 | NM_007218 // RNF139 // ring finger protein 139 // 8q24 // 11236 /// ENST00000303 | NM_007218 | −0.17 | 0.06 | 0.015 |
| 2991150 | TSPAN13 | NM_014399 // TSPAN13 // tetraspanin 13 // 7p21.1 // 27075 /// ENST00000262067 // | NM_014399 | −0.18 | 0.05 | 0.006 |
| 2875193 | P4HA2 | NM_004199 // P4HA2 // procollagen-proline, 2-oxoglutarate 4-dioxygenase (proline | NM_004199 | −0.18 | 0.05 | 0.007 |
| 4011743 | SLC7A3 | NM_032803 // SLC7A3 // solute carrier family 7 (cationic amino acid transporter, | NM_032803 | −0.18 | 0.06 | 0.009 |
| 3194015 | LCN9 | NM_001001676 // LCN9 // lipocalin 9 // 9q34.3 // 392399 /// ENST00000277526 // L | NM_001001676 | −0.18 | 0.06 | 0.011 |
| 3741040 | MNT | NM_020310 // MNT // MAX binding protein // 17p13.3 // 4335 /// ENST00000174618 / | NM_020310 | −0.18 | 0.04 | 0.003 |
| 3901851 | ABHD12 | NM_001042472 // ABHD12 // abhydrolase domain containing 12 // 20p11.21 // 26090 | NM_001042472 | −0.18 | 0.05 | 0.004 |
| 2324919 | EPHB2 | NM_017449 // EPHB2 // EPH receptor B2 // 1p36.1-p35 // 2048 /// NM_004442 // EPH | NM_017449 | −0.18 | 0.06 | 0.010 |
| 3185976 | COL27A1 | NM_032888 // COL27A1 // collagen, type XXVII, alpha 1 // 9q32 // 85301 /// ENST0 | NM_032888 | −0.18 | 0.06 | 0.009 |
| 2855434 | C5orf39 | NM_001014279 // C5orf39 // chromosome 5 | NM_001014279 | −0.18 | 0.05 | 0.007 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| | | open reading frame 39 // 5p12 // 389289 | | | | |
| 2334476 | MAST2 | NM_015112 // MAST2 // microtubule associated serine/threonine kinase 2 // 1p34.1 | NM_015112 | −0.18 | 0.02 | 0.000 |
| 3962734 | TTLL1 | NM_001008572 // TTLL1 // tubulin tyrosine ligase-like family, member 1 // 22q13. | NM_001008572 | −0.18 | 0.03 | 0.001 |
| 4017538 | COL4A6 | NM_033641 // COL4A6 // collagen, type IV, alpha 6 // Xq22 // 1288 /// NM_001847 | NM_033641 | −0.18 | 0.03 | 0.000 |
| 3141589 | IL7 | NM_000880 // IL7 // interleukin 7 // 8q12-q13 // 3574 /// ENST00000263851 // IL7 | NM_000880 | −0.19 | 0.05 | 0.006 |
| 2436826 | KCNN3 | NM_002249 // KCNN3 // potassium intermediate/small conductance calcium-activated | NM_002249 | −0.19 | 0.06 | 0.008 |
| 3521174 | ABCC4 | NM_005845 // ABCC4 // ATP-binding cassette, sub-family C (CFTR/MRP), member 4 // | NM_005845 | −0.19 | 0.07 | 0.017 |
| 3768280 | C17orf58 | NM_181656 // C17orf58 // chromosome 17 open reading frame 58 // 17q24.2 // 28401 | NM_181656 | −0.19 | 0.07 | 0.017 |
| 2363784 | HSPA6 | NM_002155 // HSPA6 // heat shock 70 kDa protein 6 (HSP70B') // 1q23 // 3310 /// E | NM_002155 | −0.19 | 0.06 | 0.011 |
| 3928211 | GRIK1 | NM_175611 // GRIK1 // glutamate receptor, ionotropic, kainate 1 // 21q22.11 // 2 | NM_175611 | −0.19 | 0.06 | 0.011 |
| 2758978 | EVC2 | NM_147127 // EVC2 // Ellis van Creveld syndrome 2 (limbin) // 4p16.2-p16.1 // 13 | NM_147127 | −0.19 | 0.06 | 0.012 |
| 3740664 | C17orf91 | NM_032895 // C17orf91 // chromosome 17 open reading frame 91 // 17p13.3 // 84981 | NM_032895 | −0.19 | 0.07 | 0.015 |
| 2782267 | NEUROG2 | NM_024019 // NEUROG2 // neurogenin 2 // 4q25 // 63973 /// ENST00000313341 // NEU | NM_024019 | −0.20 | 0.06 | 0.010 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3826542 | ZNF738 | BC034499 // ZNF738 // zinc finger protein 738 // 19p12 // 148203 /// AK291002 // | BC034499 | −0.20 | 0.05 | 0.003 |
| 3966000 | TYMP | NM_001113756 // TYMP // thymidine phosphorylase // 22q13|22q13.33 // 1890 /// NM | NM_001113756 | −0.20 | 0.05 | 0.003 |
| 3607447 | ABHD2 | NM_007011 // ABHD2 // abhydrolase domain containing 2 // 15q26.1 // 11057 /// NM | NM_007011 | −0.20 | 0.05 | 0.005 |
| 3236448 | SUV39H2 | NM_024670 // SUV39H2 // suppressor of variegation 3-9 homolog 2 (Drosophila) // | NM_024670 | −0.20 | 0.07 | 0.011 |
| 2528504 | SPEG | NM_005876 // SPEG // SPEG complex locus // 2q35 // 10290 /// ENST00000312358 // | NM_005876 | −0.20 | 0.06 | 0.009 |
| 2730746 | SLC4A4 | NM_001098484 // SLC4A4 // solute carrier family 4, sodium bicarbonate cotranspor | NM_001098484 | −0.20 | 0.06 | 0.007 |
| 2544662 | DNMT3A | NM_175629 // DNMT3A // DNA (cytosine-5-)-methyltransferase 3 alpha // 2p23 // 17 | NM_175629 | −0.20 | 0.06 | 0.007 |
| 2937625 | C6orf208 | BC101251 // C6orf208 // chromosome 6 open reading frame 208 // 6q27 // 80069 /// | BC101251 | −0.20 | 0.06 | 0.007 |
| 3233157 | UCN3 | NM_053049 // UCN3 // urocortin 3 (stresscopin) // 10p15.1 // 114131 /// ENST0000 | NM_053049 | −0.20 | 0.08 | 0.017 |
| 2548172 | FEZ2 | NM_001042548 // FEZ2 // fasciculation and elongation protein zeta 2 (zygin II) / | NM_001042548 | −0.21 | 0.03 | 0.000 |
| 3877809 | OTOR | NM_020157 // OTOR // otoraplin // 20p12.1-p11.23 // 56914 /// ENST00000246081 // | NM_020157 | −0.21 | 0.08 | 0.019 |
| 3839400 | C19orf63 | NM_175063 // C19orf63 // chromosome 19 open reading frame 63 // 19q13.33 // 2843 | NM_175063 | −0.21 | 0.04 | 0.002 |
| 3875108 | C20orf196 | AK292708 // C20orf196 // chromosome 20 open reading frame 196 // 20p12.3 // 1498 | AK292708 | −0.21 | 0.06 | 0.006 |
| 2970985 | TSPYL4 | NM_021648 // TSPYL4 // TSPY-like 4 // 6q22.1 // | NM_021648 | −0.21 | 0.07 | 0.011 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3189580 | ZBTB43 | 23270 /// ENST00000368611 // TSP NM_014007 // ZBTB43 // zinc finger and BTB domain containing 43 // 9q33-q34 // 2 | NM_014007 | −0.21 | 0.08 | 0.017 |
| 3407926 | CMAS | NM_018686 // CMAS // cytidine monophosphate N-acetylneuraminic acid synthetase / | NM_018686 | −0.21 | 0.03 | 0.000 |
| 3249886 | TET1 | NM_030625 // TET1 // tet oncogene 1 // 10q21 // 80312 /// ENST00000373644 // TET | NM_030625 | −0.21 | 0.06 | 0.007 |
| 3151970 | MTSS1 | NM_014751 // MTSS1 // metastasis suppressor 1 // 8p22 // 9788 /// ENST0000032506 | NM_014751 | −0.21 | 0.07 | 0.009 |
| 3937183 | DGCR8 | NM_022720 // DGCR8 // DiGeorge syndrome critical region gene 8 // 22q11.2 // 544 | NM_022720 | −0.21 | 0.06 | 0.008 |
| 3958253 | C22orf28 | BC016707 // C22orf28 // chromosome 22 open reading frame 28 // 22q12 // 51493 // | BC016707 | −0.22 | 0.08 | 0.019 |
| 3607503 | ABHD2 | NM_007011 // ABHD2 // abhydrolase domain containing 2 // 15q26.1 // 11057 /// NM | NM_007011 | −0.22 | 0.07 | 0.010 |
| 2799030 | SLC6A19 | NM_001003841 // SLC6A19 // solute carrier family 6 (neutral amino acid transport | NM_001003841 | −0.22 | 0.06 | 0.007 |
| 3870611 | LILRB3 | NM_001081450 // LILRB3 // leukocyte immunoglobulin-like receptor, subfamily B (w | NM_001081450 | −0.22 | 0.08 | 0.016 |
| 3857811 | C19orf12 | NM_031448 // C19orf12 // chromosome 19 open reading frame 12 // 19q12 // 83636 / | NM_031448 | −0.22 | 0.08 | 0.019 |
| 2500667 | FBLN7 | NM_153214 // FBLN7 // fibulin 7 // 2q13 // 129804 /// ENST00000331203 // FBLN7 / | NM_153214 | −0.22 | 0.08 | 0.019 |
| 3523156 | TMTC4 | NM_032813 // TMTC4 // transmembrane and tetratricopeptide repeat containing 4 // | NM_032813 | −0.22 | 0.07 | 0.010 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2612371 | EAF1 | NM_033083 // EAF1 // ELL associated factor 1 // 3p24.3 // 85403 /// ENST00000396 | NM_033083 | −0.22 | 0.07 | 0.008 |
| 3988638 | LONRF3 | NM_001031855 // LONRF3 // LON peptidase N-terminal domain and ring finger 3 // X | NM_001031855 | −0.23 | 0.08 | 0.012 |
| 3114240 | C8orf32 | BC008781 // C8orf32 // chromosome 8 open reading frame 32 // 8q24.13 // 55093 // | BC008781 | −0.23 | 0.08 | 0.016 |
| 2460368 | TTC13 | NM_024525 // TTC13 // tetratricopeptide repeat domain 13 // 1q42.2 // 79573 /// | NM_024525 | −0.23 | 0.08 | 0.014 |
| 2428425 | PPM1J | NM_005167 // PPM1J // protein phosphatase 1J (PP2C domain containing) // 1p13.2 | NM_005167 | −0.23 | 0.06 | 0.003 |
| 3194986 | LCN12 | NM_178536 // LCN12 // lipocalin 12 // 9q34.3 // 286256 /// ENST00000371633 // LC | NM_178536 | −0.23 | 0.06 | 0.004 |
| 3642875 | RAB11FIP3 | NM_014700 // RAB11FIP3 // RAB11 family interacting protein 3 (class II) // 16p13 | NM_014700 | −0.23 | 0.07 | 0.010 |
| 2532378 | CHRND | NM_000751 // CHRND // cholinergic receptor, nicotinic, delta // 2q33-q34 // 1144 | NM_000751 | −0.23 | 0.08 | 0.018 |
| 2995667 | ADCYAP1R1 | NM_001118 // ADCYAP1R1 // adenylate cyclase activating polypeptide 1 (pituitary) | NM_001118 | −0.23 | 0.05 | 0.002 |
| 3390641 | ARHGAP20 | NM_020809 // ARHGAP20 // Rho GTPase activating protein 20 // 11q22.3-q23.1 // 57 | NM_020809 | −0.23 | 0.05 | 0.003 |
| 2830465 | MYOT | NM_006790 // MYOT // myotilin // 5q31 // 9499 /// ENST00000239926 // MYOT // myo | NM_006790 | −0.23 | 0.07 | 0.007 |
| 2452069 | PIK3C2B | NM_002646 // PIK3C2B // phosphoinositide-3-kinase, class 2, beta polypeptide // | NM_002646 | −0.23 | 0.02 | 0.000 |
| 3744127 | HES7 | NM_032580 // HES7 // hairy and enhancer of split 7 (Drosophila) // 17p13.1 // 84 | NM_032580 | −0.23 | 0.09 | 0.019 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3327057 | FLJ14213 | NM_024841 // FLJ14213 // protor-2 // 11p13-p12 // 79899 /// ENST00000378867 // F | NM_024841 | −0.23 | 0.07 | 0.007 |
| 2664332 | COLQ | NM_005677 // COLQ // collagen-like tail subunit (single strand of homotrimer) of | NM_005677 | −0.23 | 0.07 | 0.006 |
| 3829160 | C19orf40 | NM_152266 // C19orf40 // chromosome 19 open reading frame 40 // 19q13.11 // 9144 | NM_152266 | −0.23 | 0.08 | 0.012 |
| 3708798 | SENP3 | NM_015670 // SENP3 // SUMO1/sentrin/SMT3 specific peptidase 3 // 17p13 // 26168 | NM_015670 | −0.23 | 0.06 | 0.005 |
| 2358700 | MGC29891 | NM_144618 // MGC29891 // hypothetical protein MGC29891 // 1q21.2 // 126626 /// E | NM_144618 | −0.23 | 0.09 | 0.019 |
| 2755111 | KLKB1 | NM_000892 // KLKB1 // kallikrein B, plasma (Fletcher factor) 1 // 4q34-q35 // 38 | NM_000892 | −0.24 | 0.08 | 0.012 |
| 2568968 | UXS1 | NM_025076 // UXS1 // UDP-glucuronate decarboxylase 1 // 2q12.2 // 80146 /// BC00 | NM_025076 | −0.24 | 0.08 | 0.011 |
| 2748923 | GUCY1B3 | NM_000857 // GUCY1B3 // guanylate cyclase 1, soluble, beta 3 // 4q31.3-q33 // 29 | NM_000857 | −0.24 | 0.07 | 0.007 |
| 3816509 | GADD45B | NM_015675 // GADD45B // growth arrest and DNA-damage-inducible, beta // 19p13.3 | NM_015675 | −0.24 | 0.09 | 0.016 |
| 3376410 | SLC22A24 | BC034394 // SLC22A24 // solute carrier family 22, member 24 // 11q12.3 // 283238 | BC034394 | −0.24 | 0.07 | 0.007 |
| 3286393 | ZNF32 | NM_006973 // ZNF32 // zinc finger protein 32 // 10q22-q25 // 7580 /// NM_0010053 | NM_006973 | −0.24 | 0.08 | 0.010 |
| 2540157 | ODC1 | NM_002539 // ODC1 // ornithine decarboxylase 1 // 2p25 // 4953 /// ENST000002341 | NM_002539 | −0.24 | 0.09 | 0.020 |
| 2994835 | CHN2 | NM_004067 // CHN2 // chimerin (chimaerin) 2 // 7p15.3 // 1124 /// NM_001039936 / | NM_004067 | −0.24 | 0.09 | 0.017 |
| 3603199 | IDH3A | NM_005530 // IDH3A // isocitrate dehydrogenase 3 (NAD+) alpha // 15q25.1-q25.2 / | NM_005530 | −0.24 | 0.05 | 0.001 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3040454 | TWISTNB | NM_001002926 // TWISTNB // TWIST neighbor // 7p15.3 // 221830 /// ENST0000022256 | NM_001002926 | −0.24 | 0.09 | 0.017 |
| 2497301 | TMEM182 | NM_144632 // TMEM182 // transmembrane protein 182 // 2q12.1 // 130827 /// ENST00 | NM_144632 | −0.24 | 0.07 | 0.007 |
| 3766716 | TEX2 | NM_018469 // TEX2 // testis expressed 2 // 17q23.3 // 55852 /// ENST00000258991 | NM_018469 | −0.25 | 0.07 | 0.007 |
| 3458819 | CYP27B1 | NM_000785 // CYP27B1 // cytochrome P450, family 27, subfamily B, polypeptide 1 / | NM_000785 | −0.25 | 0.08 | 0.009 |
| 3368940 | ABTB2 | NM_145804 // ABTB2 // ankyrin repeat and BTB (POZ) domain containing 2 // 11p13 | NM_145804 | −0.25 | 0.08 | 0.010 |
| 3298924 | MMRN2 | NM_024756 // MMRN2 // multimerin 2 // 10q23.2 // 79812 /// ENST00000372027 // MM | NM_024756 | −0.25 | 0.07 | 0.006 |
| 3529951 | KIAA1305 | NM_025081 // KIAA1305 // KIAA1305 // 14q12 // 57523 /// BC008219 // KIAA1305 // | NM_025081 | −0.25 | 0.08 | 0.011 |
| 3006572 | AUTS2 | NM_015570 // AUTS2 // autism susceptibility candidate 2 // 7q11.22 // 26053 /// | NM_015570 | −0.25 | 0.09 | 0.017 |
| 3025500 | BPGM | NM_001724 // BPGM // 2,3-bisphosphoglycerate mutase // 7q31-q34 // 669 /// NM_19 | NM_001724 | −0.25 | 0.10 | 0.018 |
| 2494709 | CNNM4 | NM_020184 // CNNM4 // cyclin M4 // 2p12-p11.2 // 26504 /// ENST00000377075 // CN | NM_020184 | −0.26 | 0.09 | 0.016 |
| 3329983 | PTPRJ | NM_002843 // PTPRJ // protein tyrosine phosphatase, receptor type, J // 11p11.2 | NM_002843 | −0.26 | 0.08 | 0.010 |
| 2769346 | LNX1 | NM_032622 // LNX1 // ligand of numb-protein X 1 // 4q12 // 84708 /// ENST0000030 | NM_032622 | −0.26 | 0.09 | 0.015 |
| 3867195 | FAM83E | NM_017708 // FAM83E // family with sequence similarity 83, member E // 19q13.32- | NM_017708 | −0.26 | 0.09 | 0.013 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3790529 | GRP | NM_002091 // GRP // gastrin-releasing peptide // 18q21.1-q21.32 // 2922 /// NM_0 | NM_002091 | −0.26 | 0.05 | 0.001 |
| 3987029 | TMEM164 | NM_032227 // TMEM164 // transmembrane protein 164 // Xq22.3 // 84187 /// ENST000 | NM_032227 | −0.26 | 0.10 | 0.018 |
| 3526454 | GRTP1 | NM_024719 // GRTP1 // growth hormone regulated TBC protein 1 // 13q34 // 79774 / | NM_024719 | −0.26 | 0.09 | 0.015 |
| 2438344 | GPATCH4 | NM_182679 // GPATCH4 // G patch domain containing 4 // 1q22 // 54865 /// NM_0155 | NM_182679 | −0.26 | 0.07 | 0.006 |
| 3132927 | NKX6-3 | NM_152568 // NKX6-3 // NK6 homeobox 3 // 8p11.21 // 157848 /// ENST00000343444 / | NM_152568 | −0.27 | 0.09 | 0.014 |
| 2672376 | TESSP2 | NM_182702 // TESSP2 // testis serine protease 2 // 3p21.31 // 339906 /// ENST000 | NM_182702 | −0.27 | 0.09 | 0.013 |
| 2730347 | C4orf35 | NM_033122 // C4orf35 // chromosome 4 open reading frame 35 // 4q13.3 // 85438 // | NM_033122 | −0.27 | 0.10 | 0.019 |
| 3921068 | ETS2 | NM_005239 // ETS2 // v-ets erythroblastosis virus E26 oncogene homolog 2 (avian) | NM_005239 | −0.27 | 0.03 | 0.000 |
| 2532894 | DGKD | NM_152879 // DGKD // diacylglycerol kinase, delta 130 kDa // 2q37.1 // 8527 /// N | NM_152879 | −0.27 | 0.07 | 0.003 |
| 4018454 | AMOT | NM_133265 // AMOT // angiomotin // Xq23 // 154796 /// NM_001113490 // AMOT // an | NM_133265 | −0.27 | 0.09 | 0.012 |
| 3070507 | RNF148 | NM_198085 // RNF148 // ring finger protein 148 // 7q31.33 // 378925 /// BC029264 | NM_198085 | −0.27 | 0.10 | 0.017 |
| 3832256 | SPINT2 | NM_021102 // SPINT2 // serine peptidase inhibitor, Kunitz type, 2 // 19q13.1 // | NM_021102 | −0.27 | 0.10 | 0.017 |
| 3371225 | CHST1 | NM_003654 // CHST1 // carbohydrate (keratan sulfate Gal-6) sulfotransferase 1 // | NM_003654 | −0.27 | 0.07 | 0.005 |
| 3870494 | TFPT | NM_013342 // TFPT // TCF3 (E2A) fusion | NM_013342 | −0.27 | 0.09 | 0.010 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3863811 | PSG9 | partner (in childhood Leukemia) // 19q13 NM_002784 // PSG9 // pregnancy specific beta-1-glycoprotein 9 // 19q13.2 // 5678 | NM_002784 | −0.28 | 0.09 | 0.011 |
| 3160175 | VLDLR | NM_003383 // VLDLR // very low density lipoprotein receptor // 9p24 // 7436 /// | NM_003383 | −0.28 | 0.08 | 0.007 |
| 2794704 | ASB5 | NM_080874 // ASB5 // ankyrin repeat and SOCS box-containing 5 // 4q34.2 // 14045 | NM_080874 | −0.28 | 0.11 | 0.019 |
| 3908901 | KCNB1 | NM_004975 // KCNB1 // potassium voltage-gated channel, Shab-related subfamily, m | NM_004975 | −0.28 | 0.09 | 0.009 |
| 3390852 | FLJ45803 | NM_207429 // FLJ45803 // FLJ45803 protein // 11q23.1 // 399948 /// ENST000003554 | NM_207429 | −0.28 | 0.10 | 0.015 |
| 2600689 | EPHA4 | NM_004438 // EPHA4 // EPH receptor A4 // 2q36.1 // 2043 /// ENST00000281821 // E | NM_004438 | −0.29 | 0.07 | 0.003 |
| 3469597 | NUAK1 | NM_014840 // NUAK1 // NUAK family, SNF1-like kinase, 1 // 12q23.3 // 9891 /// EN | NM_014840 | −0.29 | 0.09 | 0.009 |
| 3607232 | ISG20L1 | NM_022767 // ISG20L1 // interferon stimulated exonuclease gene 20 kDa-like 1 // 1 | NM_022767 | −0.29 | 0.10 | 0.015 |
| 2358426 | ADAMTSL4 | AK023606 // ADAMTSL4 // ADAMTS-like 4 // 1q21.2 // 54507 | AK023606 | −0.29 | 0.11 | 0.016 |
| 3853609 | CYP4F2 | NM_001082 // CYP4F2 // cytochrome P450, family 4, subfamily F, polypeptide 2 // | NM_001082 | −0.29 | 0.11 | 0.016 |
| 2936971 | KIF25 | NM_030615 // KIF25 // kinesin family member 25 // 6q27 // 3834 /// NM_005355 // | NM_030615 | −0.30 | 0.09 | 0.008 |
| 2997272 | EEPD1 | NM_030636 // EEPD1 // endonuclease/exonuclease/phosphatase family domain contain | NM_030636 | −0.30 | 0.09 | 0.010 |
| 3961253 | RPS19BP1 | NM_194326 // RPS19BP1 // ribosomal protein S19 binding protein 1 // 22q13.1 // 9 | NM_194326 | −0.30 | 0.10 | 0.013 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3082373 | VIPR2 | NM_003382 // VIPR2 // vasoactive intestinal peptide receptor 2 // 7q36.3 // 7434 | NM_003382 | −0.30 | 0.10 | 0.011 |
| 2340961 | IL12RB2 | NM_001559 // IL12RB2 // interleukin 12 receptor, beta 2 // 1p31.3-p31.2 // 3595 | NM_001559 | −0.30 | 0.08 | 0.005 |
| 2736462 | BMPR1B | NM_001203 // BMPR1B // bone morphogenetic protein receptor, type IB // 4q22-q24 | NM_001203 | −0.30 | 0.08 | 0.004 |
| 3774504 | — | — | | −0.30 | 0.11 | 0.016 |
| 3395958 | OR8B4 | NM_001005196 // OR8B4 // olfactory receptor, family 8, subfamily B, member 4 // | NM_001005196 | −0.30 | 0.11 | 0.018 |
| 2806231 | BXDC2 | NM_018321 // BXDC2 // brix domain containing 2 // 5p13.2 // 55299 /// ENST000003 | NM_018321 | −0.31 | 0.10 | 0.013 |
| 2396858 | NPPB | NM_002521 // NPPB // natriuretic peptide precursor B // 1p36.2 // 4879 /// ENST0 | NM_002521 | −0.31 | 0.11 | 0.016 |
| 3233322 | C10orf18 | NM_017782 // C10orf18 // chromosome 10 open reading frame 18 // 10p15.1 // 54906 | NM_017782 | −0.31 | 0.06 | 0.001 |
| 2439101 | FCRL1 | NM_052938 // FCRL1 // Fc receptor-like 1 // 1q21-q22 // 115350 /// ENST000003681 | NM_052938 | −0.31 | 0.06 | 0.001 |
| 2413907 | DHCR24 | NM_014762 // DHCR24 // 24-dehydrocholesterol reductase // 1p33-p31.1 // 1718 /// | NM_014762 | −0.31 | 0.11 | 0.014 |
| 3231186 | C9orf37 | NM_032937 // C9orf37 // chromosome 9 open reading frame 37 // 9q34.3 // 85026 // | NM_032937 | −0.31 | 0.09 | 0.008 |
| 2669955 | XIRP1 | NM_194293 // XIRP1 // xin actin-binding repeat containing 1 // 3p22.2 // 165904 | NM_194293 | −0.32 | 0.11 | 0.013 |
| 3345222 | AMOTL1 | NM_130847 // AMOTL1 // angiomotin like 1 // 11q14.3 // 154810 /// ENST0000031782 | NM_130847 | −0.32 | 0.11 | 0.012 |
| 2573326 | FLJ14816 | BC112205 // FLJ14816 // hypothetical protein FLJ14816 // 2q14.2 // 84931 /// BC1 | BC112205 | −0.32 | 0.11 | 0.016 |
| 3349437 | UNQ2550 | AY358815 // UNQ2550 // SFVP2550 // 11q23.1 // 100130653 | AY358815 | −0.32 | 0.09 | 0.005 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3951117 | ACR | NM_001097 // ACR // acrosin // 22q13-qter\| 22q13.33 // 49 /// ENST00000216139 // | NM_001097 | −0.32 | 0.12 | 0.017 |
| 2489140 | | — | — | −0.32 | 0.07 | 0.002 |
| 2562115 | LSM3 | CR457185 // LSM3 // LSM3 homolog, U6 small nuclear RNA associated (S. cerevisiae | CR457185 | −0.32 | 0.11 | 0.011 |
| 3572975 | NGB | NM_021257 // NGB // neuroglobin // 14q24.3 // 58157 /// ENST00000298352 // NGB / | NM_021257 | −0.33 | 0.09 | 0.004 |
| 2439350 | OR6N1 | NM_001005185 // OR6N1 // olfactory receptor, family 6, subfamily N, member 1 // | NM_001005185 | −0.33 | 0.10 | 0.009 |
| 3590275 | CHAC1 | NM_024111 // CHAC1 // ChaC, cation transport regulator homolog 1 (E. coli) // 15 | NM_024111 | −0.33 | 0.12 | 0.014 |
| 2397898 | HSPB7 | NM_014424 // HSPB7 // heat shock 27 kDa protein family, member 7 (cardiovascular) | NM_014424 | −0.33 | 0.12 | 0.015 |
| 2364677 | PBX1 | NM_002585 // PBX1 // pre-B-cell leukemia homeobox 1 // 1q23 // 5087 /// ENST0000 | NM_002585 | −0.34 | 0.07 | 0.001 |
| 2474409 | DNAJC5G | NM_173650 // DNAJC5G // DnaJ (Hsp40) homolog, subfamily C, member 5 gamma // 2p2 | NM_173650 | −0.34 | 0.09 | 0.004 |
| 3581373 | | — | — | −0.34 | 0.12 | 0.014 |
| 3508330 | HSPH1 | NM_006644 // HSPH1 // heat shock 105 kDa/110 kDa protein 1 // 13q12.3 // 10808 /// | NM_006644 | −0.34 | 0.13 | 0.019 |
| 3751164 | DHRS13 | NM_144683 // DHRS13 // dehydrogenase/reductase (SDR family) member 13 // 17q11.2 | NM_144683 | −0.35 | 0.10 | 0.006 |
| 2908179 | VEGFA | NM_001025366 // VEGFA // vascular endothelial growth factor A // 6p12 // 7422 // | NM_001025366 | −0.35 | 0.13 | 0.016 |
| 3962448 | dJ222E13.2 | NR_002184 // dJ222E13.2 // similar to CGI-96 // 22q13.2 // 91695 //// BC073834 // | NR_002184 | −0.35 | 0.12 | 0.014 |
| 3747638 | LOC201164 | BC031263 // LOC201164 // similar to CG12314 gene product // 17p11.2 // 201164 // | BC031263 | −0.35 | 0.09 | 0.004 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2821981 | TMEM157 | NM_198507 // TMEM157 // transmembrane protein 157 // 5q21.1 // 345757 /// ENST00 | NM_198507 | −0.35 | 0.12 | 0.015 |
| 3123675 | PPP1R3B | NM_024607 // PPP1R3B // protein phosphatase 1, regulatory (inhibitor) subunit 3B | NM_024607 | −0.35 | 0.12 | 0.014 |
| 2656837 | ST6GAL1 | NM_173216 // ST6GAL1 // ST6 beta-galactosamide alpha-2,6-sialyltranferase 1 // 3 | NM_173216 | −0.35 | 0.13 | 0.016 |
| 3746574 | PMP22 | NM_000304 // PMP22 // peripheral myelin protein 22 // 17p12-p11.2 // 5376 /// NM | NM_000304 | −0.36 | 0.09 | 0.004 |
| 2771342 | EPHA5 | NM_004439 // EPHA5 // EPH receptor A5 // 4q13.1 // 2044 /// NM_182472 // EPHA5 / | NM_004439 | −0.36 | 0.09 | 0.003 |
| 2888674 | MXD3 | NM_031300 // MXD3 // MAX dimerization protein 3 // 5q35.3 // 83463 /// ENST00000 | NM_031300 | −0.36 | 0.12 | 0.012 |
| 2353477 | ATP1A1 | NM_000701 // ATP1A1 // ATPase, Na+/K+ transporting, alpha 1 polypeptide // 1p21 | NM_000701 | −0.36 | 0.11 | 0.007 |
| 3956984 | ZMAT5 | NM_019103 // ZMAT5 // zinc finger, matrin type 5 // 22cen-q12.3 // 55954 /// NM_ | NM_019103 | −0.36 | 0.11 | 0.009 |
| 2551651 | ATP6V1E2 | NM_080653 // ATP6V1E2 // ATPase, H+ transporting, lysosomal 31 kDa, V1 subunit E2 | NM_080653 | −0.37 | 0.13 | 0.017 |
| 3578069 | C14orf139 | BC008299 // C14orf139 // chromosome 14 open reading frame 139 // 14q32.13 // 796 | BC008299 | −0.37 | 0.13 | 0.016 |
| 2428501 | SLC16A1 | NM_003051 // SLC16A1 // solute carrier family 16, member 1 (monocarboxylic acid | NM_003051 | −0.37 | 0.14 | 0.018 |
| 3061621 | TFPI2 | NM_006528 // TFPI2 // tissue factor pathway inhibitor 2 // 7q22 // 7980 /// ENST | NM_006528 | −0.37 | 0.09 | 0.002 |
| 3705516 | LOC100131454 | AF229804 // LOC100131454 // similar to hCG1646635 // 17p13.3 // 100131454 /// EN | AF229804 | −0.38 | 0.11 | 0.008 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3306299 | XPNPEP1 | NM_020383 // XPNPEP1 // X-prolyl aminopeptidase (aminopeptidase P) 1, soluble // | NM_020383 | −0.38 | 0.14 | 0.018 |
| 2763550 | PPARGC1A | NM_013261 // PPARGC1A // peroxisome proliferator-activated receptor gamma, coact | NM_013261 | −0.38 | 0.13 | 0.012 |
| 2769063 | USP46 | NM_022832 // USP46 // ubiquitin specific peptidase 46 // 4q12 // 64854 /// ENST0 | NM_022832 | −0.38 | 0.13 | 0.013 |
| 3806459 | ST8SIA5 | NM_013305 // ST8SIA5 // ST8 alpha-N-acetyl-neuraminide alpha-2,8-sialyltransfera | NM_013305 | −0.38 | 0.10 | 0.004 |
| 3190151 | SLC25A25 | NM_001006641 // SLC25A25 // solute carrier family 25 (mitochondrial carrier; pho | NM_001006641 | −0.39 | 0.09 | 0.003 |
| 2489172 | MTHFD2 | NM_001040409 // MTHFD2 // methylenetetrahydrofolate dehydrogenase (NADP+ depende | NM_001040409 | −0.39 | 0.05 | 0.000 |
| 2952065 | PPIL1 | NM_016059 // PPIL1 // peptidylprolyl isomerase (cyclophilin)-like 1 // 6p21.1 // | NM_016059 | −0.39 | 0.10 | 0.005 |
| 3382015 | CHRDL2 | NM_015424 // CHRDL2 // chordin-like 2 // 11q14 // 25884 /// ENST00000263671 // C | NM_015424 | −0.39 | 0.10 | 0.003 |
| 2711139 | ATP13A5 | NM_198505 // ATP13A5 // ATPase type 13A5 // 3q29 // 344905 /// ENST00000342358 / | NM_198505 | −0.40 | 0.11 | 0.005 |
| 2633917 | RG9MTD1 | NM_017819 // RG9MTD1 // RNA (guanine-9-) methyltransferase domain containing 1 / | NM_017819 | −0.41 | 0.14 | 0.013 |
| 2974671 | C6orf192 | NM_052831 // C6orf192 // chromosome 6 open reading frame 192 // 6q22.3-q23.3 // | NM_052831 | −0.41 | 0.15 | 0.018 |
| 2982270 | FLJ27255 | ENST00000355047 // FLJ27255 // hypothetical LOC401281 // 6q25.3 // 401281 /// AK | ENST00000355047 | −0.41 | 0.12 | 0.007 |
| 2778273 | PGDS | NM_014485 // PGDS // prostaglandin D2 synthase, hematopoietic // 4q22.3 // 27306 | NM_014485 | −0.41 | 0.08 | 0.001 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3005332 | RCP9 | NM_014478 // RCP9 // calcitonin gene-related peptide-receptor component protein | NM_014478 | −0.41 | 0.14 | 0.013 |
| 2650393 | PPM1L | NM_139245 // PPM1L // protein phosphatase 1 (formerly 2C)-like // 3q26.1 // 1517 | NM_139245 | −0.42 | 0.12 | 0.006 |
| 3463056 | CSRP2 | NM_001321 // CSRP2 // cysteine and glycine-rich protein 2 // 12q21.1 // 1466 /// | NM_001321 | −0.42 | 0.11 | 0.005 |
| 2459405 | — | — | — | −0.43 | 0.10 | 0.003 |
| 2570238 | NPHP1 | NM_000272 // NPHP1 // nephronophthisis 1 (juvenile) // 2q13 // 4867 /// NM_20718 | NM_000272 | −0.43 | 0.06 | 0.000 |
| 2840616 | NPM1 | NM_002520 // NPM1 // nucleophosmin (nucleolar phosphoprotein B23, numatrin) // 5 | NM_002520 | −0.43 | 0.14 | 0.010 |
| 3601051 | NEO1 | NM_002499 // NEO1 // neogenin homolog 1 (chicken) // 15q22.3-q23 // 4756 /// ENS | NM_002499 | −0.43 | 0.09 | 0.002 |
| 3936515 | TUBA8 | NM_018943 // TUBA8 // tubulin, alpha 8 // 22q11.1 // 51807 /// ENST00000330423 / | NM_018943 | −0.43 | 0.10 | 0.002 |
| 2725013 | UCHL1 | NM_004181 // UCHL1 // ubiquitin carboxyl-terminal esterase L1 (ubiquitin thioles | NM_004181 | −0.44 | 0.11 | 0.004 |
| 2380590 | TGFB2 | NM_003238 // TGFB2 // transforming growth factor, beta 2 // 1q41 // 7042 /// ENS | NM_003238 | −0.44 | 0.16 | 0.017 |
| 2496382 | NPAS2 | NM_002518 // NPAS2 // neuronal PAS domain protein 2 // 2q11.2 // 4862 //// ENST00 | NM_002518 | −0.46 | 0.10 | 0.002 |
| 3841574 | LILRB1 | NM_006669 // LILRB1 // leukocyte immunoglobulin-like receptor, subfamily B (with | NM_006669 | −0.46 | 0.16 | 0.015 |
| 3726960 | NME2 | NM_001018137 // NME2 // non-metastatic cells 2, protein (NM23B) expressed in // | NM_001018137 | −0.47 | 0.16 | 0.013 |
| 2649367 | PTX3 | NM_002852 // PTX3 // pentraxin-related gene, rapidly induced by IL-1 beta // 3q2 | NM_002852 | −0.47 | 0.11 | 0.002 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 2909483 | GPR111 | NM_153839 // GPR111 // G protein-coupled receptor 111 // 6p12.3 // 222611 /// EN | NM_153839 | −0.47 | 0.13 | 0.006 |
| 2881950 | SLC36A2 | NM_181776 // SLC36A2 // solute carrier family 36 (proton/amino acid symporter), | NM_181776 | −0.48 | 0.12 | 0.004 |
| 3441190 | FGF6 | NM_020996 // FGF6 // fibroblast growth factor 6 // 12p13 // 2251 /// ENST0000022 | NM_020996 | −0.48 | 0.12 | 0.004 |
| 3028911 | C7orf34 | NM_178829 // C7orf34 // chromosome 7 open reading frame 34 // 7q34 // 135927 /// | NM_178829 | −0.49 | 0.18 | 0.019 |
| 2830861 | EGR1 | NM_001964 // EGR1 // early growth response 1 // 5q31.1 // 1958 /// ENST000002399 | NM_001964 | −0.49 | 0.19 | 0.020 |
| 3323891 | GAS2 | NM_177553 // GAS2 // growth arrest-specific 2 // 11p14.3-p15.2 // 2620 /// NM_00 | NM_177553 | −0.49 | 0.16 | 0.011 |
| 2497252 | SLC9A2 | NM_003048 // SLC9A2 // solute carrier family 9 (sodium/hydrogen exchanger), memb | NM_003048 | −0.50 | 0.11 | 0.002 |
| 3018484 | GPR22 | NM_005295 // GPR22 // G protein-coupled receptor 22 // 7q22-q31.1 // 2845 /// EN | NM_005295 | −0.51 | 0.15 | 0.008 |
| 2712632 | TFRC | NM_003234 // TFRC // transferrin receptor (p90, CD71) // 3q29 // 7037 /// ENST00 | NM_003234 | −0.51 | 0.12 | 0.003 |
| 3214451 | NFIL3 | NM_005384 // NFIL3 // nuclear factor, interleukin 3 regulated // 9q22 // 4783 // | NM_005384 | −0.53 | 0.14 | 0.004 |
| 2435981 | S100A12 | NM_005621 // S100A12 // S100 calcium binding protein A12 // 1q21 // 6283 /// ENS | NM_005621 | −0.54 | 0.19 | 0.014 |
| 3320675 | RIG | U32331 // RIG // regulated in glioma // 11p15.1 // 10530 | U32331 | −0.54 | 0.10 | 0.001 |
| 3290746 | SLC16A9 | NM_194298 // SLC16A9 // solute carrier family 16, member 9 (monocarboxylic acid | NM_194298 | −0.54 | 0.15 | 0.006 |
| 3055703 | NSUN5C | NM_032158 // NSUN5C // NOL1/NOP2/Sun domain family, member 5C // 7q11.23 // 2602 | NM_032158 | −0.57 | 0.17 | 0.008 |

TABLE X1-continued

Fasting-responsive human mRNAs.

| Affymetrix ID | mRNA | Gene Assignment | Accession No. | (Fasting-Fed) | Change SEM | P |
|---|---|---|---|---|---|---|
| 3265494 | TRUB1 | NM_139169 // TRUB1 // TruB pseudouridine (psi) synthase homolog 1 (E. coli) // 1 | NM_139169 | −0.57 | 0.17 | 0.008 |
| 3374213 | OR1S2 | NM_001004459 // OR1S2 // olfactory receptor, family 1, subfamily S, member 2 // | NM_001004459 | −0.58 | 0.20 | 0.013 |
| 3318253 | OR51L1 | NM_001004755 // OR51L1 // olfactory receptor, family 51, subfamily L, member 1 / | NM_001004755 | −0.59 | 0.18 | 0.009 |
| 3294280 | DNAJC9 | NM_015190 // DNAJC9 // DnaJ (Hsp40) homolog, subfamily C, member 9 // 10q22.2 // | NM_015190 | −0.59 | 0.22 | 0.018 |
| 2899095 | HIST1H4A | NM_003538 // HIST1H4A // histone cluster 1, H4a // 6p21.3 // 8359 /// ENST000003 | NM_003538 | −0.60 | 0.16 | 0.005 |
| 2378068 | G0S2 | NM_015714 // G0S2 // G0/G1switch 2 // 1q32.2-q41 // 50486 /// ENST00000367029 // | NM_015714 | −0.63 | 0.22 | 0.016 |
| 3737677 | LOC100129503 | AF218021 // LOC100129503 // hypothetical protein LOC100129503 // 17q25.3 // 1001 | AF218021 | −0.64 | 0.19 | 0.007 |
| 3300115 | PPP1R3C | NM_005398 // PPP1R3C // protein phosphatase 1, regulatory (inhibitor) subunit 3C | NM_005398 | −0.69 | 0.26 | 0.020 |
| 3279058 | ACBD7 | NM_001039844 // ACBD7 // acyl-Coenzyme A binding domain containing 7 // 10p13 // | NM_001039844 | −0.69 | 0.13 | 0.001 |
| 4031156 | RPS4Y2 | NM_001039567 // RPS4Y2 // ribosomal protein S4, Y-linked 2 // Yq11.223 // 140032 | NM_001039567 | −0.71 | 0.17 | 0.003 |
| 2979246 | RAET1L | NM_130900 // RAET1L // retinoic acid early transcript 1L // 6q25.1 // 154064 /// | NM_130900 | −0.75 | 0.26 | 0.013 |
| 3321150 | ARNTL | NM_001178 // ARNTL // aryl hydrocarbon receptor nuclear translocator-like // 11p | NM_001178 | −0.80 | 0.20 | 0.004 |
| 3862873 | CYP2A6 | NM_000762 // CYP2A6 // cytochrome P450, family 2, subfamily A, polypeptide 6 // | NM_000762 | −1.12 | 0.34 | 0.009 |

4. Identification of Ursolic Acid as an Inhibitor of Fasting-Induced Muscle Atrophy.

The Connectivity Map describes the effects of >1300 bioactive small molecules on global mRNA expression in several cultured cell lines, and contains search algorithms that permit comparisons between compound-specific mRNA expression signatures and mRNA expression signatures of interest (Lamb J, et al. (2006) *Science* (*New York, N.Y.* 313(5795): 1929-1935). It was hypothesized herein that querying the Connectivity Map with the mRNA expression signature of fasting (muscle atrophy signature-1) would identify inhibitors of atrophy-associated gene expression and thus, potential inhibitors of muscle atrophy. It was also reasoned herein that increasing the specificity of the query would enhance the output. To this end, as described herein, an evolutionarily conserved mRNA expression signature of fasting was discovered by comparing the effect of fasting on human skeletal muscle to the effect of a 24 h fast on mouse skeletal muscle. The mouse studies were described previously (Ebert S M, et al. (2010) *Molecular endocrinology* 24(4):790-799). Altogether, 35 mRNAs that were increased by fasting and 40 mRNAs that were decreased by fasting were identified in both human and mouse skeletal muscle (Table X2; the data in column labeled "Change" show mean changes in $\log_2$ hybridization signals between fasting and fed states for the species indicated, [Mean $\log_2$ mRNA levels for fasted] minus [Mean $\log_2$ mRNA levels in unfasted]; P-values were determined with paired t-tests). The data shown in Table X2 includes all mRNAs whose levels were increased by fasting in human muscle ($P \le 0.02$) and in mouse muscle ($P \le 0.05$), and all mRNAs whose levels were decreased by fasting in human muscle ($P \le 0.02$) and in mouse muscle ($P \le 0.05$). Of the mRNAs shown in Table X2, 63 mRNAs were represented on the HG-U133A arrays used in the Connectivity Map (FIG. 6A). These mRNAs (31 increased by fasting and 32 decreased by fasting) were used to query the Connectivity Map for candidate small molecule inhibitors of muscle atrophy.

TABLE X2

Fasting-regulated mRNAs common to human and mouse skeletal muscle.

| mRNA | Protein | Human Mean Log2 Change (Fasting-Fed) | P | Mouse Mean Log2 Change (Fasting-Fed) | P |
|---|---|---|---|---|---|
| PDK4 | pyruvate dehydrogenase kinase, isozyme 4 | 2.15 | 0.000 | 1.91 | 0.000 |
| TXNIP | thioredoxin interacting protein | 0.85 | 0.004 | 0.60 | 0.038 |
| FBXO32 | F-box protein 32 | 0.82 | 0.002 | 2.13 | 0.000 |
| SLC38A2 | solute carrier family 38, member 2 | 0.62 | 0.001 | 0.33 | 0.036 |
| UCP3 | uncoupling protein 3 (mitochondrial, proton carrier) | 0.59 | 0.000 | 1.02 | 0.001 |
| ZFAND5 | zinc finger, AN1-type domain 5 | 0.51 | 0.005 | 0.57 | 0.001 |
| HMOX1 | heme oxygenase (decycling) 1 | 0.46 | 0.006 | 0.17 | 0.035 |
| SESN1 | sestrin 1 | 0.46 | 0.004 | 1.51 | 0.001 |
| GABARAPL1 | GABA(A) receptor-associated protein like 1 | 0.39 | 0.004 | 1.18 | 0.000 |
| CAT | catalase | 0.39 | 0.003 | 0.85 | 0.001 |
| CITED2 | Cbp/p300-interacting transactivator, with Glu/Asp-rich carboxy-terminal domain | 0.37 | 0.005 | 0.29 | 0.010 |
| ABCA1 | ATP-binding cassette, sub-family A (ABC1), member 1 | 0.37 | 0.016 | 0.26 | 0.018 |
| FBXL20 | F-box and leucine-rich repeat protein 20 | 0.35 | 0.002 | 0.46 | 0.001 |
| XPO4 | exportin 4 | 0.31 | 0.009 | 0.22 | 0.022 |
| HERPUD1 | homocysteine-inducible, endoplasmic reticulum stress-inducible, ubiquitin-like domain 1 | 0.29 | 0.003 | 0.27 | 0.029 |
| ACOX1 | acyl-Coenzyme A oxidase 1, palmitoyl | 0.29 | 0.013 | 0.53 | 0.006 |
| NOX4 | NADPH oxidase 4 | 0.28 | 0.002 | 0.41 | 0.018 |
| UBE4A | ubiquitination factor E4A (UFD2 homolog, yeast) | 0.27 | 0.004 | 1.08 | 0.010 |
| INSR | insulin receptor | 0.24 | 0.014 | 0.58 | 0.003 |
| IGF1R | insulin-like growth factor 1 receptor | 0.23 | 0.013 | 0.40 | 0.001 |
| PANK1 | pantothenate kinase 1 | 0.21 | 0.007 | 0.78 | 0.000 |
| NBR1 | neighbor of BRCA1 gene 1 | 0.21 | 0.017 | 0.39 | 0.009 |
| RORA | RAR-related orphan receptor A | 0.21 | 0.006 | 0.39 | 0.006 |
| TMEM71 | transmembrane protein 71 | 0.21 | 0.009 | 0.40 | 0.008 |

TABLE X2-continued

Fasting-regulated mRNAs common to human and mouse skeletal muscle.

| mRNA | Protein | Human Mean Log2 Change (Fasting-Fed) | P | Mouse Mean Log2 Change (Fasting-Fed) | P |
|---|---|---|---|---|---|
| CPT1A | carnitine palmitoyltransferase 1A (liver) | 0.21 | 0.001 | 0.21 | 0.020 |
| UCP2 | uncoupling protein 2 (mitochondrial, proton carrier) | 0.20 | 0.005 | 0.33 | 0.024 |
| TULP3 | tubby like protein 3 | 0.19 | 0.008 | 0.22 | 0.008 |
| MED13L | mediator complex subunit 13-like | 0.18 | 0.000 | 0.23 | 0.011 |
| CALCOCO1 | calcium binding and coiled coil domain 1 | 0.16 | 0.010 | 0.31 | 0.028 |
| MYO5A | myosin VA (heavy chain 12, myoxin) | 0.14 | 0.006 | 0.36 | 0.012 |
| PPAP2B | phosphatidic acid phosphatase type 2B | 0.13 | 0.007 | 0.09 | 0.029 |
| SRRM2 | serine/arginine repetitive matrix 2 | 0.13 | 0.007 | 0.24 | 0.040 |
| ADPGK | ADP-dependent glucokinase | 0.13 | 0.007 | 0.16 | 0.009 |
| SUPT6H | suppressor of Ty 6 homolog (S. cerevisiae) | 0.11 | 0.005 | 0.26 | 0.036 |
| SFRS8 | splicing factor, arginine/serine-rich 8 | 0.08 | 0.016 | 0.13 | 0.011 |
| NFYA | nuclear transcription factor Y, alpha | −0.07 | 0.011 | −0.31 | 0.045 |
| MRPS15 | mitochondrial ribosomal protein S15 | −0.11 | 0.003 | −0.25 | 0.001 |
| PDE7B | phosphodiesterase 7B | −0.12 | 0.013 | −0.51 | 0.011 |
| WDR1 | WD repeat domain 1 | −0.14 | 0.019 | −0.21 | 0.047 |
| ACACA | acetyl-Coenzyme A carboxylase alpha | −0.15 | 0.010 | −0.22 | 0.041 |
| AXIN2 | axin 2 (conductin, axil) | −0.15 | 0.013 | −0.12 | 0.046 |
| CASQ1 | calsequestrin 1 (fast-twitch, skeletal muscle) | −0.16 | 0.015 | −0.26 | 0.015 |
| ZNF280B | zinc finger protein 280B | −0.16 | 0.005 | −0.34 | 0.046 |
| JTB | jumping translocation breakpoint | −0.16 | 0.014 | −0.42 | 0.030 |
| CACNB1 | calcium channel, voltage-dependent, beta 1 subunit | −0.17 | 0.013 | −0.43 | 0.003 |
| ALG2 | asparagine-linked glycosylation 2 homolog | −0.17 | 0.011 | −0.39 | 0.019 |
| TSPAN13 | tetraspanin 13 | −0.18 | 0.006 | −0.30 | 0.028 |
| P4HA2 | procollagen-proline, 2-oxoglutarate 4-dioxygenase, alpha II polypeptide | −0.18 | 0.007 | −0.12 | 0.012 |
| TTLL1 | tubulin tyrosine ligase-like family, member 1 | −0.18 | 0.001 | −0.29 | 0.043 |
| SUV39H2 | suppressor of variegation 3-9 homolog 2 (Drosophila) | −0.20 | 0.011 | −0.26 | 0.014 |
| SLC4A4 | solute carrier family 4, sodium bicarbonate cotransporter, member 4 | −0.20 | 0.007 | −0.69 | 0.003 |
| DNMT3A | DNA (cytosine-5-)-methyltransferase 3 alpha | −0.20 | 0.007 | −0.48 | 0.000 |
| FEZ2 | fasciculation and elongation protein zeta 2 (zygin II) | −0.21 | 0.000 | −0.50 | 0.019 |
| MTSS1 | metastasis suppressor 1 | −0.21 | 0.009 | −0.22 | 0.033 |
| TMTC4 | transmembrane and tetratricopeptide repeat containing 4 | −0.22 | 0.010 | −0.17 | 0.035 |
| PPM1J | protein phosphatase 1J (PP2C domain containing) | −0.23 | 0.003 | −0.30 | 0.012 |
| ARHGAP20 | Rho GTPase activating protein 20 | −0.23 | 0.003 | −0.22 | 0.013 |
| ABTB2 | ankyrin repeat and BTB (POZ) domain containing 2 | −0.25 | 0.010 | −0.18 | 0.005 |
| CNNM4 | cyclin M4 | −0.26 | 0.016 | −0.27 | 0.005 |
| GRTP1 | growth hormone regulated TBC protein 1 | −0.26 | 0.015 | −0.54 | 0.002 |

TABLE X2-continued

Fasting-regulated mRNAs common to human and mouse skeletal muscle.

| mRNA | Protein | Human Mean Log2 Change (Fasting-Fed) | P | Mouse Mean Log2 Change (Fasting-Fed) | P |
| --- | --- | --- | --- | --- | --- |
| RNF148 | ring finger protein 148 | −0.27 | 0.017 | −0.35 | 0.014 |
| SPINT2 | serine peptidase inhibitor, Kunitz type, 2 | −0.27 | 0.017 | −0.23 | 0.026 |
| PBX1 | pre-B-cell leukemia homeobox 1 | −0.34 | 0.001 | −0.22 | 0.000 |
| HSPH1 | heat shock 105 kDa/110 kDa protein 1 | −0.34 | 0.019 | −0.20 | 0.043 |
| VEGFA | vascular endothelial growth factor A | −0.35 | 0.016 | −0.26 | 0.002 |
| PMP22 | peripheral myelin protein 22 | −0.36 | 0.004 | −0.13 | 0.012 |
| PPARGC1A | peroxisome proliferative activated receptor, gamma, coactivator 1 alpha | −0.38 | 0.012 | −0.39 | 0.030 |
| ST8SIA5 | ST8 alpha-N-acetyl-neuraminide alpha-2,8-sialyltransferase 5 | −0.38 | 0.004 | −0.48 | 0.011 |
| PPIL1 | peptidylprolyl isomerase (cyclophilin)-like 1 | −0.39 | 0.005 | −0.52 | 0.016 |
| PPM1L | protein phosphatase 1 (formerly 2C)-like | −0.42 | 0.006 | −0.46 | 0.000 |
| NEO1 | neogenin homolog 1 (chicken) | −0.43 | 0.002 | −0.31 | 0.037 |
| TGFB2 | transforming growth factor, beta 2 | −0.44 | 0.017 | −0.30 | 0.003 |
| PTX3 | pentraxin-related gene, rapidly induced by IL-1 beta | −0.47 | 0.002 | −0.48 | 0.000 |
| GAS2 | growth arrest-specific 2 | −0.49 | 0.011 | −0.23 | 0.044 |
| TFRC | transferrin receptor (p90, CD71) | −0.51 | 0.003 | −1.37 | 0.011 |

Figure 6B:
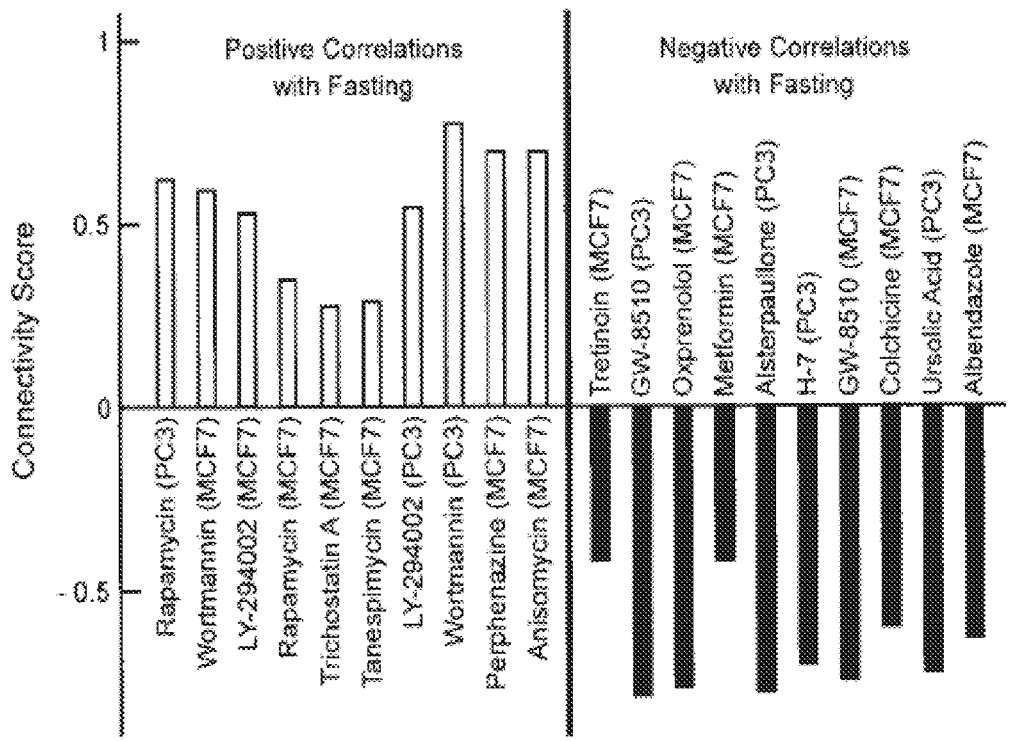
Figure 6C:
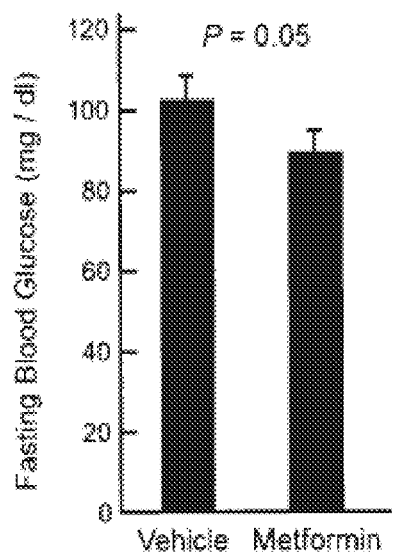
Figure 6D:
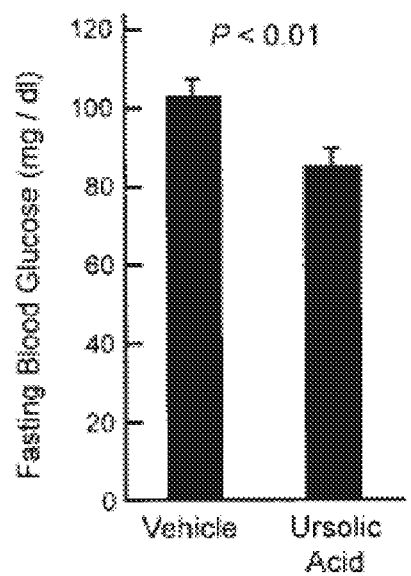
Figure 6E:
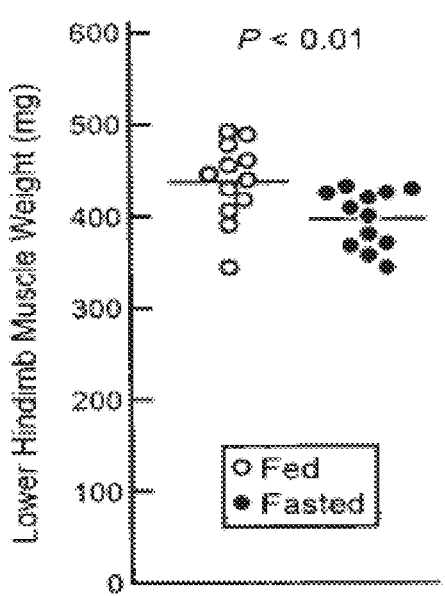
Figures 6F, 6G:
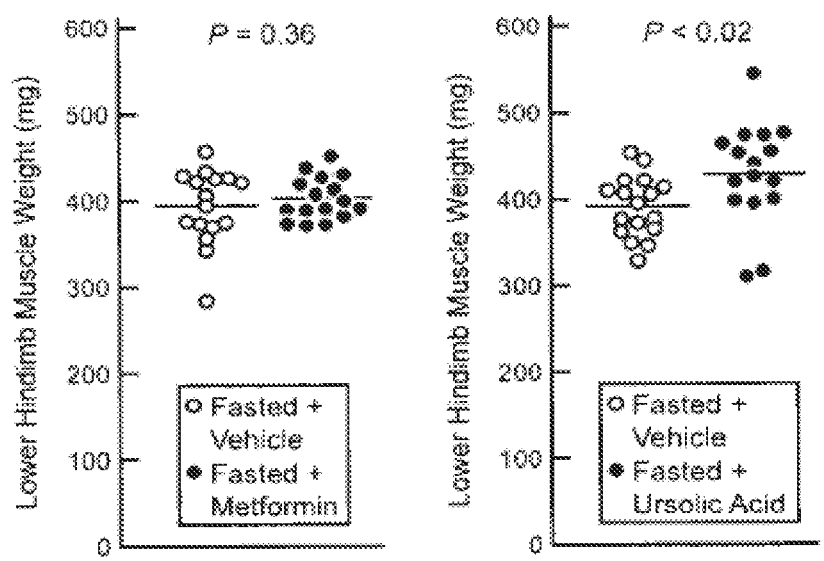

The left side of FIG. 6B shows the 10 Connectivity Map instances (or data sets) with the most significant positive correlations (P<0.004) to the effect of fasting in skeletal muscle. The connectivity score, represented on the y-axis, is a measure of the strength of the correlation (Lamb J, et al. (2006) Science (New York, N.Y. 313(5795):1929-1935); the compound and cell-line is shown below the bar representing the Connectivity Score. Of these, 6 involved wortmannin or LY-294002 (inhibitors of phosphoinositide 3-kinase (PI3K)) or rapamycin (an inhibitor of the mammalian target of rapamycin complex 1 (mTORC1)). Since PI3K and mTORC1 mediate effects of insulin and IGF-I, and since insulin/IGF-I signaling inhibits muscle atrophy and atrophy-associated changes in skeletal muscle mRNA expression (Bodine S C, et al. (2001) Nat Cell Biol 3(11):1014-1019; Sandri M, et al. (2004) Cell 117(3):399-412), these results lent confidence that the Connectivity Map might be used to identify potential inhibitors of muscle atrophy. The right side of FIG. 6B shows the 10 Connectivity Map instances with the most significant negative correlations (P<0.004) to the effect of fasting in skeletal muscle. These compounds, whose effects on cultured cell lines were opposite to the effect of fasting on muscle, included metformin (an insulin-sensitizing agent widely used to treat type 2 diabetes), as well as ursolic acid. Further experiments focused on metformin and ursolic acid. To test the hypothesis that metformin and ursolic acid might reduce fasting-induced muscle atrophy, each compound was administered, or vehicle alone, via i.p. injection to C57BL/6 mice. The mice were then fasted, and after 12 hours of fasting, the mice received a second dose of the compound or vehicle. After 24 hours of fasting, the blood glucose was measured and muscles were harvested. The data shown in FIGS. 6C-6H are means±SEM from ≤16 mice per condition. Both metformin (250 mg/kg) and ursolic acid (200 mg/kg) significantly reduced fasting blood glucose (FIGS. 6C and 6D). The effects of metformin and ursolic acid on fasting-induced muscle atrophy were also examined, i.e. the effect of 24 h fast (relative to ad lib feeding) on wet weight of lower hindlimb skeletal muscle (bilateral tibialis anterior ("TA" muscle), gastrocnemius, and soleus; see FIGS. 6E-6G). In the absence of metformin and ursolic acid, fasting reduced muscle weight by 9% (FIG. 6E). Although metformin did not alter muscle weight in fasted mice (FIG. 6F), ursolic acid increased it by 7±2% (FIG. 6G). Moreover, consistent with the predicted inhibitory effect on fasting-induced gene expression described herein, ursolic acid reduced fasting levels of atrogin-1 and MuRF1 mRNA levels in the TA muscles of fasted mice (FIG. 6H; the data shown are normalized to the levels in vehicle-treated mice, which were set at 1). In FIGS. 6E-6H, each data point represents one mouse and the horizontal bars denote the means. In FIGS. 6C-6H, P-values were determined using unpaired t-tests. Thus, ursolic acid, but not metformin, decreased fasting-induced muscle atrophy.

5. Ursolic Acid Reduces Denervation-Induced Muscle Atrophy.

The Connectivity Map was queried with a second mRNA expression signature, muscle atrophy signature-2 (described above), to determine if this muscle atrophy signature would also correlate with ursolic acid, among other compounds. As described above, muscle atrophy signature-2 was an mRNA expression signature identified as described herein for human skeletal muscle mRNAs that were induced or repressed by fasting and also by spinal cord injury ("SCI"). The studies of the effects of SCI on human skeletal muscle gene expression were described previously (Adams C M, et al. (2011) *Muscle Nerve*. 43(1):65-75). Using this approach with the muscle atrophy expression signatures described herein, there were 18 human mRNAs that were increased by fasting and SCI, and 17 human mRNAs that were decreased by fasting and SCI, and are shown in Table X3 ("Change" represents mean changes in $\log_2$ hybridization signals for pairs as indicated, e.g. fasting and fed states for column labeled "(Fasting-Fed)" or untrained and trained for the column labeled "(Untrained-Trained)"). The data in Table X3 include all mRNAs whose levels were increased by fasting (P≤0.02) and by SCI (P≤0.05), and all mRNAs whose levels were decreased by fasting (P≤0.02) and by SCI (P≤0.05). P-values in Table X3 were determined with paired t-tests.

TABLE X3

Human skeletal muscle mRNAs induced or repressed by fasting and SCI.

| | | EFFECT OF FASTING | | EFFECT OF SCI | |
|---|---|---|---|---|---|
| mRNA | Protein | Change (Fasting-Fed) | P | Change (Untrained-Trained) | P |
| OR1D4 | olfactory receptor, family 1, subfamily D, member 4 | 0.50 | 0.019 | 0.65 | 0.030 |
| RHOBTB1 | Rho-related BTB domain containing 1 | 0.48 | 0.001 | 0.71 | 0.032 |
| TSPAN8 | tetraspanin 8 | 0.39 | 0.015 | 1.79 | 0.023 |
| FLJ33996 | hypothetical protein FLJ33996 | 0.39 | 0.019 | 0.68 | 0.020 |
| NUPR1 | nuclear protein 1 | 0.35 | 0.007 | 0.65 | 0.030 |
| IRS2 | insulin receptor substrate 2 | 0.34 | 0.004 | 0.21 | 0.035 |
| NPC2 | Niemann-Pick disease, type C2 | 0.30 | 0.011 | 0.39 | 0.042 |
| KLF11 | Kruppel-like factor 11 | 0.29 | 0.011 | 0.22 | 0.034 |
| ZNF682 | zinc finger protein 682 | 0.28 | 0.017 | 0.72 | 0.013 |
| NOX4 | NADPH oxidase 4 | 0.28 | 0.002 | 0.56 | 0.007 |
| PLXDC2 | plexin domain containing 2 | 0.26 | 0.013 | 0.38 | 0.022 |
| CTDSP2 | CTD small phosphatase 2 | 0.25 | 0.003 | 0.34 | 0.021 |
| CAV3 | caveolin 3 | 0.24 | 0.007 | 0.56 | 0.020 |
| IGF1R | insulin-like growth factor 1 receptor | 0.23 | 0.013 | 0.63 | 0.040 |
| FLJ14154 | hypothetical protein FLJ14154 | 0.22 | 0.005 | 0.30 | 0.021 |
| CUGBP2 | CUG triplet repeat, RNA binding protein 2 | 0.21 | 0.004 | 0.14 | 0.034 |
| MLL | myeloid/lymphoid or mixed-lineage leukemia | 0.14 | 0.016 | 0.30 | 0.040 |
| SUPT6H | suppressor of Ty 6 homolog | 0.11 | 0.005 | 0.19 | 0.024 |
| MRPS15 | mitochondrial ribosomal protein S15 | −0.11 | 0.003 | −0.33 | 0.001 |
| RFXDC2 | regulatory factor X domain containing 2 | −0.12 | 0.012 | −0.10 | 0.037 |
| PDE7B | phosphodiesterase 7B | −0.12 | 0.013 | −0.39 | 0.011 |
| PFDN6 | prefoldin subunit 6 | −0.14 | 0.014 | −0.42 | 0.021 |
| ZNF280B | zinc finger protein 280B | −0.16 | 0.005 | −0.30 | 0.028 |
| TSPAN13 | tetraspanin 13 | −0.18 | 0.006 | −0.56 | 0.023 |
| TTLL1 | tubulin tyrosine ligase-like family, member 1 | −0.18 | 0.001 | −0.37 | 0.020 |
| CMAS | cytidine monophosphate N-acetylneuraminic acid synthetase | −0.21 | 0.000 | −0.22 | 0.025 |
| C8orf32 | chromosome 8 open reading frame 32 | −0.23 | 0.016 | −0.11 | 0.049 |
| GUCY1B3 | guanylate cyclase 1, soluble, beta 3 | −0.24 | 0.007 | −0.24 | 0.008 |
| ZNF32 | zinc finger protein 32 | −0.24 | 0.010 | −0.21 | 0.030 |
| VLDLR | very low density lipoprotein receptor | −0.28 | 0.007 | −0.16 | 0.015 |
| HSPB7 | heat shock 27 kDa protein family, member 7 (cardiovascular) | −0.33 | 0.015 | −0.77 | 0.032 |
| VEGFA | vascular endothelial growth factor A | −0.35 | 0.016 | −0.43 | 0.020 |
| SLC16A1 | solute carrier family 16, member 1 | −0.37 | 0.018 | −0.94 | 0.015 |
| PPARGC1A | peroxisome proliferative activated receptor, gamma, coactivator 1 alpha | −0.38 | 0.012 | −0.74 | 0.001 |
| C6orf192 | chromosome 6 open reading frame 192 | −0.41 | 0.018 | −0.39 | 0.042 |

Figures 7A, 7B:
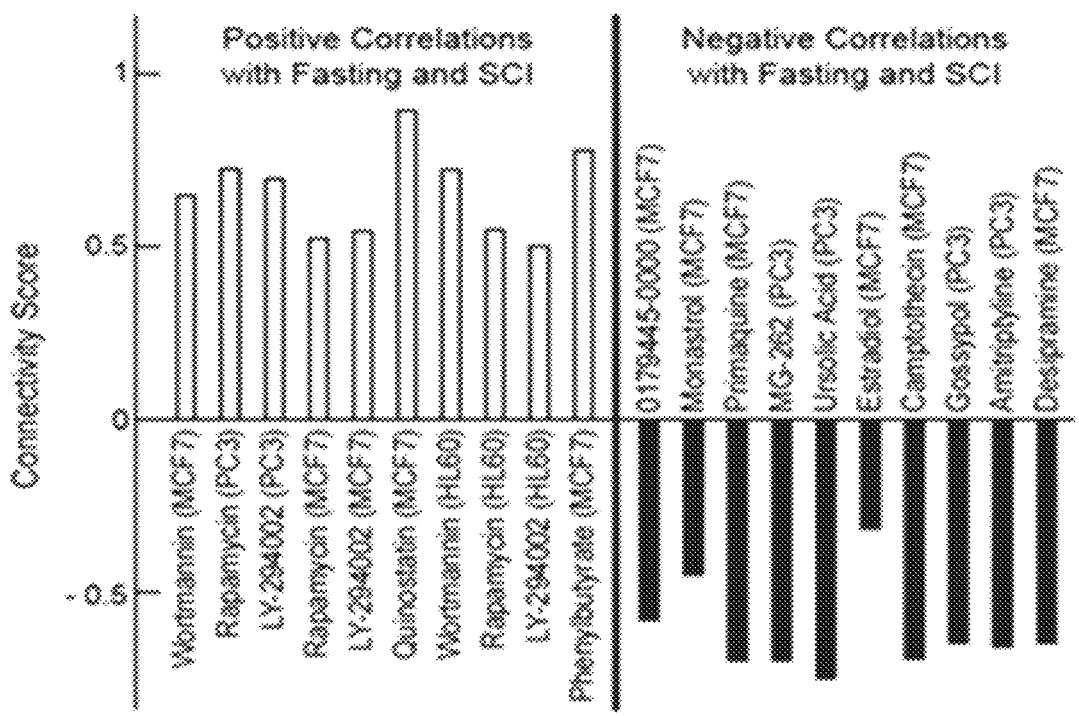
FIGS. 7A-7E show representative data on the identification of ursolic acid as an inhibitor of denervation-induced muscle atrophy.

Of the mRNAs listed in Table X3, 29 were represented on the HG-U133A arrays used in the Connectivity Map (FIG. 7A), but only 10 were common to the 63 mRNAs used in the first Connectivity Map query described above for muscle atrophy signature-1 (IGF-IR, NOX4, SUPT6H, MRPS15, PDE7B, PGC-1a, TSPAN13, TTLL1, VEGFA and ZNF280B). The mRNAs listed in FIG. 7A represent human muscle atrophy signature-2: mRNAs altered by both fasting and SCI in human muscle. These mRNAs, as described above, were used to query the Connectivity Map. Inclusion criteria were: $P \leq 0.02$ in fasted human muscle (by t-test), $P \leq 0.05$ in untrained, paralyzed muscle (by t-test), and the existence of complimentary probes on HG-U133A arrays. Connectivity Map instances with the most significant positive and negative correlations to the effect of fasting and SCI in human muscle. $P<0.005$ for all compounds are shown in FIG. 7B. The results partially overlapped with the results of the first search: both search strategies identified LY-294002, wortmannin and rapamycin as predicted mimics of atrophy-inducing stress, and ursolic acid (but not metformin) as a predicted inhibitor (FIG. 7B).

Figure 7C:
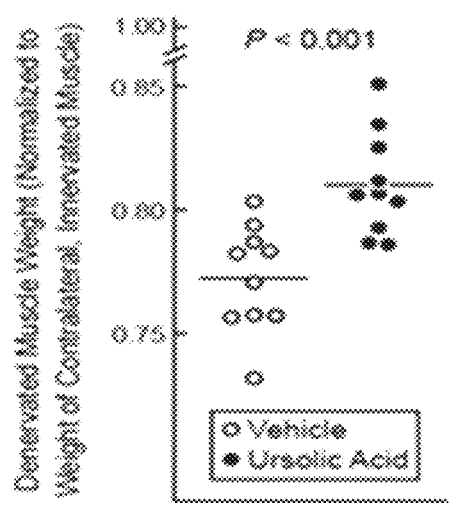
Figure 7D:
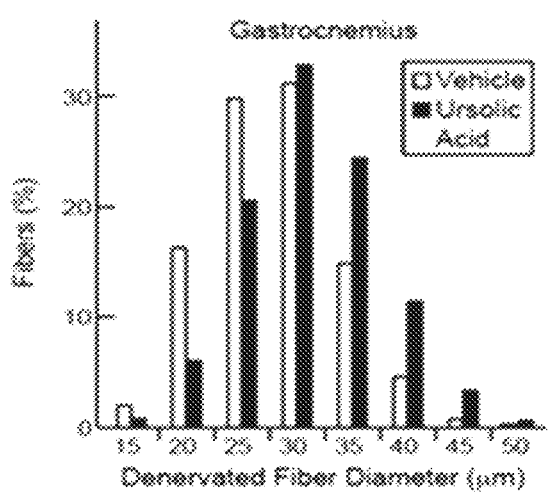
Figure 7E:
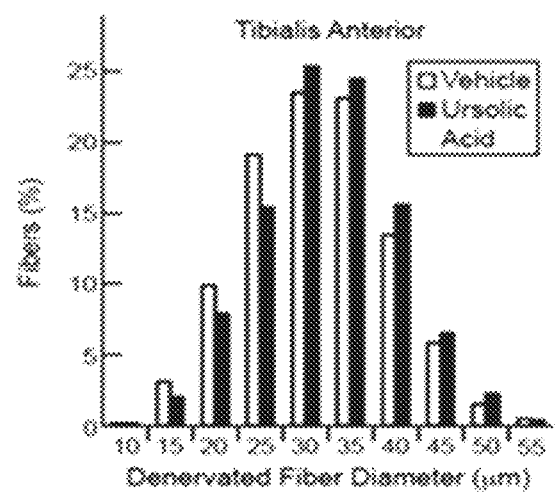

Because muscle atrophy signature-2 utilized data from SCI subjects, it was hypothesized that ursolic acid might reduce denervation-induced muscle atrophy. To test this, a denervation-induced skeletal muscle atrophy model in mouse was used. Briefly, on day 0, the left hindlimbs of C57BL/6 mice were denervated by transsecting the left sciatic nerve. This approach allowed the right hindlimb to serve as an intra-subject control. Mice were then administered ursolic acid (200 mg/kg) or an equivalent volume of vehicle alone (corn oil) via i.p. injection twice daily for seven days. During this time, mice continued to have ad libitum access to food. On day 7, muscle tissues were harvested for analysis, and the left (denervated) and right (innervated) hindlimb muscles in both groups (ursolic acid vs. vehicle administration) were compared. Ursolic acid significantly decreased denervation-induced muscle loss (FIG. 7C). In FIG. 7C, weights of the left (denervated) lower hindlimb muscles were normalized to weights of the right (innervated) lower hindlimb muscles from the same mouse. Each data point represents one mouse, and horizontal bars denote the means and the P-value was determined using an unpaired t-test. Histologically, this effect of ursolic acid was reflected as an increase in the size of denervated skeletal muscle fiber diameter in denervated gastrocnemius and TA muscles (FIGS. 7D and 7E, respectively). The data shown in FIGS. 7D and 7E are from >2500 muscle fibers per condition; $P<0.0001$ by unpaired t-test. Thus, ursolic acid reduced denervation-induced muscle atrophy.

6. Ursolic Acid Induces Skeletal Muscle Hypertrophy.

Figure 8A:
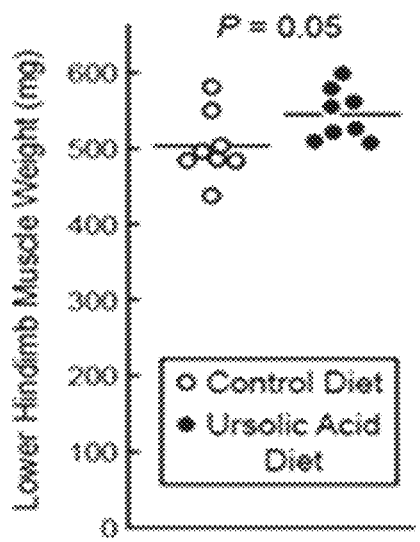
FIGS. 8A-8E show representative data on ursolic acid-mediated induction of muscle hypertrophy.
Figure 8B:
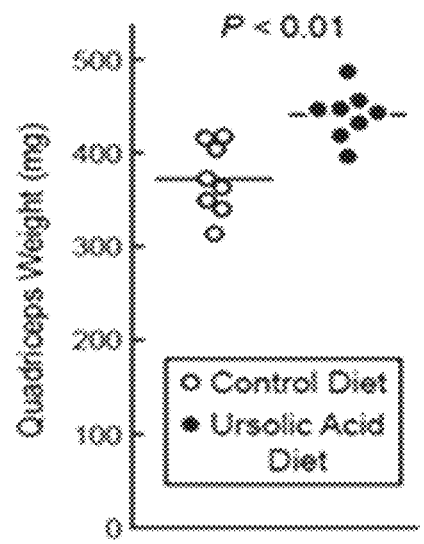
Figure 8C:
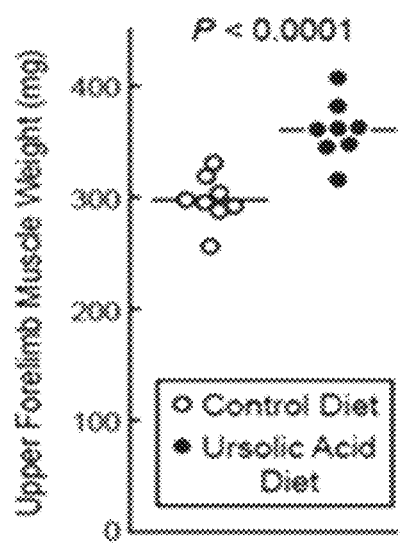
Figure 8D:
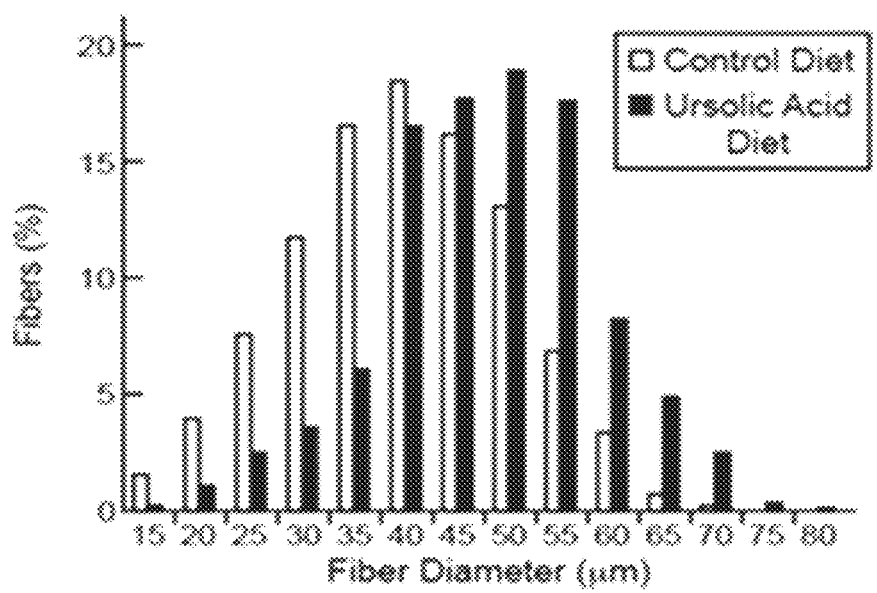
Figure 8E:
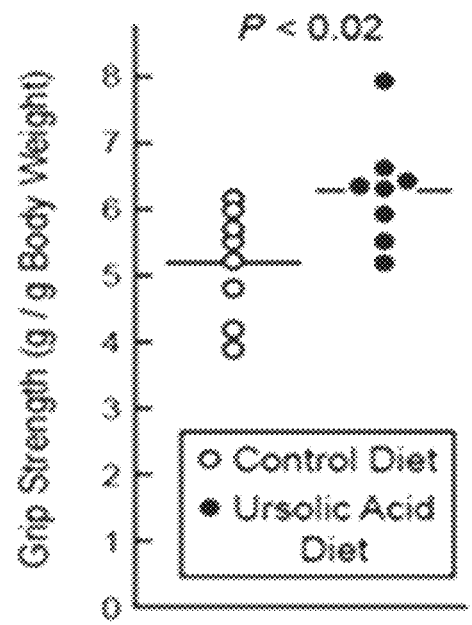

The results from the denervation-induced muscle atrophy model suggested that ursolic acid reduced muscle atrophy, thus the hypothesis that ursolic acid might promote muscle hypertrophy in the absence of an atrophy-inducing stress was reasonable. Mice were provided ad lib access to either standard chow (control diet) or standard chow supplemented with 0.27% ursolic acid (ursolic acid diet) for 5 weeks before grip strength was measured and tissues were harvested. After five weeks, mice administered ursolic had increased lower hindlimb muscle weight (FIG. 8A), quadriceps weight (FIG. 8B), and upper forelimb muscle (triceps and biceps) weight (FIG. 8C). Each data point in FIGS. 8A-8C represents one mouse, and horizontal bars denote the means. The effect of ursolic acid in this study on skeletal muscle fiber size distribution is shown in FIG. 8D. Each distribution represents measurements of >800 triceps muscle fibers from 7 animals (>100 measurements/animal); $P<0.0001$. The effect of ursolic acid on peak grip strength (normalized to body weight) is shown in FIG. 8E. Each data point represents one mouse, and horizontal bars denote the means. Non-normalized grip strength data were 157±9 g (control diet) and 181±6 g (ursolic acid diet) ($P=0.04$).

Figure 9:
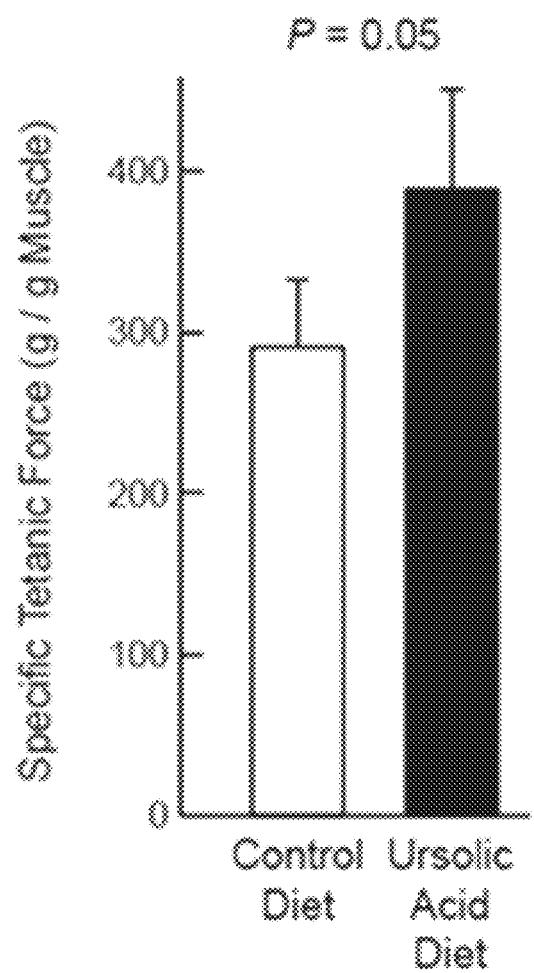
FIG. 9 shows representative data on the effect of ursolic acid on mouse skeletal muscle specific tetanic force.

Moreover, dietary ursolic acid increased the specific force generated by muscles ex vivo (FIG. 9). Briefly, six-week old male C57BL/6 mice were provided either standard diet or diet containing 0.27% ursolic acid for 16 weeks before being euthanized. The lower hindlimb was removed (by transsecting the upper hindlimb mid-way through the femur), and placed in Krebs solution aerated with 95% O2 and 5% CO2. The gastrocnemius, soleus and tibialis anterior muscles, as well as the distal half of the tibia and fibula were then removed and discarded, leaving the extensor digitorum longus and peroneus muscles with their origins and insertions intact. A suture was placed through the proximal tendon and secured to the distal femur fragment. This ex vivo preparation was then mounted vertically in a water jacket bath (Aurora Scientific 1200A Intact Muscle Test System, filled with aerated Krebs solution) by attaching the suture to a servo-controlled lever (superiorly) and clamping the metatarsals (inferiorly). Passive muscle force was adjusted to a baseline of 1 g, and then muscles were stimulated with supramaximal voltage (80 V) at 100 Hz. The mean time from euthanasia to maximal force measurements was 10 min. After force measurements, muscles were removed and weighed in order to calculate specific titanic force. Maximal tetanic force and muscle weight did not differ between the two groups ($P=0.20$ and 0.26, respectively). Data are means±SEM from 5-6 mice per diet. P-values were determined with a t-test. Together, the data in FIGS. 8 and 9 provide morphological and functional evidence that ursolic acid induced skeletal muscle hypertrophy.

7. Ursolic Acid Induces Trophic Changes in Skeletal Muscle Gene Expression.

The foregoing results suggested that ursolic acid might alter skeletal muscle gene expression. To test this hypothesis, an unbiased approach was used, specifically exon expression arrays were used to analyze gastrocnemius muscle mRNA expression in mice that had been fed diets lacking or containing ursolic acid for 5 weeks. Mice were provided ad lib access to either standard chow (control diet) or standard chow supplemented with 0.27% ursolic acid (ursolic acid diet) for 5 weeks before gastrocnemius muscle RNA was harvested and analyzed by Affymetrix Mouse Exon 1.0 ST arrays (n=4 arrays per diet). Each array assessed pooled gastrocnemius RNA from two mice. Stringent criteria were used for ursolic acid-induced effects on mRNA levels ($P<0.005$), and mRNAs with low levels of expression were disregarded (i.e. only transcripts that were increased to a mean $\log_2$ hybridization signal $\geq 8$, or repressed from a mean $\log_2$ hybridization signal $\geq 8$ were included). The results were that ursolic acid decreased 18 mRNAs and increased 51 mRNAs (out of >16,000 mRNAs analyzed. The results are shown in Table X4 ("Change" is the mean $\log_2$ change or difference between mice on ursolic acid diet and control diet, i.e. [Mean $\log_2$ mRNA levels in ursolic acid diet] minus [Mean $\log_2$ mRNA levels in control diet]).

TABLE X4

Mouse skeletal muscle mRNAs induced or repressed by ursolic acid.

| mRNA | Protein | Change | P |
|---|---|---|---|
| Smox | spermine oxidase | 0.81 | 0.001 |
| Lyz2 | lysozyme 2 | 0.71 | 0.001 |
| C3 | complement component 3 | 0.70 | 0.000 |
| Tyrobp | TYRO protein tyrosine kinase binding protein | 0.69 | 0.001 |
| Lum | lumican | 0.61 | 0.001 |
| Igf1 | insulin-like growth factor 1 | 0.56 | 0.005 |
| Fmo1 | flavin containing monooxygenase 1 | 0.47 | 0.000 |
| Ostn | osteocrin | 0.43 | 0.001 |
| Nampt | nicotinamide phosphoribosyltransferase | 0.41 | 0.003 |
| H19 | H19 fetal liver mRNA | 0.39 | 0.004 |
| Hipk2 | homeodomain interacting protein kinase 2 | 0.38 | 0.002 |
| Fbp2 | fructose bisphosphatase 2 | 0.37 | 0.003 |
| Gpx1 | glutathione peroxidase 1 | 0.36 | 0.001 |
| Sepp1 | selenoprotein P, plasma, 1 | 0.35 | 0.004 |
| Parp3 | poly (ADP-ribose) polymerase family, member 3 | 0.32 | 0.001 |
| Hspb8 | heat shock protein 8 | 0.32 | 0.000 |
| Musk | muscle, skeletal, receptor tyrosine kinase | 0.31 | 0.004 |
| Fhl3 | four and a half LIM domains 3 | 0.31 | 0.005 |
| Hsph1 | heat shock 105 kDa/110 kDa protein 1 | 0.30 | 0.001 |
| Arfgap2 | ADP-ribosylation factor GTPase activating protein 2 | 0.30 | 0.001 |
| Cd24a | CD24a antigen | 0.28 | 0.002 |
| Sepx1 | selenoprotein X 1 | 0.28 | 0.003 |
| Hk2 | hexokinase 2 | 0.26 | 0.003 |
| Ggct | gamma-glutamyl cyclotransferase | 0.24 | 0.005 |
| Trip10 | thyroid hormone receptor interactor 10 | 0.23 | 0.001 |
| Npc1 | Niemann Pick type C1 | 0.22 | 0.001 |
| Asb5 | ankyrin repeat and SOCs box-containing 5 | 0.21 | 0.001 |
| Vps29 | vacuolar protein sorting 29 (*S. pombe*) | 0.20 | 0.000 |
| Ahsa2 | AHA1, activator of heat shock protein ATPase homolog 2 | 0.18 | 0.001 |
| Lsm14a | LSM14 homolog A (SCD6, *S. cerevisiae*) | 0.18 | 0.004 |
| Pdha1 | pyruvate dehydrogenase E1 alpha 1 | 0.18 | 0.001 |
| Trappc2l | trafficking protein particle complex 2-like | 0.16 | 0.004 |
| Ube2l3 | ubiquitin-conjugating enzyme E2L 3 | 0.16 | 0.003 |
| Ctsb | cathepsin B | 0.16 | 0.003 |
| D0H4S114 | DNA segment, human D4S114 | 0.15 | 0.004 |
| Psma2 | proteasome (prosome, macropain) subunit, alpha type 2 | 0.15 | 0.005 |
| Mrpl46 | mitochondrial ribosomal protein L46 | 0.15 | 0.001 |
| Eef1e1 | eukaryotic translation elongation factor 1 epsilon 1 | 0.15 | 0.002 |
| Krr1 | KRR1, small subunit (SSU) processome component, homolog | 0.15 | 0.005 |
| Ndufaf4 | NADH dehydrogenase (ubiquinone) 1 alpha subcomplex, assembly factor 4 | 0.14 | 0.005 |
| Ndufs2 | NADH dehydrogenase (ubiquinone) Fe—S protein 2 | 0.14 | 0.002 |
| 2610507B11Rik | RIKEN cDNA 2610507B11 gene | 0.14 | 0.000 |
| Ssr4 | signal sequence receptor, delta | 0.14 | 0.000 |
| Ndufs4 | NADH dehydrogenase (ubiquinone) Fe—S protein 4 | 0.14 | 0.003 |
| Sqstm1 | sequestosome 1 | 0.12 | 0.001 |
| Gfm1 | G elongation factor, mitochondrial 1 | 0.12 | 0.003 |
| 2310016M24Rik | RIKEN cDNA 2310016M24 gene | 0.12 | 0.004 |
| Sod2 | superoxide dismutase 2, mitochondrial | 0.12 | 0.001 |
| Prdx5 | peroxiredoxin 5 | 0.10 | 0.005 |
| BC004004 | cDNA sequence BC004004 | 0.06 | 0.001 |
| Ghitm | growth hormone inducible transmembrane protein | 0.05 | 0.005 |
| Foxn3 | forkhead box N3 | −0.09 | 0.000 |
| Klhl31 | kelch-like 31 (*Drosophila*) | −0.09 | 0.001 |
| Acadm | acyl-Coenzyme A dehydrogenase, medium chain | −0.11 | 0.001 |
| Eif4g3 | eukaryotic translation initiation factor 4 gamma, 3 | −0.12 | 0.005 |
| Nrap | nebulin-related anchoring protein | −0.14 | 0.003 |
| Golga4 | golgi autoantigen, golgin subfamily a, 4 | −0.14 | 0.003 |
| Paip2b | poly(A) binding protein interacting protein 2B | −0.16 | 0.000 |
| Pde4dip | phosphodiesterase 4D interacting protein (myomegalin) | −0.18 | 0.001 |
| Sfpq | splicing factor proline/glutamine rich | −0.18 | 0.005 |
| Pnn | pinin | −0.18 | 0.002 |
| D4Wsu53e | DNA segment, Chr 4, Wayne State University 53, expressed | −0.18 | 0.003 |
| Mlec | malectin | −0.19 | 0.003 |

TABLE X4-continued

Mouse skeletal muscle mRNAs induced or repressed by ursolic acid.

| mRNA | Protein | Change | P |
|---|---|---|---|
| Cacna1s | calcium channel, voltage-dependent, L type, alpha 1S | −0.22 | 0.001 |
| Sfrs5 | splicing factor, arginine/serine-rich 5 (SRp40, HRS) | −0.22 | 0.005 |
| Nnt | nicotinamide nucleotide transhydrogenase | −0.24 | 0.002 |
| Adprhl1 | ADP-ribosylhydrolase like 1 | −0.26 | 0.002 |
| Ddit4l | DNA-damage-inducible transcript 4-like | −0.32 | 0.000 |
| Fbxo32 | F-box protein 32 (Atrogin-1) | −0.35 | 0.001 |

Figure 6H:
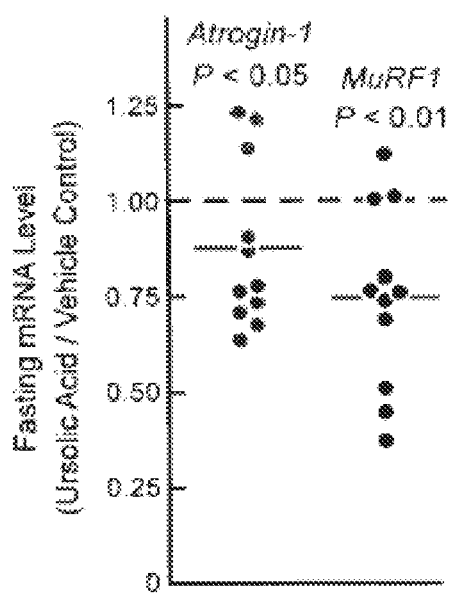
Figure 10D:
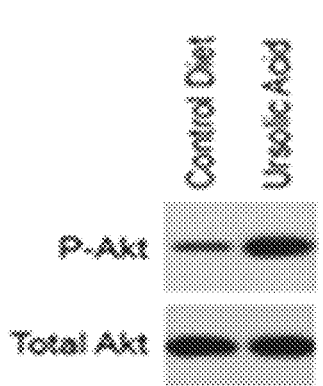
Figure 11B:
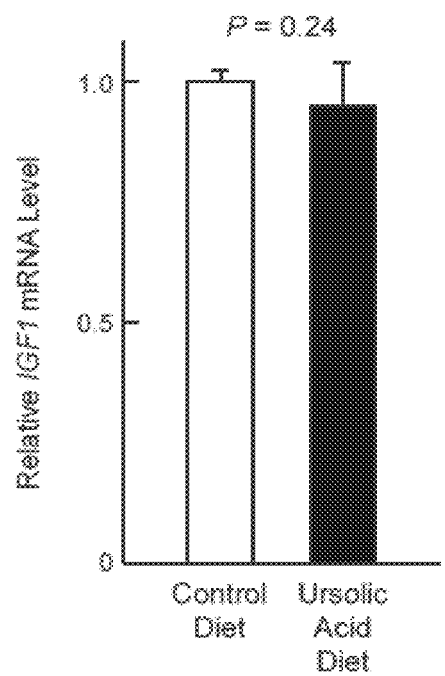
Figure 12A:
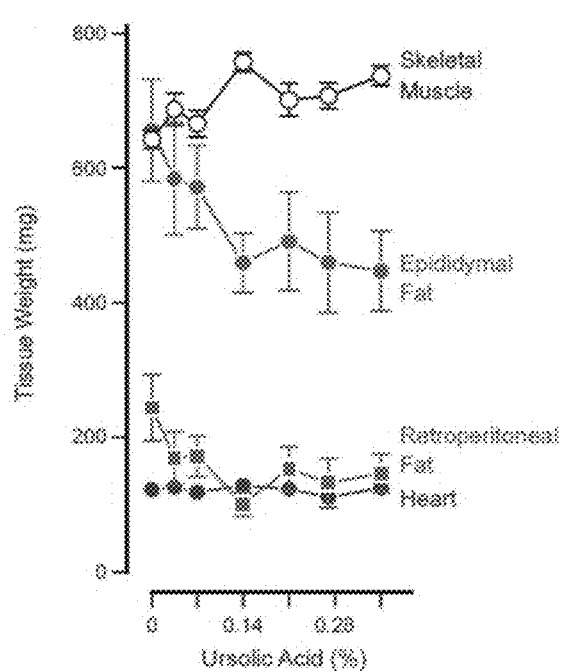
FIGS. 12A-12J show representative data on the effect of ursolic acid on adiposity and plasma lipids.
Figure 12B:
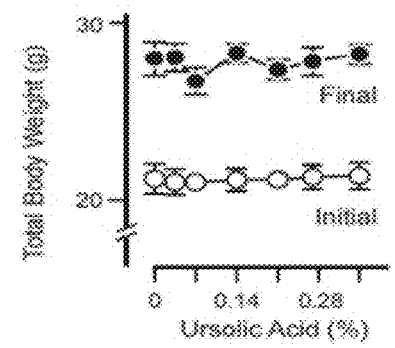

As discussed above, atrogin-1 and MuRF1 are transcriptionally up-regulated by atrophy-inducing stresses (see FIG. 4B and Sacheck J M, et al. (2007) *Faseb J* 21(1): 140-155), and they are required for muscle atrophy (Bodine S C, et al. (2001) *Science (New York, N.Y.* 294(5547):1704-1708). Moreover, in the studies of fasted mice as described herein above, ursolic acid reduced atrogin-1 and MuRF1 mRNAs (FIG. 6H). Consistent with that finding, the arrays indicated that dietary ursolic acid reduced atrogin-1 mRNA, which was the most highly repressed mRNA (FIG. 10A). The results shown in FIG. 10A represent a subset of the mRNAs from Table X4 which had the greatest increase or decrease in expression level in response to ursolic acid. Although MuRF1 mRNA was not measured by the arrays used in these experiments, qPCR analysis confirmed that dietary ursolic acid repressed both atrogin-1 and MuRF1 mRNAs (FIG. 10B; data are means±SEM). Interestingly, one of the most highly up-regulated muscle mRNAs was IGF1 (FIGS. 10A and 10B), which encodes insulin-like growth factor-I (IGF-I), a locally generated autocrine/paracrine hormone. IGF1 mRNA is known to be transcriptionally induced in hypertrophic muscle (Hameed M, et al. (2004) *The Journal of physiology* 555(Pt 1):231-240; Adams G R & Haddad F (1996) *J Appl Physiol* 81(6):2509-2516; Gentile M A, et al. (2010) *Journal of molecular endocrinology* 44(1):55-73). In addition, increased skeletal muscle IGF1 expression reduces denervation-induced muscle atrophy (Shavlakadze T, et al. (2005) *Neuromuscul Disord* 15(2): 139-146), and stimulates muscle hypertrophy (Barton-Davis E R, et al. (1998) *Proceedings of the National Academy of Sciences of the United States of America* 95(26): 15603-15607; Musaro A, et al. (2001) *Nature Genetics* 27(2):195-200). Moreover, by stimulating skeletal muscle insulin/IGF-I signaling, IGF-I represses atrogin-1 and MuRF mRNAs (Sacheck J M, et al. (2004) *Am J Physiol Endocrinol Metab* 287(4):E591-601; Frost R A, et al. (2009) *J Cell Biochem* 108(5):1192-1202.), as well as DDIT4L mRNA (ibid), which, after atrogin-1 mRNA, was the second most highly repressed mRNA in muscle from ursolic acid-treated mice (FIG. 10A). Thus, 5 weeks of dietary ursolic acid altered skeletal muscle gene expression in a manner known to reduce atrophy and promote hypertrophy, and muscle-specific IGF1 induction emerged as a likely contributing mechanism in ursolic acid-induced muscle hypertrophy. The effect of ursolic acid on plasma IGF-I levels was also determined, which primarily reflect growth hormone-mediated hepatic IGF-I production (Yakar S, et al. (1999) *Proceedings of the National Academy of Sciences of the United States of America* 96(13): 7324-7329). Although diets containing 0.14% or 0.27% ursolic acid increased muscle mass (described in greater detail below; FIG. 12A), neither increased plasma IGF-I (FIG. 10C). For the data in FIG. 10C, mice were provided ad lib access to either standard chow (control diet) or standard chow supplemented with the indicated concentration of ursolic acid for 7 weeks before plasma IGF-I levels were measured. Each data point represents one mouse, and horizontal bars denote the means. P-values were determined by one-way ANOVA with Dunnett's post-test. Of note, exon expression arrays indicated that ursolic acid increased levels of all measured IGF1 exons (exons 2-6; FIG. 11A). The data in FIG. 11A are mean exon-specific $\log_2$ hybridization signals from the arrays described in Table X4. However, ursolic acid did not alter levels of mRNAs encoding myostatin (which reduces muscle mass, for example see Lee S J (2004) *Annu Rev Cell Dev Biol* 20:61-86), or twist or myogenin (which are induced by IGF-I during development, for example see Dupont J, et al. (2001) *The Journal of biological chemistry* 276(28):26699-26707; Tureckova J, et al. (2001) *The Journal of biological chemistry* 276(42): 39264-39270). Moreover, ursolic acid did not alter the amount of IGF1 mRNA in adipose tissue (FIG. 11B). Briefly, the data shown in FIG. 11B were obtained as follows: mice were provided ad lib access to either standard chow (control diet) or standard chow supplemented with 0.27% ursolic acid (ursolic acid diet) for 7 weeks before retroperitoneal adipose tissue was harvested for qPCR quantification of IGF1 mRNA. The data shown are means±SEM from 5 mice per group. Without wishing to be bound by a particular theory, ursolic acid-mediated IGF1 induction may be localized to skeletal muscle.

8. Ursolic Acid Enhances Skeletal Muscle IGF-I Signaling.

Figure 10E:
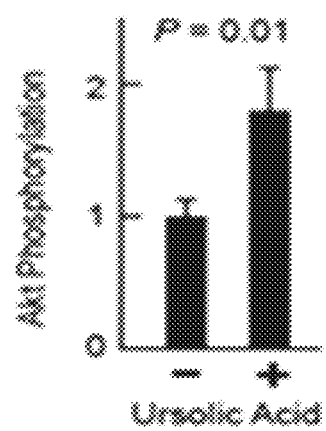

Although muscle-specific IGF1 induction is characteristic of, and contributes to, muscle hypertrophy, it may be a relatively late event that promotes hypertrophy after it has been initiated by other stimuli (Adams G R, et al. (1999) *J Appl Physiol* 87(5):1705-1712). Without wishing to be bound by a particular theory, it is possible that ursolic acid might have a more proximal effect on insulin/IGF-I signaling. In a previous study of non-muscle cell lines (CHO/IR and 3T3-L1 cells), ursolic acid enhanced insulin-mediated Akt activation (Jung S H, et al. (2007) *The Biochemical journal* 403(2):243-250). To determine whether ursolic acid might have a similar effect in skeletal muscle, the level of phosphorylated Akt was assessed in quadriceps muscles of mice fed diets lacking or containing ursolic acid. Briefly, mice were provided ad lib access to either standard chow (control diet) or standard chow supplemented with 0.27% ursolic acid for 16 weeks. Total protein extracts from quadriceps muscles were subjected to SDS-PAGE, followed by immunoblot analysis for phosphorylated and total Akt, as indicated. A representative immunoblot is shown in FIG. 10D. Immunoblot data were quantitated as follows: in each mouse, the level of phospho-Akt was normalized to the level of total Akt; these ratios were then normalized to the average phospho-Akt/total Akt ratio from control mice and the results are shown in FIG. 10E (data are means±SEM from 9 mice per diet. P-value was determined by unpaired t-test). The data show that in quadriceps, ursolic acid increased Akt phosphorylation by 1.8-fold.

The effect of ursolic acid on Akt activation was examined in C2C12 skeletal myotubes, a well-established in vitro model of skeletal muscle (Sandri M, et al. (2004) *Cell* 117(3):399-412; Stitt T N, et al. (2004) *Mol Cell* 14(3):395-403). Use of an in vitro system, such as C2C12 skeletal myotubes, circumvented potentially confounding effects from non-muscle tissues, and enabled a determination of whether IGF-I or insulin was required for ursolic acid's effect. The latter consideration was important because circulating IGF-I and insulin are always present in healthy animals. Use of an in vitro system also allowed testing of a clearly defined concentration of ursolic acid (10 μM, similar what was used in the Connectivity Map (8.8 μM)) for a clearly defined time of incubation (20 min). These considerations were important because the in vivo pharmacokinetic properties of ursolic acid are not yet known.

Figure 10F:
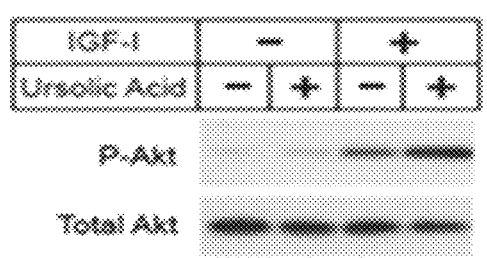
Figure 10G:
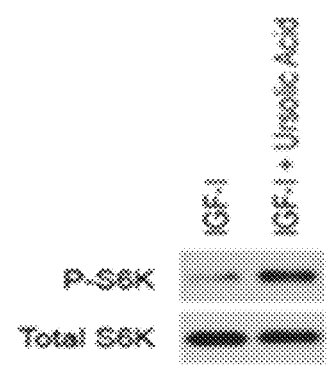
Figure 10H:
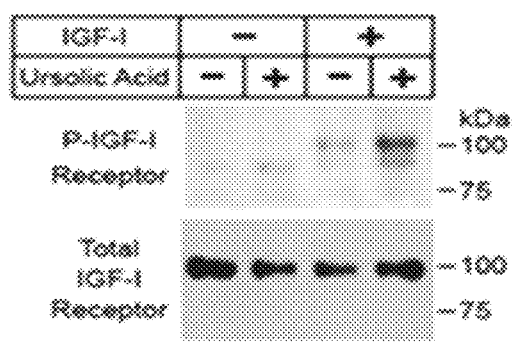
Figure 10I:
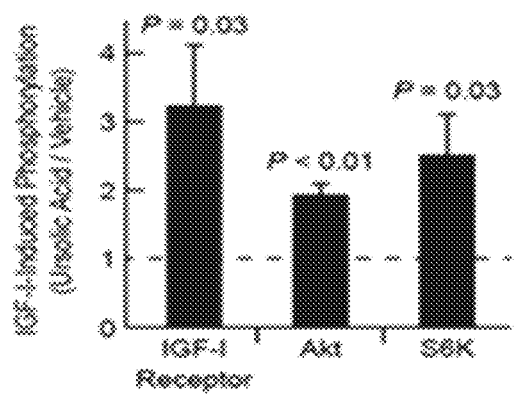

For the data shown in FIGS. 10F-10K, serum-starved C2C12 myotubes were treated in the absence or presence of ursolic acid (10 μM) and/or IGF-I (10 nM), as indicated. For studies of the IGF-I receptor, cells were harvested 2 min later, and protein extracts were subjected to immunoprecipitation with anti-IGF-I receptor β antibody, followed by immunoblot analysis with anti-phospho-tyrosine or anti-IGF-I receptor β antibodies to assess phospho- and total IGF-I receptor, respectively. For other studies, cells were harvested 20 min after addition of ursolic acid and/or IGF-I, and immunoblot analyses were performed using total cellular protein extracts and antibodies specific for the phosphorylated or total proteins indicated. Representative immunoblots showing effect of ursolic acid on IGF-I-mediated phosphorylation of Akt (FIG. 10F), S6K (FIG. 10G) and IGF-I receptor (FIG. 10H). Data from immunoblots was quantitated as follows: levels in the presence of ursolic acid and IGF-I were normalized to levels in the presence of IGF-I alone, which were set at 1 and are indicated by the dashed line. The data shown in FIG. 10I are means±SEM from ≥3 experiments.

For the data shown in FIGS. 11C-11F, serum-starved C2C12 myotubes were treated in the absence or presence of ursolic acid (10 μM), insulin (10 nM) and/or IGF-I (10 nM), as indicated. For studies of the insulin receptor, cells were harvested 2 min later, and protein extracts were subjected to immunoprecipitation with anti-insulin receptor β antibody, followed by immunoblot analysis with anti-phospho-insulin receptor β (Y1162/1163) or anti-insulin receptor β antibodies to assess phospho- and total insulin receptor, respectively. For other studies, cells were harvested 20 min after addition of ursolic acid, insulin and/or IGF-I, and immunoblot analyses were performed using total cellular protein extracts and antibodies specific for the phosphorylated or total proteins indicated.

Figure 11C:
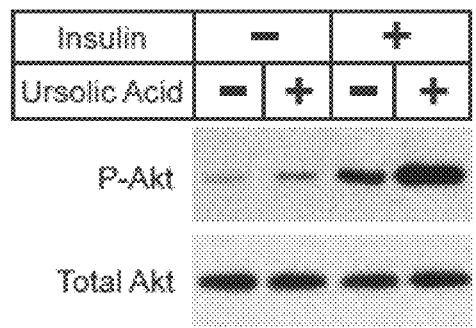

When serum-starved myotubes were treated with ursolic acid alone, Akt phosphorylation did not increase (FIG. 10F). However, in the presence of IGF-I, ursolic acid increased Akt phosphorylation by 1.9-fold (FIGS. 10F and 10I). Ursolic acid also increased Akt phosphorylation in the presence of insulin (FIG. 11C). Thus, ursolic acid enhanced IGF-I-mediated and insulin-mediated Akt phosphorylation. The finding that ursolic acid enhanced muscle Akt activity in vivo and in vitro was consistent with the finding that ursolic acid's mRNA expression signature negatively correlated with the mRNA expression signatures of LY-294002 and wortmannin (FIGS. 6B and 7B), which inhibit insulin/IGF-I signaling upstream of Akt. However, ursolic acid's signature also negatively correlated with the signature of rapamycin, which inhibits insulin/IGF-I signaling downstream of Akt.

Figure 10J:
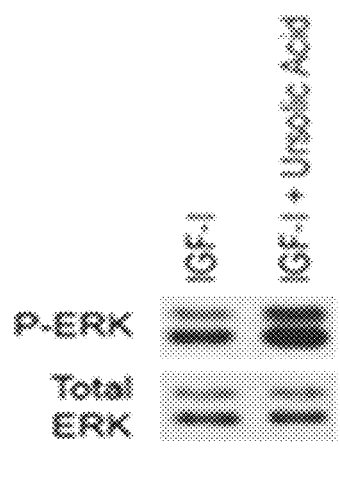
Figure 10K:
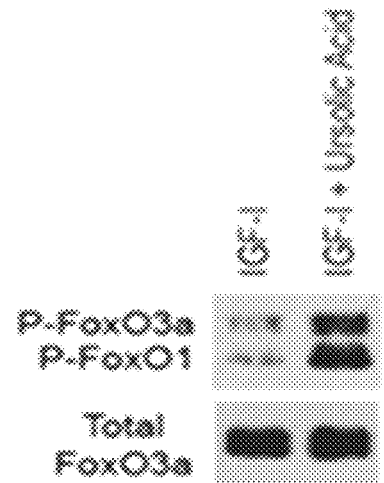
Figure 11D:
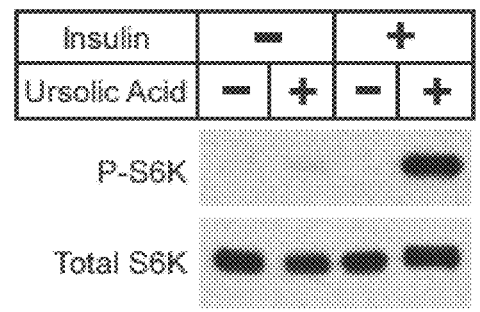
Figure 11E:
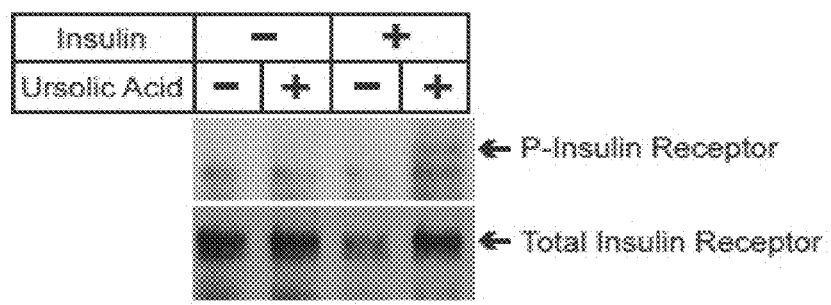
Figure 11F:
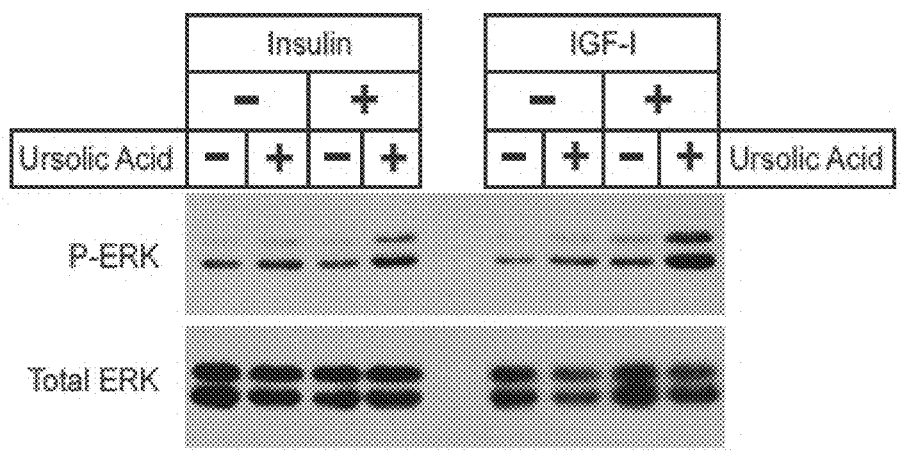

Although ursolic acid alone did not increase S6K phosphorylation (FIG. 11D), it enhanced IGF-I-mediated and insulin-mediated S6K phosphorylation (FIGS. 10G, 10I and 11D). To further investigate the mechanism, the effect of ursolic acid on the IGF-I receptor was examined. Ursolic acid increased IGF-I receptor phsophorylation in the presence but not the absence of IGF-I (FIGS. 10H and 10I). Similarly, ursolic acid increased insulin receptor phosphorylation in the presence but not the absence of insulin (FIG. 11E). Both of these effects were rapid, occurring within 2 minutes after the addition of ursolic acid and either IGF-I or insulin. Consistent with enhanced signaling at the level of the IGF-I and insulin receptors, ursolic acid also enhanced IGF-I-mediated and insulin-mediated ERK phosphorylation (FIGS. 10J and 11F). Moreover, ursolic acid enhanced IGF-I-mediated phosphorylation (inhibition) of FoxO transcription factors, which activate transcription of atrogin-1 and MuRF1 mRNAs (FIG. 10K; Sandri M, et al. (2004) *Cell* 117(3):399-412; Stitt T N, et al. (2004) *Mol Cell* 14(3):395-403.). Without wishing to be bound by a particular theory, ursolic acid represses atrophy-associated gene expression and promotes muscle hypertrophy by increasing activity of the IGF-I and insulin receptors.

9. Ursolic Acid Reduces Adiposity.

Mice were provided ad lib access to standard chow supplemented with the indicated concentration (weight percent in chow as indicated in FIG. 12) of ursolic acid for 7 weeks before tissues were harvested for analysis. Data are means±SEM from 10 mice per diet. Data for the effects of ursolic acid on weights of skeletal muscle (quadriceps+triceps), epididymal fat, retroperitoneal fat and heart are shown in FIG. 12A. The P-values, determined by one-way ANOVA with post-test for linear trend, were <0.001 for muscle; 0.01 and 0.04 for epididymal and retroperitoneal fat, respectively; and 0.46 for heart. The data show that 7 weeks of dietary ursolic acid increased skeletal muscle weight in a dose-dependent manner, with a peak effect at 0.14% ursolic acid. Interestingly, although ursolic acid increased muscle weight, it did not increase total body weight (FIG. 12B; P-values were 0.71 and 0.80 for initial and final weights, respectively).

Figure 12C:
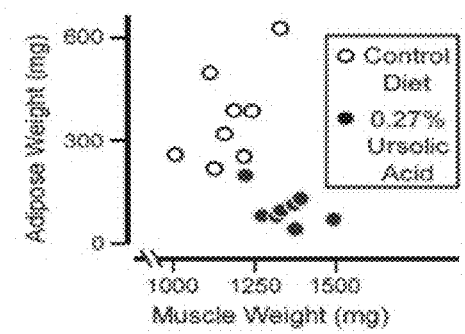

The data in FIG. 12A also show that 7 weeks of dietary ursolic acid reduced the weight of epididymal and retroperitoneal fat depots, with a peak effect at 0.14%. In another study, mice were provided ad lib access to either standard chow (control diet) or standard chow supplemented with 0.27% ursolic acid (ursolic acid diet) for 5 weeks. The relationship between skeletal muscle weight (quadriceps, triceps, biceps, TA, gastrocnemius and soleus) and retroperitoneal adipose weight is shown in FIG. 12C. Each data point in FIG. 12C represents one mouse; P<0.001 for both muscle and adipose by unpaired t-test. The data show that 5 weeks of ursolic acid administration (0.14%) also reduced adipose weight. Thus, muscle and fat weights were inversely related. Without wishing to be bound by a particular theory, ursolic acid-treated mice contain less fat because, in part, ursolic acid increases Akt activity (see FIGS. 10 and 11), and muscle-specific increases in Akt activity reduce adiposity as a secondary consequence of muscle hypertrophy (Lai K M, et al. (2004) *Molecular and cellular biology* 24(21):9295-9304; Izumiya Y, et al. (2008) *Cell metabolism* 7(2):159-172).

Figure 12D:
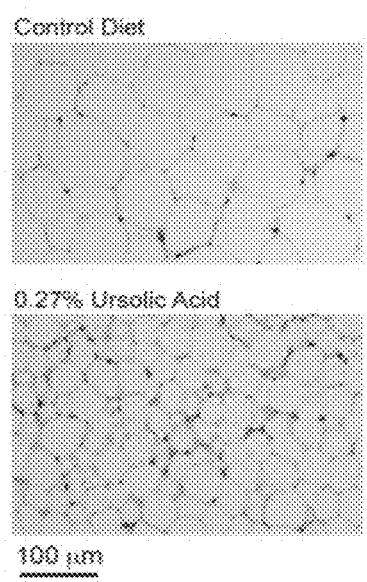
Figure 12E:
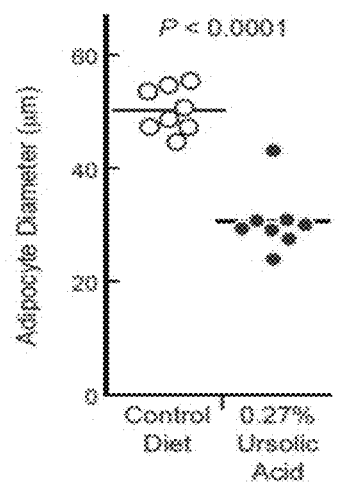
Figure 12F:
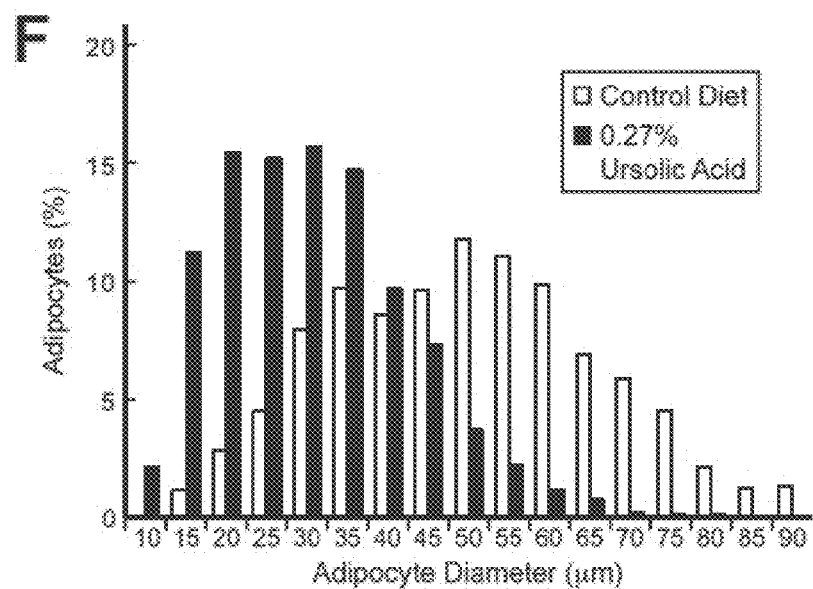

Ursolic acid reduced adipose weight by reducing adipocyte size as shown by data in FIGS. 12D-12F. FIG. 12D shows a representative H&E stain of retroperitoneal fat for animals feed a control data or a chow with 0.27% ursolic acid as indicated. The data in FIG. 12D are shown quantitatively in FIG. 12E in terms of adipocyte diameter, where data point represents the average diameter of ≥125 retroperitoneal adipocytes from one mouse. FIG. 12F shows the retroperitoneal adipocyte size distribution. Each distribution represents combined adipocyte measurements (>1000 per diet) from FIG. 12E.

Figure 12G:
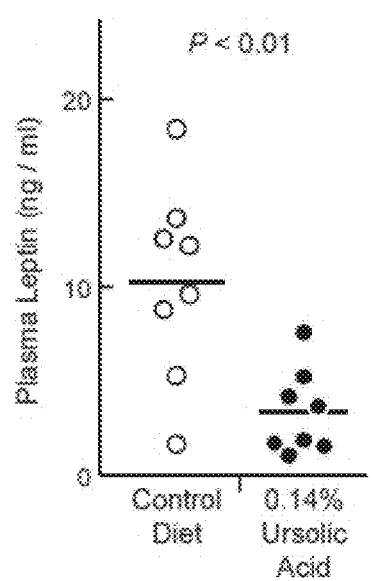
Figure 12H:
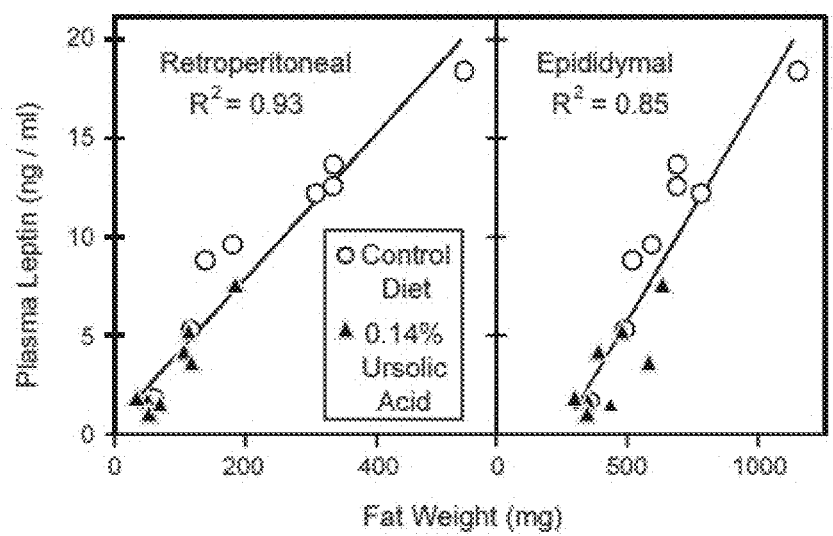
Figure 12I:
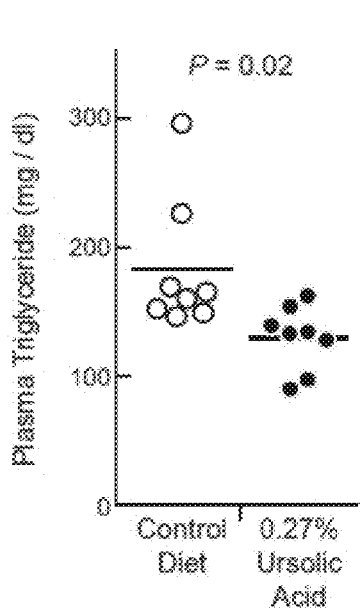
Figure 12J:
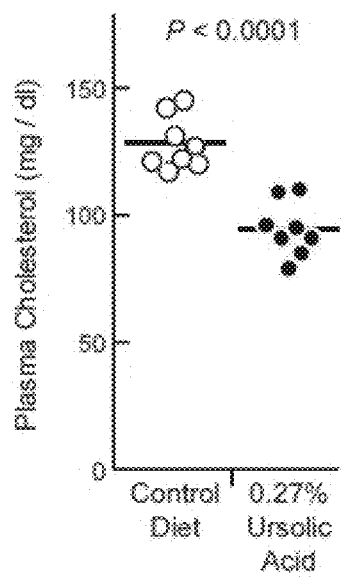
Figure 13C:
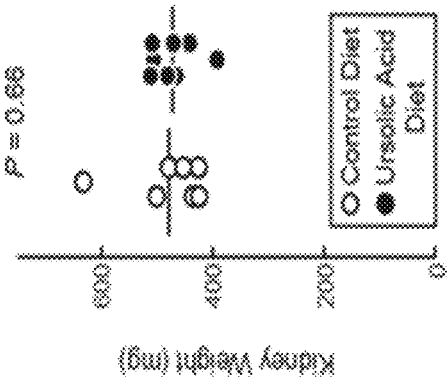
FIGS. 13A-13F show representative data on the effect of ursolic acid on food consumption, liver weight, kidney weight, and plasma ALT, bilirubin, and creatinine concentrations.
Figure 13F:
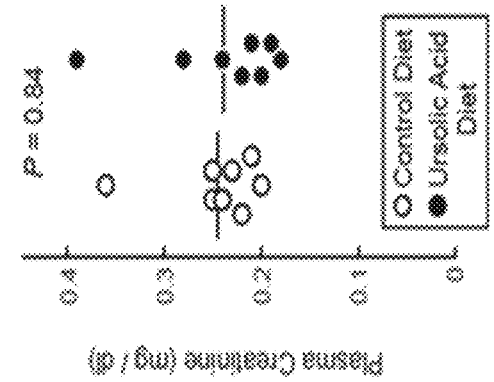
Figure 13B:
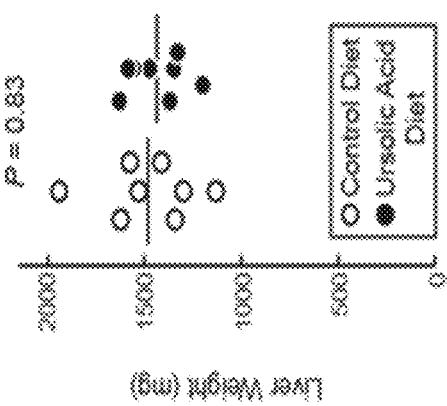
Figure 13E:
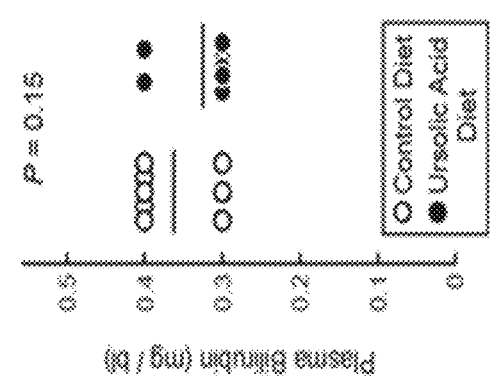
Figure 13A:
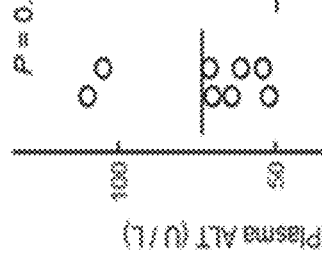
Figure 13D:
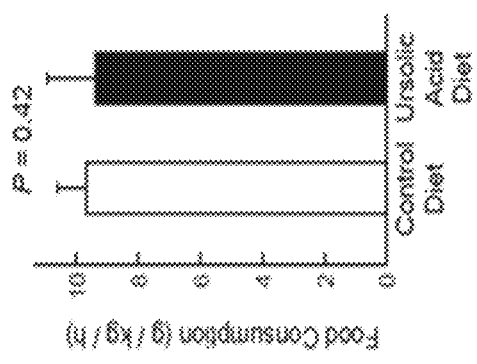

The changes in adipocyte size were accompanied by a significant reduction in plasma leptin levels, which correlated closely with adipose weight (see FIGS. 12G and 12H). In FIG. 12G, each data point represents one mouse, and horizontal bars denote the means. P-values were determined by t-test. In FIG. 12H, each data point represents one mouse. Importantly, ursolic acid also significantly reduced plasma triglyceride (FIG. 12I) and cholesterol (FIG. 12J). In FIGS. 12I and 12J, each data point represents one mouse, and horizontal bars denote the means. P-values were determined by unpaired t-test. Although ursolic acid reduced leptin, it did not alter food intake (FIG. 13A). In this study, mice were provided ad lib access to either standard chow (control diet) or standard chow supplemented with 0.27% ursolic acid (ursolic acid diet) for 4 weeks. Mice were then moved to a comprehensive animal metabolic monitoring system (CLAMS; Columbus Instruments, Columbus, Ohio) and provided with ad lib access to the same diets. Food consumption was measured for 48 hours. Data are means±SEM from 6 mice per group. However, ursolic acid did not alter weights of heart (FIG. 12A), liver or kidney (FIGS. 13B and 13C), nor did it elevate plasma markers of hepatotoxicity or nephrotoxicity (alanine aminotransferase, bilirubin and creatinine; see FIGS. 13D-13F). The data in FIGS. 13B-13F were obtained as follows: mice were provided ad lib access to either standard chow (control diet) or standard chow supplemented with 0.27% ursolic acid (ursolic acid diet) for 5 weeks before tissues and plasma were harvested for the indicated measurements; each data point represents one mouse, and horizontal bars denote the means. For FIG. 13, P-values were determined with unpaired t-tests. Thus, dietary ursolic acid had two major effects: skeletal muscle hypertrophy and reduced adiposity.

10. Ursolic Acid Reduces Weight Gain and White Adipose Tissue.

Figure 14A:
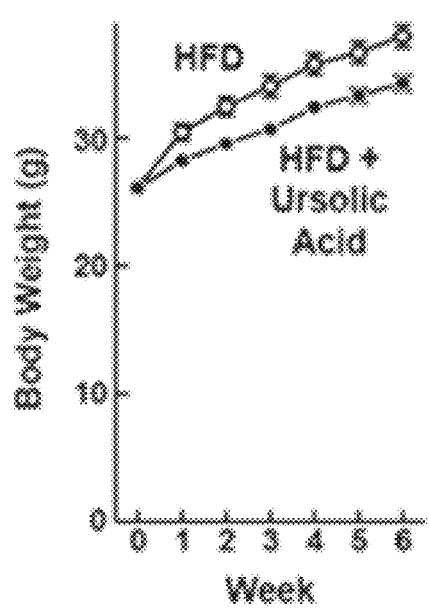
Figure 14B:
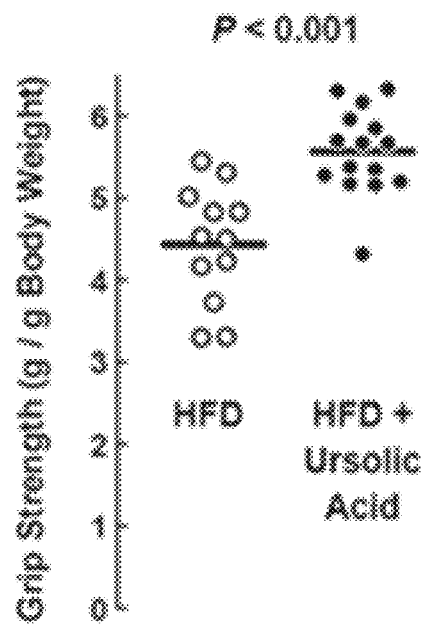
Figure 14C:
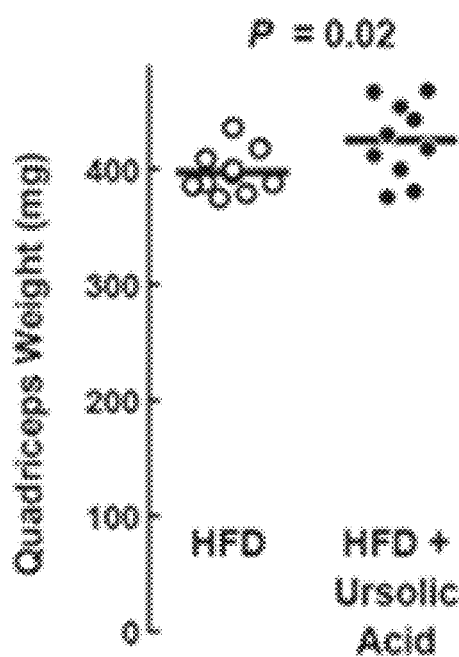
Figure 14D:
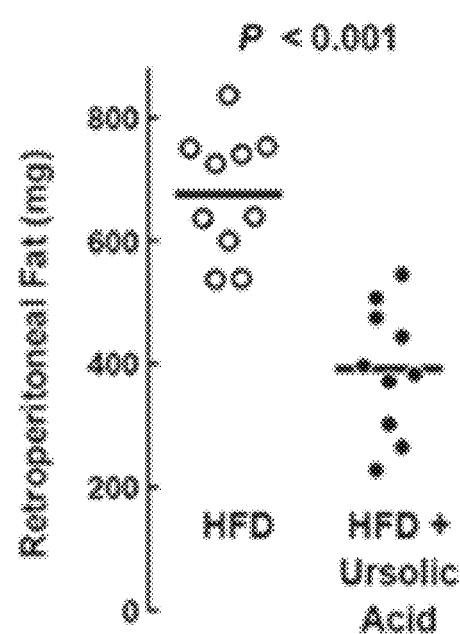
Figure 14E:
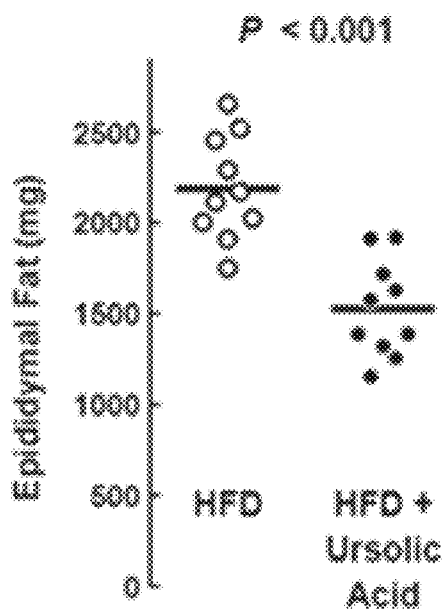
Figure 14F:
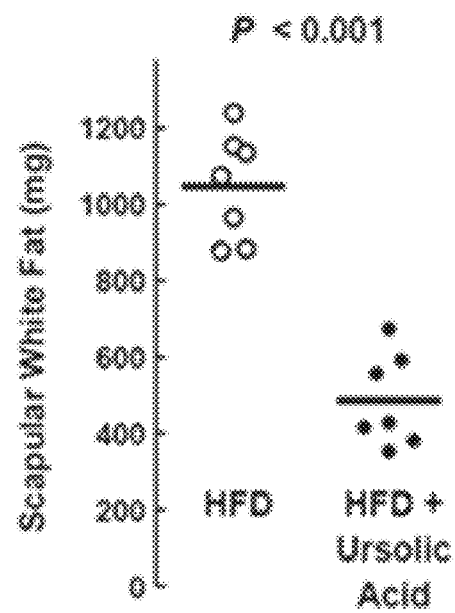
Figure 14G:
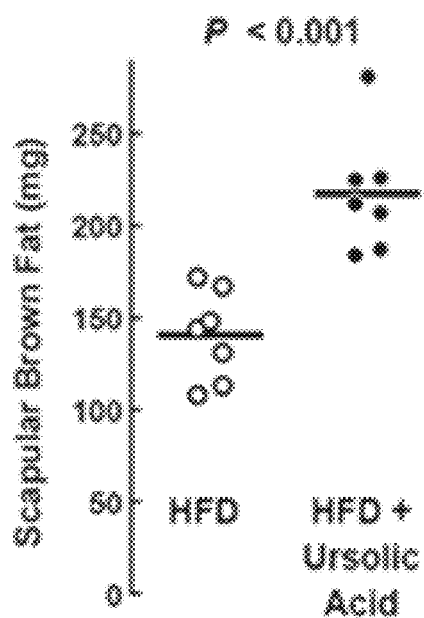
Figure 14H:
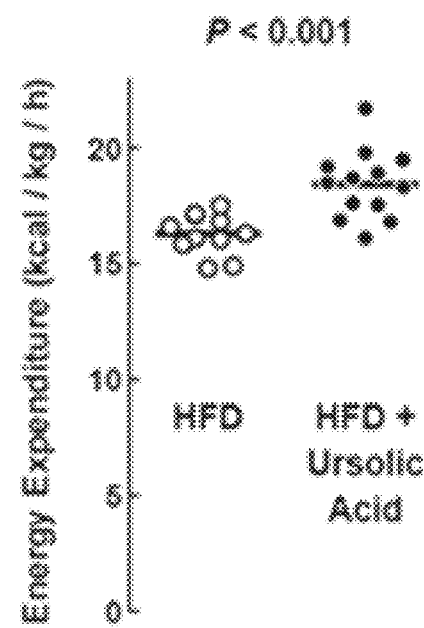

The findings that ursolic acid increased skeletal muscle and decreased adiposity suggested that ursolic acid might increase energy expenditure, which would lead to obesity resistance. To test this, C57BL/6 mice were given ad libitum access to a high fat diet (HFD; Teklad TD.93075; 55% calories from fat) lacking or containing 0.27% ursolic acid. After 7 weeks, mice from each group were studied for three days in comprehensive lab animal monitoring systems ("CLAMS"; Columbus Instruments). In the CLAMS, mice were maintained on the same diet they had been eating since the beginning of the experiment. Following CLAMS, tissues were harvested for analysis. In high fat-fed mice, ursolic acid dramatically reduced weight gain, and this effect was apparent within one week (FIG. 14A). As previously observed in mice fed ursolic acid and standard chow (FIG. 8), ursolic acid increased grip strength and muscle mass (FIGS. 14B and 14C). Moreover, ursolic acid reduced retroperitoneal and epididymal fat (FIGS. 14D and 14E). Interestingly, in the scapular fat pad, which contains a mixture of white and thermogenic brown fat, ursolic acid reduced white fat (FIG. 14F), but increased brown fat (FIG. 14G). Importantly, increased skeletal muscle and brown adipose tissue would be predicted to increase energy expenditure. Indeed, CLAMS revealed that ursolic acid increased energy expenditure (FIG. 14H), providing an explanation for how ursolic acid reduces adiposity and obesity. Remarkably, CLAMS analysis revealed that ursolic acid-treated mice consumed more food (FIG. 14I), even though they gained less weight (FIG. 14A). For the data shown in FIG. 14A, data are means±SEM from 12 control mice and 15 treated mice, but it should be noted that some error bars are too small to see; $P<0.01$ at 1 wk and each subsequent time point. In FIGS. 14B-14I, each data point represents one mouse and horizontal bars denote the means. P-values were determined with unpaired t-tests.

11. Ursolic Acid Reduces Obesity-Related Pre-Diabetes, Diabetes, Fatty Liver Disease and Hypercholesterolemia.

Figure 15C:
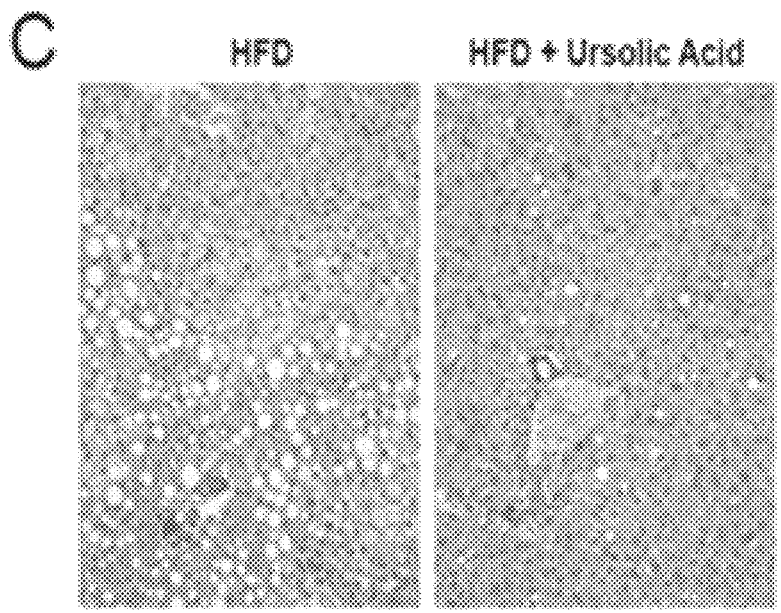
Figure 15D:
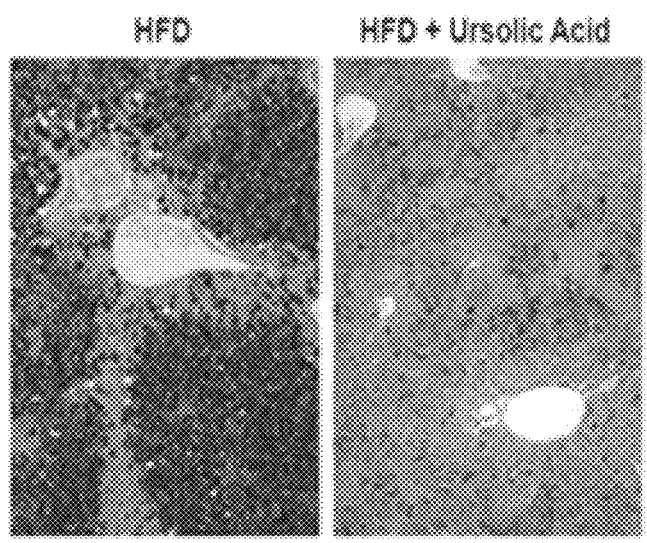
Figures 15E, 15F:
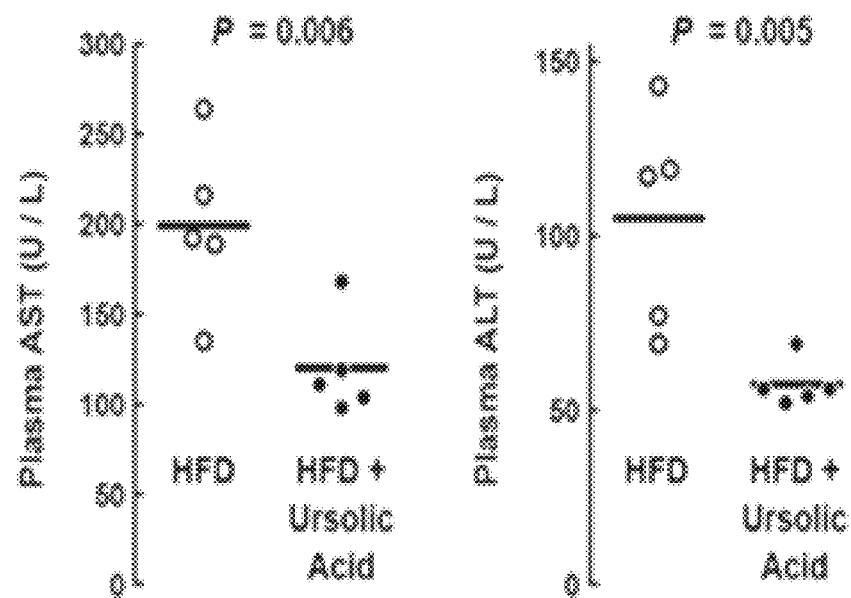
Figures 15G, 15H:
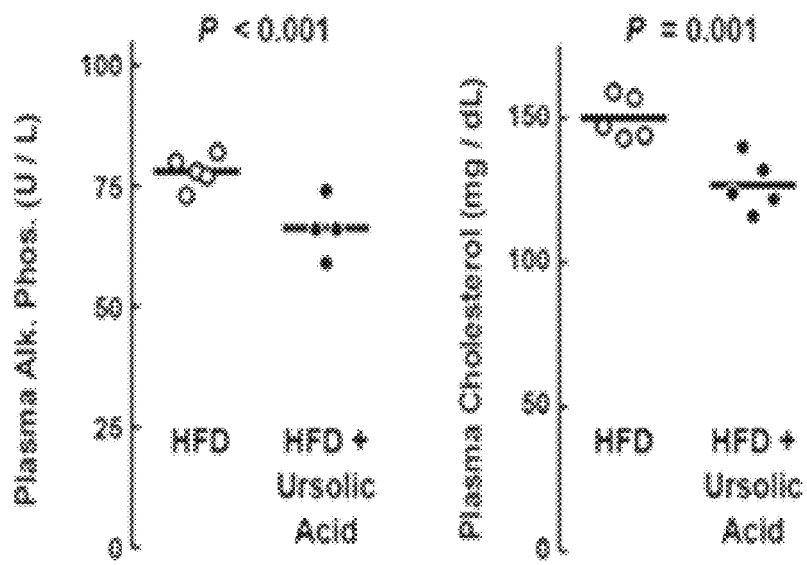

The study was carried out as follows: C57BL/6 mice were given ad libitum access to a high fat diet ("HFD"; Teklad TD.93075; 55% calories from fat) lacking or containing 0.27% ursolic acid. After 5 weeks, mice were fasted for 16 h before blood glucose was measured via the tail vein (FIG. 15A). Normal fasting blood glucose: ≤100 mg/dl. (B-I) After 7 weeks, liver and plasma were harvested for analysis (FIGS. 15B-15H). The data shown in FIG. 15A suggest that most mice fed HFD without ursolic acid for 6 weeks developed impaired fasting glucose (pre-diabetes) or diabetes. Importantly, this was prevented by ursolic acid (FIG. 15A). In addition, mice fed HFD without ursolic acid developed fatty liver disease, as evidenced by increased liver weight (>30% increase above normal mouse liver weight of 1500 mg; FIG. 15B), hepatocellular lipid accumulation (FIG. 15C, H&E stain at 20× magnification; FIG. 15D, lipid-staining osmium at 10× magnification), and elevated plasma liver function tests (FIG. 15E, AST; 15F, ALT; 15G, alkaline phosphatase (labeled as "Alk. Phos. in figure); and, 15H, cholesterol). However, ursolic acid prevented all of these hepatic changes (FIG. 15B-15G). In addition, ursolic acid reduced obesity-related hypercholesterolemia (FIG. 15H). In FIGS. 15A, 15B, and 15E-15H, each data point represents one mouse and horizontal bars denote the means.

12. Oleanolic Acid does not Increase Skeletal Muscle Mass.

Figure 16A:
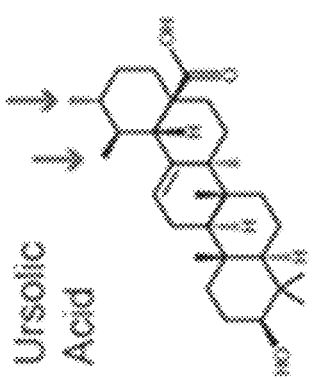

The effect of ursolic acid on skeletal muscle weight and liver weight was compared to the effects by oleanolic acid and metformin. Metformin was a compound identified from muscle atrophy signature-1, but not muscle atrophy signature-2. Oleanolic acid, like ursolic acid is a pentacyclic acid triterpane. This is a structurally similar compound to ursolic acid. However, the two compounds are distinct: oleanolic acid has two methyl groups at position 20, whereas ursolic acid has a single methyl group at each of positions 19 and 20 (compare FIGS. 16A and 16D). Both ursolic acid and oleanolic acid reduce blood glucose, adiposity and hepatic steatosis (Wang Z H, et al. (2010) *European journal of pharmacology* 628(1-3):255-260; Jayaprakasam B, et al. (2006) *J Agric Food Chem* 54(1):243-248; de Melo C L, et al. (2010) *Chem Biol Interact* 185(1):59-65). In addition, both ursolic acid and oleanolic acid possess a large number of cellular effects and biochemical targets, including nearly equivalent inhibition of protein tyrosine phosphatases ("PTPs"; see Zhang W, et al. (2006) *Biochimica et biophysica acta* 1760(10):1505-1512; Qian S, et al. (2010) *J Nat Prod* 73(11):1743-1750; Zhang Y N, et al. (2008) *Bioorg Med Chem* 16(18):8697-8705). However, the effects of these compounds on skeletal muscle mass were not known.

Because some PTPs (particularly PTP1B) dephosphorylate (inactivate) the insulin receptor, PTP inhibition represented a potential mechanism to explain ursolic acid-mediated enhancement of insulin signaling. Thus, because oleanolic acid and ursolic acid inhibit PTP1B and other PTPs with similar efficacy and potency in vitro (Qian S, et al. (2010) *J Nat Prod* 73(11):1743-1750; Zhang Y N, et al. (2008) *Bioorg Med Chem* 16(18):8697-8705), testing oleanolic acid's effects on skeletal mass tests the potential role of PTP inhibition. It should be noted that neither ursolic acid nor oleanolic acid is known to inhibit PTPs in vivo, and neither of these compounds are known to enhance IGF-I signaling. Moreover, ursolic acid's capacity to inhibit PTPs has been disputed based on ursolic acid's failure to delay insulin receptor de-phosphorylation in cultured cells (Jung S H, et al. (2007) *The Biochemical journal* 403(2):243-250), and ursolic acid's capacity to act as an insulin mimetic (Jung S H, et al. (2007) *The Biochemical journal* 403(2):243-250). In addition, global and muscle-specific PTP1B knockout mice do not possess increased muscle mass, although they are resistant to obesity and obesity-related disorders (Delibegovic M, et al. (2007) *Molecular and cellular biology* 27(21):7727-7734; Klaman L D, et al. (2000) *Molecular and cellular biology* 20(15):5479-5489). Furthermore, ursolic acid increases pancreatic beta cell mass and serum insulin levels in vivo, perhaps via its anti-inflammatory effects (Wang Z H, et al. (2010) *European journal of pharmacology* 628(1-3):255-260; Jayaprakasam B, et al. (2006) *J Agric Food Chem* 54(1):243-248; de Melo C L, et al. (2010) *Chem Biol Interact* 185(1):59-65). Importantly, inflammation is now recognized as a central pathogenic mechanism in muscle atrophy, metabolic syndrome, obesity, fatty liver disease and type 2 diabetes. Thus, the existing data suggest at least four mechanisms to explain ursolic acid's capacity to increase insulin signaling in vivo: PTP inhibition, direct stimulation of the insulin receptor, increased insulin production, and reduced inflammation. Of these four potential mechanisms, only the latter three have been demonstrated in vivo.

Figure 16B:
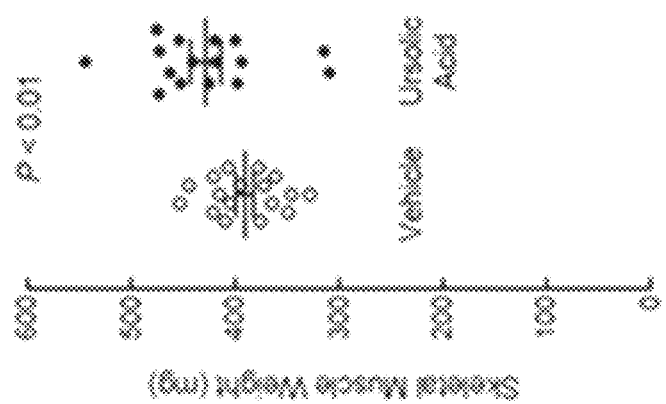
Figure 16C:
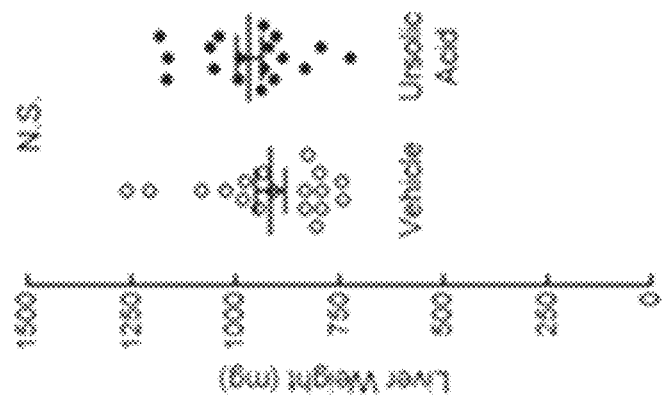
Figure 16I:
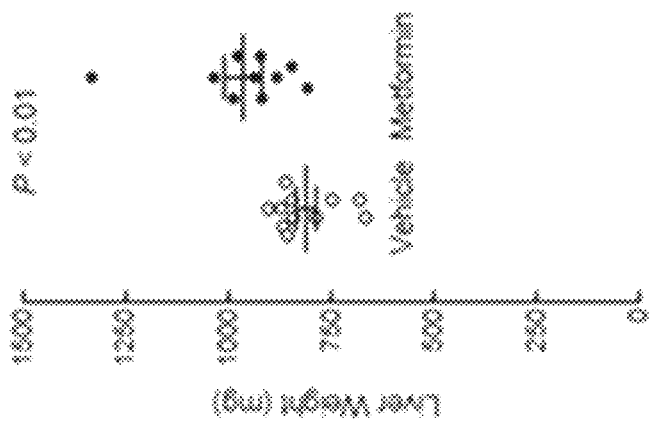
Figure 16H:
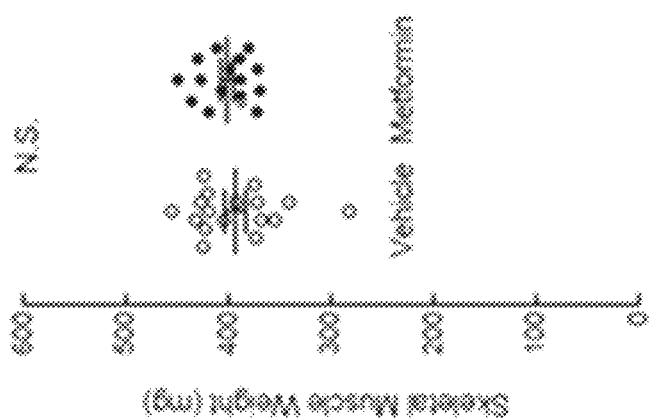
Figure 16G:
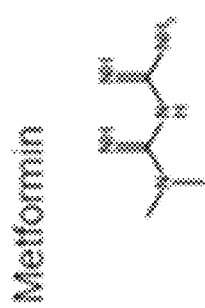

To compare the effects of ursolic acid and oleanolic acid on skeletal muscle and liver weight, C57BL/6 mice were administered ursolic acid (200 mg/kg), oleanolic acid (200 mg/kg), or vehicle alone (corn oil) via i.p. injection. Mice were then fasted, and after 12 hours of fasting, mice received a second dose of ursolic acid, oleanolic acid, or vehicle. After 24 hours of fasting, lower hindlimb skeletal muscles and liver were harvested and weighed. As shown previously, ursolic acid increased skeletal muscle weight (FIG. 16B), but not liver weight (FIG. 16C). In contrast, oleanolic acid increased liver weight (FIG. 16F), but not skeletal muscle weight (FIG. 16E). Interestingly, metformin (250 mg/kg) resembled oleanolic acid in biological effect: it increased liver weight (FIG. 16I), but not muscle weight (FIG. 16H). Without wishing to be bound by a particular theory, ursolic acid increases skeletal muscle and inhibit muscle atrophy by a pathway that does not involve PTP inhibition.

13. Targeted Inhibition of PTP1B does not Induce Skeletal Muscle Hypertrophy.

To further rule out the potential role of PTP1B inhibition in skeletal muscle hypertrophy, PTP1B expression was specifically reduced in mouse skeletal muscle by transfecting plasmid DNA constructed to express RNA interference constructs. Briefly, C57BL/6 mouse tibialis anterior muscles were transfected with 20 µg pCMV-miR-control (control plasmid transfected in the left TA) or either 20 µg pCMV-miR-PTP1B #1 (encoding miR-PTP1B #1; transfected in the right TA) or 20 µg pCMV-miR-PTP1B #2 (encoding miR-PTP1B #2; transfected in the right TA). miR-PTP1B #1 and miR-PTP1B #2 encode two distinct RNA interference (RNAi) constructs targeting distinct regions of PTP1B mRNA. Tissue was harvested 10 days following transfection.

Of note with regard to FIG. 17A, mRNA measurements were taken from the entire TA muscle. Because electroporation transfects only a portion of muscle fibers, the data underestimate PTP1B knockdown in transfected muscle fibers. In FIG. 17A, mRNA levels in the right TA were normalized to levels in the left TA, which were set at 1; data are means±SEM from 3 mice. In FIG. 17B, in each TA muscle, the mean diameter of >300 transfected fibers was determined; data are means±SEM from 3 TA muscles per condition. For both FIGS. 17A and 17B, P-values were determined with one-tailed paired t-tests.

Although both miR-PTP1B constructs reduced PTP1B mRNA (FIG. 17A), neither increased skeletal muscle fiber diameter (FIG. 17B). These data demonstrate that targeted PTP1B inhibition does not cause muscle fiber hypertrophy. Without wishing to be bound by a particular theory, ursolic acid does not increase skeletal muscle by inhibiting PTP1B.

14. Ursolic Acid Serum Levels Associated with Increased Muscle Mass and Decreased Adiposity.

To determine the dose-response relationship between dietary ursolic acid and muscle and adipose weight, C57BL/6 mice were fed standard chow containing varying amounts of ursolic acid for 7 weeks. Serum ursolic acid levels from mice were determined as described above. As shown previously in FIG. 12A, ursolic acid increased skeletal muscle weight and decreased weight of retroperitoneal and epididymal fat pads in a dose-dependent manner, but did not alter heart weight (FIG. 18A; data are means±SEM). These effects of ursolic acid were discernable at 0.035% ursolic acid and were maximal at doses ≥0.14% ursolic acid. Serum was collected from these same mice at the time of necropsy, and then measured random serum ursolic acid levels via ultra high performance liquid chromatography (UPLC). The data indicate that ursolic acid serum levels in the range of 0.25-0.5 µg/ml are sufficient to increase muscle mass and decrease adiposity (FIG. 18B; data are means±SEM). Of note, 0.5 µg/ml equals 1.1 µM ursolic acid, close to the dose used in the Connectivity Map (8.8 µM) and in the C2C12 experiments (10 µM) described above.

The data described herein indicate that ursolic acid reduced muscle atrophy and stimulated muscle hypertrophy in mice. Importantly, ursolic acid's effects on muscle were accompanied by reductions in adiposity, fasting blood glucose and plasma leptin, cholesterol and triglycerides, as well as increases in the ratio of skeletal muscle to fat, the amount of brown fat, the ratio of brown fat to white fat, and increased energy expenditure. Without wishing to be bound by a particular theory, ursolic acid reduced muscle atrophy and stimulated muscle hypertrophy by enhancing skeletal muscle IGF-I expression and IGF-I signaling, and inhibiting atrophy-associated skeletal muscle mRNA expression.

All of the compositions and/or methods disclosed and claimed herein can be made and executed without undue experimentation in light of the present disclosure. It will be apparent to those skilled in the art that various modifications and variations can be made in the present invention without departing from the scope or spirit of the invention. More specifically, certain agents which are both chemically and physiologically related can be substituted for the agents described herein while the same or similar results can be achieved. All such similar substitutes and modifications apparent to those skilled in the art are deemed to be within the spirit, scope and concept of the invention as defined by the appended claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

15. Treatment of Muscle Atrophy

Several compounds have been shown to treat muscle atrophy as shown below.

a. Betulinic Acid

Betulinic acid has the following structure:

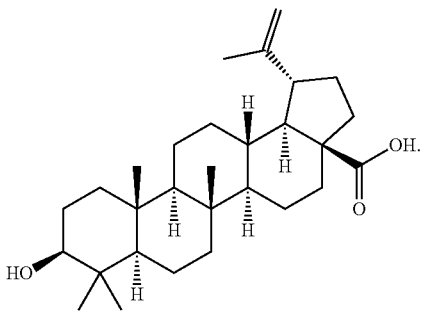

Figure 19A:
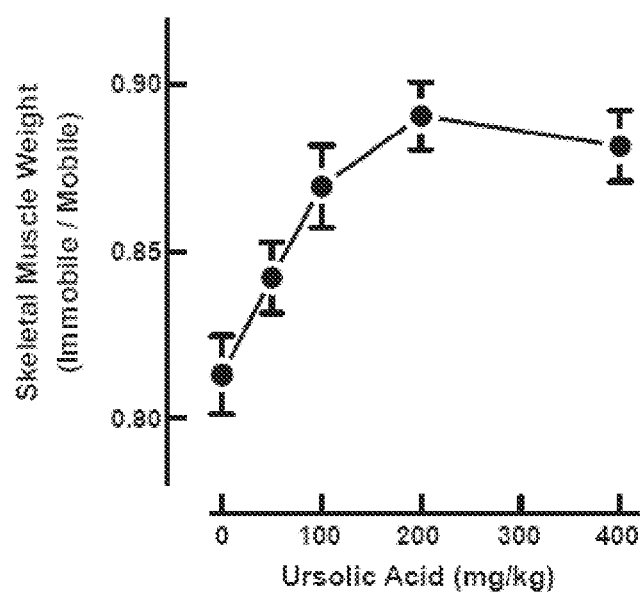
FIGS. 19A and 19B show that betulinic acid, like ursolic acid, reduces immobilization-induced skeletal muscle atrophy. Mice were administered vehicle (corn oil) or the indicated concentration of ursolic acid (A) or betulinic acid (B) via intraperitoneal injection twice a day for two days. One tibialis anterior (TA) muscle was immobilized with a surgical staple, leaving the contralateral mobile TA as an intrasubject control. Vehicle, or the same dose of ursolic acid or betulinic acid was administered via i.p. injection twice daily for six days before comparing weights of the immobile and mobile TAs. Data are means±SEM from 9-10 mice per condition. A, ursolic acid dose-response relationship. B, betulinic acid dose-response relationship.
Figure 19B:
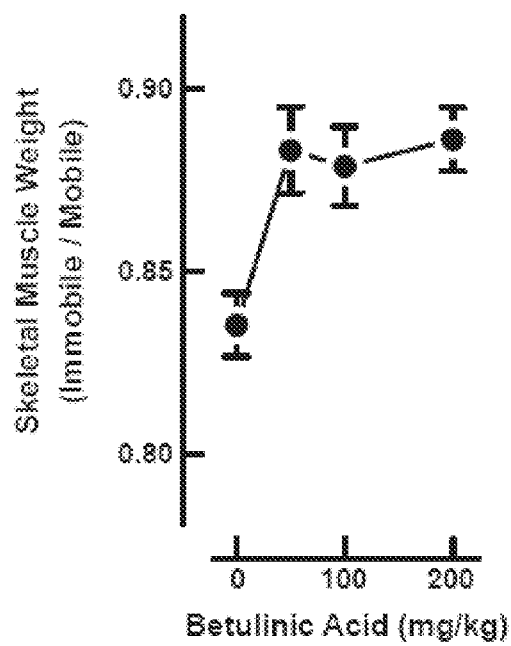

The mRNA expression signature of betulinic acid negatively correlated to human muscle atrophy signature-2. Therefore betulinic acid, like ursolic acid, could inhibit skeletal muscle atrophy. To test this, a mouse model of immobilization-induced skeletal muscle atrophy was used: mice were administered vehicle (corn oil) or varying doses of ursolic acid (positive control) or betulinic acid via intraperitoneal injection twice a day for two days. One tibialis anterior (TA) muscle was immobilized with a surgical staple, leaving the contralateral mobile TA as an intrasubject control. The vehicle or the same dose of ursolic acid or betulinic acid was continuously administered via i.p. injection twice daily for six days before comparing weights of the immobile and mobile TAs. As expected, immobilization caused muscle atrophy, and ursolic acid reduced muscle atrophy in a dose-dependent manner, with maximal inhibition at 200 mg/kg (FIG. 19A). Betulinic acid also reduced muscle atrophy in a dose-dependent manner, with maximal inhibition at ≤50 mg/kg (FIG. 19B). These data indicate that betulinic acid reduces immobilization-induced muscle atrophy, and it is more potent than ursolic acid.

b. Naringenin

Naringenin has the following structure:

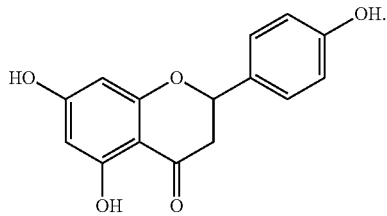 [SMILES: O=C1CC(c2ccc(O)cc2)Oc2cc(O)cc(O)c21]

Figure 20:
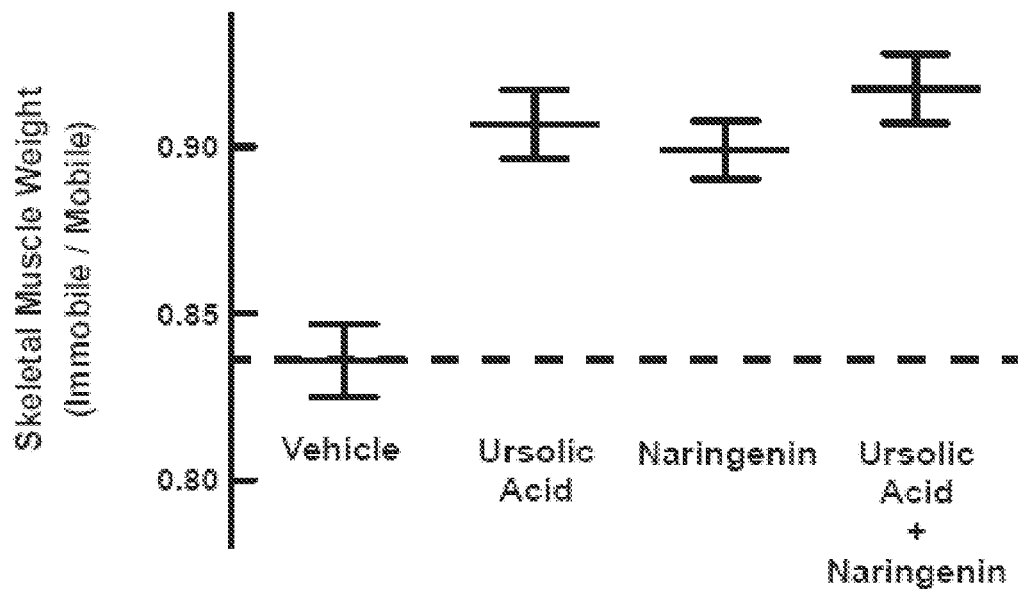
FIG. 20 shows that naringenin reduces immobilization-induced skeletal muscle atrophy. Mice were administered vehicle (corn oil), ursolic acid (200 mg/kg), naringenin (200 mg/kg) or ursolic acid plus naringenin (both at 200 mg/kg) via intraperitoneal injection twice a day for two days. One tibialis anterior (TA) muscle was immobilized with a surgical staple, leaving the contralateral mobile TA as an intrasubject control. Vehicle, or the same dose of ursolic acid and/or naringenin was administered via i.p. injection twice daily for six days before comparing weights of the immobile and mobile TAs. Data are means±SEM from 9-10 mice per condition.

The mRNA expression signature of naringenin negatively correlated to human muscle atrophy signatures-1 and -2. Therefore naringenin could inhibit skeletal muscle atrophy. To test this, mice were administered vehicle (corn oil), ursolic acid (200 mg/kg), naringenin (200 mg/kg), or the combination of ursolic acid and naringenin (each at 200 mg/kg) via i.p injection twice a day for two days. One tibialis anterior (TA) muscle was immobilized with a surgical staple, leaving the contralateral mobile TA as an intrasubject control. Vehicle or the same doses of ursolic acid and/or naringenin was continuously administered via i.p. injection twice daily for six days before comparing weights of the immobile and mobile TAs. Like ursolic acid, naringenin reduced muscle atrophy (FIG. 20). The combination of ursolic acid and naringenin also reduced muscle atrophy, but not more than either compound alone (FIG. 20). These data indicate that naringenin reduces skeletal muscle atrophy.

Figure 21A:
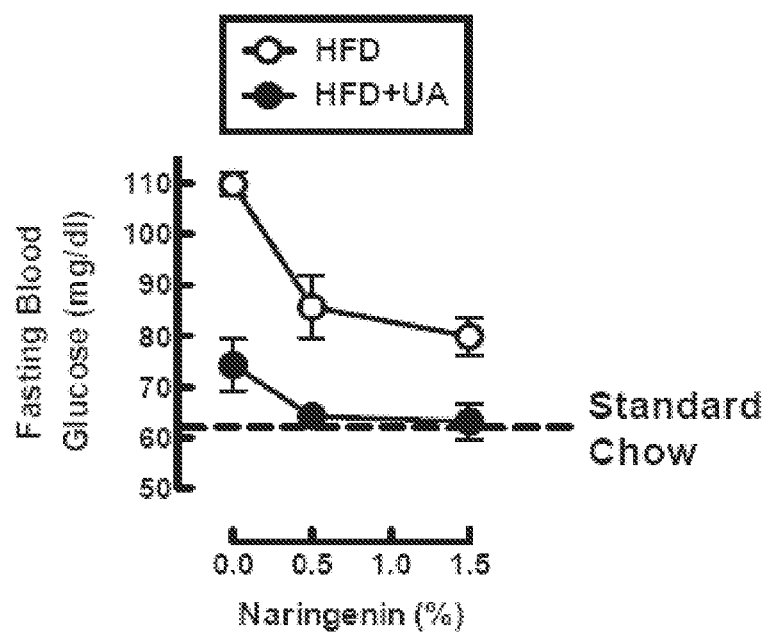
FIGS. 21A-21F show that the combination of ursolic acid and naringenin normalizes fasting blood glucose levels in a mouse model of glucose intolerance, obesity and fatty liver disease. Mice were fed standard chow, high fat diet (HFD) plus the indicated concentrations of naringenin, or HFD containing 0.15% ursolic acid (UA) plus the indicated concentrations of naringenin for 5 weeks before measurement of fasting blood glucose (A), total body weight (B), fat mass by NMR (C), liver weight (D), grip strength (E) and skeletal muscle weight (bilateral tibialis anterior, gastrocnemius, soleus, quadriceps and triceps muscle; F). Dashed line indicates levels in control mice that were fed standard chow. Open symbols indicate levels in mice fed HFD containing the indicated concentrations of naringenin. Closed symbols indicate levels in mice fed HFD containing 0.15% UA plus the indicated concentrations of naringenin. Data are means±SEM from ≥12 mice per condition.
Figure 21B:
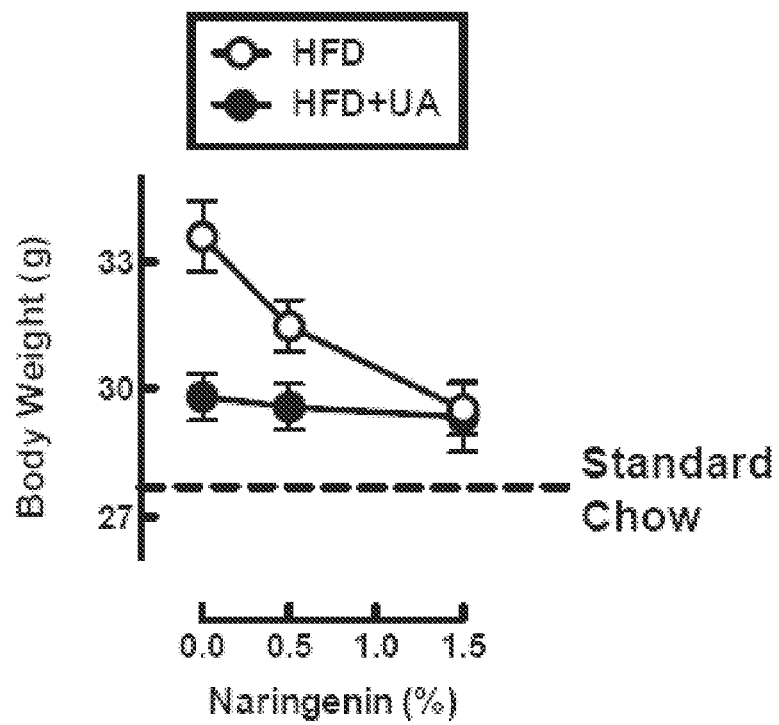
Figure 21C:
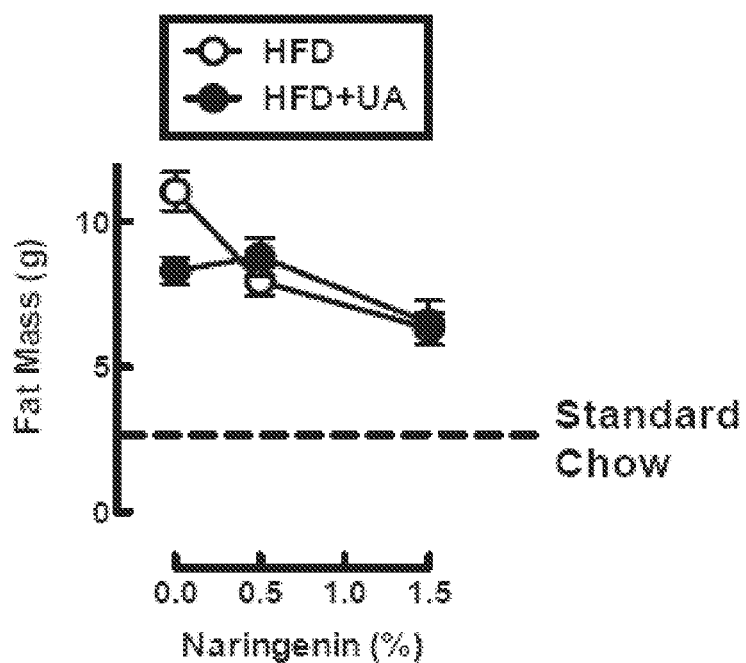
Figure 21D:
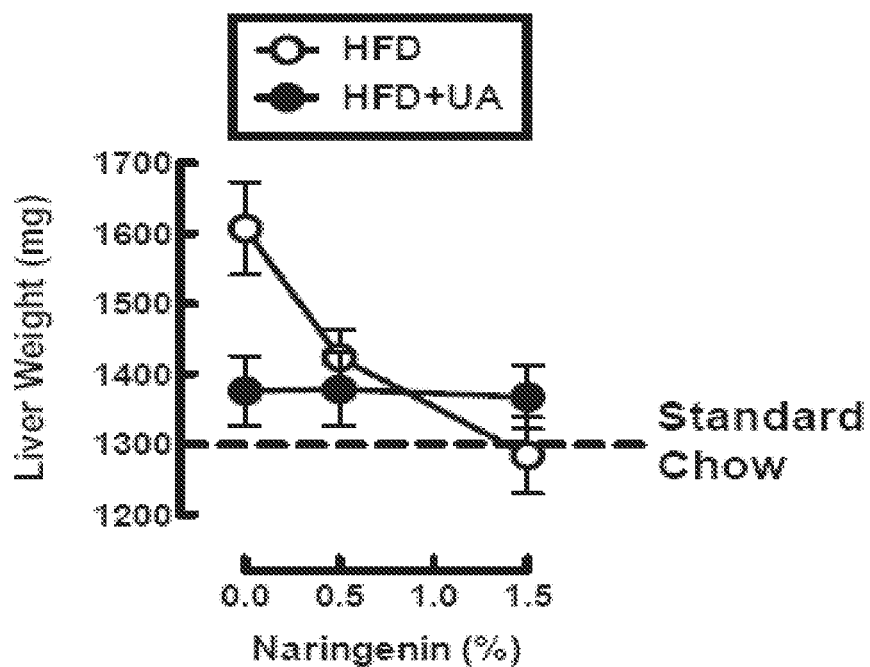
Figure 21E:
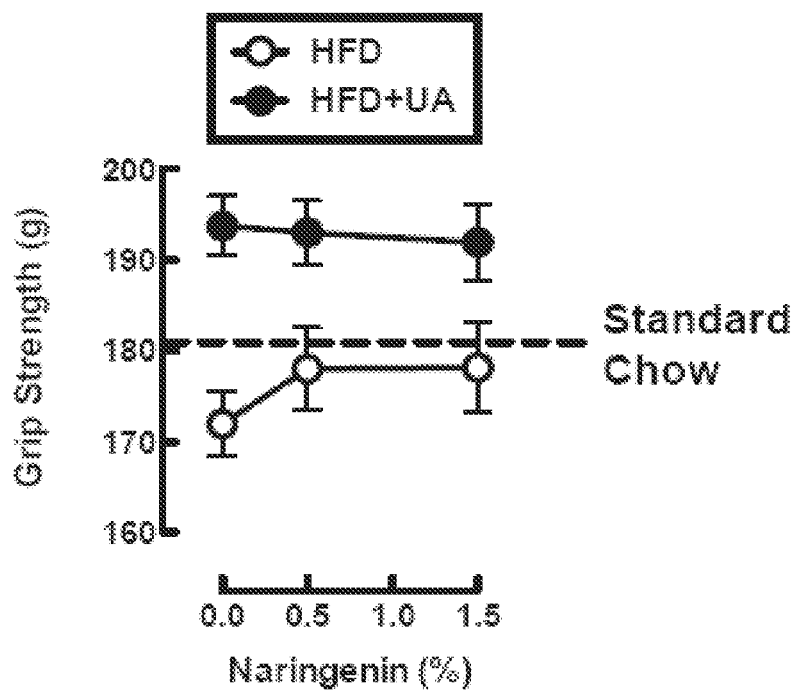
Figure 21F:
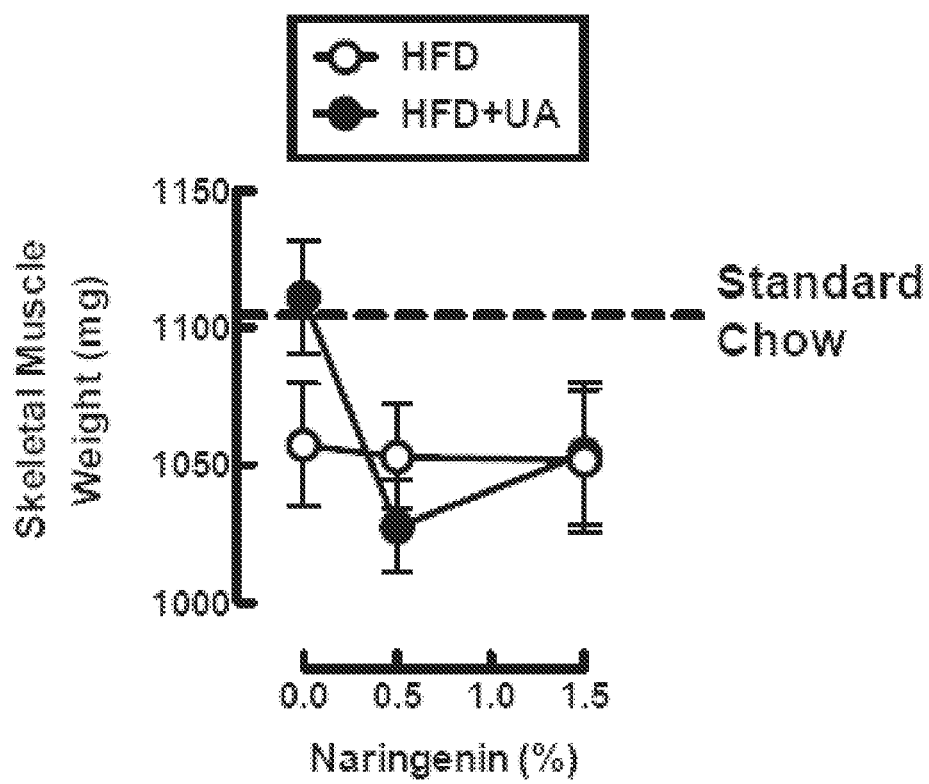

Like ursolic acid, naringenin reduces blood glucose, as well as obesity and fatty liver disease. Therefore ursolic acid and naringenin could have additive effects. To determine this, weight-matched mice were provided ad libitum access to standard (Harlan Teklad formula 7013), high fat diet (HFD; Harlan Teklad formula TD93075), or HFD containing varying concentrations of ursolic acid (0.15%) and/or naringenin (0.5% or 1.5%). After the mice consumed these diets for 5 weeks, fasting blood glucose, total body weight, fat mass, liver weight, grip strength, and skeletal muscle weight was measured. As expected, HFD increased blood glucose, and this increase in blood glucose was partially prevented by ursolic acid and naringenin (FIG. 21A). The combination of ursolic acid plus either dose of naringenin reduced blood glucose more than either compound alone, and it restored blood glucose to normal levels (FIG. 21A). Importantly, ursolic acid and naringenin did not have additive effects on total body weight (FIG. 21B), fat mass (FIG. 21C), liver weight (FIG. 21D), grip strength (FIG. 21E), or skeletal muscle weight (FIG. 21F). In addition, ursolic acid increased strength to a greater extent than naringenin (FIG. 21E), and ursolic acid, but not naringenin, increased muscle weight (FIG. 21F). These differences between ursolic acid and naringenin in high fat fed mice indicates that ursolic acid and naringenin have differences in their mechanisms of action, which could explain their additive effects on fasting blood glucose.

c. Tomatidine

Tomatidine has the following structure:

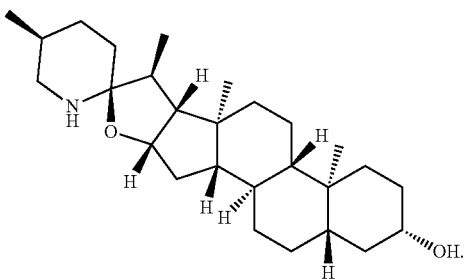 [SMILES: C[C@H]1CC[C@]2(NC1)O[C@H]1C[C@H]3[C@@H]4CC[C@H]5C[C@@H](O)CC[C@]5(C)[C@H]4CC[C@]3(C)[C@H]1[C@@H]2C]

Figure 22A:
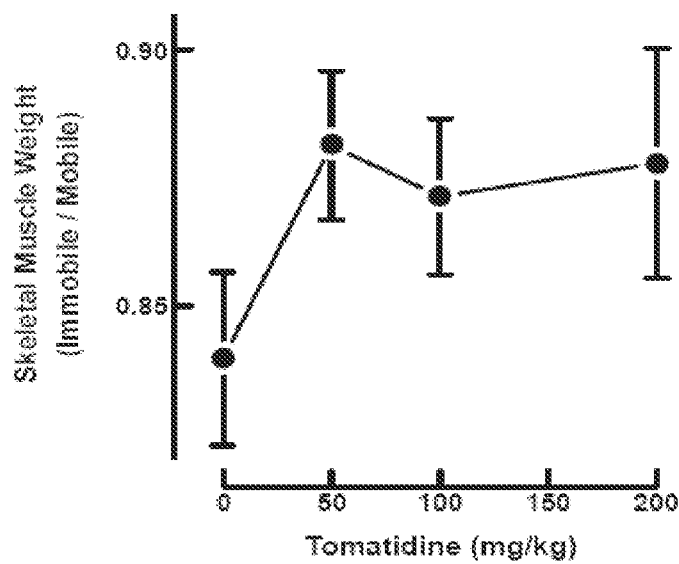
FIGS. 22A and 22B show that tomatidine reduces immobilization-induced muscle atrophy. Mice were administered vehicle (corn oil) or the indicated concentration of tomatidine via intraperitoneal injection twice a day for two days. One tibialis anterior (TA) muscle was immobilized with a surgical staple, leaving the contralateral mobile TA as an intrasubject control. Vehicle, or the same dose of tomatidine was administered via i.p. injection twice daily for six days before comparing weights of the immobile and mobile TAs. Data are means±SEM from 9-10 mice per condition. A, effects of 50, 100 and 200 mg/kg tomatidine. B, effects of 5, 15 and 50 mg/kg tomatidine.
Figure 22B:
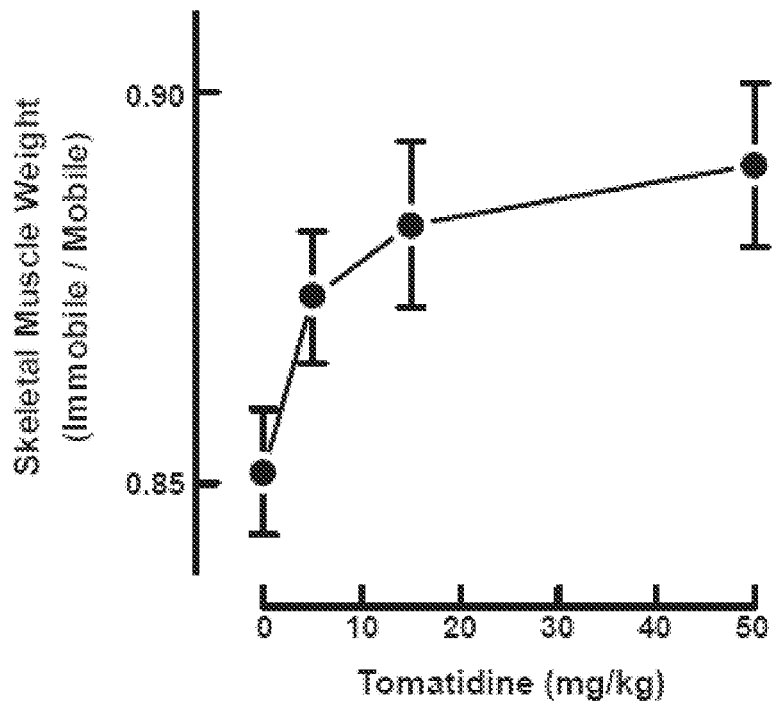

The mRNA expression signature of tomatidine negatively correlated to human muscle atrophy signatures-1 and -2. Therefore tomatidine could inhibit skeletal muscle atrophy. To test this, mice were administered vehicle (corn oil) or tomatidine (50, 100 or 200 mg/kg) via i.p injection twice a day for two days. One tibialis anterior (TA) muscle was immobilized with a surgical staple, leaving the contralateral mobile TA as an intrasubject control. Vehicle or the same doses of tomatidine was administered via i.p. injection twice daily for six days before comparing weights of the immobile and mobile TAs. All 3 doses of tomatidine reduced muscle atrophy, and the effect was maximal at 50 mg/kg (FIG. 22A). The same protocol was used to compare the effects of vehicle (corn oil) and tomatidine (5, 15 or 50 mg/kg) on immobilization-induced muscle atrophy. Tomatidine reduced muscle atrophy in dose-dependent manner, with maximal effect at 50 mg/kg and EC50<5 mg/kg (FIG. 22B). These data indicate that tomatidine reduces immobilization-induced muscle atrophy, and it is more potent than ursolic acid.

Figure 23A:
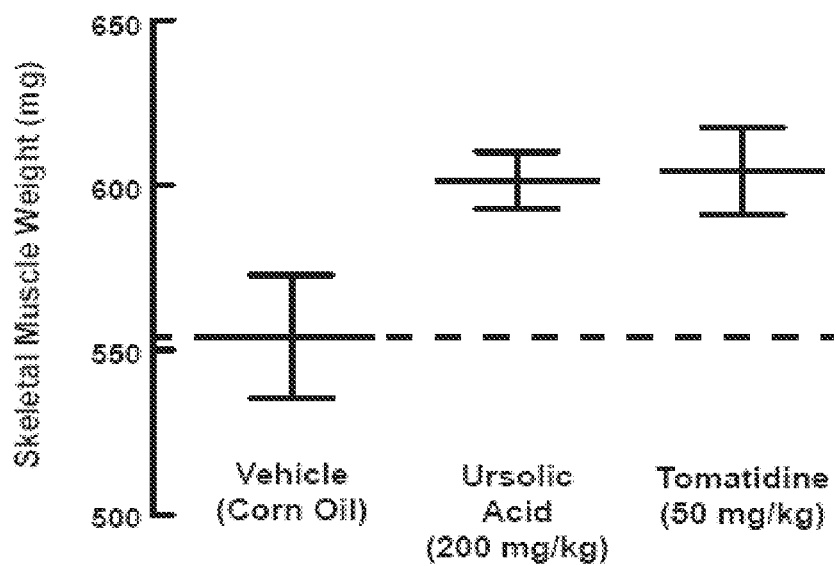
FIGS. 23A and 23B show that tomatidine reduces fasting-induced muscle atrophy. Data are means±SEM from 9-12 mice per condition. Food was withdrawn from mice, and then vehicle (corn oil), or the indicated concentrations of ursolic acid or tomatidine, were administered by i.p. injection. Twelve hours later, mice received another i.p. injection of vehicle or the same dose of ursolic acid or tomatidine. Twelve hours later, skeletal muscles (bilateral tibialis anterior, gastrocnemius, soleus, quadriceps muscles) were harvested and weighed. A, comparison of 200 mg/kg ursolic acid and 50 mg/kg tomatidine. B, effects of 5, 15 and 50 mg/kg tomatidine.
Figure 23B:
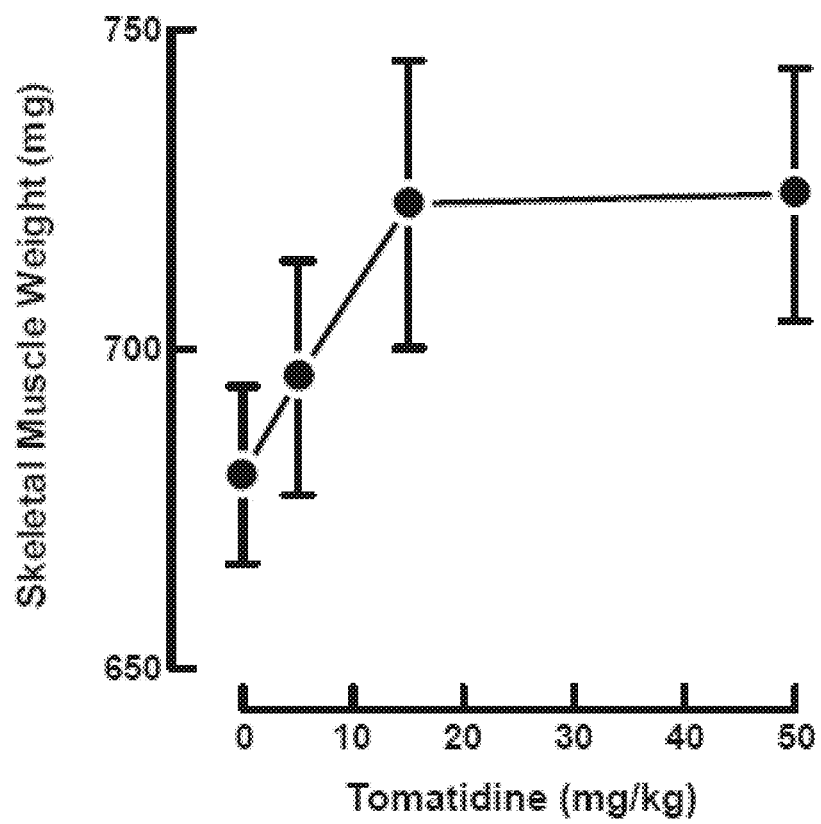

Tomatidine could also inhibit skeletal muscle atrophy induced by fasting. To test this, food was withdrawn from mice, and then vehicle, ursolic acid (200 mg/kg) or tomatidine (50 mg/kg) were administered by i.p. injection. Twelve hours later, mice received another i.p. injection of vehicle or the same dose of ursolic acid or tomatidine. Twelve hours later, skeletal muscles were harvested and weighed. Both ursolic acid and tomatidine increased skeletal muscle, indicating decreased fasting-induced skeletal muscle atrophy (FIG. 23A). We next used the same protocol to compare the effects of vehicle (corn oil) and tomatidine (5, 15 and 50 mg/kg). Tomatidine reduced muscle atrophy in dose-dependent manner, with maximal effect at 50 mg/kg and EC50 between 5 and 15 mg/kg (FIG. 23B).

d. Allantoin, Tacrine, Ungerine, Hippeastrine and Conessine

Allantoin has the following structure:

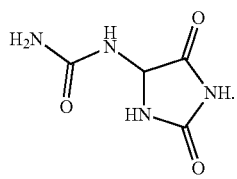 [SMILES: NC(=O)NC1NC(=O)NC1=O]

Tacrine has the following structure:

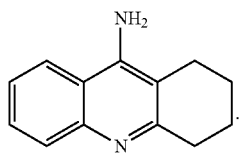 [SMILES: Nc1c2c(nc3ccccc13)CCCC2]

Ungerine has the following structure:

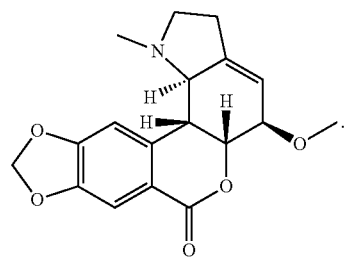

Hippeastrine has the following structure:

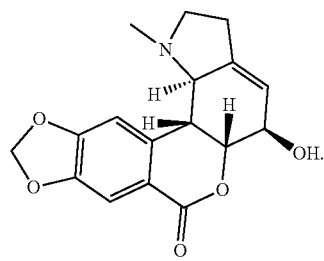

Conessine has the following structure:

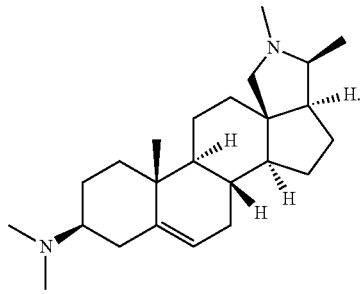

Figure 24:
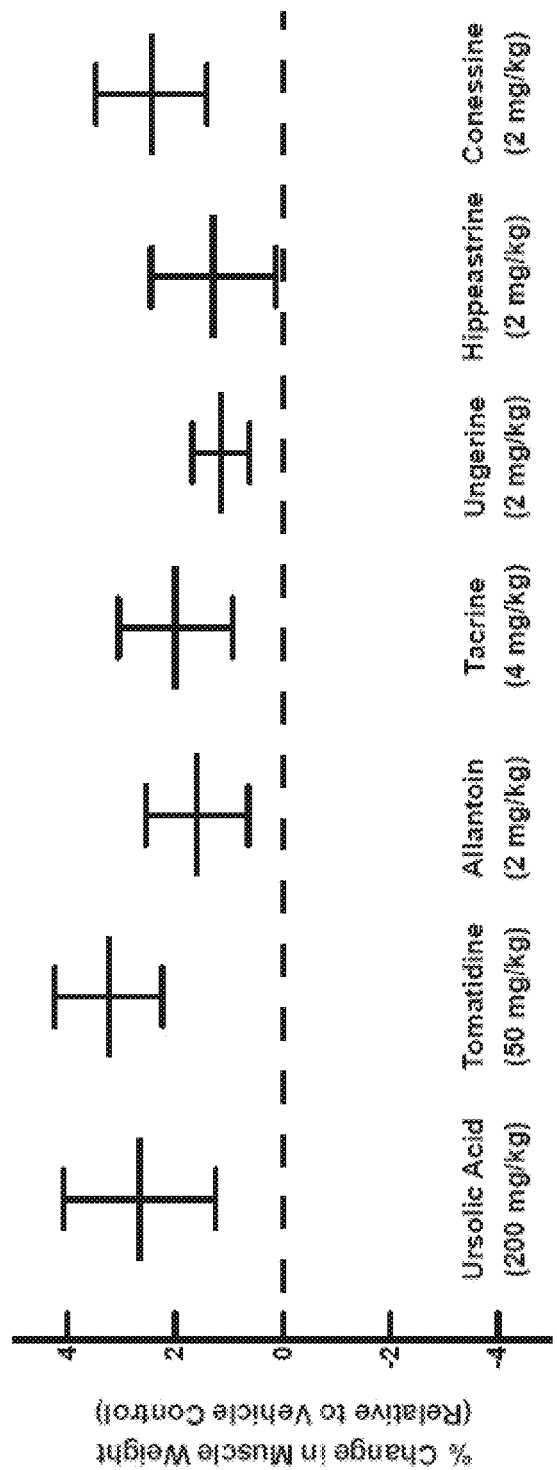
FIG. 24 shows that allantoin, tacrine, ungerine, hippeastrine and conessine reduce fasting-induced muscle atrophy. Food was withdrawn from mice, and then vehicle or the indicated dose of ursolic acid, tomatidine, allantoin, tacrine, ungerine, hippeastrine or conessine was administered by i.p. injection. Twelve hours later, mice received another i.p. injection of vehicle or the same dose of ursolic acid, tomatidine, allantoin, tacrine, ungerine, hippeastrine or conessine. Twelve hours later, skeletal muscles (bilateral tibialis anterior, gastrocnemius and soleus muscles) were harvested and weighed. Data are means±SEM from ≥9 mice per condition and show the percent change in skeletal muscle weight relative to vehicle-treated animals in the same experiment. The vehicle for ursolic acid, tomatidine, ungerine, hippeastrine and conessine was corn oil. The vehicle for tacrine and allantoin was saline.

The mRNA expression signatures of allantoin, tacrine, ungerine (Prestwick-689), hippeastrine (Prestwick-675) and conessine also negatively correlated to human muscle atrophy signatures-1 and -2. Therefore these compounds could inhibit skeletal muscle atrophy. To test this, the fasting-induced muscle atrophy model described above was used to compare the effects of ursolic acid (200 mg/kg), tomatidine (50 mg/kg), allantoin (2 mg/kg), tacrine (4 mg/kg), ungerine (2 mg/kg), hippeastrine (2 mg/kg) and conessine (2 mg/kg). Like ursolic acid and tomatidine, allantoin, tacrine, ungerine, hippeastrine and conessine increased muscle weight in fasted mice (FIG. 24), indicating that these compounds decrease skeletal muscle atrophy.

Figure 25:
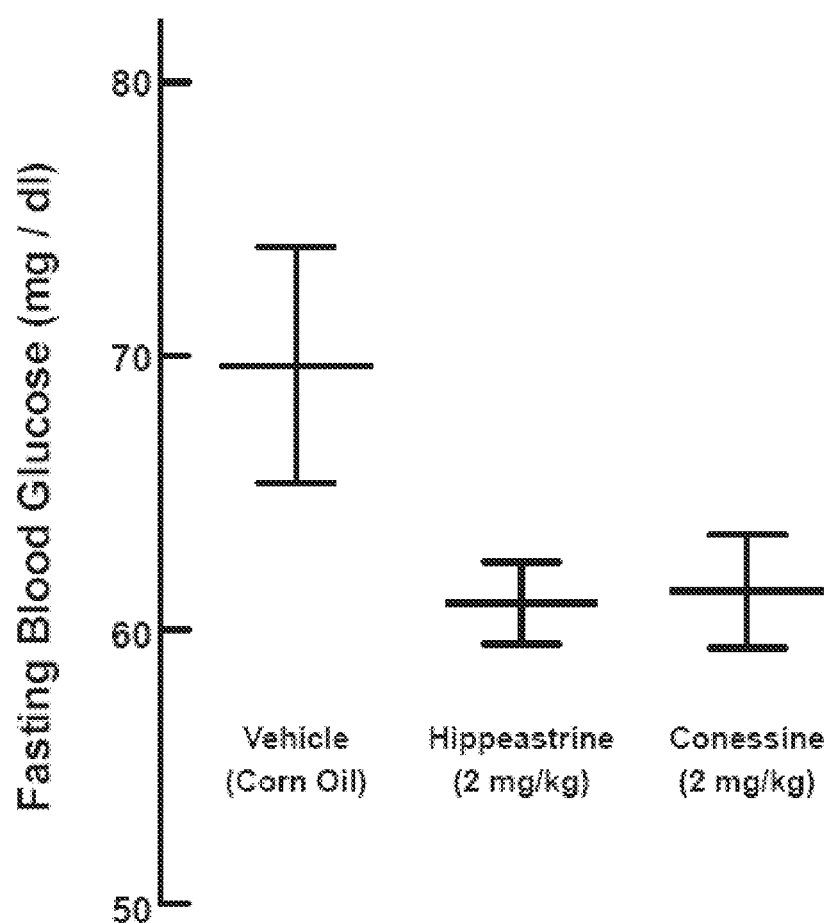
FIG. 25 shows that hippeastrine and conessine reduce fasting blood glucose. Food was withdrawn from mice, and then vehicle or the indicated dose of hippeastrine or conessine was administered by i.p. injection. Twelve hours later, mice received another i.p. injection of vehicle or the same dose of hippeastrine or conessine. Twelve hours later, blood glucose was measured via tail vein. Data are means±SEM from ≥9 mice per condition.

Since ursolic acid and naringenin reduced fasting blood glucose, hippeastrine (2 mg/kg) and conessine (2 mg/kg) could have a similar effect. Hippeastrine and conessine reduced fasting blood glucose (FIG. 25).

16. Prophetic Synthesis of Tacrine and Analogs

The formulas disclosed herein could be synthesized by reacting an anthranilonitrile derivative with a cyclohexanone derivative in the presence of zinc chloride (Proctor et al., *Curr Medici. Chem.*, 2000, 7, 295-302). Such reaction is shown in Scheme 1A.

SCHEME 1A

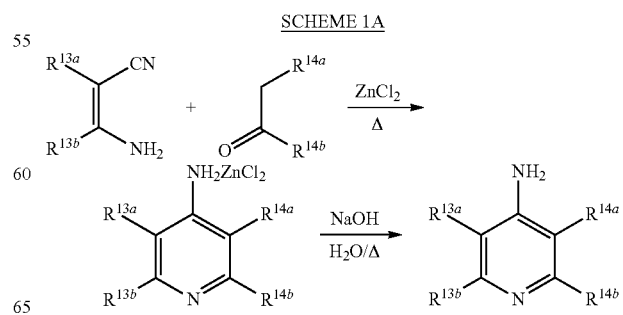

Thus, tacrine can be synthesized as shown in scheme 1B.

SCHEME 1B

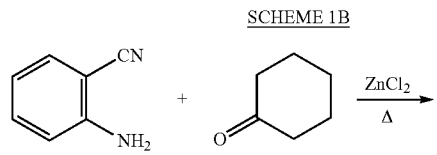

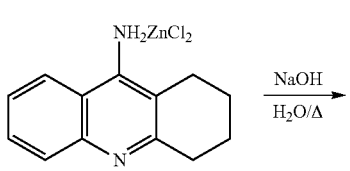

The formulas disclosed herein could also be synthesized by reacting an t-cyanocyclonones with a vide variety of anilines using either TiCl$_4$ or AlCl$_3$ as reagents (Proctor et al., *Curr Medici. Chem.*, 2000, 7, 295-302). An example of such reaction is shown in Scheme 1C.

SCHEME 1C

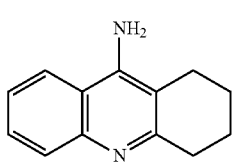

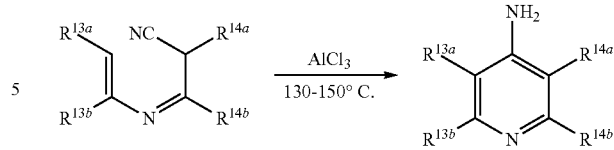

Thus, tacrine could be synthesized as shown in scheme 1D.

SCHEME 1D

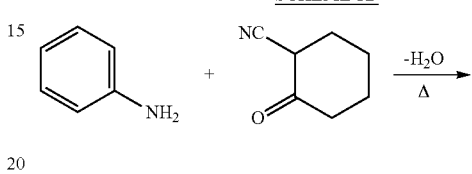

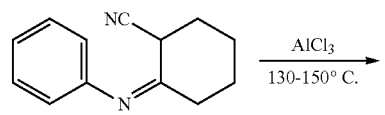

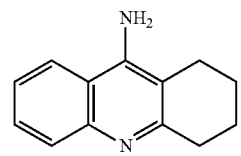

17. Prophetic Synthesis of Naringenin and Analogs

The disclosed formulas could be synthesized as described in PCT application WO 2007/053915 by De Keukkeleire et al. which is hereby incorporated in its entirety by reference. In another example, Glucoyl substituted naringenin could be extracted as described in U.S. Pat. No. 6,770,630 by Kashiwaba et al. which is hereby incorporated in its entirety by reference. As described by De Keukkeleire et al. the disclosed formulas could be synthesized as shown in Scheme 2A:

SCHEME 2A

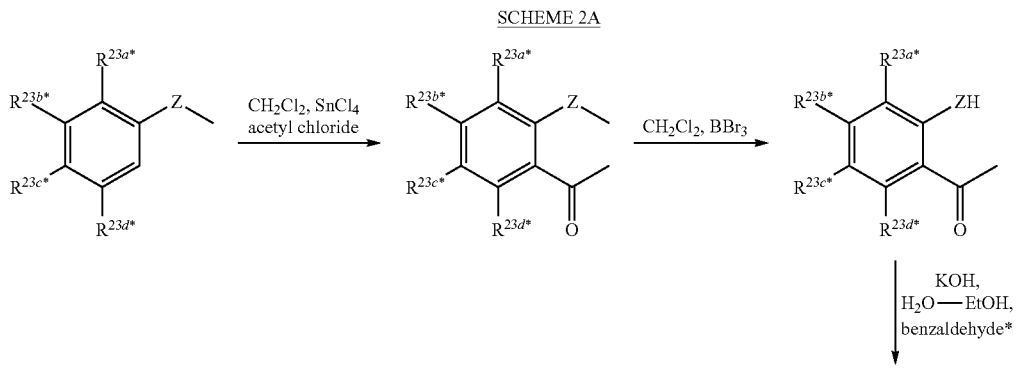

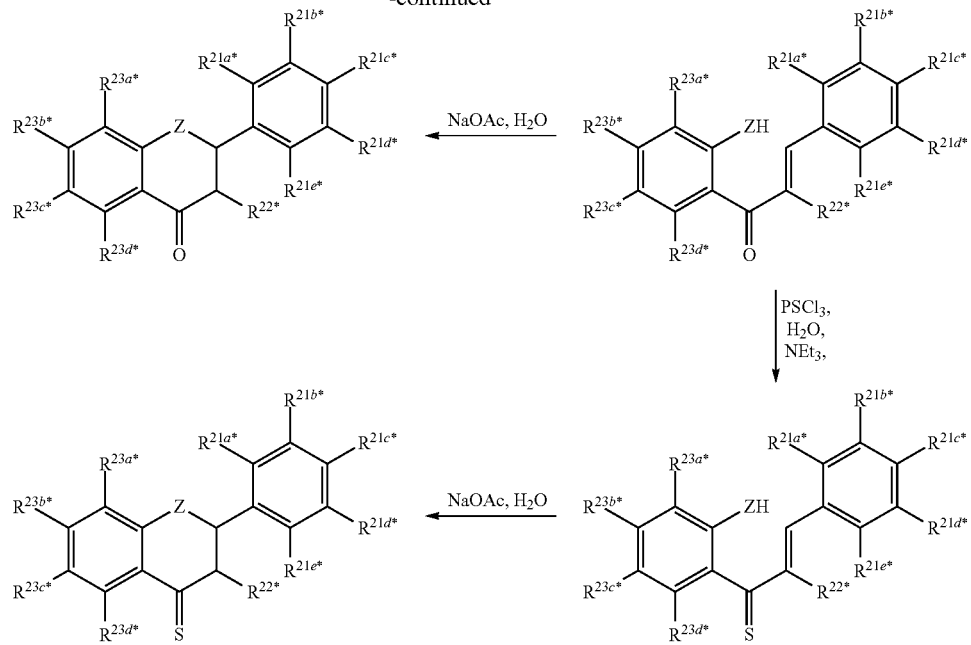
The formation of the thioketone was described by Pathak, et al. (*J. Org. Chem.*, 2008, 73, 2890-2893). The * in the scheme denotes moieties that is or can be converted, using known chemistry, into the disclosed R moieties. For example, the synthesis of naringenin is shown in Scheme 2B.
SCHEME 2B
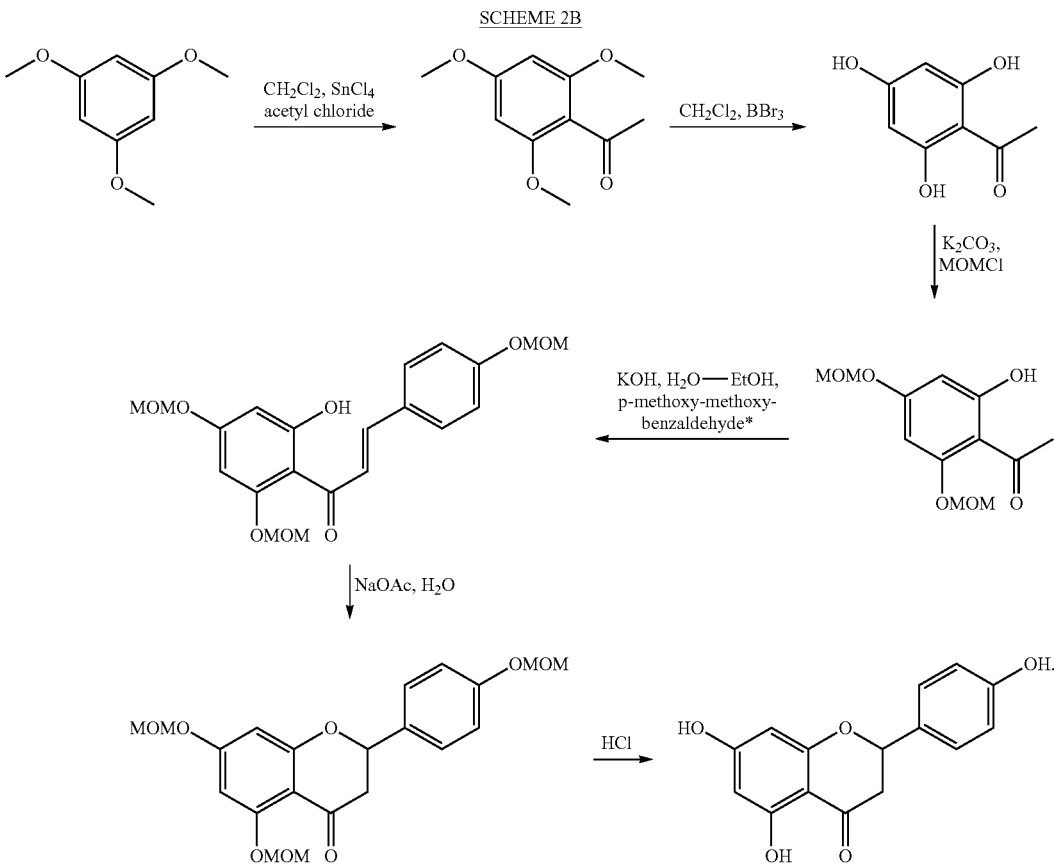

18. Prophetic Synthesis of Allantoin and Analogs

The disclosed formulas could be made using a variety of chemistry known in the art. For example, one set of the disclosed formulas could be made as shown in Scheme 3A and as described in U.S. Pat. No. 4,647,574 by Ineaga et al, which is hereby incorporated herein by reference in its entirety.

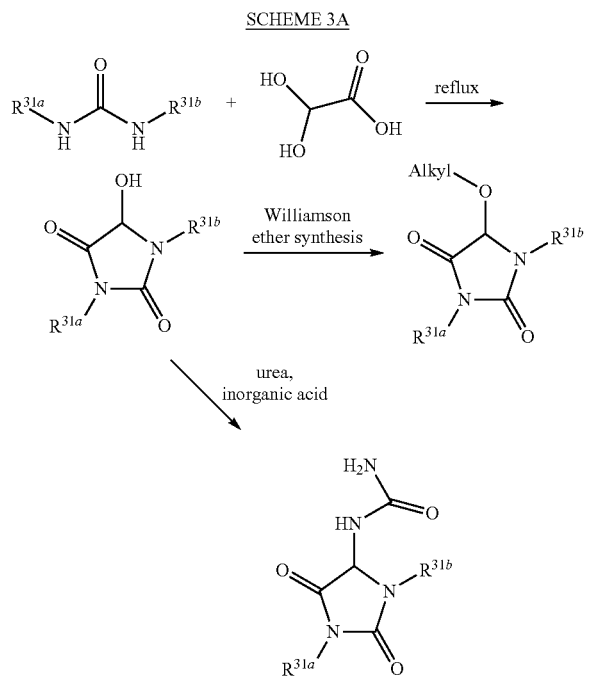

Allantoin could be prepared as described in U.S. Pat. No. 5,196,545 by Schermanz, which is hereby incorporated herein by reference in its entirety, and as shown in Scheme 3B.

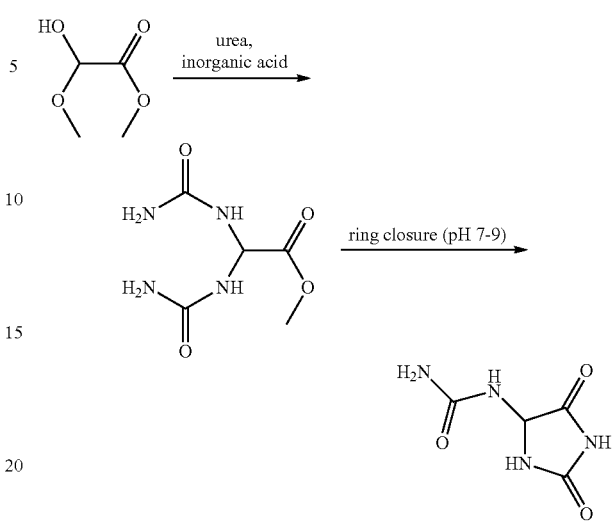

A comprehensive guide for how to make the disclosed formulas can be found in Kirk-Othmer Encyclopedia of Chemical Technology under the chapter Hydantoin and Its Derivatives by Avendafio et al (2000), which is hereby incorporated herein by reference in its entirety.

19. Prophetic Synthesis of Conessine and Analogs

Conessine is a steroid alkaloid found in plant species from the Apocynaceae family, for example in *Holarrhena floribunda*. Conessine derivatives could be prepared as described in U.S. Pat. Nos. 3,539,449, 3,466,279, and 3,485,825 by Marx, which are hereby incorporated by reference in their entirety. As described in U.S. Pat. Nos. 3,539,449, 3,466,279, and 3,485,825 by Marx, conessine derivatives could be prepared using microorganisms such as the fungus *Stachybotrys parvispora* and enzymes from *Gloeosporium, Colletotrichum*, and *Myrothecium*. For example, see Scheme 4A.

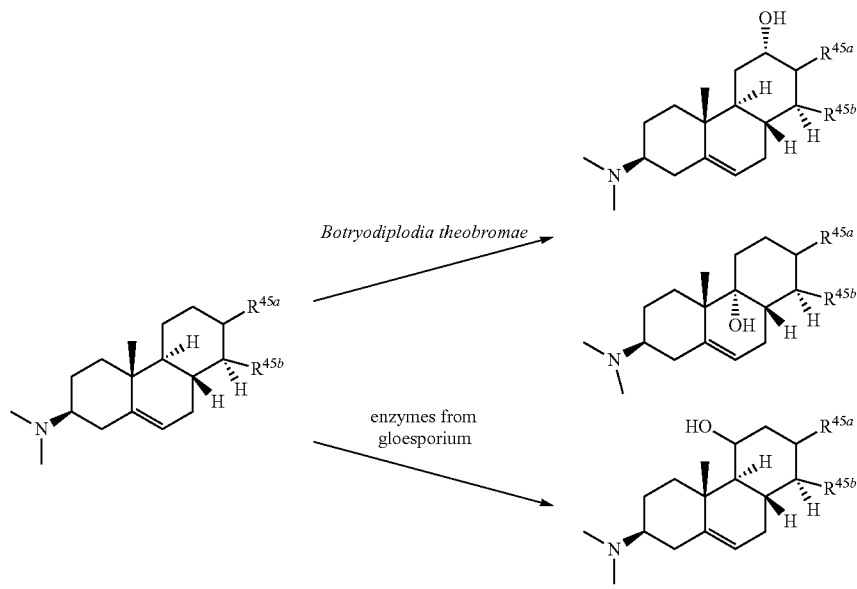

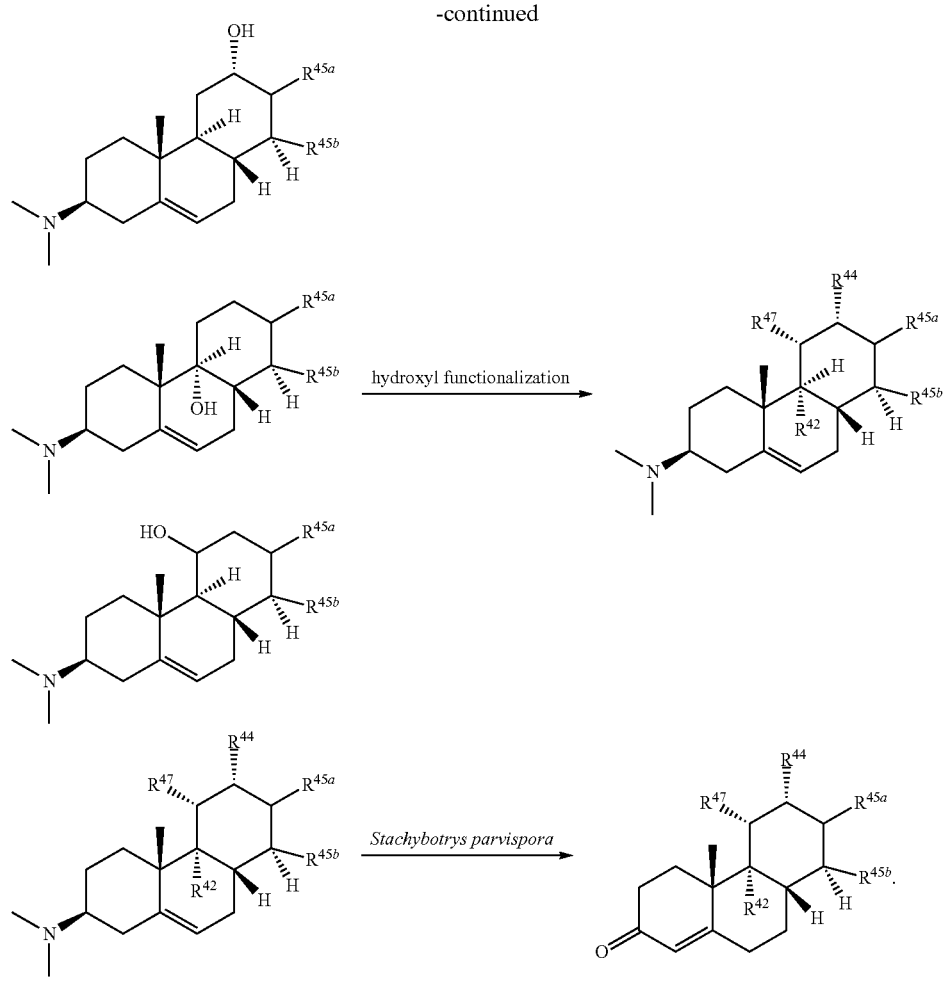

The conessine oxo derivatives could be further modified via a reduction and subsequent chemistry known to one skilled in the art, as shown in Scheme 4B.

SCHEME 4B

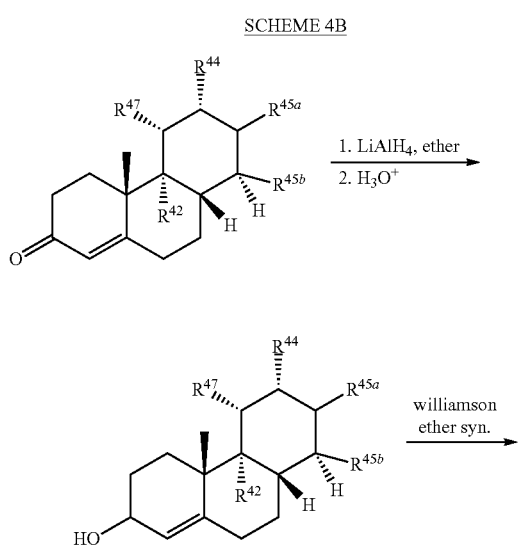

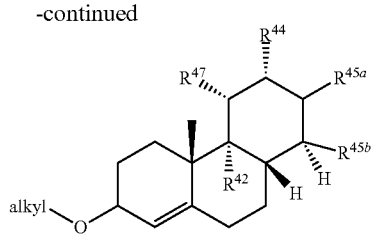

The hydroxyl functionality could undergo a number of chemical reactions known in the art. One example, as shown in Scheme 4B, is a Williamson ether synthesis.

Conessine derivatives could be prepared synthetically as described in U.S. Pat. No. 2,910,470, which is hereby incorporated by reference in its entirety. Conessine derivatives are also described in WO 2011/046978 by Orlow, which is hereby incorporated by reference in its entirety. Synthesis of the disclosed formulas is also described in U.S. Pat. No. 3,625,941 by Pappo, which is hereby incorporated in its entirety by reference.

20. Prophetic Synthesis of Tomatidine and Analogs

The formulas disclosed herein could be synthesized by the method disclosed by Uhle, and Moore, *J. Am. Chem. Soc.* 76, 6412 (1954); Uhle, *J. Am. Chem. Soc.* 83, 1460 (1961); and Kessar et al., *Tetrahedron* 27, 2869 (1971), which are all hereby incorporated by reference in their entirety. The disclosed compounds can also be made as shown in Scheme 5A.

SCHEME 5A
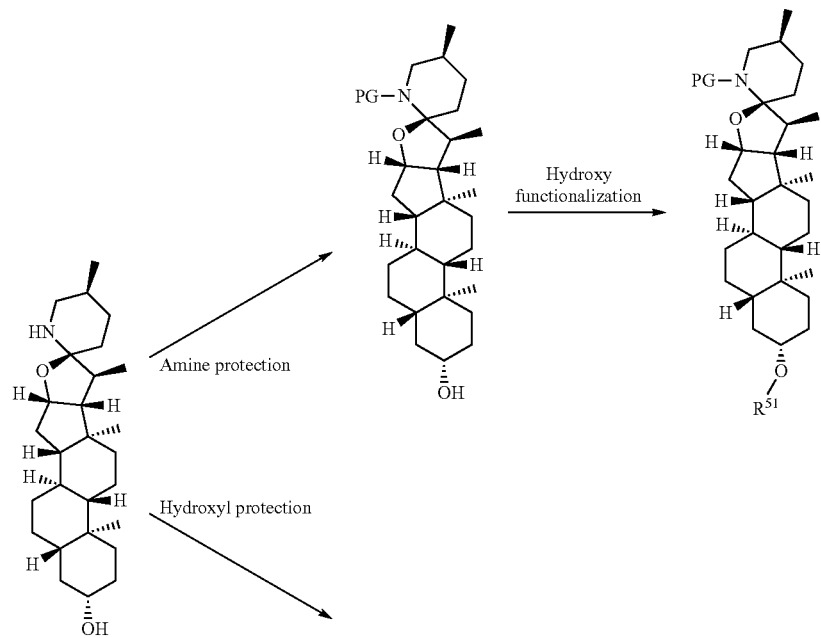
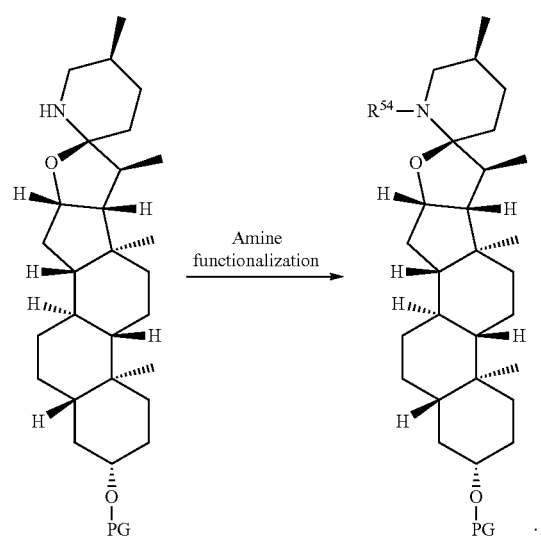

21. Prophetic Synthesis of Hippeastrine/Ungerine and Analogs
The disclosed formulas can be synthesized by method disclosed by Mafias et al. (*J. Am. Chem. Soc.* 2010, 132, 5176-78), which is hereby incorporated by reference in its entirety. Thus, disclosed formulas can be synthesized as shown in Scheme 6A.
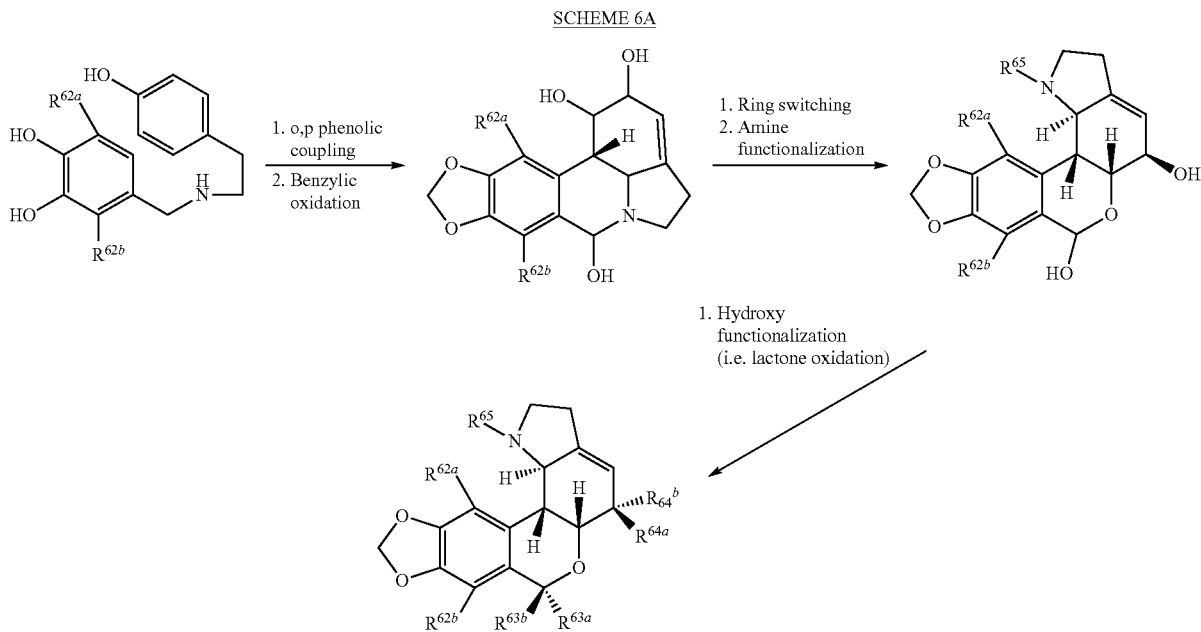
Thus, for example, Hippeastrine can be made as shown in Scheme 6B.
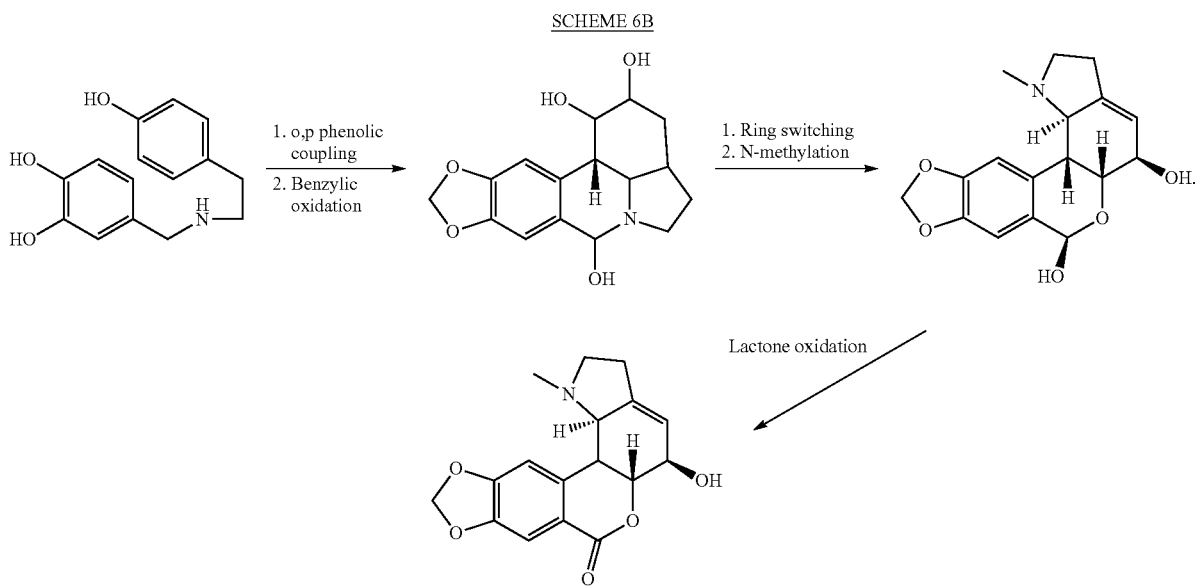

Another route to make the disclosed formulas is shown in Scheme 6C, as demonstrated by Mafias et al.

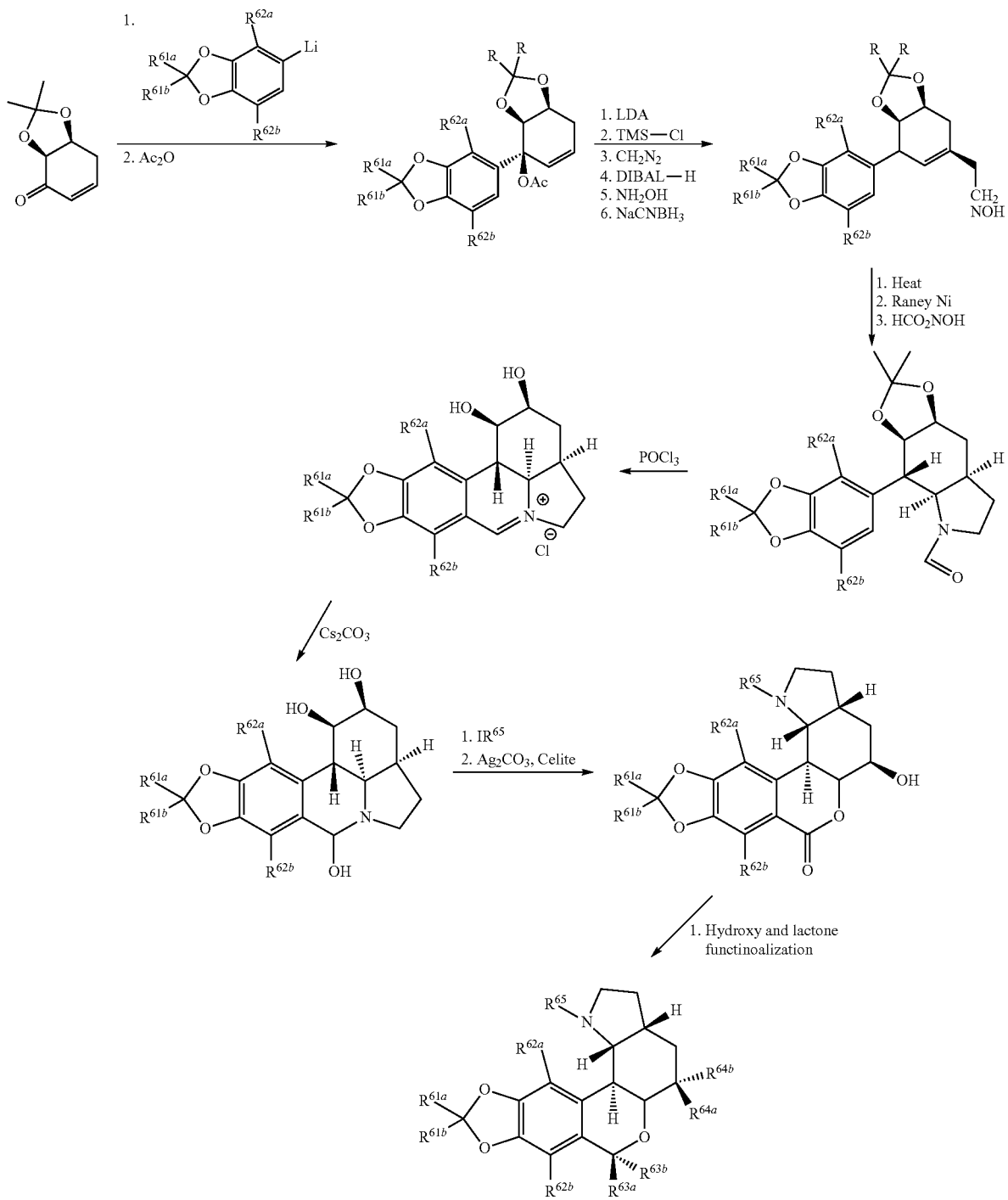

The disclosed derivatives can also be made using methods disclosed by Haning et al (*Org. Biomolec. Chem.* 2011, 9, 2809-2820).

22. Prophetic Synthesis of Betulinic Acid and Analogs

Betulininc acid analogs are also described in International Published application WO 2011/153315 by Regueiro-Ren et al. and in International Published application WO 2008/063318 by Safe et al. which are hereby incorporated by reference in its entirety. Betulinic acid analogs of the present invention of the present invention could be prepared generically as shown below in scheme 7A. The starting materials could be made with methods known in the art.

SCHEME 7A
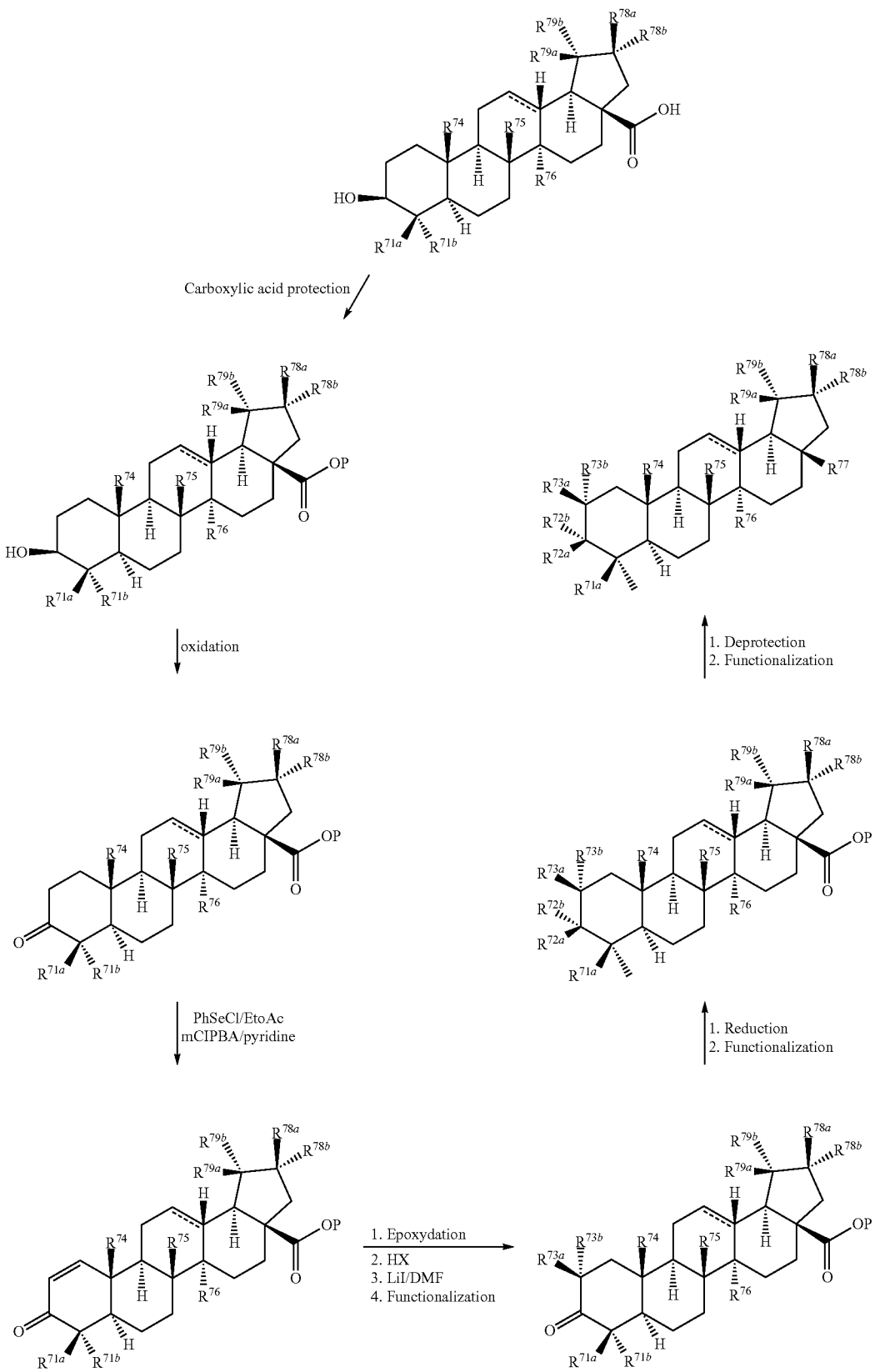

Compounds are represented in generic form, with substituents as noted in compound descriptions elsewhere herein. A more specific example is set forth below in scheme 7B.

SCHEME 7B

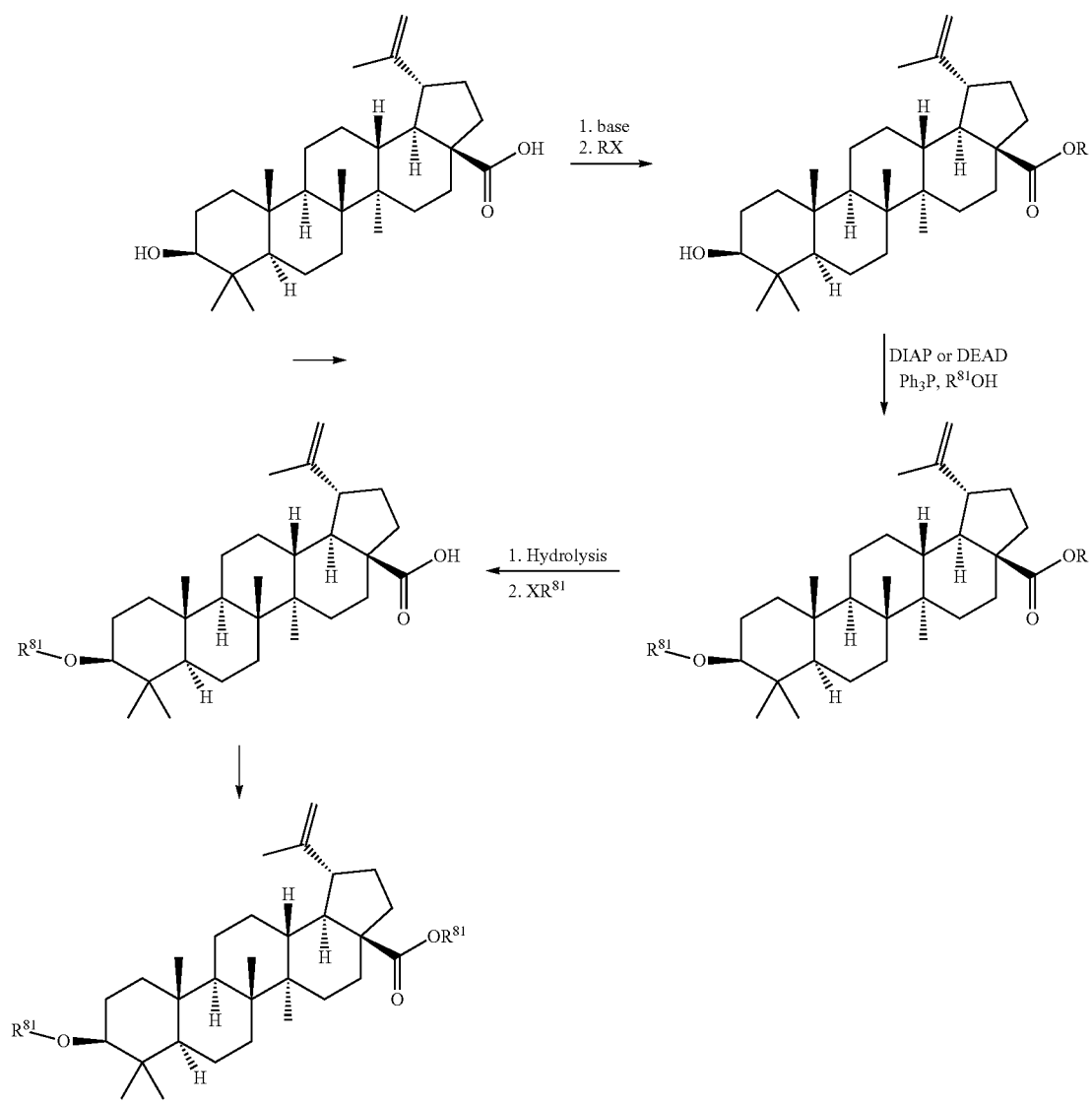

23. Muscle Atrophy Signature—3

Induced and repressed mRNA were evaluated for muscle atrophy signature-3. The statisitical significance for the identified mRNAs was defined as P≤0.01.

For induced mRNAs: mouse tibialis anterior mRNAs significantly induced by 1 week of denervation and significantly induced by 24 h fasting.

For repressed mRNAs: mouse tibialis anterior mRNAs significantly repressed by 1 week of denervation and significantly repressed by 24 h fasting.

The identified induced mRNAs included 1200011I18Rik, 2310004I24Rik, Akap81, Als2, Anapc7, Apod, Arrdc3, Atp6v1h, BC027231, Bsdc1, Ccdc77, Cd68, Cdkn1a, Ctps2, Ctsl, D930016D06Rik, Ddx21, Depdc7, Dido1, nttip2, Ece1, Eda2r, Egln3, Elk4, Erbb2ip, Errfi1, Fbxo30, Fbxo32, Fip1l1, Frg1, Gabarap1l, Gadd45a, Gnl2, Gnl3, Herpud2, Hpgd, Hspb7, Htatip2, Impact, Kdm3a, Klhl5, Lpin2, Medl2, Mfap1b, Mgea5, Mknk2, Nmd3, Nup93, ORF19, Pacrg1, Parp4, Pdk4, Phc3, Plaa, Ppfibp1, Psma2, Ranbp10, Ranbp9, Rassf4, Riok1, Rlim, Sf3b1, Sik1, Slc20a1, Sln, Spag5, Srsf2ip, Syf2, Tbc1d15, Tbk1, Tekt1, Tgif1, Tmem140, Tmem71, Tnks, Trim25, Trmt1, Tspyl2, Tsr1, Tulp3, Txlng, Ubfd1, Ubxn4, Utp14a, Wdr3, and Xpo4.

The identified repressed mRNAs included 1600014C10Rik, 1700021F05Rik, 2310003L22Rik, 2310010M20Rik, 2310028O11Rik, 2310061C15Rik, 2610528E23Rik, 2810432L12Rik, Abcd2, Acvrl, Aimp2, Ank1, Aqp4, Arl3, Asb10, Aurka, Bhlhe41, Bpnt1, Camk2a, Cby1, Cc2d2a, Cdc14a, Cdc42ep2, Clcn1, Cntfr, Col15a1, Col6a3, Cox11, Cox7b, Crhr2, DOH4S114, Ddit3, Deb1, Dexi, Dhrs7c, Eif4e, Endog, Epha7, Exd2, Fam69a, Fhod3, Fn3k, Fndc5, Fsd2, Gcom1, Gdap1, Gm4841, Gm5105, Gm9909, Gnb5, Gpd2, Grtp1, Heatr5a, Hlf, Homer1, Ikzf2, Inppl1, Irx3, Itgb6, Jarid2, Jph2, Khdrbs3, Klf7, Klhl23, Ky, Lrp2 bp, Lrrfip1, Map2k6, Map3k4, Mat2a, Mkks, Mkl1, Mrc2, Mreg, Mrpl39, Narf, Ntf5, Nudt3, Osbpl6, Ostc, Parp8, Pkia, Plcd4, Podxl, Polk, Polr3k, Ppml1, Pppde2, Prss23, Psd3, Psph, Ptpmt1, Ptx3, Qrsl1, Rasgrp3, Rhobtb3, Ric8b, Rnf150, Rsph1, Rundc1, Rxrg, Sel1l3, Sema3a, Sgcd, Shisa2, Sirt5, Slc25a19, Slc41a3, Slc4a4, Slco5a1, Snrnp35, Stac3, Ston2, Stradb, Stxbp4, Tfrc, Tmc7, Tmem218, Tmtc1, Tnfaip2, Tob1, Trim35, Ttl, Vegfa, and Vgll4.

24. Muscle Atrophy Signature—4

Induced and repressed mRNA were evaluated for muscle atrophy signature-4. The statisitical significance for the identified mRNAs was defined as P≤0.01.

For induced mRNAs: mouse tibialis anterior mRNAs significantly induced by 1 week of denervation and significantly induced by 1 week of Gadd45a overexpression.

For repressed mRNAs: mouse tibialis anterior mRNAs significantly repressed by 1 week of denervation and significantly repressed by 1 week of Gadd45a overexpression.

The identified induced mRNAs included 2410089E03Rik, 6720456H20Rik, Abca1, Abhd2, Abr, Aifl1, Akap6, Alg8, Alox5ap, mpd3, Ankrd1, Anxa4, Aoah, App, Araf, Arfgap3, Arhgef2, Arpc3, Arpp21, Atf7ip, Atp6ap2, Atp6vlh, Atp7a, Atp8b1, B4galt5, Bax, Baz2a, Bhlhb9, Bmp2k, C3ar1, Canx, Casp3, Ccdc111, Ccdc122, Ccdc93, Ccndbp1, Cct4, Cd68, Cd82, Cdkn1a, Cep192, Cgref1, Chd4, Chrna1, Chrnb1, Chrng, Chuk, Clec12a, Clec4a3, Col19a1, Copb2, Cpne2, Cstb, Ctnna1, Ctps2, Ctsd, Ctsl, Ctss, Ctsz, Cyb5r3, Cybb, Cyr61, D10Wsu52e, D930016D06Rik, Dcaf13, Dclre1c, Dctn5, Ddb1, Ddhd1, Decr2, Derl1, Dhx9, Dido1, Dnajc1, Eda2r, Eef1b2, Eef2, Emr1, Epb4.113, Erbb2ipm, Erlin1, Esyt1, Fam108c, Fam115a, Fbxo30, Frrs1, Fst, Fubp1, Fyb, Gab2, Gabarap, Gadd45a, Galc, Galnt7, Ganab, Gigyf2, Gm3435, Gnb211, Gng2, Gnl2, Gnl3, Gprasp1, Gpsm2, Gramd1b, H19, H2-Aa, Hmgn3, Hn1, Hnrnpu, Hprt, Hsp90ab1, Hsp90b1, Hspa2, Hspa4, Hspb8, Htatip2, Id2, Ifi30, Igbp1, Igdcc4, Ilf3, Imp4, Impact, Irak4, Itm2b, Ivns1abp, Kcnn3, Kdm3a, Khdrbs1, Kif5b, Klhl5, Krt18, Lbh, Lgals3, Lgmn, Lpar6, Lpin2, Lyz2, Macf1, Map1lc3a, Map3k1, Map4k4, Marveld2, Matr3, Mcm6, Mdm2, Mdm4, Me2, Med12, Mgea5, Micall1, Mpp1, Mrc1, Mtap1b, Myf6, Myl4, Myo5a, Ncam1, Nip7, Nln, Nop58, Nrcam, Nup93, Nvl, Obfc2a, Osbpl8, Palm2, Parp4, Pcbd1, Pcgf3, Pdlim3, Pfn1, Pgd, Pik3r3, Plaa, Plekha5, Plxdc2, Plxna1, Polr2a, Polr3b, Ppfibp1, Ppib, Prep, Prkdc, Prmt1, Prss48, Prune2, Psmb1, Psmd5, Rad50, Rassf4, Rb1, Rbm45, Reep5, Rgs2, Riok3, Rlim, Rnasel, Rpl31, Rps3, Rps9, Rrad, Rras2, Rspry1, Runx1, Sap30 bp, Sema4d, Sema6a, Serf1, Serpinb6a, Sesn3, Sf3b1, Sf3b3, Sgpl1, Sh3d19, Sh3pxd2a, Sh3rf1, Sik1, Sirpa, Slc20al, Slc25a24, Slc9a7, Slc9a9, Sln, Smarcad1, Smc1a, Smc5, Snd1, Snx5, Spin1, Srp14, Ssu72, Stam, Supt5h, Tbc1d8, Tbcd, Tbxas1, Tec, Tgfbr1, Tgs1, Thoc5, Thumpd3, Tiam2, Tlr4, Tlr6, Tmeff1, Tmem176b, Tmem179b, Tmem209, Tmem38b, Tnc, Tnfrsf22, Tnfrsf23, Tnnt2, Trim25, Trp63, Tubb5, Tubb6, Tyrobp, Uchl1, Ugcg, Usp11, Usp5, Wasf2, Wbp5, Wbscr27, Wdr36, Wdr61, Wdr67, Wdr77, Wdyhv1, Wsb1, Ylpm1, Ypel2, Ywhab, Zfp280d, Zfp318, Zfp346, Zfp3611, and Zmynd8.

The identified repressed mRNAs included 0610012G03Rik, 1110001J03Rik, 1110067D22Rik, 2010106G01Rik, 2310002L09Rik, 2310003L22Rik, 2310010M20Rik, 2610507B11Rik, 2610528E23Rik, 2810407C02Rik, 4931409K22Rik, 4933403F05Rik, 5730437N04Rik, 9630033F20Rik, A21d1, A930018M24Rik, Abcb1a, Abcb4, Abcd2, Abi3 bp, Acaa2, Acadm, Acadvl, Acat1, Acot13, Adal, Adcy10, Adk, Adssl1, Aes, AI317395, Aimp2, Ak1, Alas2, Aldh1a1, Ank, Ank1, Ankrd9, Ano2, Ano5, Aplp2, Apobec2, Aqp4, Ar, Arhgap19, Arhgap20, Arhgap31, Arl3, Asb10, Asb11, Asb12, Asb14, Asb15, Atp11a, Atp13a5, Atp1b1, Atp5al, Atp5e, Atp8al, Atxn1, B4galt4, Bckdk, Bhlhe41, Bpgm, Bpil1, Brp44, Btbd1, C2cd2, Camk2a, Camk2g, Capn5, Car8, Cast, Cc2d2a, Ccng1, Ccnk mCd34, Cd36, Cdc14a, Cdc42ep3, Cdh5, Cdnf, Ces1d, Chchd10, Chchd3, Cib2, Ckm, Clcn1, Clic5, Cmbl, Cntfr, Col11a1, Coq9, Cox11, Cox6a2, Cox8b, Cpt1b, Csrp2 bp, Cuedc1, Cyb5b, Cyyr1, DOH4S114, D1Ertd622e, Dab2ip, Dcunld2, Deb1, Decr1, Dgkb, Dhrs7c, Dlat, Dlc1, Dlg1, Dlst, Dnajb5, Dusp28, Ecsit, Eef1a2, Eepd1, Efcab2, Eif4e, Endog, Eno3, Epas1, Epha7, Etfb, Exd2, Eya1, Fam132a, Fastkd3, Fbp2, Fbxo3, Fdx1, Fez2, Fgfbp1, Fh1, Fitm2, Flt1, Fmo5, Fsd2, Fxyd1, Fzd4, G3bp2, Ganc, Gbas, Gcom1, Gdap1, Ghr, Gjc3, Glb112, Gm4841, Gm4861, Gm4951, Gm5105, Gmpr, Gpcpd1, Gpd1, Gpd2, Gpt2, Grsf1, Gucy1a3, Gys1, Hadh, Hfe2, Hivep2, Hk2, Hlf, Homer1, Hsdl2, Idh3a, Idh3g, Il15ra, Inpp5a, Irx3, Jak2, Jam2, Jph1, Kcna7, Kcnj2, Kcnn2, Kdr, Khdrbs3, Kif1b, Kif1c, Kitl, Klf12, Klh123, Klhl31, Klhl31, Klhl7, Ky, Ldb3, Lifr, Lmbr1, Lphn1, Lpin1, Lpl, Lrig1, Lrrc39, Lynx1, Man2a2, Maob, Map2k6, Map2k7, Map3k4, Mapkapk2, Mbnl1, Mccc1, Mdh1, Mdh2, Me3, Mfn1, Mfn2, Mgst3, Mlf1, Mpnd, Mpz, Mr1, Mreg, Mtus1, Mybpc2, Myo5c, Myom2, Myoz1, Narf, Ndrg2, Ndufa3, Ndufa5, Ndufa8, Ndufb8, Ndufb9, Ndufs1, Ndufs2, Ndufs6, Ndufs8, Ndufv1, Nf2, Nos1, Nr1d1, Nudt3, Oat, Ociad2, Ocrl, Osbpl6, Osgepl1, Ostn, Paqr9, Parp3, Pcmtd1, Pent, Pcnx, Pdgfd, Pdha1, Pdpr, Pfkfb3, Pfkm, Pfn2, Pgam2, Phb, Phka1, Phkg1, Phtf2, Phyh, Pitpnc1, Pkdcc, Pkia, Pla2g12a, Pla2g4e, Plcb1, Plcd4, Pln, Pmp22, Ppara, Ppargc1a, Ppat, Ppm1a, Ppm11, Ppp1cb, Ppp1r1a, Ppp2r2a, Ppp3cb, Prelp, Prkab2, Prkca, Prkg1, Ptp4a3, Ptprb, Pttg1, Pxmp2, Pygm, Rab28, Rasgrp3, Rcan2, Rgs5, Rhot2, Rnf123, Rpa1, Rpl3l, Rtn4ip1, Samd12, Samd5, Satb1, Scn4a, Scn4b, Sdha, Sdhb, Sdr39u1, Sel1l3, Sema6c, Serpine2, Shisa2, Slc15a5, Slc16a3, Slc19a2, Slc24a2, Slc25a11, Slc25a12, Slc25a3, Slc25a4, Slc2a12, Slc2a4, Slc35f1, Slc37a4, Slc43a3, Slc4a4, Slc6a13, Slc6a8, Slc9a3r2, Slco3a1, Smarca1, Smox, Smyd1, Snrk, Sorbs2, Spop, Srl, St3ga13, St3gal6, St6galnac6, Stk381, Stradb, Strbp, Strbp, Stxbp4, Suclg1, Tab2, Taf3, Tarsl2, Tcea3, Thra, Tiam1, Timp4, Tln2, Tmem126a, Tmem126b, Tmem65, Tnfaip2, Tnmd, Tnnc2, Tnni2, Tnxb, Tomm401, Trak1, Trak2, Trim24, Trpc3, Tuba8, Txlnb, Txnip, U05342, Uaca, Ulk2, Uqcrc1, Uqcrfs1, Uqcrq, Vamp5, Vdac1, Vegfa, Vegfb, Xpr1, Yipf7, Zfand5, Zfp191, and Zfp238.

F. REFERENCES

The following references, to the extent that they provide exemplary procedural or other details supplementary to those set forth herein, are specifically incorporated herein by reference.

1. Bodine S C, et al. (2001) Akt/mTOR pathway is a crucial regulator of skeletal muscle hypertrophy and can prevent muscle atrophy in vivo. *Nat Cell Biol* 3(11): 1014-1019.
2. Sandri M, et al. (2004) Foxo transcription factors induce the atrophy-related ubiquitin ligase atrogin-1 and cause skeletal muscle atrophy. *Cell* 117(3):399-412.
3. Stitt T N, et al. (2004) The IGF-1/PI3K/Akt pathway prevents expression of muscle atrophy-induced ubiquitin ligases by inhibiting FOXO transcription factors. *Mol Cell* 14(3):395-403.

4. Hu Z, et al. (2009) Endogenous glucocorticoids and impaired insulin signaling are both required to stimulate muscle wasting under pathophysiological conditions in mice. *The Journal of clinical investigation* 119(10):3059-3069.
5. Dobrowolny G, et al. (2005) Muscle expression of a local Igf-1 isoform protects motor neurons in an ALS mouse model. *The Journal of cell biology* 168(2):193-199.
6. Kandarian S C & Jackman R W (2006) Intracellular signaling during skeletal muscle atrophy. *Muscle & nerve* 33(2):155-165.
7. Hirose M, et al. (2001) Long-term denervation impairs insulin receptor substrate-1-mediated insulin signaling in skeletal muscle. *Metabolism: clinical and experimental* 50(2):216-222.
8. Pallafacchina G, et al. (2002) A protein kinase B-dependent and rapamycin-sensitive pathway controls skeletal muscle growth but not fiber type specification. *Proceedings of the National Academy of Sciences of the United States of America* 99(14):9213-9218.
9. Sandri M (2008) Signaling in muscle atrophy and hypertrophy. *Physiology (Bethesda)* 23:160-170.
10. Glass D J (2005) Skeletal muscle hypertrophy and atrophy signaling pathways. *The international journal of biochemistry & cell biology* 37(10): 1974-1984.
11. Lecker S H, et al. (2004) Multiple types of skeletal muscle atrophy involve a common program of changes in gene expression. *Faseb J* 18(1):39-51.
12. Sacheck J M, et al. (2007) Rapid disuse and denervation atrophy involve transcriptional changes similar to those of muscle wasting during systemic diseases. *Faseb J* 21(1): 140-155.
13. Jagoe R T, et al. (2002) Patterns of gene expression in atrophying skeletal muscles: response to food deprivation. *Faseb J* 16(13): 1697-1712.
14. Sandri M, et al. (2006) PGC-1alpha protects skeletal muscle from atrophy by suppressing FoxO3 action and atrophy-specific gene transcription. *Proceedings of the National Academy of Sciences of the United States of America* 103(44): 16260-16265.
15. Wenz T, et al. (2009) Increased muscle PGC-1alpha expression protects from sarcopenia and metabolic disease during aging. *Proceedings of the National Academy of Sciences of the United States of America* 106(48): 20405-20410.
16. Bodine S C, et al. (2001) Identification of ubiquitin ligases required for skeletal muscle atrophy. *Science (New York, N.Y.* 294(5547):1704-1708.
17. Lagirand-Cantaloube J, et al. (2008) The initiation factor eIF3-f is a major target for atrogin1/MAFbx function in skeletal muscle atrophy. *The EMBO journal* 27(8):1266-1276.
18. Cohen S, et al. (2009) During muscle atrophy, thick, but not thin, filament components are degraded by MuRF1-dependent ubiquitylation. *The Journal of cell biology* 185(6):1083-1095.
19. Adams V, et al. (2008) Induction of MuRF1 is essential for TNF-alpha-induced loss of muscle function in mice. *Journal of molecular biology* 384(1):48-59.
20. Leger B, et al. (2006) Human skeletal muscle atrophy in amyotrophic lateral sclerosis reveals a reduction in Akt and an increase in atrogin-1. *Faseb J* 20(3):583-585.
21. Doucet M, et al. (2007) Muscle atrophy and hypertrophy signaling in patients with chronic obstructive pulmonary disease. *American journal of respiratory and critical care medicine* 176(3):261-269.
22. Levine S, et al. (2008) Rapid disuse atrophy of diaphragm fibers in mechanically ventilated humans. *The New England journal of medicine* 358(13): 1327-1335.
23. Adams C M, et al. (2011) Altered mRNA expression after long-term soleus electrical stimulation training in humans with paralysis. *Muscle & nerve* 43(1):65-75.
24. Ebert S M, et al. (2010) The transcription factor ATF4 promotes skeletal myofiber atrophy during fasting. *Molecular endocrinology* 24(4):790-799.
25. Lamb J, et al. (2006) The Connectivity Map: using gene-expression signatures to connect small molecules, genes, and disease. *Science (New York, N.Y.* 313(5795): 1929-1935.
26. Frighetto R T S, et al. (2008) Isolation of ursolic acid from apple peels by high speed counter-current chromatography. *Food Chemistry* 106:767-771.
27. Liu J (1995) Pharmacology of oleanolic acid and ursolic acid. *Journal of ethnopharmacology* 49(2): 57-68.
28. Liu J (2005) Oleanolic acid and ursolic acid: research perspectives. *Journal of ethnopharmacology* 100(1-2):92-94.
29. Wang Z H, et al. (2010) Anti-glycative effects of oleanolic acid and ursolic acid in kidney of diabetic mice. *European journal of pharmacology* 628(1-3):255-260.
30. Jang S M, et al. (2009) Ursolic acid enhances the cellular immune system and pancreatic beta-cell function in streptozotocin-induced diabetic mice fed a high-fat diet. *Int Immunopharmacol* 9(1): 113-119.
31. Jung S H, et al. (2007) Insulin-mimetic and insulin-sensitizing activities of a pentacyclic triterpenoid insulin receptor activator. *The Biochemical journal* 403(2):243-250.
32. Zhang W, et al. (2006) Ursolic acid and its derivative inhibit protein tyrosine phosphatase 1B, enhancing insulin receptor phosphorylation and stimulating glucose uptake. *Biochimica et biophysica acta* 1760(10): 1505-1512.
33. Goldstein B J, et al. (2000) Tyrosine dephosphorylation and deactivation of insulin receptor substrate-1 by protein-tyrosine phosphatase 1B. Possible facilitation by the formation of a ternary complex with the Grb2 adaptor protein. *The Journal of biological chemistry* 275(6):4283-4289.
34. Delibegovic M, et al. (2007) Improved glucose homeostasis in mice with muscle-specific deletion of protein-tyrosine phosphatase 1B. *Molecular and cellular biology* 27(21):7727-7734.
35. Zabolotny J M, et al. (2004) Transgenic overexpression of protein-tyrosine phosphatase 1B in muscle causes insulin resistance, but overexpression with leukocyte antigen-related phosphatase does not additively impair insulin action. *The Journal of biological chemistry* 279(23): 24844-24851.
36. Sivakumar G, et al. (2009) Plant-based corosolic acid: future anti-diabetic drug? *Biotechnol J* 4(12):1704-1711.
37. Ebert S M, et al. (2010) The transcription factor ATF4 promotes skeletal myofiber atrophy during fasting. *Molecular Endocrinology* 24(4):790-799.
38. Dubowitz V, et al. (2007) *Muscle biopsy: a practical approach* (Saunders Elsevier, Philadelphia) 3rd Ed pp XIII, 611 s.
39. Hishiya A, et al. (2006) A novel ubiquitin-binding protein ZNF216 functioning in muscle atrophy. *The EMBO journal* 25(3):554-564.
40. Adams C M, et al. (2011) Altered mRNA expression after long-term soleus electrical stimulation training in humans with paralysis. *Muscle Nerve.* 43(1):65-75

41. Hameed M, et al. (2004) The effect of recombinant human growth hormone and resistance training on IGF-I mRNA expression in the muscles of elderly men. *The Journal of physiology* 555(Pt 1):231-240.
42. Adams G R & Haddad F (1996) The relationships among IGF-1, DNA content, and protein accumulation during skeletal muscle hypertrophy. *J Appl Physiol* 81(6):2509-2516.
43. Gentile M A, et al. (2010) Androgen-mediated improvement of body composition and muscle function involves a novel early transcriptional program including IGF1, mechano growth factor, and induction of {beta}-catenin. *Journal of molecular endocrinology* 44(1):55-73.
44. Shavlakadze T, et al. (2005) Insulin-like growth factor I slows the rate of denervation induced skeletal muscle atrophy. *Neuromuscul Disord* 15(2):139-146.
45. Sacheck J M, et al. (2004) IGF-I stimulates muscle growth by suppressing protein breakdown and expression of atrophy-related ubiquitin ligases, atrogin-1 and MuRF1. *Am J Physiol Endocrinol Metab* 287(4):E591-601.
46. Frost R A, et al. (2009) Regulation of REDD1 by insulin-like growth factor-1 in skeletal muscle and myotubes. *J Cell Biochem* 108(5):1192-1202.
47. Lee S J (2004) Regulation of muscle mass by myostatin. *Annu Rev Cell Dev Biol* 20:61-86.
48. Dupont J, et al. (2001) Insulin-like growth factor 1 (IGF-1)-induced twist expression is involved in the anti-apoptotic effects of the IGF-1 receptor. *The Journal of biological chemistry* 276(28):26699-26707.
49. Tureckova J, et al. (2001) Insulin-like growth factor-mediated muscle differentiation: collaboration between phosphatidylinositol 3-kinase-Akt-signaling pathways and myogenin. *The Journal of biological chemistry* 276 (42):39264-39270.
50. Yakar S, et al. (1999) Normal growth and development in the absence of hepatic insulin-like growth factor I. *Proceedings of the National Academy of Sciences of the United States of America* 96(13):7324-7329.
51. Adams G R, et al. (1999) Time course of changes in markers of myogenesis in overloaded rat skeletal muscles. *J Appl Physiol* 87(5): 1705-1712.
52. Lai K M, et al. (2004) Conditional activation of akt in adult skeletal muscle induces rapid hypertrophy. *Molecular and cellular biology* 24(21):9295-9304.
53. Izumiya Y, et al. (2008) Fast/Glycolytic muscle fiber growth reduces fat mass and improves metabolic parameters in obese mice. *Cell metabolism* 7(2):159-172.
54. Jayaprakasam B, et al. (2006) Amelioration of obesity and glucose intolerance in high-fat-fed C57BL/6 mice by anthocyanins and ursolic acid in Cornelian cherry (*Cornus mas*). *J Agric Food Chem* 54(1):243-248.
55. de Melo C L, et al. (2010) Oleanolic acid, a natural triterpenoid improves blood glucose tolerance in normal mice and ameliorates visceral obesity in mice fed a high-fat diet. *Chem Biol Interact* 185(1):59-65.
56. Qian S, et al. (2010) Synthesis and biological evaluation of oleanolic acid derivatives as inhibitors of protein tyrosine phosphatase 1B. *J Nat Prod* 73(11):1743-1750.
57. Zhang Y N, et al. (2008) Oleanolic acid and its derivatives: new inhibitor of protein tyrosine phosphatase 1B with cellular activities. *Bioorg Med Chem* 16(18):8697-8705.
58. Klaman L D, et al. (2000) Increased energy expenditure, decreased adiposity, and tissue-specific insulin sensitivity in protein-tyrosine phosphatase 1B-deficient mice. *Molecular and cellular biology* 20(15):5479-5489.
59. Reagan-Shaw S, Nihal M, & Ahmad N (2008) Dose translation from animal to human studies revisited. *Faseb J* 22(3):659-661.
60. Barton-Davis E R, et al. (1998) Viral mediated expression of insulin-like growth factor I blocks the aging-related loss of skeletal muscle function. *Proceedings of the National Academy of Sciences of the United States of America* 95(26): 15603-15607.
61. Musaro A, et al. (2001) Localized Igf-1 transgene expression sustains hypertrophy and regeneration in senescent skeletal muscle. *Nature Genetics* 27(2): 195-200.
62. Zhou X, et al. (2010) Reversal of cancer cachexia and muscle wasting by ActRIIB antagonism leads to prolonged survival. *Cell* 142(4):531-43.

The invention claimed is:

1. A method for:

(a) increasing skeletal muscle mass;

(b) reducing skeletal muscle atrophy;

(c) increasing muscular strength;

(d) promoting muscle growth;

(e) decreasing muscle wasting; or (f) increasing strength per unit of muscle mass in an animal identified or having been identified to be in need of one or more of (a)-(f), the method comprising administering to the animal an effective amount of a compound of formula:

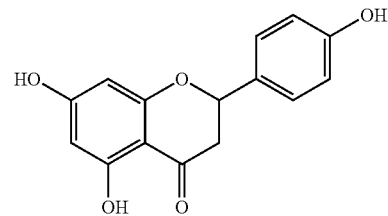 [SMILES: O=C1CC(c2ccc(O)cc2)Oc2cc(O)cc(O)c21]

or a stereoisomer, solvate, or pharmaceutically acceptable salt thereof, thereby accomplishing one or more of (a)-(f).

2. The method according to claim 1, for increasing skeletal muscle mass, wherein the compound is

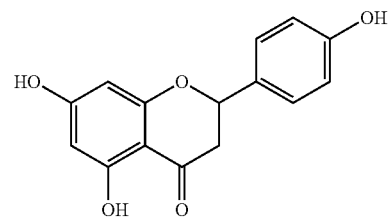 [SMILES: O=C1CC(c2ccc(O)cc2)Oc2cc(O)cc(O)c21]

or a stereoisomer or pharmaceutically acceptable salt thereof.

3. The method according to claim 1, for reducing skeletal muscle atrophy, wherein the compound is

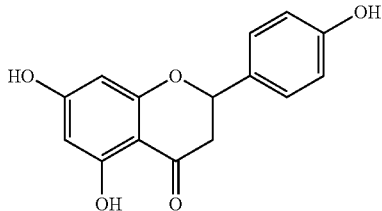 [SMILES: O=C1CC(c2ccc(O)cc2)Oc2cc(O)cc(O)c21]

or a stereoisomer or pharmaceutically acceptable salt thereof.

4. The method according to claim 1, for increasing muscular strength, wherein the compound is

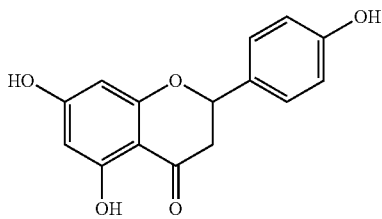 [SMILES: O=C1CC(c2ccc(O)cc2)Oc2cc(O)cc(O)c21]

or a stereoisomer or pharmaceutically acceptable salt thereof.

5. The method according to claim 1, for promoting muscle growth, wherein the compound is

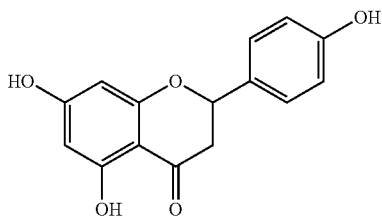 [SMILES: O=C1CC(c2ccc(O)cc2)Oc2cc(O)cc(O)c21]

or a stereoisomer or pharmaceutically acceptable salt thereof.

6. The method according to claim 1, for decreasing muscle wasting, wherein the compound is:

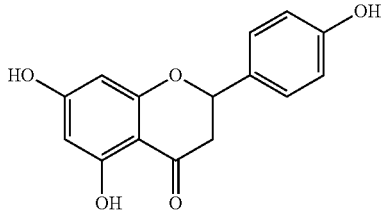 [SMILES: O=C1CC(c2ccc(O)cc2)Oc2cc(O)cc(O)c21]

or a stereoisomer or pharmaceutically acceptable salt thereof.

7. The method according to claim 1, for increasing strength per unit of muscle mass, wherein the compound is

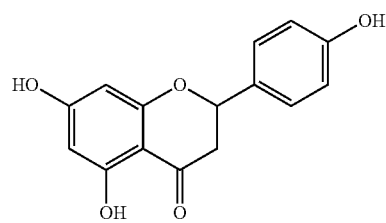 [SMILES: O=C1CC(c2ccc(O)cc2)Oc2cc(O)cc(O)c21]

or a stereoisomer or pharmaceutically acceptable salt thereof.

8. The method according to claim 1, comprising administering to the animal greater than 75 mg per day of the compound or stereoisomer, solvate, or pharmaceutically acceptable salt thereof.

9. The method according to claim 1, comprising administering to the animal greater than 100 mg per day of the compound or stereoisomer, solvate, or pharmaceutically acceptable salt thereof.

10. The method according to claim 1, wherein the compound is

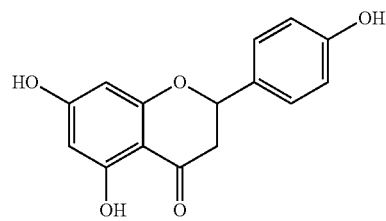 [SMILES: O=C1CC(c2ccc(O)cc2)Oc2cc(O)cc(O)c21]

or a stereoisomer or pharmaceutically acceptable salt thereof.

11. The method according to claim 1, comprising administering to the animal greater than 150 mg per day of the compound or stereoisomer, solvate, or pharmaceutically acceptable salt thereof.

12. The method according to claim 11, wherein the compound is

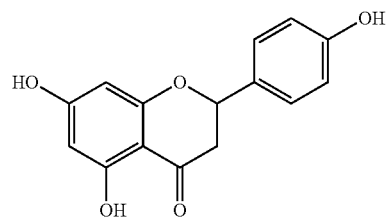 [SMILES: O=C1CC(c2ccc(O)cc2)Oc2cc(O)cc(O)c21]

or a stereoisomer or pharmaceutically acceptable salt thereof.

13. The method according to claim 1, comprising administering to the animal at least 5.0 mg/kg per day of the compound or stereoisomer, solvate, or pharmaceutically acceptable salt thereof.

14. The method according to claim 13, wherein the compound is

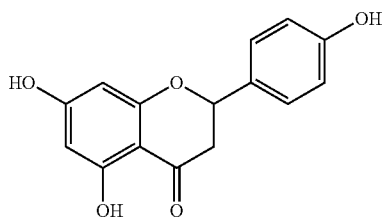 [SMILES: O=C1CC(c2ccc(O)cc2)Oc2cc(O)cc(O)c21]

or a stereoisomer or pharmaceutically acceptable salt thereof.

15. The method according to claim 1, comprising administering to the animal 0.5 to 250 mg/kg per day of the compound or stereoisomer, solvate, or pharmaceutically acceptable salt thereof.

16. The method according to claim 15, wherein the compound is

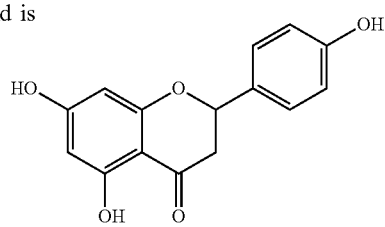

or a stereoisomer or pharmaceutically acceptable salt thereof.

17. The method according to claim 1, wherein said animal is selected from the group consisting of a non-human primate, domesticated fish, domesticated crustacean, domesticated mollusk, poultry, dog, cat, guinea pig, and livestock.

18. The method according to claim 17, wherein the compound is

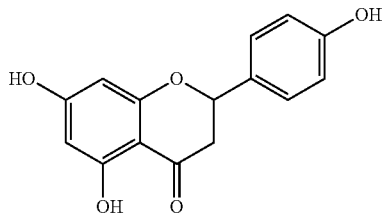 [SMILES: O=C1CC(c2ccc(O)cc2)Oc2cc(O)cc(O)c21]

or a stereoisomer or pharmaceutically acceptable salt thereof.

19. The method according to claim 1, wherein said animal is a human.

20. The method according to claim 19, wherein the compound is

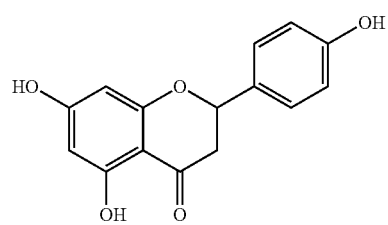 [SMILES: O=C1CC(c2ccc(O)cc2)Oc2cc(O)cc(O)c21]

or a stereoisomer or pharmaceutically acceptable salt thereof.

21. The method according to claim 1, wherein the compound of formula:

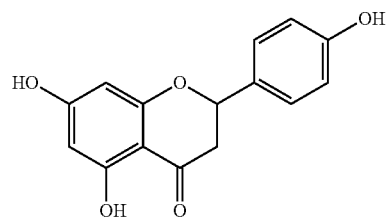 [SMILES: O=C1CC(c2ccc(O)cc2)Oc2cc(O)cc(O)c21]

is administered to the animal in a composition that does not comprise an antibacterial phenol.

* * * * *